United States Patent
Wang et al.

(10) Patent No.: US 9,856,262 B2
(45) Date of Patent: Jan. 2, 2018

(54) ANALOGUES OF 4H-PYRAZOLO[1,5-A] BENZIMIDAZOLE COMPOUND AS PARP INHIBITORS

(71) Applicants: HUBEI BIO-PHARMACEUTICAL INDUSTRIAL TECHNOLOGICAL INSTITUTE INC., Wuhan, Hubei (CN); HUMANWELL HEALTHCARE (GROUP) CO., LTD., Wuhan, Hubei (CN); MEDSHINE DISCOVERY INC., Nanjing, Jiangsu (CN)

(72) Inventors: Xuehai Wang, Wuhan (CN); Zhaozhong Ding, Shanghai (CN); Yong Xu, Wuhan (CN); Shuhui Chen, Shanghai (CN); Lie Li, Wuhan (CN); Gang Li, Shanghai (CN); Ronghua Tu, Wuhan (CN); Cailin Wang, Shanghai (CN); Yang Yue, Wuhan (CN); Zhibo Zhang, Shanghai (CN); Hailiang Chen, Wuhan (CN); Wenjie Sun, Wuhan (CN); Lu Huang, Wuhan (CN)

(73) Assignees: Hubei Bio-Pharmaceutical Industrial Technological Institute Inc., Wuhan, Hubei (CN); Humanwell Healthcare (Group) Co., Ltd., Wuhan, Hubei (CN); Medshine Discovery Inc., Nanjing, Jiangsu (CN)

( * ) Notice: Subject to any disclaimer, the term of this patent is extended or adjusted under 35 U.S.C. 154(b) by 0 days.

(21) Appl. No.: 15/302,588

(22) PCT Filed: Mar. 30, 2015

(86) PCT No.: PCT/CN2015/075363
§ 371 (c)(1),
(2) Date: Oct. 7, 2016

(87) PCT Pub. No.: WO2015/154630
PCT Pub. Date: Oct. 15, 2015

(65) Prior Publication Data
US 2017/0029430 A1   Feb. 2, 2017

(30) Foreign Application Priority Data

Apr. 10, 2014 (CN) .......... 2014 1 0144173
Mar. 13, 2015 (CN) .......... 2015 1 0113090

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
None
See application file for complete search history.

(56) References Cited

U.S. PATENT DOCUMENTS

2015/0166544 A1   6/2015 Zhang et al.

FOREIGN PATENT DOCUMENTS

| CN | 104974161 A | 10/2015 |
|---|---|---|
| EP | 2656843 A1 | 10/2013 |
| JP | 2009541346 A | 11/2009 |
| WO | WO-2007076127 A2 | 7/2007 |
| WO | WO-2007/149907 A2 | 12/2007 |
| WO | WO-2007144669 A1 | 12/2007 |
| WO | WO-2008090379 A1 | 7/2008 |
| WO | WO-2013164061 A1 | 11/2013 |
| WO | WO-2013174822 A1 | 11/2013 |
| WO | WO-2013182580 A1 | 12/2013 |
| WO | WO-2014009872 A1 | 1/2014 |
| WO | WO-2014019468 A1 | 2/2014 |
| WO | WO-2014023390 A2 | 2/2014 |

OTHER PUBLICATIONS

Helen E. Bryant, etc., Specific killing of BRCA2-deficient tumours with inhibitors of poly(ADP-ribose) polymerase; Nature 434, 913-917 (2005).
Dana V. Ferraris; Evolution of Poly(ADP-ribose) Polymerase-1 (PARP-1) Inhibitors. From Concept to Clinic; J. Med. Chem. 2010, 53, 4561-4584.
Laszlo Virag et al.; The Therapeutic Potential of Poly(ADP-Ribose) Polymerase Inhibitors; Pharmacol Rev 54:375-429, 2002.
Stephen M. Berge, etc.; Pharmaceutical Salts; Journal of Pharmaceutical Sciences vol. 66, No. 1, Jan. 1977, 1-19.
Hubert Maehr; A Proposed Hew Convention for Graphic Presentation of Molecular Geometry and Topography; Journal of Chemical Education vol. 62 No. 2 Feb. 1985.
Remington:The Science and Practice of Pharmacy, 21st Ed., Lippincott, Williams &Wilkins (2005).
Chinese Priority Application No. 201510113090.X—English translation.
First Office Action issued in SG11201608438Y.
First Office Action issued in JP2017-504223.
Second OA issued in AU2015245786.
Wang et al. Design and Synthesis of New Templates Derived from Pyrrolopyrimidine as Selective Multidrug-Resistance-Associated Protein Inhibitors in Multidrug Resistance; J. Med. Chem. 2004, 47, 1339-1350.
Tong et al. Synthesis and Evaluation of a New Generation of Orally Efficacious Benzimidazole-Based Poly(ADP-ribose) Polymerase-1 (PARP-1) Inhibitors as Anticancer Agents; J. Med. Chem. 2009, 52, 6803-6813.

*Primary Examiner* — Samantha Shterengarts
(74) *Attorney, Agent, or Firm* — Harness, Dickey & Pierce P.L.C.

(57) ABSTRACT

Disclosed is a series of analogs of 4H-pyrazolo[1,5-α] benzimidazole compound as PARP inhibitors. In particular, disclosed in the invention is a compound as shown by formula (I) or a pharmaceutically acceptable salt thereof as a PARP inhibitor.

21 Claims, No Drawings

ANALOGUES OF 4H-PYRAZOLO[1,5-A] BENZIMIDAZOLE COMPOUND AS PARP INHIBITORS

CROSS-REFERENCE TO RELATED APPLICATIONS

This application is a National Stage of International Application No. PCT/CN2015/075363, filed on Mar. 30, 2015 and published in Chinese as WO 2015/154630 on Oct. 15, 2015. This application claims the priority to Chinese Application No. 201410144173.0, filed on Apr. 10, 2014 and Chinese Application No. 201510113090.X, filed on Mar. 13, 2015. The entire disclosures of the above applications are incorporated herein by reference.

FIELD OF THE INVENTION

This invention relates to a series of analogs of 4H-Pyrazolo[1,5-α]benzimidazole compounds as PARP inhibitors. To be specific, this invention relates to the compounds of formula (I) or pharmaceutically acceptable salts thereof as PARP inhibitors.

BACKGROUND OF THE INVENTION

PARP is a family of enzymes that catalyzes the addition of an ADP-ribose residue to various target proteins. To date, as many as 18 isoforms have been identified and characterized. Despite the large number of enzymes in the family, PARP-1 is responsible for more than 90% of the ADP-ribosylation within cells.

PARP-1 has long been associated with DNA repair and maintenance of genomic function. Following DNA damage, PARP-1 becomes instantly activated by binding to DNA breaks. After the structural changes, it begins to utilize NAD+ to synthesize poly(ADP) ribose as a signal for the other repairing enzymes (such as DNA ligase III, DNA polymerase beta). This process of PARP-1 binding and activation (known as base excision repair) helps amplify the repair process in which single-strand DNA breaks (SSB) are targeted. SSB are generally initiated by oxidative damages that are caused by cell's own metabolic processes as well as by exogenous chemotherapeutical agents and radiation. It is well-known that many types of anti-cancer therapies, such as DNA alkylating agents, platinum-based drugs, topoisomerase inhibitors and radiotherapy, are concomitant with DNA damages. These therapies are shadowed by the emergence of drug resistance, particularly in PARP-1 dominated DNA repair pathway. Recent studies have confirmed that selective PARP-1 inhibitors greatly enhance the antitumor efficacies of TMZ and cisplatin.

BRCA1 and BRCA2 play an essential role in homologous recombination (HR). DNA breaks arising during DNA replication can only be repaired by HR. In 2005, Bryant and Farmer (Nature, 2005, 913 and 917) independently discovered that cell lines deficient in BACA1 and BACA2 were very sensitive to PARP-1 inhibitors, resulting in cells death. Breast cancer genes BRCA1/2 have long been characterized as tumor suppressor genes that play an indispensable role in the repair of DNA double strand breaks. BRCA1/2 mutation carriers in ovarian cancer and prostate cancer are also at an elevated risk. Therefore PARP-1 inhibitors could also be used as a standalone therapy for such types of tumors that are already deficient in certain types of DNA repair mechanism.

PARP-1 has been an actively pursued oncology target for 30 years and Ferraris has entirely summarized the progress in this field (J. Med. Chem. 2010, 4561). A series compounds are in clinical studies regardless as a single agent or a synergist, such as veliparib (ABT-888), niraparib (MK-4827), BMN-673, CEP-977, BGP-15, E-7016, MP-124 and IND-1022. Recently certain heterocyclic compounds have also been disclosed as being useful in the treatment of a variety of cancers in some patents, for example, WO2014009872 (A1), WO2014019468 (A1), WO2014023390 (A2), WO2013182580, WO2013164061 (A1), EP2656843 (A1).

In addition, PARP-1 inhibition has been an actively pursued drug discovery target in wide ranges of therapeutic areas compassing stroke, cardiac ischemia, inflammation, and diabetes (Pharmacol. Rev. 2002, 54, 375.).

Although efforts have always been made to develop PARP-1 inhibitors for treating cancer and other diseases, satisfactory treatment has not yet been achieved. Thus, there exists a need for the development of new PARP-1 inhibitors.

SUMMARY OF THE INVENTION

An objective of the present invention is to provide compounds shown in formula (I) or pharmaceutically acceptable salts thereof,

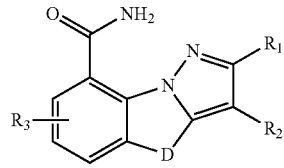

wherein,

D is selected from the group consisting of —C($R_{d1}$)($R_{d2}$)—, —C(=O)N($R_{d3}$)—, —N($R_{d4}$)—, —C(=N$R_{d5}$)—, —S(=O)$_2$N($R_{d6}$)—, —S(=O) N($R_{d7}$)—, —O—, —S—, —C(=O)O—, —C(=O)—, —C(=S)—, —S(=O)—, or —S(=O)$_2$—;

$R_{1-3}$, $R_{d1}$, and $R_{d2}$ are separately and independently selected from the group consisting of H, F, Cl, Br, I, CN, OH, SH, and NH$_2$, or selected from the group, optionally substituted by $R_{01}$, consisting of $C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl.

$R_{01}$ is selected from the group consisting of F, Cl, Br, I, CN, OH, SH, NH$_2$, and $R_{02}$;

$R_{02}$ is selected from the group consisting of $C_{1-10}$ alkyl, $C_{1-10}$ alkylamino, N,N-di($C_{1-10}$ alkyl) amino, $C_{1-10}$ alkyloxyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl; the heteroatom or heteroatomic group is separately and independently selected from the group consisting of —C(=O)N($R_{d3}$)—, —N($R_{d4}$)—, —C(=N$R_{d5}$)—, —S(=O)$_2$N($R_{d6}$)—, —S(=O) N($R_{d7}$)—, —O—, —S—, —C(=O)O—, —C(=O)—, —C(=S)—, —S(=O)—, and —S(=O)$_2$—;

$R_{d3-d7}$ are separately and independently selected from the group consisting of H, and $R_{o3}$;

$R_{o3}$ is selected from the group consisting of $C_{1-10}$ alkyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

$R_{o2}$, and $R_{o3}$ are optionally substituted by $R_{oo1}$;

$R_{oo1}$ is selected from the group consisting of F, Cl, Br, I, CN, OH, $N(CH_3)_2$, $NH(CH_3)$, $NH_2$, $CF_3$, $(NH_2)CH_2$, $(HO)CH_2$, $CH_3$, $CH_3O$, $HC(=O)$, $CH_3OC(=O)$, $CH_3S(=O)_2$, and $CH_3S(=O)$; and the number of $R_{o1}$, $R_{oo1}$, heteroatom, or heteroatomic group is separately and independently selected from 0, 1, 2, or 3.

In an embodiment of this invention, D is selected from —NH—, —N(CH₃)—, —C(F)₂—, —C(H) (F)—, and —C(H)(OH)—.

In an embodiment of this invention, $R_{1-3}$ are separately and independently selected from the group consisting of H, F, Cl, Br, I, CN, OH, SH, $NH_2$, $C_{1-6}$ alkyl, $C_{1-6}$ alkyloxyl, benzyloxyl, —CH₂N(R₂₁)(R₂₂),

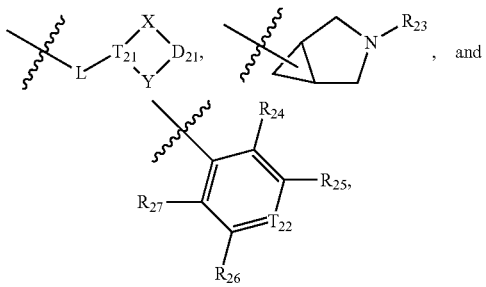, and in which,

L and $D_{21}$ are separately and independently selected from the group consisting of —C(R_{d1})(R_{d2})—, —C(=O)N(R_{d3})—, —N(R_{d4})—, —C(=NR_{d5})—, —S(=O)₂N(R_{d6})—, —S(=O) N(R_{d7})—, —O—, —S—, —C(=O)—, —C(=O)O—, —C(=S)—, —S(=O)—, or —S(=O)₂—;

L may also be a single bond for a linkage purpose only;

$T_{21-22}$ are separately and independently selected from the group consisting of C(R_t) and N;

X is selected from $(CH2)_n$ optionally substituted by $R_{o1}$, and n is selected from 0, 1, 2, or 3, and preferably 0, 1, or 2;

Y is selected from $(CH2)_m$ optionally substituted by $R_{o1}$, and m is selected from 0, 1, 2, or 3, and preferably 1, 2, or 3;

$R_{21-23}$ and $R_{d3-d7}$ are separately and independently selected from the group consisting of H and $R_{o3}$;

$R_{24-27}$, $R_{d1}$, $R_{d2}$, and $R_t$ are separately and independently selected from the group consisting of H, F, Cl, Br, I, CN, OH, SH, and $NH_2$, or selected from the group, optionally substituted by $R_{o1}$, consisting of $C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl;

$R_{o1}$ is selected from the group consisting of F, Cl, Br, I, CN, OH, SH, $NH_2$, and $R_{o2}$;

$R_{o2}$ is selected from the group consisting of $C_{1-10}$ alkyl, $C_{1-10}$ alkylamino, N,N-di($C_{1-10}$ alkyl)amino, $C_{1-10}$ alkyloxyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

the heteroatom or heteroatomic group is separately and independently selected from the group consisting of —C(=O)N(R_{d3})—, —N(R_{d4})—, —C(=NR_{d5})—, —S(=O)₂N(R_{d6})—, —S(=O) N(R_{d7})—, —O—, —S—, —C(=O)O—, —C(=O)—, —C(=S)—, —S(=O)—, and/or —S(=O)₂—;

$R_{d3-d7}$ are separately and independently selected from the group consisting of H, and $R_{o3}$;

$R_{o3}$ is selected from the group consisting of $C_{1-10}$ alkyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

$R_{o2}$, and $R_{o3}$ are optionally substituted by $R_{oo1}$;

$R_{oo1}$ is selected from the group consisting of F, Cl, Br, I, CN, OH, $N(CH_3)_2$, $NH(CH_3)$, $NH_2$, $CF_3$, $(NH_2)CH_2$, $(HO)CH_2$, $CH_3$, $CH_3O$, $HC(=O)$, $CH_3OC(=O)$, $CH_3S(=O)_2$, and $CH_3S(=O)$; and the number of $R_{o1}$, $R_{oo1}$, heteroatom, or heteroatomic group is separately and independently selected from 0, 1, 2, or 3.

In an embodiment of this invention, $R_1$ and $R_3$ are separately and independently selected from the group consisting of H, F, Cl, Br, I, CN, OH, SH, $NH_2$, $C_{1-3}$ alkyl, $C_{1-3}$ alkyloxyl, benzyloxyl, and

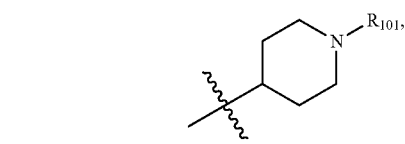

in which R101 is selected from the group consisting of H, methyl, ethyl, n-propyl, or isopropyl.

In an embodiment of this invention, $R_1$ is selected from the group consisting of H, methyl, methyloxyl, benzyloxyl,

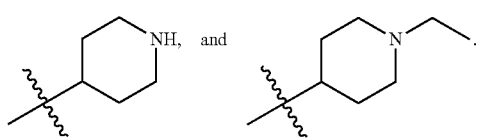

In an embodiment of this invention, $R_3$ is selected from the group consisting of H, F, Cl, Br, CN, and methyl.

In an embodiment of this invention, $R_2$ is selected from —CH₂N(R₂₀₁)(R₂₀₂), in which $R_{201}$ and $R_{202}$ are separately and independently selected from the group consisting of H, $C_{1-3}$ alkyl, $C_{1-3}$ alkylacyl, $C_{3-6}$ cycloalkylacyl, or $C_{3-6}$ cycloalkyl.

In an embodiment of this invention, $R_{201}$ and $R_{202}$ are separately and independently selected from the group consisting of H or cyclopropylacyl.

In an embodiment of this invention, $R_2$ is selected from the group consisting of

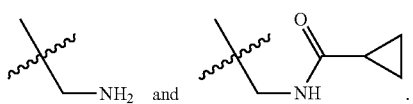

In an embodiment of this invention, R₂ is selected from the group consisting of

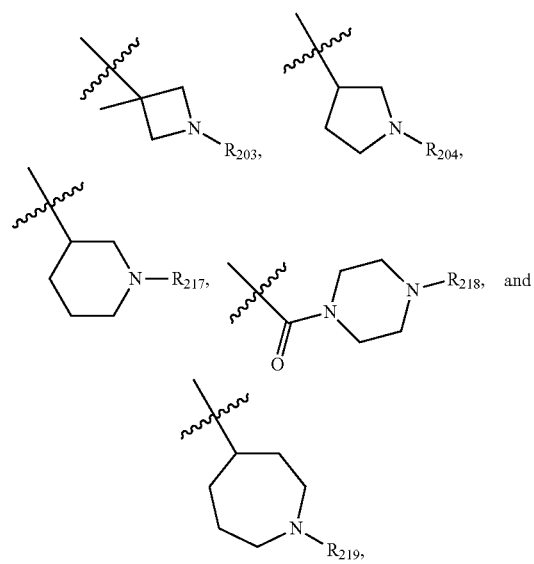

in which $R_{203}$, $R_{204}$, $R_{217}$, and $R_{218}$ are separately and independently selected from the group consisting of H, substituted or unsubstituted $C_{1-3}$ alkyl, cyclopropyl, or cyclopropylmethylene, wherein the substituent is selected from the group consisting of F, Cl, Br, I, CN, OH, $NH_2$, methyl, or methyloxyl, and the number of substituents is 0, 1, 2, or 3.

In an embodiment of this invention, $R_{203}$ is selected from the group consisting of methyl, ethyl, n-propyl, isopropyl, —$CH_2C(CH_3)(CH_3)(OH)$, and cyclopropylalkylene.

In an embodiment of this invention, $R_{204}$ is selected from the group consisting of methyl, ethyl, n-propyl, and isopropyl.

In an embodiment of this invention, $R_{217-219}$ are separately and independently selected from the group consisting of methyl and ethyl.

In an embodiment of this invention, $R_2$ is selected from the group consisting of

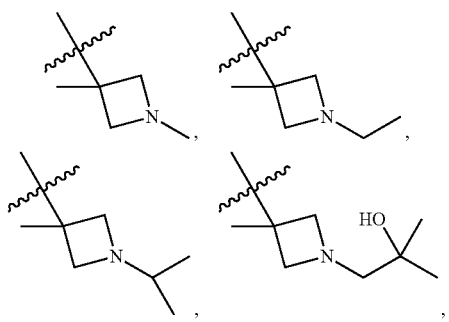

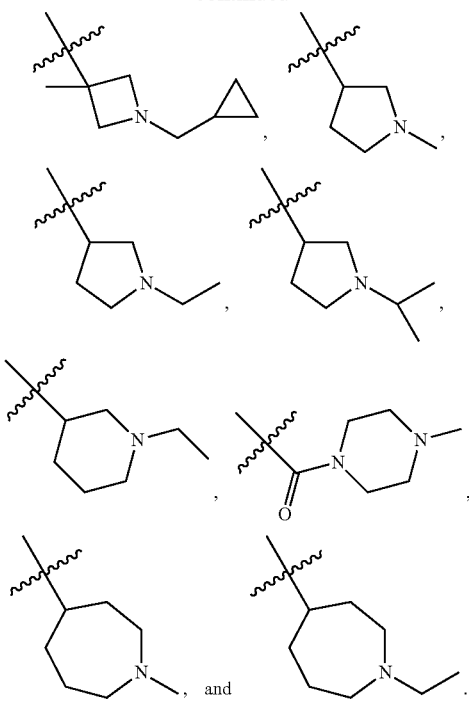

In an embodiment of this invention, $R_2$ is selected from

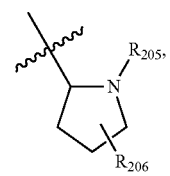

in which $R_{205}$ and $R_{206}$ are separately and independently selected from the group consisting of H, substituted or unsubstituted $C_{1-3}$ alkyl, cyclopropyl, or cyclopropylmethylene, wherein the substituent is selected from the group consisting of F, Cl, Br, I, CN, OH, $NH_2$, methyl, or methyloxyl, and the number of substituents is 0, 1, 2, or 3.

In an embodiment of this invention, $R_{205}$ and $R_{206}$ are separately, independently and preferably selected from the group consisting of H, methyl, ethyl, n-propyl, and isopropyl, and $R_{206}$ is also preferably selected from the group consisting of F, Cl, Br, I, CN, OH, and $NH_2$.

In an embodiment of this invention, $R_2$ is selected from

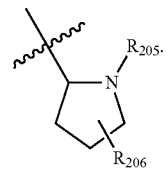

In an embodiment of this invention, $R_2$ is selected from the group consisting of

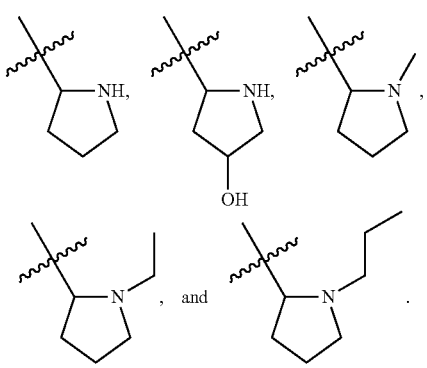

In an embodiment of this invention, $R_2$ is selected from

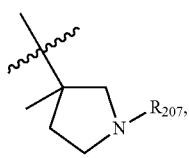

in which $R_{207}$ is selected from the group consisting of H, substituted or unsubstituted $C_{1-3}$ alkyl, cyclopropyl, cyclopropylmethylene, cyclobutyl, cyclobutylmethylene, oxacyclobutyl or oxacyclobutylalkylene, wherein the substituent is selected from the group consisting of F, Cl, Br, I, CN, OH, $NH_2$, methyl, $CF_3$, methyloxyl, and methylsulfonyl, and the number of substituents is 0, 1, 2, or 3.

In an embodiment of this invention, $R_{207}$ is selected from the group consisting of H, methyl, ethyl, n-propyl, isopropyl, $-CH_2CF_3$, $-CH_2CH_2CF_3$, $-CH_2CH_2F$, $-CH_2CH_2S(=O)_2CH_3$, $-CH_2CH_2CN$,

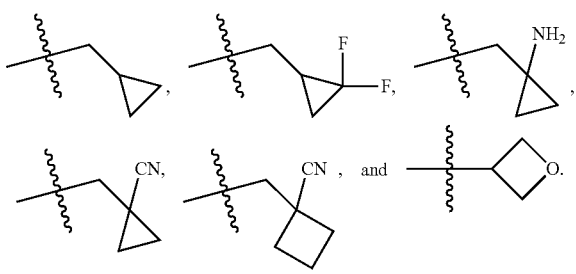

In an embodiment of this invention, $R_2$ is selected from the group consisting of

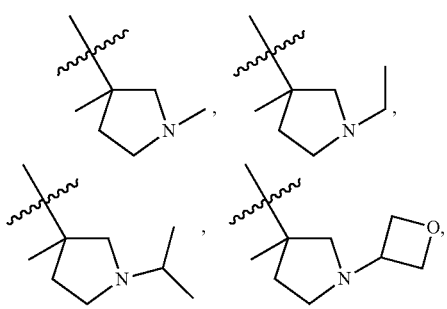

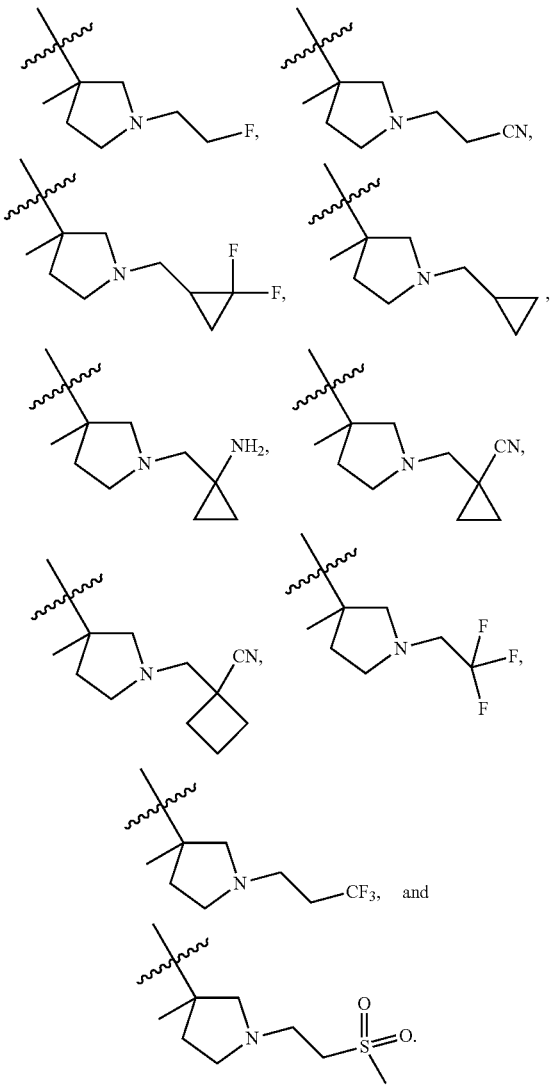

In an embodiment of this invention, $R_2$ is selected from the group consisting of in which $R_{208}$ is selected from the group consisting of H, substituted or unsubstituted $C_{1-4}$ alkyl, wherein the substituent is selected from the group consisting of F, Cl, Br, I, CN, OH, $NH_2$, methyl, $CF_3$, methyloxyl, and methylsulfonyl, and the number of substituents is 0, 1, 2, or 3.

In an embodiment of this invention, $R_{208}$ is selected from the group consisting of H, methyl, ethyl, n-propyl, isopropyl, cyclopropylmethylene, and cyclobutyl.

In an embodiment of this invention, $R_2$ is selected from the group consisting of

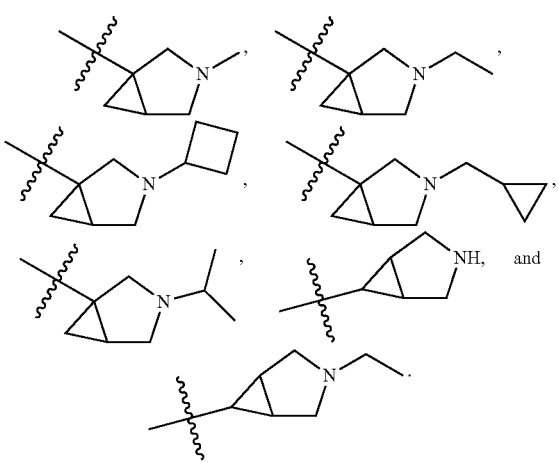

In an embodiment of this invention, $R_2$ is selected from

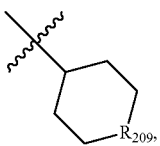

in which $R_{209}$ is selected from the group consisting of —C($R_{d1}$)($R_{d2}$)—, —C(=O)N($R_{d3}$)—, —N($R_{d4}$)—, —C(=N$R_{d5}$)—, —S(=O)$_2$N($R_{d6}$)—, —S(=O) N($R_{d7}$)—, —O—, —S—, —C(=O)O—, —C(=O)—, —C(=S)—, —S(=O)—, or —S(=O)$_2$—, wherein $R_{d1-d7}$ are as defined in claim 1.

In an embodiment of this invention, $R_{209}$ is selected from the group consisting of O and S(=O)$_2$.

In an embodiment of this invention, $R_2$ is selected from

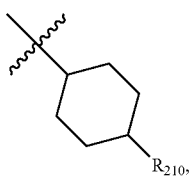

in which $R_{210}$ is selected from the group consisting of H, F, Cl, Br, I, CN, OH, SH, NH$_2$, N,N-di($C_{1-3}$ alkyl)amino, and $C_{1-3}$ alkylamino.

In an embodiment of this invention, $R_{210}$ is selected from the group consisting of dimethylamino, methylamino, H, F, Cl, Br, I, CN, OH, and NH$_2$.

In an embodiment of this invention, $R_2$ is selected from

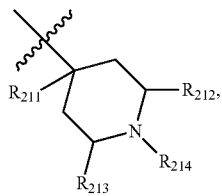

in which $R_{211-214}$ are selected from the group consisting of H, or substituted or unsubstituted $C_{1-4}$ alkyloxylcarbonyl, $C_{1-4}$ alkyl, 3-6 membered cycloalkyl, 3-6 membered cycloalkylmethylene, or unsaturated 5-6 membered heterocyclohydrocarbyl, wherein the substitutent includes $R_{215}$, and $R_{211-213}$ are also selected from the group consisting of H, F, Cl, Br, I, CN, OH, and NH$_2$, in which the cycloalkyl or unsaturated heterocyclohydrocarbyl has O, S or NR$_{216}$ with a number of 0, 1 or 2 wherein $R_{216}$ is selected from the group consisting of H and $C_{1-4}$alkyl substituted by $R_{215}$, $R_{215}$ is selected from the group consisting of F, Cl, Br, I, CN, OH, NH$_2$, methyl, ethyl, methyloxyl, ethyloxyl, formyl, acetyl, methylsulfonyl, ethylsulfonyl, methyloxylcarbonyl, ethyloxylcarbonyl, dimethylamino, diethylamino, dimethylaminocarbonyl, diethylaminocarbonyl, oxo, the number of $R_{215}$ is 1, 1, 2, or 3, optionally, $R_{212}$ and $R_{213}$ may join together to form a linker selected from the group consisting of —CH$_2$—, —CH$_2$CH$_2$—, or —CH$_2$CH$_2$CH$_2$—;

In an embodiment of this invention, $R_{211}$ is selected from the group consisting of H, F, Cl, Br, I, CN, OH, NH$_2$, methyl, ethyl, hydroxylmethyl, and methyloxylcarbonyl, $R_{212}$ is selected from the group consisting of H, F, Cl, Br, I, CN, OH, NH$_2$, and methyl, $R_{213}$ is selected from the group consisting of H, F, Cl, Br, I, CN, OH, and NH$_2$, $R_{214}$ is selected from the group consisting of H, methyl, ethyl, n-propyl, isopropyl, n-butyl, isobutyl, tert-butyl, —CH$_2$C(OH)(CH$_3$)$_2$, —CH$_2$C(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$CN, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$,

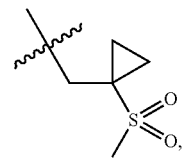 [SMILES: *CC1(S(C)(=O)=O)CC1]

cyclopropyl, cyclopropylmethylene,

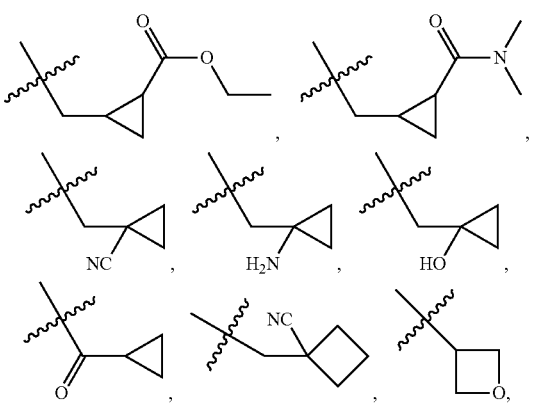

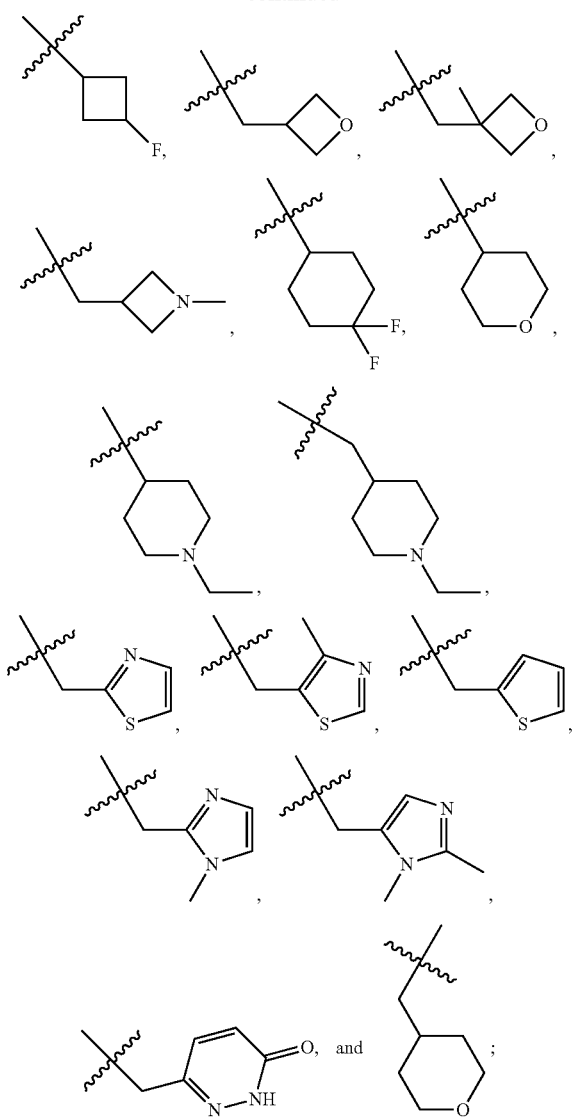
In an embodiment of this invention, R₂ is selected from the group consisting of
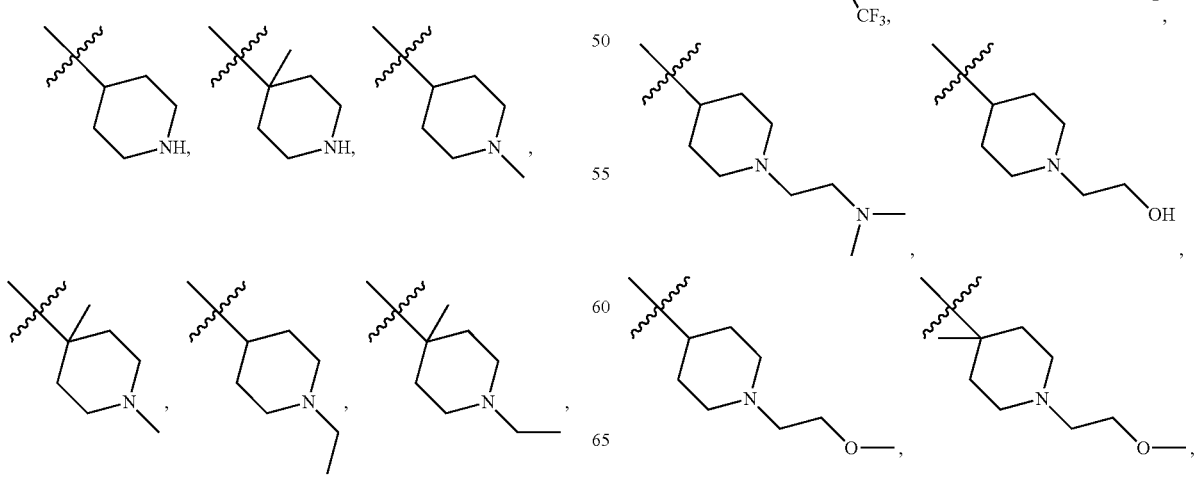
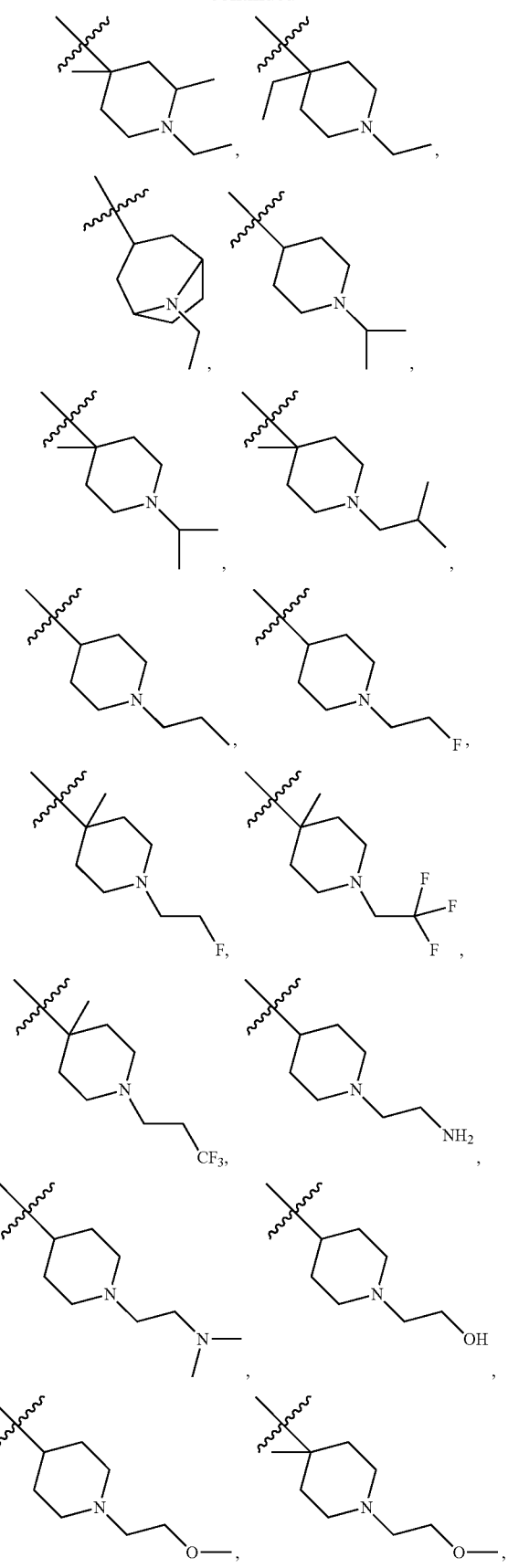

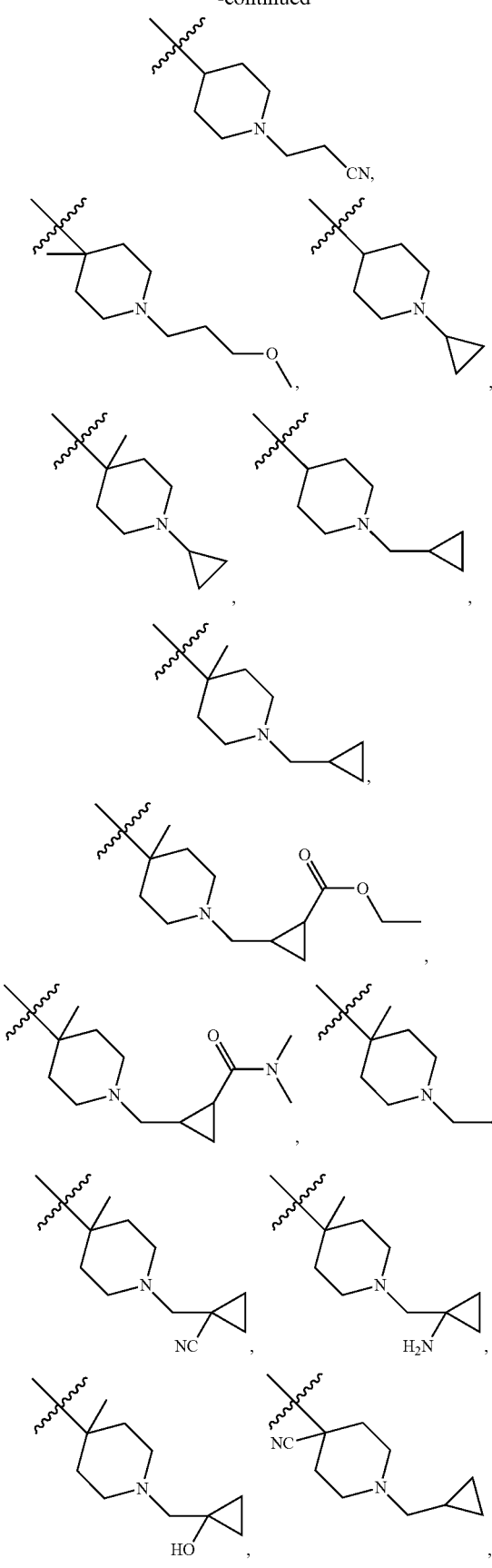
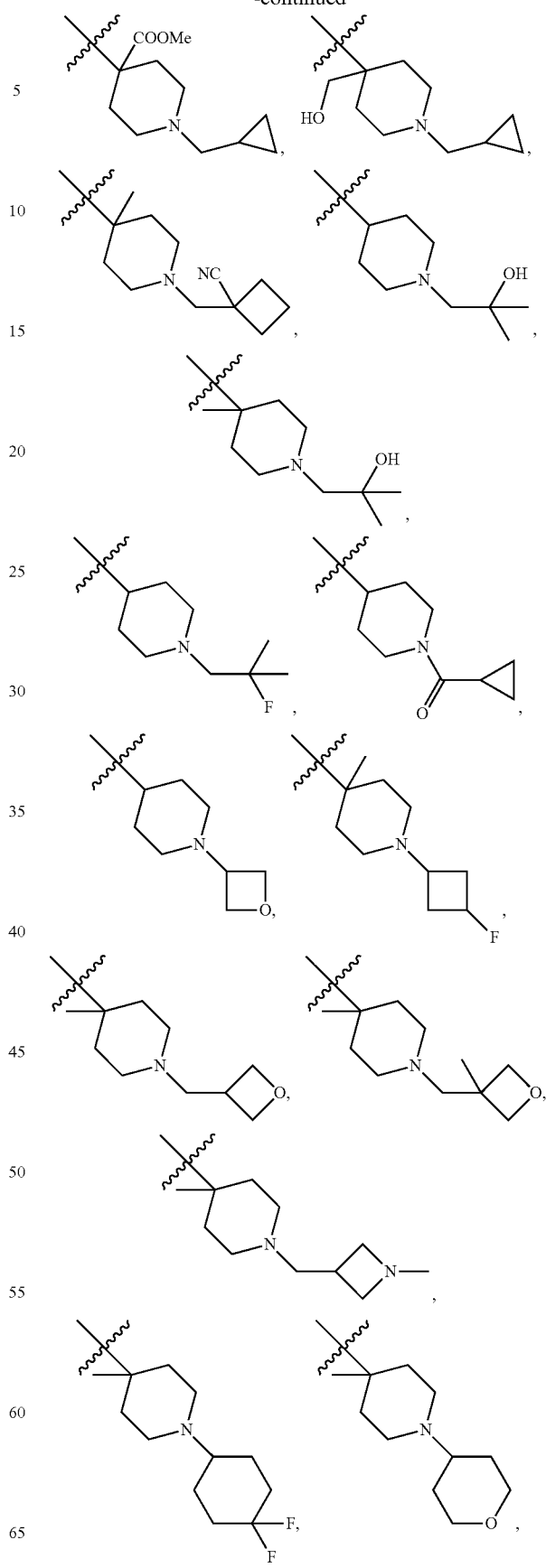

-continued

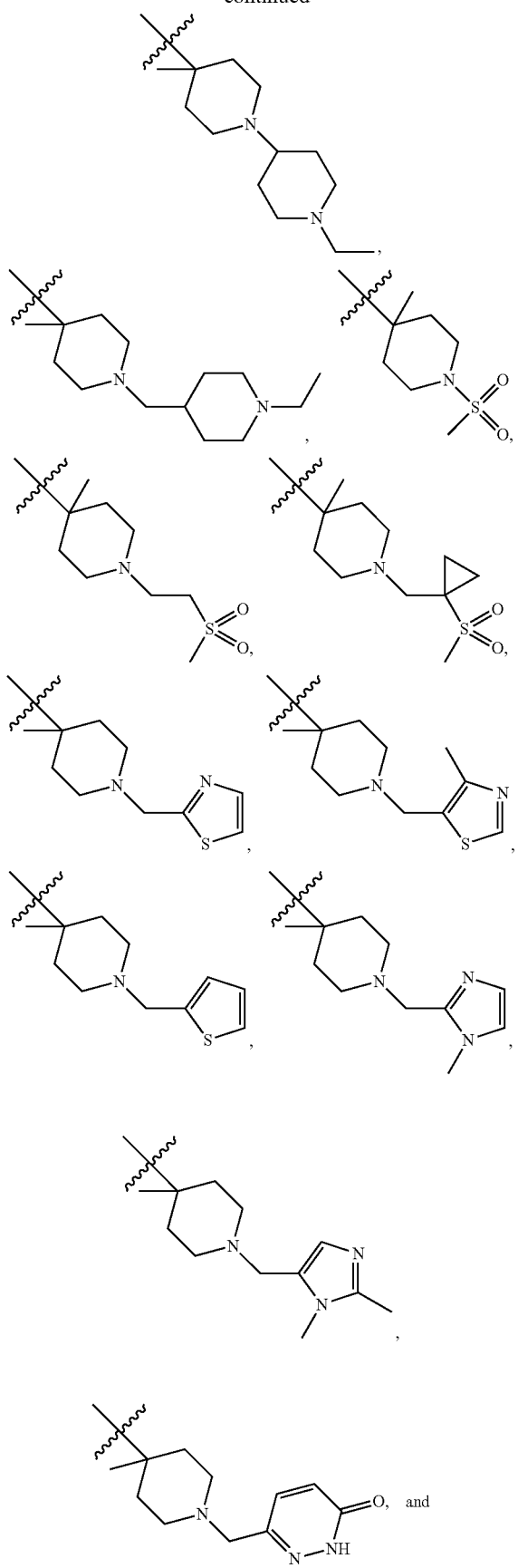

-continued

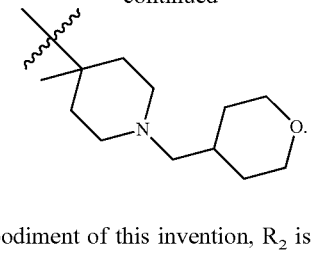

In an embodiment of this invention, $R_2$ is selected from

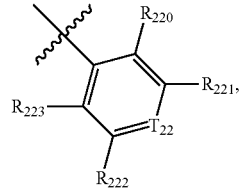

in which $T_{22}$ is selected from the group consisting of N or $C(R_{224})$, and $R_{220\text{-}224}$ are separately and independently selected from the group consisting of H, F, Cl, Br, I, CN, OH, SH, $NH_2$, $C_{1\text{-}3}$ alkylamino-$C_{1\text{-}3}$ alkyl, and

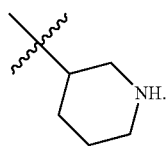 [SMILES: *C1CCCNC1]

In an embodiment of this invention, the $C_{1\text{-}3}$ alkylamino-$C_{1\text{-}3}$ alkyl is selected from methylaminomethylene.

In an embodiment of this invention,
$R_2$ is selected from the group consisting of

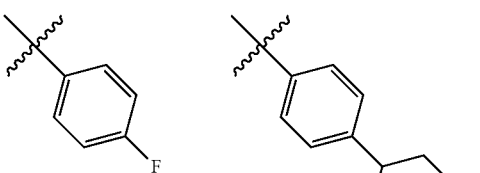

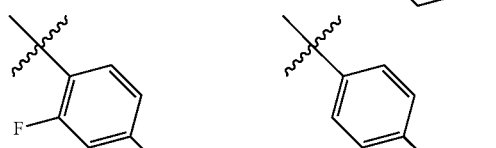

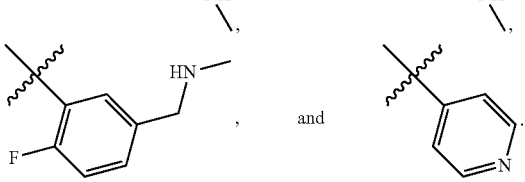
and
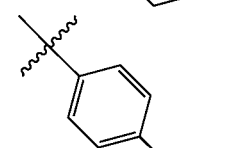

In an embodiment of this invention, the compounds or pharmaceutically acceptable salts thereof are selected from:
1) 6-fluoro-3-(piperidin-4-yl)-4H-benzo[4,5]imidazo[1,2-b]pyrazole-8-carboxamide;

2) 3-(1-ethylpiperidin-4-yl)-6-fluoro-4H-benzo[4,5]imidazo[1,2-b]pyrazole-8-carboxamide;
3) 6-fluoro-3-(1-(2-fluoroethyl)piperidin-4-yl)-4H-benzo[4,5]imidazo[1,2-b]pyrazole-8-carboxamide;
4) 3-(1-cyclopropylpiperidin-4-yl)-6-fluoro-4H-benzo[4,5]imidazo[1,2-b]pyrazole-8-carboxamide;
5) 3-(1-(cyclopropylmethyl)piperidin-4-yl)-6-fluoro-4H-benzo[4,5]imidazo[1,2-b]pyrazole-8-carboxamide;
6) 6-fluoro-3-(1-(2-hydroxy-2-methylpropyl)piperidin-4-yl)-4H-benzo[4,5]imidazo[1,2-b]pyrazole-8-carboxamide;
7) 6-fluoro-3-(1-(2-fluoro-2-methylpropyl)piperidin-4-yl)-4H-benzo[4,5]imidazo[1,2-b]pyrazole-8-carboxamide;
8) 3-(1-(cyclopropanecarbonyl)piperidin-4-yl)-6-fluoro-4H-benzo[4,5]imidazo[1,2-b]pyrazole-8-carboxamide;
9) 6-fluoro-3-(1-methylpiperidin-4-yl)-4H-benzo[4,5]imidazo[1,2-b]pyrazole-8-carboxamide;
10) 6-fluoro-3-(1-isopropylpiperidin-4-yl)-4H-benzo[4,5]imidazo[1,2-b]pyrazole-8-carboxamide;
11) 6-fluoro-3-(1-(oxetan-3-yl)piperidin-4-yl)-4H-benzo[4,5]imidazo[1,2-b]pyrazole-8-carboxamide;
12) 6-fluoro-3-(1-propylpiperidin-4-yl)-4H-benzo[4,5]imidazo[1,2-b]pyrazole-8-carboxamide;
13) 3-(1-(2-aminoethyl)piperidin-4-yl)-6-fluoro-4H-benzo[4,5]imidazo[1,2-b]pyrazole-8-carboxamide;
14) 3-(1-(2-(dimethylamino)ethyl)piperidin-4-yl)-6-fluoro-4H-benzo[4,5]imidazo[1,2-b]pyrazole-8-carboxamide;
15) 6-fluoro-3-(1-(2-methoxyethyl)piperidin-4-yl)-4H-benzo[4,5]imidazo[1,2-b]pyrazole-8-carboxamide
16) 6-fluoro-3-(1-(2-hydroxyethyl)piperidin-4-yl)-4H-benzo[4,5]imidazo[1,2-b]pyrazole-8-carboxamide;
17) 3-(1-ethylpiperidin-3-yl)-6-fluoro-4H-benzo[4,5]imidazo[1,2-b]pyrazole-8-carboxamide;
18) 3-(1-ethylazepan-4-yl)-6-fluoro-4H-benzo[4,5]imidazo[1,2-b]pyrazole-8-carboxamide;
19) 6-fluoro-3-(1-methylazepan-4-yl)-4H-benzo[4,5]imidazo[1,2-b]pyrazole-8-carboxamide;
20) 6-fluoro-3-(1-methylpyrrolidin-3-yl)-4H-benzo[4,5]imidazo[1,2-b]pyrazole-8-carboxamide;
21) 3-(1-ethylpyrrolidin-3-yl)-6-fluoro-4H-benzo[4,5]imidazo[1,2-b]pyrazole-8-carboxamide;
22) 6-fluoro-3-(1-isopropylpyrrolidin-3-yl)-4H-benzo[4,5]imidazo[1,2-b]pyrazole-8-carboxamide;
23) 6-fluoro-3-(pyrrolidin-2-yl)-4H-benzo[4,5]imidazo[1,2-b]pyrazole-8-carboxamide;
24) 6-fluoro-3-(1-propylpyrrolidin-2-yl)-4H-benzo[4,5]imidazo[1,2-b]pyrazole-8-carboxamide; 6-fluoro-3-(1-methylpyrrolidin-2-yl)-4H-benzo[4,5]imidazo[1,2-b]pyrazole-8-carboxamide;
25) 3-(1-ethylpyrrolidin-2-yl)-6-fluoro-4H-benzo[4,5]imidazo[1,2-b]pyrazole-8-carboxamide;
26) 3-(1-ethylpiperidin-4-yl)-4H-benzo[4,5]imidazo[1,2-b]pyrazole-8-carboxamide;
27) 6-fluoro-3-(1-propylpyrrolidin-2-yl)-4H-benzo[4,5]imidazol[1,2-b]pyrazole-8-carboxamide;
28) 6-fluoro-3-(3-methyl-3-azabicyclo[3.1.0]hexan-1-yl)-4H-benzo[4,5]imidazo[1,2-b]pyrazole-8-carboxamide;
29) 3-(3-ethyl-3-azabicyclo[3.1.0]hexan-1-yl)-6-fluoro-4H-benzo[4,5]imidazo[1,2-b]pyrazole-8-carboxamide;
30) 3-(3-cyclobutyl-3-azabicyclo[3.1.0]hexan-1-yl)-6-fluoro-4H-benzo[4,5]imidazo[1,2-b]pyrazole-8-carboxamide;
31) 3-(3-(cyclopropylmethylene)-3-azabicyclo[3.1.0]hexan-1-yl)-6-fluoro-4H-benzo[4,5]imidazo[1, 2-b]pyrazole-8-carboxamide;
32) 6-fluoro-3-(3-isopropyl-3-azabicyclo[3.1.0]hexan-1-yl)-4H-benzo[4,5]imidazo[1,2-b]pyrazole-8-carboxamide;
33) 3-(3-azabicyclo[3.1.0]hexan-6-yl)-6-fluoro-4H-benzo[4,5]imidazo[1,2-b]pyrazole-8-carboxamide;
34) 3-(3-ethyl-3-azabicyclo[3.1.0]hexan-6-yl)-6-fluoro-4H-benzo[4,5]imidazo[1,2-b]pyrazole-8-carboxamide;
35) 3-(8-ethyl-8-azabicyclo[3.2.1]octan-3-yl)-6-fluoro-4H-benzo[4,5]imidazo[1,2-b]pyrazole-8-carboxamide;
36) 6-fluoro-3-(4-hydroxypyrrolidin-2-yl)-4H-benzo[4,5]imidazo[1,2-b]pyrazole-8-carboxamide;
37) 3-cyano-6-fluoro-4H-benzo[4,5]imidazo[1,2-b]pyrazole-8-carboxamide;
38) 3-cyano-4H-benzo[4,5]imidazo[1,2-b]pyrazole-8-carboxamide;
39) 3-(aminomethyl)-6-fluoro-4H-benzo[4,5]imidazo[1,2-b]pyrazole-8-carboxamide;
40) 3-(cyclopropanecarboxamidomethylene)-6-fluoro-4H-benzo[4,5]imidazo[1,2-b]pyrazole-8-carboxamide;
41) 6-fluoro-3-(4-fluorophenyl)-4H-benzo[4,5]imidazo[1,2-b]pyrazole-8-carboxamide;
42) 6-fluoro-3-(2-fluoro-4-((methylamino)methylene)phenyl)-4H-benzo[4,5]imidazo[1,2-b]pyrazole-8-carboxamide;
43) 6-fluoro-3-(4-((methylamino)methyl)phenyl)-4H-benzo[4,5]imidazo[1,2-b]pyrazole-8-carboxamide;
44) 6-fluoro-3-(2-fluoro-5-((methylamino)methyl)phenyl)-4H-benzo[4,5]imidazo[1,2-b]pyrazole-8-carboxamide;
45) 6-fluoro-3-(pyridin-4-yl)-4H-benzo[4,5]imidazo[1,2-b]pyrazole-8-carboxamide;
46) 6-fluoro-3-(4-(piperidin-3-yl)phenyl)-4H-benzo[4,5]imidazo[1,2-b]pyrazole-8-carboxamide;
47) 6-fluoro-3-(tetrahydro-2H-pyran-4-yl)-4H-benzo[4,5]imidazo[1,2-b]pyrazole-8-carboxamide;
48) 3-(4-(dimethylamino)cyclohexyl)-6-fluoro-4H-benzo[4,5]imidazo[1,2-b]pyrazole-8-carboxamide;
49) 6-fluoro-3-(4-methylpiperazine-1-carbonyl)-4H-benzo[4,5]imidazo[1,2-b]pyrazole-8-carboxamide;
50) 3-(1-(cyclopropylmethyl)piperidin-4-yl)-4,4,6-trifluoro-4H-pyrazolo[1,5-α]indole-8-carboxamide;
51) 3-(1-ethylpiperidin-4-yl)-6-fluoro-4-hydroxy-4H-pyrazolo[1,5-α]indole-8-carboxamide;
52) 3-(1-ethylpiperidin-4-yl)-6-fluoro-4-methyl-4H-benzo[4,5]imidazo[1,2-b]pyrazole-8-carboxamide;
53) 6-fluoro-3-(4-methylpiperidin-4-yl)-4H-benzo[4,5]imidazo[1,2-b]pyrazole-8-carboxamide;
54) 3-(1-ethyl-4-methylpiperidin-4-yl)-6-fluoro-4H-benzo[4,5]imidazo[1,2-b]pyrazole-8-carboxamide;
55) 3-(1-cyclopropyl-4-methylpiperidin-4-yl)-6-fluoro-4H-benzo[4,5]imidazo[1,2-b]pyrazole-8-carboxamide;
56) 6-fluoro-3-(1-(2-hydroxy-2-methylpropyl)-4-methylpiperidin-4-yl)-4H-benzo[4,5]imidazo[1,2-b]pyrazole-8-carboxamide;
57) 3-(1-(cyclopropylmethylene)-4-methylpiperidin-4-yl)-6-fluoro-4H-benzo[4,5]imidazo[1,2-b]pyrazole-8-carboxamide;
58) 3-(1-(4,4-difluorocyclohexyl)-4-methylpiperidin-4-yl)-6-fluoro-4H-benzo[4,5]imidazo[1,2-b]pyrazole-8-carboxamide;
59) 6-fluoro-3-(4-methyl-1-(tetrahydro-2H-pyran-4-yl)piperidin-4-yl)-4H-benzo[4,5]imidazo[1,2-b]pyrazole-8-carboxamide;
60) 6-fluoro-3-(1-(2-fluoroethyl)-4-methylpiperidin-4-yl)-4H-benzo[4,5]imidazo[1,2-b]pyrazole-8-carboxamide;
61) 6-fluoro-3-(4-methyl-1-(2,2,2-trifluoroethyl)piperidin-4-yl)-4H-benzo[4,5]imidazo[1,2-b]pyrazole-8-carboxamide;

62) 6-fluoro-3-(4-methyl-1-(3,3,3-trifluoropropyl)piperidin-4-yl)-4H-benzo[4,5]imidazo[1,2-b]pyrazole-8-carboxamide;
63) 3-(1-((1-cyanocyclopropyl)methyl)-4-methylpiperidin-4-yl)-6-fluoro-4H-benzo[4,5]imidazo[1,2-b]pyrazole-8-carboxamide;
64) 3-(1-((1-cyanocyclobutyl)methyl)-4-methylpiperidin-4-yl)-6-fluoro-4H-benzo[4,5]imidazo[1,2-b]pyrazole-8-carboxamide;
65) 6-fluoro-3-(4-methyl-1-(2-(methylsulfonyl)ethyl)piperidin-4-yl)-4H-benzo[4,5]imidazo[1,2-b]pyrazole-8-carboxamide;
66) 6-fluoro-3-(4-methyl-1-((tetrahydro-2H-pyran-4-yl)methyl)piperidin-4-yl)-4H-benzo[4,5]imidazo[1,2-b]pyrazole-8-carboxamide;
67) 3-(1-((1-aminocyclopropyl)methyl)-4-methylpiperidin-4-yl)-6-fluoro-4H-benzo[4,5]imidazo[1,2-b]pyrazole-8-carboxamide;
68) 6-fluoro-3-(4-methyl-1-(oxetan-3-ylmethyl)piperidin-4-yl)-4H-benzo[4,5]imidazo[1,2-b]pyrazole-8-carboxamide;
69) 6-fluoro-3-(1-(2-methoxyethyl)-4-methylpiperidin-4-yl)-4H-benzo[4,5]imidazo[1,2-b]pyrazole-8-carboxamide;
70) 6-fluoro-3-(1-((1-hydroxycyclopropyl)methyl)-4-methylpiperidin-4-yl)-4H-benzo[4,5]imidazo[1,2-b]pyrazole-8-carboxamide;
71) 6-fluoro-3-(4-methyl-1-((3-methyloxetan-3-yl)methyl)piperidin-4-yl)-4H-benzo[4,5]imidazo[1, 2-b]pyrazole-8-carboxamide;
72) 6-fluoro-3-(1-(3-methoxypropyl)-4-methylpiperidin-4-yl)-4H-benzo[4,5]imidazo[1,2-b]pyrazole-8-carboxamide;
73) 6-fluoro-3-(4-methyl-1-((1-(methylsulfonyl)cyclopropyl)methyl)piperidin-4-yl)-4H-benzo[4,5]imidazo[1,2-b]pyrazole-8-carboxamide;
74) 6-fluoro-3-(4-methyl-1-(thiazol-2-ylmethyl)piperidin-4-yl)-4H-benzo[4,5]imidazo[1,2-b]pyrazole-8-carboxamide;
75) 6-fluoro-3-(4-methyl-1-(methylsulfonyl)piperidin-4-yl)-4H-benzo[4,5]imidazo[1,2-b]pyrazole-8-carboxamide;
76) 6-fluoro-3-(1-(3-fluorocyclobutyl)-4-methylpiperidin-4-yl)-4H-benzo[4,5]imidazo[1,2-b]pyrazole-8-carboxamide;
77) 6-fluoro-3-(4-methyl-1-(thiophen-2-ylmethyl)piperidin-4-yl)-4H-benzo[4,5]imidazo[1,2-b]pyrazole-8-carboxamide;
78) 3-(1-((1-ethylpiperidin-4-yl)methyl)-4-methylpiperidin-4-yl)-6-fluoro-4H-benzo[4,5]imidazo[1, 2-b]pyrazole-8-carboxamide;
79) 6-fluoro-3-(4-methyl-1-((1-methylazetidin-3-yl)methyl)piperidin-4-yl)-4H-benzo[4,5]imidazo[1, 2-b]pyrazole-8-carboxamide;
80) ethyl2-((4-(8-carbamoyl-6-fluoro-4H-benzo[4,5]imidazo[1,2-b]pyrazol-3-yl)-4-methylpiperidin-1-yl)methyl)cyclopropanecarboxylate;
81) 3-(1-((2-(dimethylcarbamoyl)cyclopropyl)methyl)-4-methylpiperidin-4-yl)-6-fluoro-4H-benzo[4,5]imidazo[1, 2-b]pyrazole-8-carboxamide;
82) 6-fluoro-3-(1-isobutyl-4-methylpiperidin-4-yl)-4H-benzo[4,5]imidazo[1,2-b]pyrazole-8-carboxamide;
83) 6-fluoro-3-(4-methyl-1-((4-methylthiazol-5-yl)methyl)piperidin-4-yl)-4H-benzo[4,5]imidazo[1, 2-b]pyrazole-8-carboxamide;
84) 6-fluoro-3-(4-methyl-1-((1-methyl-1H-imidazol-2-yl)methyl)piperidin-4-yl)-4H-benzo[4,5]imidazo[1,2-b]pyrazole-8-carboxamide;
85) 3-(1-((1,2-dimethyl-1H-imidazol-5-yl)methyl)-4-methylpiperidin-4-yl)-6-fluoro-4H-benzo[4,5]imidazo[1,2-b]pyrazole-8-carboxamide
86) 3-(1'-ethyl-4-methyl-[1,4'-bipiperidin]-4-yl)-6-fluoro-4H-benzo[4,5]imidazo[1,2-b]pyrazole-8-carboxamide;
87) 6-fluoro-3-(4-methyl-1-((6-oxo-1,6-dihydropyridazin-3-yl)methyl)piperidin-4-yl)-4H-benzo[4,5]imidazo[1,2-b]pyrazole-8-carboxamide;
88) 3-(1-(2-cyanoethyl)-4-methylpiperidin-4-yl)-6-fluoro-4H-benzo[4,5]imidazo[1,2-b]pyrazole-8-carboxamide;
89) 6-chloro-3-(1-ethyl-4-methylpiperidin-4-yl)-4H-benzo[4,5]imidazo[1,2-b]pyrazole-8-carboxamide;
90) 3-(1-ethyl-3-methylpyrrolidin-3-yl)-6-fluoro-4H-benzo[4,5]imidazo[1,2-b]pyrazole-8-carboxamide;
91) 3-(1,3-dimethylpyrrolidin-3-yl)-6-fluoro-4H-benzo[4,5]imidazo[1,2-b]pyrazole-8-carboxamide;
92) 6-fluoro-3-(1-isopropyl-3-methylpyrrolidin-3-yl)-4H-benzo[4,5]imidazo[1,2-b]pyrazole-8-carboxamide;
93) 3-(1-(cyclopropylmethyl)-3-methylpyrrolidin-3-yl)-6-fluoro-4H-benzo[4,5]imidazo[1,2-b]pyrazole-8-carboxamide;
94) 6-fluoro-3-(3-methyl-1-(oxetan-3-yl)pyrrolidin-3-yl)-4H-benzo[4,5]imidazo[1,2-b]pyrazole-8-carboxamide;
95) 6-fluoro-3-(1-(2-fluoroethyl)-3-methylpyrrolidin-3-yl)-4H-benzo[4,5]imidazo[1,2-b]pyrazole-8-carboxamide;
96) 3-(1-((2,2-difluorocyclopropyl)methyl)-3-methylpyrrolidin-3-yl)-6-fluoro-4H-benzo[4,5]imidazo[1,2-b]pyrazole-8-carboxamide;
97) 6-fluoro-3-(3-methyl-1-(2,2,2-trifluoroethyl)pyrrolidin-3-yl)-4H-benzo[4,5]imidazo[1,2-b]pyrazole-8-carboxamide;
98) 6-fluoro-3-(3-methyl-1-(2-(methylsulfonyl)ethyl)pyrrolidin-3-yl)-4H-benzo[4,5]imidazo[1,2-b]pyrazole-8-carboxamide;
99) 6-fluoro-3-(3-methyl-1-(3,3,3-trifluoropropyl)pyrrolidin-3-yl)-4H-benzo[4,5]imidazo[1,2-b]pyrazole-8-carboxamide;
100) 3-(1-((1-aminocyclopropyl)methyl)-3-methylpyrrolidin-3-yl)-6-fluoro-4H-benzo[4,5]imidazo[1, 2-b]pyrazole-8-carboxamide;
101) 3-(1-((1-cyanocyclobutyl)methyl)-3-methylpyrrolidin-3-yl)-6-fluoro-4H-benzo[4,5]imidazo[1,2-b]pyrazole-8-carboxamide;
102) 3-(1-((1-cyanocyclopropyl)methyl)-3-methylpyrrolidin-3-yl)-6-fluoro-4H-benzo[4,5]imidazo[1, 2-b]pyrazole-8-carboxamide;
103) 3-(1-(2-cyanoethyl)-3-methylpyrrolidin-3-yl)-6-fluoro-4H-benzo[4,5]imidazo[1,2-b]pyrazole-8-carboxamide;
104) 3-(1-(cyclopropylmethyl)-3-methylazetidin-3-yl)-6-fluoro-4H-benzo[4,5]imidazo[1,2-b]pyrazole-8-carboxamide;
105) 6-fluoro-3-(1-isopropyl-4-methylpiperidin-4-yl)-4H-benzo[4,5]imidazo[1,2-b]pyrazole-8-carboxamide;
106) 6-fluoro-3-(4-methyl-1,1-dioxido-2H-thiopyran-4-yl)-4H-benzo[4,5]imidazo[1,2-b]pyrazole-8-carboxamide;
107) 3-(1,4-diethylpiperidin-4-yl)-6-fluoro-4H-benzo[4,5]imidazo[1,2-b]pyrazole-8-carboxamide;
108) 3-(4-cyano-1-(cyclopropylmethyl)piperidin-4-yl)-6-fluoro-4H-benzo[4,5]imidazo[1,2-b]pyrazole-8-carboxamide;
109) 3-(1-(cyclopropylmethyl)-4-(hydroxymethyl)piperidin-4-yl)-6-fluoro-4H-benzo[4,5]imidazo[1,2-b]pyrazole-8-carboxamide;

110) Methyl 4-(8-carbamoyl-6-fluoro-4H-benzo[4,5]imidazo[1,2-b]pyrazol-3-yl)-1-(cyclopropylmethyl)piperidine-4-carboxylate;
111) 3-(1-(cyclopropylmethyl)-4-methylpiperidin-4-yl)-6-fluoro-2-methyl-4H-benzo[4,5]imidazo[1,2-b]pyrazole-8-carboxamide;
112) 3-(1-ethyl-4-methylpiperidin-4-yl)-6-fluoro-2-methyl-4H-benzo[4,5]imidazo[1,2-b]pyrazole-8-carboxamide;
113) 6-fluoro-3-(1-isobutyl-4-methylpiperidin-4-yl)-2-methyl-4H-benzo[4,5]imidazo[1,2-b]pyrazole-8-carboxamide;
114) 6-fluoro-3-(1-isopropyl-4-methylpiperidin-4-yl)-2-methyl-4H-benzo[4,5]imidazo[1,2-b]pyrazole-8-carboxamide;
115) 3-(1,4-dimethylpiperidin-4-yl)-6-fluoro-2-methyl-4H-benzo[4,5]imidazo[1,2-b]pyrazole-8-carboxamide;
116) 6-fluoro-3-(1-(2-hydroxy-2-methylpropyl)-4-methylpiperidin-4-yl)-2-methyl-4H-benzo[4,5]imidazo[1,2-b]pyrazole-8-carboxamide;
117) 3-(1-ethyl-2,4-dimethylpiperidin-4-yl)-6-fluoro-2-methyl-4H-benzo[4,5]imidazo[1,2-b]pyrazole-8-carboxamide;
118) 3-(1-ethyl-3-methylpyrrolidin-3-yl)-6-fluoro-2-methyl-4H-benzo[4,5]imidazo[1,2-b]pyrazole-8-carboxamide;
119) 6-fluoro-3-(1-isopropyl-3-methylpyrrolidin-3-yl)-2-methyl-4H-benzo[4,5]imidazo[1,2-b]pyrazole-8-carboxamide;
120) 3-(1-(cyclopropylmethyl)-3-methylpyrrolidin-3-yl)-6-fluoro-2-methyl-4H-benzo[4,5]imidazo[1,2-b]pyrazole-8-carboxamide;
121) 3-(1,3-dimethylazetidin-3-yl)-6-fluoro-2-methyl-4H-benzo[4,5]imidazo[1,2-b]pyrazole-8-carboxamide;
122) 3-(1-ethyl-3-methylazetidin-3-yl)-6-fluoro-2-methyl-4H-benzo[4,5]imidazo[1,2-b]pyrazole-8-carboxamide;
123) 6-fluoro-3-(1-isopropyl-3-methylazetidin-3-yl)-2-methyl-4H-benzo[4,5]imidazo[1,2-b]pyrazole-8-carboxamide;
124) 3-(1-(cyclopropylmethyl)-3-methylazetidin-3-yl)-6-fluoro-2-methyl-4H-benzo[4,5]imidazo[1,2-b]pyrazole-8-carboxamide;
125) 6-fluoro-3-(1-(2-hydroxy-2-methylpropyl)-3-methylazetidin-3-yl)-2-methyl-4H-benzo[4,5]imidazo[1,2-b]pyrazole-8-carboxamide;
126) 6-fluoro-3-(1-isopropyl-4-methylpiperidin-4-yl)-2-methoxy-4H-benzo[4,5]imidazo[1,2-b]pyrazole-8-carboxamide;
127) 2-(benzyloxy)-6-fluoro-3-(1-isopropyl-4-methylpiperidin-4-yl)-4H-benzo[4,5]imidazo[1,2-b]pyrazole-8-carboxamide;
128) 6-fluoro-2-(piperidin-4-yl)-4H-benzo[4,5]imidazo[1,2-b]pyrazole-8-carboxamide; and
129) 2-(1-ethylpiperidin-4-yl)-6-fluoro-4H-benzo[4,5]imidazo[1,2-b]pyrazole-8-carboxamide.

Definitions $C_{1-10}$ is selected from the group consisting of $C_1$, $C_2$, $C_3$, $C_4$, $C_5$, $C_6$, $C_7$, $C_8$, $C_9$, and $C_{10}$; $C_{3-10}$ is selected from the group consisting of $C_3$, $C_4$, $C_5$, $C_6$, $C_7$, $C_8$, $C_9$, and $C_{10}$.

$C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, or $C_{1-10}$ heteroalkyl substituted by $C_{3-10}$ cyclohydrocarbyl or $C_{3-10}$ heterocyclohydrocarbyl include, but are not limited to:

$C_{1-10}$ alkyl, $C_{1-10}$ alkylamino, N,N-di($C_{1-10}$ alkyl) amino, $C_{1-10}$ alkyloxyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

methyl, ethyl, n-propyl, isopropyl, —$CH_2C(CH_3)(CH_3)$(OH), cyclopropyl, cyclobutyl, propylmethylene, cycropropylacyl, benzyloxyl, trifluoromethyl, aminomethyl, hydroxylmethyl, methyloxyl, formyl, methyloxylcarbonyl, methylsulfonyl, methylsulfinyl, ethyloxyl, acetyl, ethylsulfonyl, ethyloxylcarbonyl, dimethylamino, diethylamino, dimethylaminocarbonyl, and diethylaminocarbonyl;

$N(CH_3)_2$, $NH(CH_3)$, —$CH_2CF_3$, —$CH2CH_2CF_3$, —$CH_2CH_2F$, —$CH_2CH_2S(=O)_2CH_3$, —$CH_2CH_2CN$,

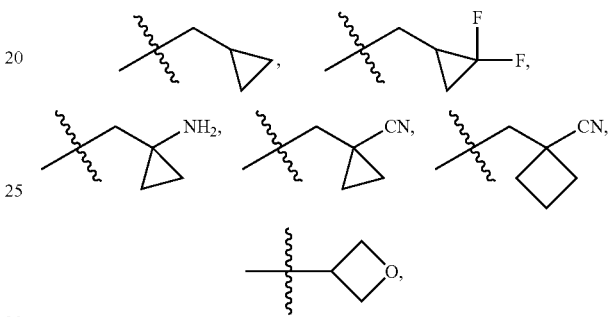

—$CH_2CH(OH)(CH_3)_2$—$CH_2CH(F)(CH_3)_2$, —$CH_2CH_2F$, —$CH_2CF_3$, —$CH_2CH_2CF_3$, —$CH_2CH_2NH_2$, —$CH_2CH_2OH$, —$CH_2CH_2OCH_3$, —$CH_2CH_2CH_2OCH_3$, —$CH_2CH_2N(CH_3)_2$, —$S(=O)_2CH_3$, —$CH_2CH_2S(=O)_2CH_3$,

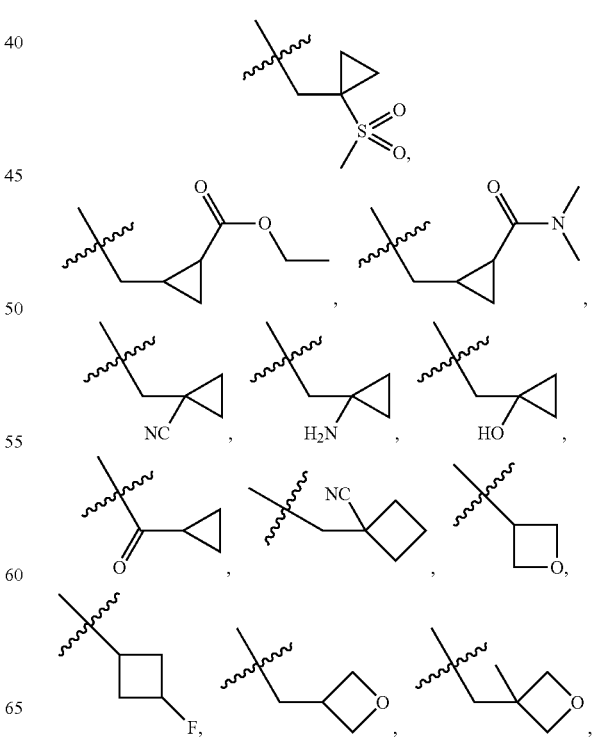

-continued

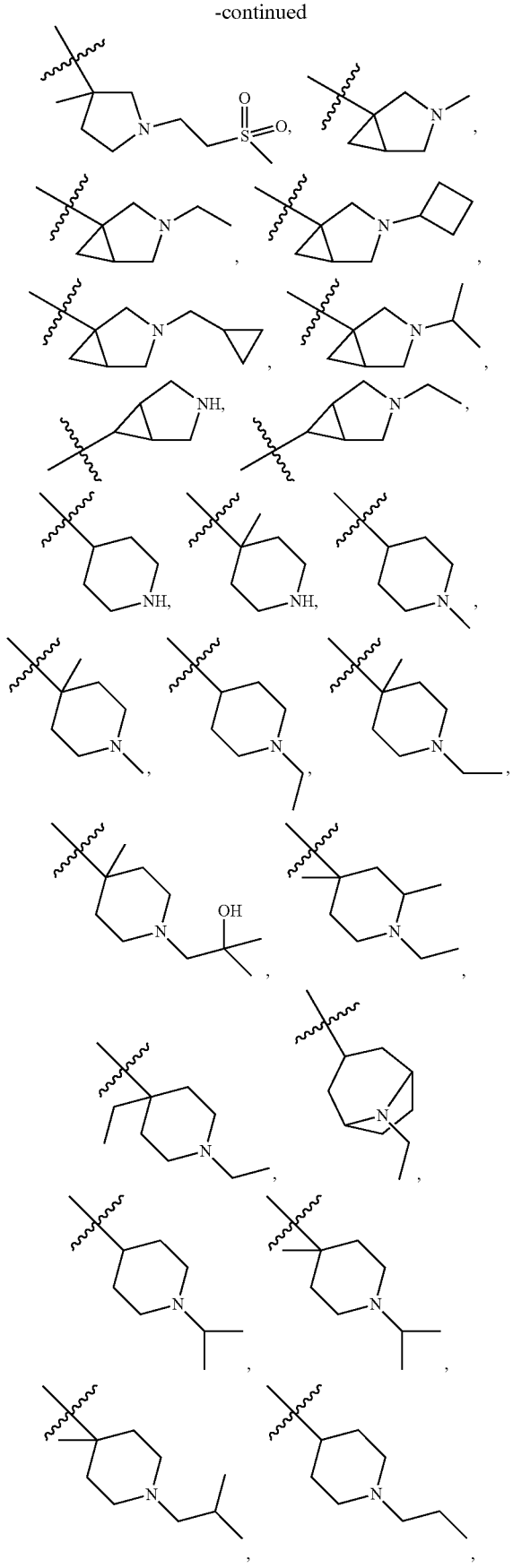
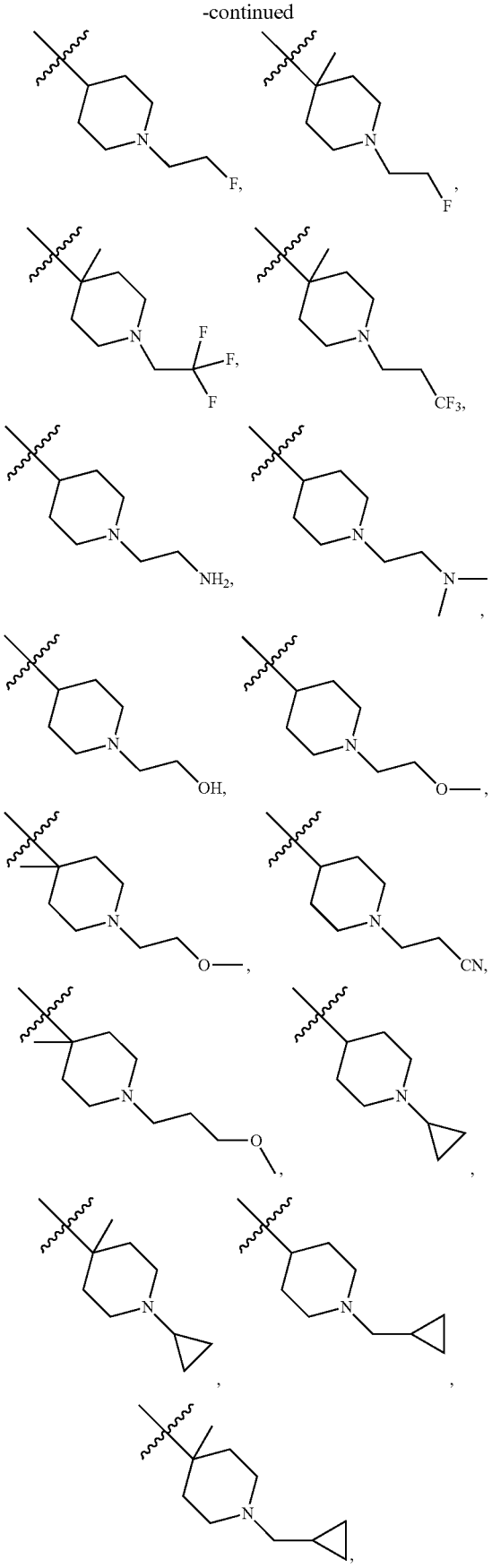

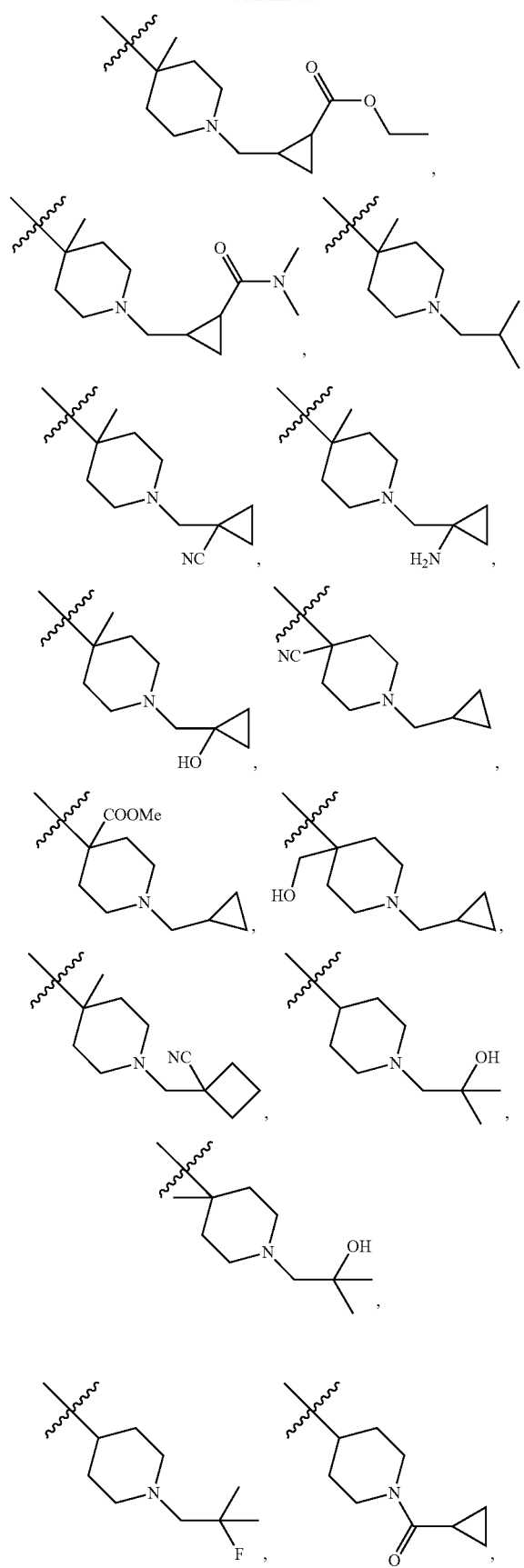
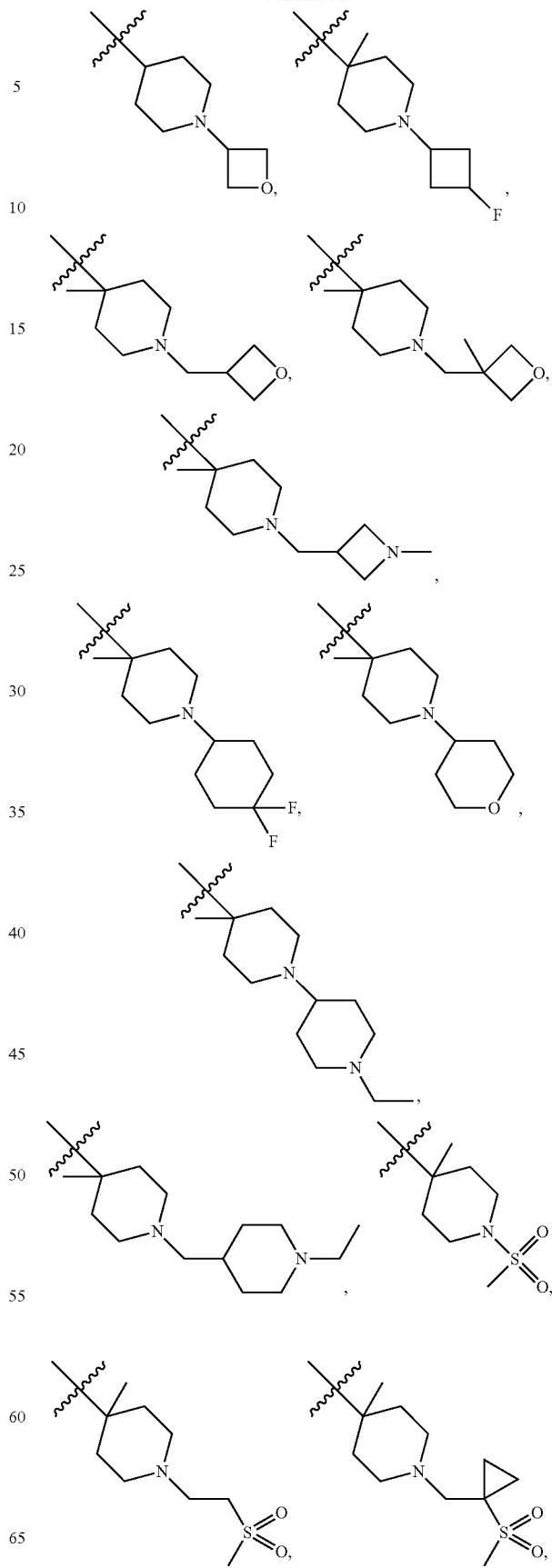

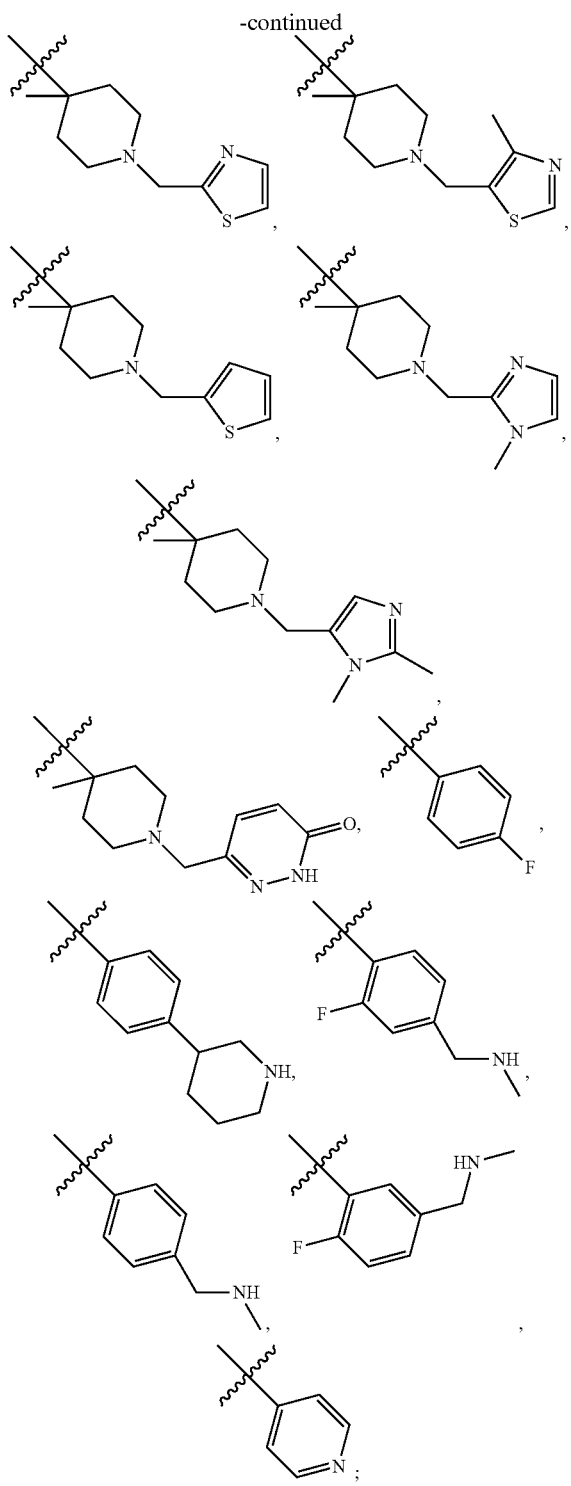

phenyl, thiazolyl, biphenyl, naphthyl, cyclopentyl, furyl, 3-pyrrolinyl, pyrrolidinyl, 1,3-oxolanyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridyl, piperidinyl, 1,4-dioxanyl, morpholinyl, pyridazinyl, pyrimidinyl, pyrazinyl, piperazinyl, 1,3 5-trithianyl, 1,3,5-triazinyl, benzofuranyl, benzothienyl, indolyl, benzimidazolyl, benzothiazolyl, purinyl, quinolinyl, iso-quinolinyl, cinnolinyl, or quinoxalinyl;

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" is meant to include a salt of a compound of the invention which is prepared by a relatively nontoxic acid or base and the compound of the invention having particular substituents. When the compound of the invention contains a relatively acidic functional group, a base addition salt can be obtained by contacting a neutral form of such compounds with a sufficient amount of a desired base, either neat or in a suitable inert solvent. Examples of the pharmaceutically acceptable base addition salts include salts of sodium, potassium, calcium, ammonium, organic amine, or magnesium, or similar salts. When the compound of the invention contains a relatively basic functional group, an acid addition salt can be obtained by contacting a neutral form of such compounds with a sufficient amount of a desired acid, either neat or in a suitable inert solvent. Examples of the pharmaceutically acceptable acid addition salts include salts of inorganic acids including hydrochloric, hydrobromic, nitric, carbonic, hydrocarbonic, phosphoric, hydrophosphoric, dihydrophosphoric, sulfuric, hydrosulfuric, hydriodic, or phosphorous acids and the like; as well as salts of organic acids including acetic, propionic, isobutyric, maleic, malonic, benzoic, succinic, suberic, fumaric, lactic, mandelic, phthalic, benzenesulfonic, p-tolylsulfonic, citric, tartaric, methanesulfonic acid, or the like; and also salts of amino acids (such as arginate and the like), and salts of organic acids like glucuronic acid and the like (see, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral form of the compound is preferably regenerated by contacting the salt with a base or acid and then isolating the parent compound in the conventional manner. The parent form of the compound differs from the various salt forms thereof in certain physical properties, such as solubility in polar solvents.

As used herein, "pharmaceutically acceptable salts" refers to derivatives of the compounds of the invention wherein the parent compound is modified by making a salt with an acid or base.

Examples of pharmaceutically acceptable salts include, but are not limited to, mineral or organic acid salts of basic groups such as amines; alkali or organic salts of acidic groups such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodide, hydroxyl acids, hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic acid.

The pharmaceutically acceptable salts of the present invention can be synthesized from the parent compound that contains a basic or acidic moiety by conventional chemical methods.

Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile or the like are preferred.

In addition to salt forms, the present invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an in vivo environment.

Certain compounds of the invention can exist in unsolvated forms or solvated forms, including hydrated forms. In general, the solvated forms are equivalent to unsolvated forms and all are encompassed within the scope of the present invention. Certain compounds of the invention may exist in polycrystalline or amorphous forms.

Certain compounds of the invention may possess asymmetric carbon atoms (optical centers) or double bonds; the racemates, diastereomers, geometric isomers and individual isomers are all encompassed within the scope of the present invention.

The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included within the scope of the invention.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, and all these mixtures as falling within the scope of the invention. Additional asymmetric carbon atoms can be present in a substituent such as an alkyl group. All such isomers, as well as mixtures thereof, are intended to be included in this invention.

Optically active (R)- and (S)-isomers and D and L isomers can be prepared by chiral synthons or chiral reagents, or other conventional techniques. If a particular enantiomer of a compound of the present invention is desired, it can be prepared by asymmetric synthesis, or by derivatization with a chiral auxiliary, where the resultant diastereomeric mixture is separated and the auxiliary group is cleaved to provide the pure desired enantiomers. Alternatively, where the molecule contains a basic functional group (such as an amino group) or an acidic functional group (such as a carboxyl group) diastereomeric salts can be formed with an appropriate optically active acid or base, followed by resolution of the diastereomers by fractional crystallization or chromatographic means known in the art, and subsequent recovery of the pure enantiomers. In addition, separation of enantiomers and diastereomers is frequently accomplished by chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, regardless of radioactivity, are intended to be encompassed within the scope of the present invention.

The term "pharmaceutically acceptable carrier or vehicle" refers to any formulation or carrier medium that is capable of delivery of an effective amount of an active agent of the invention without toxic side effects on a host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) which is incorporated herein by reference.

The term "excipients" conventionally means carriers, diluents and/or vehicles needed in formulating effective pharmaceutical compositions.

The terms "effective amount" or "therapeutically effective amount" for a drug or pharmacologically active agent refers to a nontoxic but sufficient amount of the drug or agent to provide the desired effect. In the oral dosage forms of the present disclosure, an "effective amount" of an active agent of the composition refers to the amount of the active agent required to provide the desired effect when used in combination with the other active agent of the composition. The amount that is "effective" will vary from subject to subject, depending on the age and general condition of a recipient, and also a particular active agent, and an appropriate effective amount in an individual case may be determined by one of ordinary skill in the art using routine experimentation.

The terms "active ingredient," "therapeutic agent," "active substance," or "active agent" mean a chemical entity which can be effective in treating a targeted disorder, disease or condition.

The term "substituted" means that any one or more hydrogens on a designated atom is replaced with a substituent including deuterium and a variant of hydrogen, provided that the designated atom's valency is normal, and that the substituted compound is stable. When a substituent is keto (i.e., =O), it means that 2 hydrogen atoms are replaced. Keto substituents are not present on aromatic moieties. The term "optionally substituted" means that the designated atom can be substituted or unsubstituted, and unless otherwise stated, the species and number of the substituents may be arbitrary provided that they can be achieved in Chemistry.

When any variable (e.g., R) occurs more than once in the constituent or structure of a compound, its definition at each occurrence is independent. Thus, for example, if a group is substituted with 0-2 Rs, then said group may optionally be substituted with up to two R groups and R at each occurrence has independent options. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating via which atom such substituent is bonded to the compound of a general formula including unspecified ones, then such substituent may be bonded via any atom therein. Combinations of substituents and/or variables are permissible only if such combinations result in stable compounds.

Substituents of the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more selected from, but not limited to the following groups: —R', —OR', =O, =NR', =N—OR', —NR'R", —SR', -halogen, —SiR'R"R"', OC(O)R', —C(O)R', —CO$_2$R', —CONR'R", —OC(O)NR'R", —NR"C(O)R', NR'C(O)NR"R"', —NR"C(O)$_2$R', —NR""-C(NR'R"R"')=NR"", NR"" C(NR'R")=NR"', —S(O)R', —S(O)$_2$R', —S(O)$_2$NR'R", NR"SO$_2$R', —CN, —NO$_2$, —N$_3$, —CH(Ph)$_2$, and fluoro(C$_1$-C$_4$)alkyl, with a number of substitutents ranging from zero to (2m'+1), where m' is the total number of carbon atoms in such radical. R', R", R"', R"" and R""' are each preferably independently hydrogen, substituted or unsubstituted heteroalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"', R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion on substituents, one of skill in the art will understand that the term "alkyl" is meant to include groups constituted by carbon atoms bonding to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents of the aryl and heteroaryl groups are generically referred to as "aryl group substituents." The substituents are selected from, for example: —R', —OR', —NR'R", —SR', -halogen, —SiR'R"R"', OC(O)R', —C(O)R', —CO2R', —CONR'R", —OC(O)NR'R", —NR"C(O)R', NR'C(O)NR"R"', —NR"C(O)$_2$R', —NR""—C(NR'R"R"')=NR"", NR"" C(NR'R")=NR"', —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$)alkoxy, and fluoro(C$_1$-C$_4$)alkyl, etc., with a number of substitutents ranging from zero to the total number of open valences on the aromatic ring; where R', R", R"', R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R""' groups when more than one of these groups is present.

Two of the substituents on adjacent atoms of the aryl or heteroaryl ring may optionally be replaced with a substituent of the formula -T-C(O)—(CRR')q-U—, wherein T and U are independently selected from —NR—, —O—, —CRR'— or a single bond, and q is an integer from 0 to 3.

Alternatively, two of the substituents on adjacent atoms of the aryl or heteroaryl ring may optionally be replaced with a substituent of the formula -A(CH$_2$)rB—, wherein A and B are independently selected from —CRR'—, —O—, —NR—, —S—, —S(O)—, —S(O)$_2$—, —S(O)$_2$NR'— or a single bond, and r is an integer from 1 to 4. One of the single bonds of the thus formed new ring may optionally be replaced with a double bond. Alternatively, two of the substituents on adjacent atoms of the aryl or heteroaryl ring may optionally be replaced with a substituent of the formula -A(CH$_2$)rB—, where s and d are separately and independently selected from integers from 0 to 3, and X is —O—, —NR'—, —S—, —S(O)—, —S(O)$_2$—, or —S(O)$_2$NR'—. The substituents R, R', R" and R"' are separately, preferably and independently selected from hydrogen and substituted or unsubstituted (C$_1$-C$_6$)alkyl.

The term "hydrocarbyl" or its hyponyms (such as alkyl, alkenyl, alkynyl and phenyl etc.) by itself or as part of another substituent, means, unless otherwise stated, a straight or branched chain, or cyclic hydrocarbon radical, or combination thereof, which may be fully saturated, mono- or polyunsaturated, and may be mono-, di-, or multi-substituted, and can include di- or multi-valent radicals, having the designated number of carbon atoms (e.g., C$_1$-C$_{10}$ meaning one to ten carbons). "Hydrocarbyl" include, but are not limited to, aliphatic hydrocarbyl and aromatic hydrocarbyl, and the aliphatic hydrocarbyl include linear and cyclic ones, specifically including but not limited to, alkyl, alkenyl, and alkynyl, and the aromatic hydrocarbyl include, but are not limited to, 6-12 membered aromatic hydrocarbyl, for example, benzene, and naphthalene, etc. In some embodiments, the term "alkyl" means a straight or branched chain radical, or combinations thereof, which may be fully saturated, mono- or polyunsaturated and can include di- and multivalent radicals. Examples of saturated hydrocarbon radicals include, but are not limited to, methyl, ethyl, n-propyl, isopropyl, n-butyl, t-butyl, isobutyl, sec-butyl, isobutyl, cyclohexyl, (cyclohexyl)methyl, cyclopropylmethyl, homologs and isomers of radicals such as n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its hyponymshyponyms (such as heteroalkyl, heteroalkenyl, heteroalkynyl and heteroaryl etc.) by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain hydrocarbyl radical, or combinations thereof, consisting of the stated number of carbon atoms and at least one heteroatom. In a typical embodiment, the heteroatoms are selected from the group consisting of B, O, N and S, wherein the nitrogen and sulfur atoms may optionally be oxidized and the nitrogen heteroatom may optionally be quaternized. The heteroatom(s) B, O, N and S may be placed at any internal position of the heterohydrocarbyl group (except the position at which the hydrocarbyl group is attached to the remainder of the molecule). Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH═CH—N(CH₃)—CH₃. Up to two heteroatoms may be consecutive, such as, for example, —CH₂—NH—OCH₃.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cyclohydrocarbyl," "heterocyclohydrocarbyl" or "cyclohydrocarbylheteroyl" or its hyponyms (such as aryl, heteroaryl, arylheteroyl, cycloalkyl, heterocycloalkyl, cycloalkylheteroyl, cycloalkenyl, heterocycloalkenyl, cycloalkenylheteroyl, cycloalkynyl, heterocycloalkynyl and cycloalkynylheteroyl, etc.) by themselves or in combination with other terms, represent, unless otherwise stated, cyclic versions of "hydrocarbyl," "heterohydrocarbyl" or "hydrocarbylheteroyl," respectively. Additionally, for heterohydrocarbyl or heterocyclohydrocarbyl (such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocycle moieties include 1-(1,2,5,6-tetra-hydropyridyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydrothien-2-yl, tetrahydrothien-3-yl, 1-piperazinyl, and 2-piperazinyl.

The term "halo" or "halogen," by themselves or as part of another substituent, means, unless otherwise stated, a fluorine, chlorine, bromine, or iodine atom. Additionally, the term "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a poly-unsaturated, aromatic substituent that may be mono-, di- or poly-substituted, and can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents of any of the above-described aryl and heteroaryl ring systems are selected from the acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom, e.g., phenoxymethyl, 2-pyridyloxymethyl, 3-(1-naphthyloxy)propyl, and the like.

"Ring or cyclo" means a substituted or unsubstituted cycloalkyl, substituted or unsubstituted heterocycloalkyl, substituted or unsubstituted aryl, or substituted or unsubstituted heteroaryl. The so-called ring includes fused ring moieties. The number of atoms in a ring is typically defined as the number of members of the ring. For example, a "5- to 7-membered ring" means there are 5 to 7 atoms in the encircling arrangement. Unless otherwise specified, the ring optionally includes one to three heteroatoms. Thus, the term "5- to 7-membered ring" includes, for example phenyl, pyridinyl and piperidinyl. The term "5- to 7-membered heterocycloalkyl ring," on the other hand, include pyridinyl and piperidinyl, but not phenyl. The term "ring" further includes a ring system comprising at least one ring, wherein each "ring" is independently defined as above.

As used herein, the term "heteroatom" includes atoms other than carbon (C) and hydrogen (H), including e.g., oxygen (O), nitrogen (N) sulfur (S), silicon (Si), germanium (Ge), aluminum (Al) and boron (B), etc.

The term "leaving group" means a functional group or atom which can be displaced by another functional group or atom in a substitution reaction (such as a nucleophilic substitution reaction). For example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "protecting group" includes but is not limited to "amino-protecting group," "hydroxy-protecting group" or "thiol-protecting group." The term "amino-protecting group" means a protecting group suitable for preventing side reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. The term "hydroxy-protecting group" means a protecting group suitable for preventing side reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. 3-7 cycloalkyl is intended to include $C_3$, $C_4$, $C_5$, $C_6$, and $C_7$ cycloalkyl groups. "Alkenyl" is intended to include hydrocarbon chains of either straight or branched configuration and one or more unsaturated carbon-carbon bonds that may occur in any stable point along the chain, such as ethenyl and propenyl. The term "Halo" or "halogen" refers to fluoro, chloro, bromo, and iodo.

The term "heterocycle" or "heterocyclo" is intended to mean a stable monocyclic or bicyclic or bicyclic heterocyclic ring which may be saturated, partially unsaturated or unsaturated (aromatic), and include carbon atoms and 1, 2, 3, or 4 ring heteroatoms independently selected from the group consisting of N, O and S in which any of the above-defined heterocyclic rings may be fused to a benzene ring to form a bicyclic group. The nitrogen and sulfur heteroatoms may optionally be oxidized (i. e., NO and S(O) p). The nitrogen atom may be substituted or unsubstituted (i.e., N or NR wherein R is H or other substituents already defined herein). The heterocyclic ring may be attached to its pendant group at any heteroatom or carbon atom that results in a stable structure. The heterocyclic rings described herein may be substituted on a carbon or on a nitrogen atom if the resultant compound is stable. A nitrogen atom in the heterocycle may optionally be quaternized. In a preferred embodiment, when the total number of S and O atoms in the heterocycle exceeds 1, then these heteroatoms are not adjacent to one another. In another preferred embodiment, the total number of S and O atoms in the heterocycle is not more than 1. As used herein, the term "aromatic heterocyclic group" or "heteroaryl" is intended to mean a stable 5-, 6-, or 7-membered monocyclic or bicyclic or 7-, 8-, 9-, or 10-membered bicyclic heterocyclic aromatic ring which includes carbon atoms and 1, 2, 3, or 4 heteroatoms independently selected from the group consisting of N, O and S. The nitrogen atom may be substituted or unsubstituted (i.e., N or NR wherein R is H or other substituents already defined herein). The nitrogen and sulfur heteroatoms may optionally be oxidized (i.e., NO and S(O) p). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridged rings include, but are not limited to, one carbon atom, two carbon atoms, one nitrogen atom, two nitrogen atoms, and a carbon-nitrogen group. It is to be noted that a bridge always converts a monocyclic ring into a tricyclic ring. In a bridged ring, the substituents on the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1, 5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2, 4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds.

The compounds of the present invention can be prepared in a number of synthetic methods known to one skilled in the art, including the specific embodiments described below, the embodiments formed by combining them with other chemical synthetic methods known in the art, and equivalents well known to those skilled in the art. Preferred embodiments include, but are not limited to, examples of the invention.

All solvents used herein are commercially available and are used without further purification. Reactions are typically run in anhydrous solvents under an inert atmosphere of nitrogen. Proton NMR data are recorded on Bruker Avance III 400 (400 MHz) spectrometer and chemical shifts are reported as δ (ppm) down field from tetramethylsilane. Mass spectra are determined on Agilent 1200 series plus 6110 (& 1956A). LC/MS, or Shimadzu MS includes a DAD:SPD-M20A (LC) and Shimadzu Micromass 2020 detector. The mass spectrometer is equipped with an electrospray ion source (ESI) operated in a positive or negative mode.

The following abbreviations are used herein: aq represents aqueous; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride, m-CPBA represents 3-chloroperoxybenzoic acid; eq. represents equivalent; CDI represents carbonyl diimidaole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, a amine protecting group; BOC represents tert-butylcarbonyl, an amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents sulfurous dichloride; $CS_2$ represents carbon disulfide; TsOH represents 4-methylbenzenesulfonic acid; NFSI represents N-fluoro-N-(phenylsulfonyl)benzenesulfonamide; NCS represents N-chlorosuccinimide; n-$Bu_4NF$ represents tetrabutylammonium fluoride; i-PrOH represents 2-propanol and mp represents melting point.

Compounds were named either manually or by using ChemDraw®, or using vendors catalogue name if commercially available.

HPLC analyses were performed on a Shimadzu LC20AB system with a Shimadzu SIL-20A Autosampler and a Shimadzu DAD:SPD-M20A Detector. The column used was a Xtimate C18, 3 μm, 2.1×300 mm. Method 0-60AB_6 min included: applying a linear gradient, starting elution at 100% A (A: 0.0675% TFA in water) and ending elution at 60% B (B: 0.0625% TFA in MeCN) overall for 4.2 min and then eluting at 60% B for 1.0 min. The column was then re-equilibrated over 0.8 min to 100:0 with a total run time of 6 min. Method 10-80AB_6 min included: applying a linear gradient, starting elution at 90% A (A: 0.0675% TFA in water) and ending elution at 80% B (B: 0.0625% TFA in MeCN) overall for 4.2 min and then eluting at 80% B for 1.0 min. The column was then re-equilibrated over 0.8 min to 90:10 with a total run time of 6 min. The column temperature was at 50° C. with a flow rate of 0.8 mL/min. The Diode Array Detector scanned from 200-400 nm.

Thin layer chromatography (TLC) was performed on Silica gel GF254 from Sanpont-group and UV was typically used to visualize the spots. Additional visualization methods were also employed in some cases. In these cases the TLC plate was developed with iodine (prepared by adding approximately 1 g of $I_2$ to 10 g silica gel and thoroughly mixing), vanillin (prepared by dissolving about 1 g vanillin in 100 mL 10% $H_2SO_4$), ninhydrin (available commercially from Aldrich), or Magic Stain (prepared by thoroughly mixing $(NH_4)_6Mo_7O_{24}\cdot 4H_2O$, 5 g $(NH_4)_2Ce(IV)(NO_3)_6$, 450 mL $H_2O$ and 50 mL concentrated $H_2SO_4$) to visualize the compound. Flash chromatography was performed using 40-63 μm (230-400 mesh) silica gel from Silicycle following analogous techniques to those disclosed in Still, W. C.; Kahn, M.; and Mitra, M. Journal of Organic Chemistry, 1978, 43, 2923-2925. Typical solvents used for flash chromatography or thin layer chromatography were mixtures such as dichloromethane/methanol, ethyl acetate/methanol and hexanes/ethyl acetate.

Preparative chromatography was performed on a Gilson-281 Prep LC 322 System using a Gilson UV/VIS-156 Detector. The column used was a Agella Venusil ASB Prep C18, 5 μm, 150×21.2 mm or Phenomenex Gemini C18, 5 μm, 150×30 mm or Boston Symmetrix C18, 5 μm, 150×30 mm or Phenomenex Synergi C18, 4 μm, 150×30 mm. Narrow gradients with acetonitrile/water, with the water containing 0.05% HCl or 0.25% HCOOH or 0.5% $NH_3\cdot H_2O$, were used to elute the compounds at a flow rate of approximately 25 mL/min and a total run time of 8-15 min.

SFC analyses were performed on an Agilent 1260 Infinity SFC system with an Agilent 1260 Autosampler and an Agilent DAD:1260 Detector. The column used was Chiralcel OD-H 250×4.6 mm I.D., 5 um or Chiralpak AS-H 250×4.6 mm I.D., 5 μm or Chiralpak AD-H 250×4.6 mm I.D., 5 um. Method OD-H_5_40_2.35 ML Column included: Chiralcel OD-H 250×4.6 mm I.D., 5 μm Mobile phase: 40% ethanol (0.05% DEA) in $CO_2$ Flow rate: 2.35 mL/min Wavelength: 220 nm. Method AS-H_3_40_2.35 ML Column included: Chiralpak AS-H 250×4.6 mm I.D., 5 μm Mobile phase: 40% methanol (0.05% DEA) in $CO_2$ Flow rate: 2.35 mL/min Wavelength: 220 nm. Method OD-H_3_40_2.35M Column included: Chiralcel OD-H 250×4.6 mm I.D., 5 μm Mobile phase: 40% methanol (0.05% DEA) in $CO_2$ Flow rate: 2.35 mL/min Wavelength: 220 nm. Method AD-H_2_50_2.35 ML Column included: Chiralpak AD-H 250×4.6 mm I.D., 5 mm Mobile phase: 50% methanol (0.1% MEA) in $CO_2$ Flow rate: 2.35 mL/min Wavelength: 220 nm.

Preparative SFC analysis was performed on a Waters Thar 80 Pre-SFC System using a Gilson UV Detector. The column used was Chiralcel OD-H 250×4.6 mm I.D., 5 m or Chiralpak AD-H 250×4.6 mm I.D., 5 m. Narrow gradients with ethanol or methanol in $CO_2$, with the ethanol or methanol containing 0.05% $NH_3\cdot H_2O$ or 0.05% DEA or 0.1% MEA, were used to elute the compound at a flow rate between 40-80 mL/min and a total run time between 20-30 min.

The PARP-1 inhibitors provided herein can be used for the treatment of wide rages of diseases comprising cancer, stroke, cardiac ischemia, inflammation, and diabetes. The PARP-1 inhibitors can be used as a standalone agent or in combination with other chemotherapeutical agents to enhance the effect of these standard chemotherapeutical agents.

Cancers that can be treated by the PARP-1 inhibitors include, but are not limited to breast cancer, ovarian cancer, pancreatic cancer, prostate cancer, clone cancer, and leukemia, etc.

DETAILED DESCRIPTION OF THE INVENTION

To describe the present invention in more detail, the following examples are provided. However, the scope of the present invention is not limited to these.

Scheme A

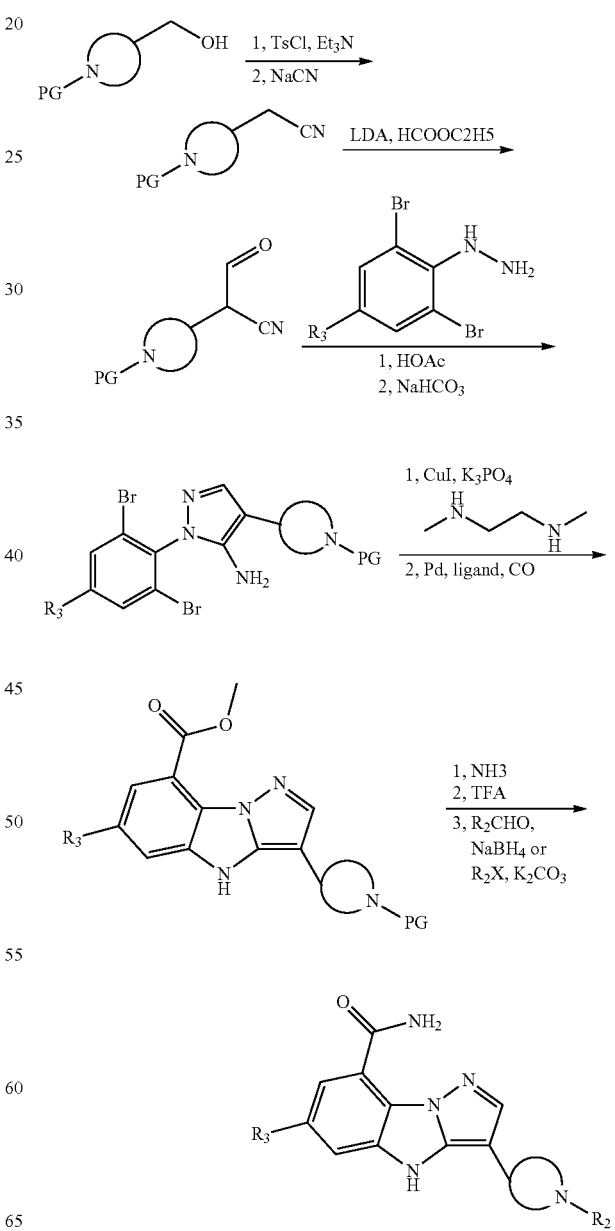

Example 1

6-fluoro-3-(piperidin-4-yl)-4H-benzo[4,5]imidazo[1,2-b]pyrazole-8-carboxamide

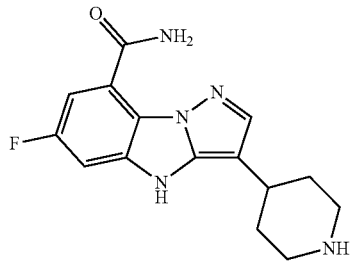 [SMILES: NC(=O)c1cc(F)cc2[nH]c3c(C4CCNCC4)cnn3c12]

Example 1A tert-butyl 4-((tosyloxy)methyl)piperidine-1-carboxylate

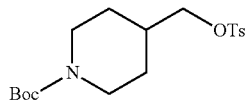 [SMILES: Cc1ccc(S(=O)(=O)OCC2CCN(C(=O)OC(C)(C)C)CC2)cc1]

To a solution of tert-butyl 4-(hydroxymethyl)piperidine-1-carboxylate (10 g, 46.5 mmol), Et₃N (5.64 g, 55.8 mmol) and DMAP (1.13 g, 9.3 mmol) in DCM (100 mL) was added in protions TosCl (9.73 g, 51.2 mmol) at 0° C. under N₂ atmosphere. After stirring at 17° C. for 2 h, water (100 mL) was added to quench. The aqueous layer was extracted with DCM (100 mL×2). The combined organic layers were dried over Na₂SO₄, filtered and evaporated to give the residue which was purified by column chromatography to give the title compound (17 g, 99% yield) as a white solid. LCMS (ESI) m/z: 370 (M+1).

Example 1B tert-butyl 4-(cyanomethyl)piperidine-1-carboxylate

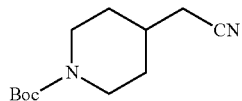 [SMILES: CC(C)(C)OC(=O)N1CCC(CC#N)CC1]

A mixture of EXAMPLE 1A (19 g, 55.7 mmol), sodium cyanide (8.19 g, 167 mmol) in dimethylsulfoxide (100 mL) was reacted at 100° C. for 16 h. After being cooled to room temperature, the mixture was diluted with water (200 ml). The aqueous layer was extracted with EtOAc (100 mL×3). The combined organic layers were washed with water (50 mL), and brine (50 mL), then dried over Na₂SO₄, filtered and evaporated to provide the title compound (11 g) which could be used directly in the next step without further purification. LCMS (ESI) m/z: 225 (M+1)

Example 1C tert-butyl 4-(1-cyano-2-oxoethyl)piperidine-1-carboxylate

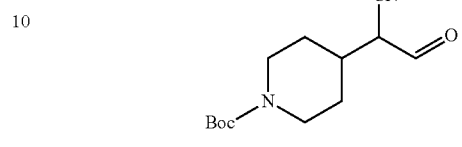

To a mixture of EXAMPLE 1B (11 g, 49 mmol), t-BuOK (32.9 g, 294 mmol) in DMF (80 mL) was added dropwise a solution of ethyl formate (21.7 g, 294 mmol) in DMF (50 mL) at −10° C. under N₂ atmosphere. After the dropwise addition completed, the mixture was stirred at 17° C. for 16 h, and then neutralized with 1N HCl. The aqueous layer was extracted with EtOAc (100 mL×4). The combined organic layers were dried over Na₂SO₄, filtered and evaporated to provide the title compound (11 g, 89%) which could be used directly in the next step without further purification. LCMS (ESI) m/z: 253 (M+1)

Example 1D (2,6-dibromo-4-fluorophenyl)hydrazine

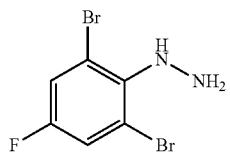 [SMILES: NNc1c(Br)cc(F)cc1Br]

To a solution of 2,6-dibromo-4-fluoroaniline (5 g, 18.6 mmol) in 35 ml 20% aq HCl (35 mL) was added dropwise a solution of NaNO₂ (1.41 g, 20.45 mmol) in water (40 mL) at −5° C. with a rate of the dropwise addition to keep the internal temperature below 5° C. After 0.5 h, the above-mentioned solution was added dropwise into a solution of SnCl₂ (10.49 g, 46 mmol) in concentrate HCl solution (40 mL) at −15° C. After the dropwise addition completed, the mixture was allowed to warm to 35° C. and stirred for 12 h. The mixture was cooled to 0° C. and adjusted to pH=9 with concentrate ammonia aqueous solution. The aqueous layer was extracted with EtOAc (150 mL×3). The organic layers were washed with water (100 mL), dried over Na₂SO₄, filtered and evaporated to give the residue which was purified by column chromatography to provide the title compound (4 g, yield: 76%). ¹H NMR (400 MHz, CDCl3-d): δ ppm 3.91 (br. s., 1H), 5.37 (br. s., 1H), 7.31 (d, J=7.37 Hz, 2H).

Example 1E tert-butyl 4-(1-cyano-2-(2-(2,6-dibromo-4-fluoro-phenyl)hydrazono)ethyl)piperidine-1-carboxylate

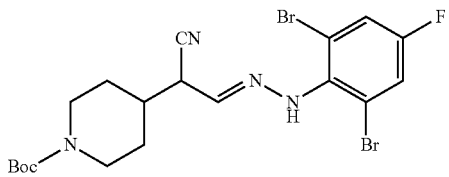 [SMILES: CC(C)(C)OC(=O)N1CCC(C(C#N)/C=N/Nc2c(Br)cc(F)cc2Br)CC1]

A mixture of EXAMPLE 1C (3.5 g, 13.87 mmol) and EXAMPLE 1D (3.94 g, 13.87 mmol) in EtOH (30 mL) was stirred at 80° C. for 0.5 h. After removal of solution in vacuum, the residue was purified by column chromatography to provide the title compound as a white solid (3.8 g, 53%). LCMS (ESI) m/z: 519 (M+1).

Example 1F tert-butyl 4-(5-amino-1-(2,6-dibromo-4-fluorophe-nyl)-1H-pyrazol-4-yl)piperidine-1-carboxylate

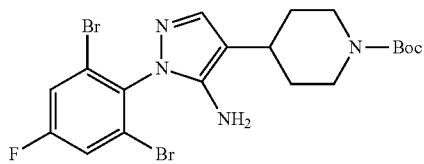 [SMILES: CC(C)(C)OC(=O)N1CCC(c2cnn(-c3c(Br)cc(F)cc3Br)c2N)CC1]

A mixture of EXAMPLE 1E (3.8 g, 7.33 mmol) and $Et_3N$ (1.48 g, 14.67 mmol) in EtOH (30 mL) was stirred at 80° C. for 16 h. The mixture was evaporated under vacuum to provide the title compound which could be used directly in the next step without further purification. (3.8 g, 100%).

Example 1G tert-butyl 4-(8-bromo-6-fluoro-4H-benzo[4,5]imi-dazo[1,2-b]pyrazol-3-yl)piperidine-1-carboxylate

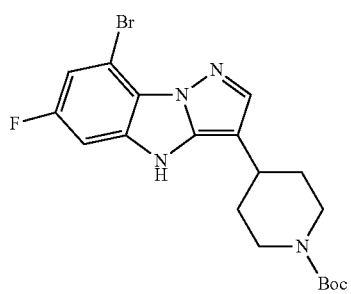 [SMILES: CC(C)(C)OC(=O)N1CCC(c2cnn3c2[nH]c2cc(F)cc(Br)c23)CC1]

A mixture of EXAMPLE 1F (2.4 g, 4.63 mmol), $N^1,N^2$-dimethylethane-1,2-diamine (40.83 g, 0.463 mmol), CuI (88 g, 0.463 mmol) and $K_3PO_4$ (983 g, 4.63 mmol) in DMF (30 mL) was stirred at 60° C. for 1 h by microwave under $N_2$ atmosphere. The mixture was cooled to room temperature and then filtrated through a pad of Celite, and the filtrate was evaporated under vacuum to give a residue which was purified by column chromatography to provide the title compound as a white solid (0.4 g, 15%). LCMS (ESI) m/z: 437, 439 (M, M+2).

Example 1H methyl 3-(1-(tert-butoxycarbonyl)piperidin-4-yl)-6-fluoro-4H-benzo[4,5]imidazo[1,2-b]pyrazole-8-car-boxylate

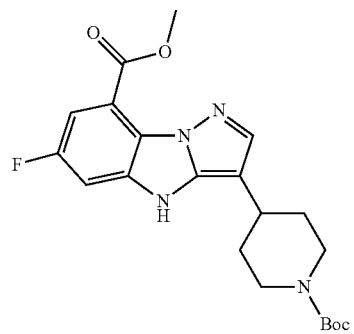 [SMILES: COC(=O)c1cc(F)cc2[nH]c3c(C4CCN(C(=O)OC(C)(C)C)CC4)cnn3c12]

A mixture of EXAMPLE 1G (200 g, 0.457 mmol), $Pd(OAc)_2$ (10.27 g, 0.0457 mmol), $Pd(dppf)Cl_2$ (33.46 g, 0.0457 mmol), Xantphos (53 g, 0.0914 mmol), DPPP (38 g, 0.0914 mmol), $PPh_3$ (24 mg, 0.0914 mmol) and $Et_3N$ (232 g, 2.29 mmol) in DMF (40 mL) and MeOH (20 mL) was stirred at 120° C. for 12 h under CO atmosphere (3 MPa). The mixture was cooled to room temperature and then filtrated through a pad of Celite. The filtrate was evaporated to give the residue which was purified by column chromatography to provide the title compound as a white solid (100 g, 52%). LCMS (ESI) m/z: 417 (M+1).

Example 1I tert-butyl 4-(8-carbamoyl-6-fluoro-4H-benzo[4,5]imidazo[1,2-b]pyrazol-3-yl)piperidine-1-carboxylate

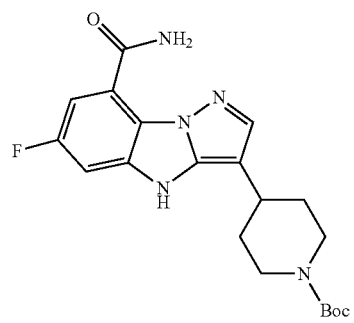

A mixture of EXAMPLE 1H (100 g, 0.24 mmol) and $NH_3$-MeOH (30 mL) in DMF (100 mL) was reacted at 120° C. for 16 h in a closed tube. The mixture was cooled and then removed of solution in vacuum, and the residue was purified by column chromatography to provide the title compound as a white solid (70 g, 73%). LCMS (ESI) m/z: 402 (M+1).

Example 1J 6-fluoro-3-(piperidin-4-yl)-4H-benzo[4,5]imidazo[1,2-b]pyrazole-8-carboxamide

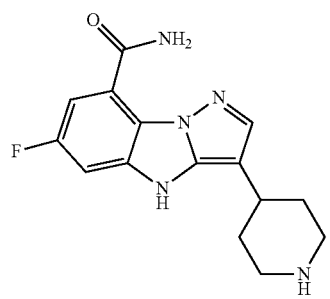 [SMILES: NC(=O)c1cc(F)cc2[nH]c3c(C4CCNCC4)cnn3c12]

A mixed solution of EXAMPLE 1I (70 g, 0.174 mmol) in DCM (3 mL) and TFA (1 mL) was stirred at 15° C. for 1 h, and removed of solution in vacuum. The residue was purified by prep-HPLC to provide the title compound (25 g, 49%). $^1$H NMR (400 MHz, METHANOL-d4) δ ppm 1.93-1.96 (m, 2H), 2.37-2.36 (d, 2H), 3.09-3.22 (m, 3H), 3.31-3.53 (t, 2H), 7.37-7.39 (m, 1H), 7.68-7.74 (m, 2H). LCMS (ESI) m/z: 302 (M+1).

Example 2

3-(1-ethylpiperidin-4-yl)-6-fluoro-4H-benzo[4,5]imidazo[1,2-b]pyrazole-8-carboxamide

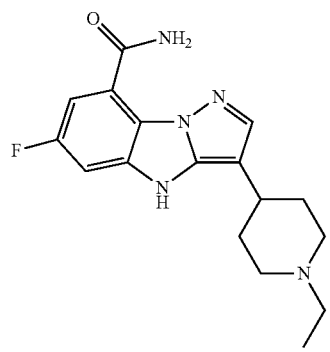 [SMILES: CCN1CCC(c2cnn3c2[nH]c2cc(F)cc(C(N)=O)c23)CC1]

A mixture of EXAMPLE 1J (750 g, 2.49 mmol) and acetaldehyde (1.1 g, 24.9 mmol) in MeOH (15 mL) was stirred at 50° C. for 0.5 h. Thereafter, NaCNBH$_3$ (3.13 g, 49.8 mmol) was added thereto. The resulting mixture was stirred at 50° C. for 16 h. After removal of solution in vacuum, the residue was purified by column chromatography to provide the title compound as a white solid. (563.1 g, 69%). $^1$H NMR (400 MHz, METHANOL-d4) δ ppm 1.31-1.34 (t, 3H), 1.94-1.97 (m, 2H), 2.27-2.31 (d, 2H), 2.82 (t, 2H), 2.97-3.02 (m, 3H), 3.47-3.48 (d, 2H), 7.34-7.37 (m, 1H), 7.67-7.72 (m, 2H). LCMS (ESI) m/z: 330 (M+1).

Example 3

6-fluoro-3-(1-(2-fluoroethyl)piperidin-4-yl)-4H-benzo[4,5]imidazo[1,2-b]pyrazole-8-carboxamide

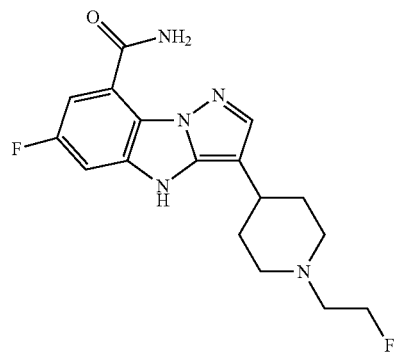 [SMILES: NC(=O)c1cc(F)cc2[nH]c3c(C4CCN(CCF)CC4)cnn3c12]

A mixture of EXAMPLE 1J (112 g, 0.372 mmol), 1-bromo-2-methoxyethane (71 g, 0.558 mmol) and potassium carbonate (154 g, 1.116 mmol) in acetonitrile (20 mL) was stirred at 40° C. for 16 hours. The mixture was cooled and filtrated, and the filtrate was evaporated under vacuum to give a residue which was purified by prep-HPLC to provide the title compound (4.6 g, 3.6%). $^1$H NMR (400 MHz, METHANOL-d$_4$) ppm 1.94-2.15 (m, 2H), 2.17-2.37 (m, 2H), 2.86-3.07 (m, 3H), 3.27-3.32 (m, 1H), 3.35-3.39 (m, 1H), 3.46-3.61 (m, 2H), 4.71-4.80 (m, 1H), 4.89 (br. s., 1H), 7.28-7.41 (m, 1H), 7.60-7.76 (m, 2H), 8.24-8.69 (m, 1H). LCMS (ESI) m/z: 348 (M+1).

Example 4

3-(1-cyclopropylpiperidin-4-yl)-6-fluoro-4H-benzo[4,5]imidazo[1,2-b]pyrazole-8-carboxamide

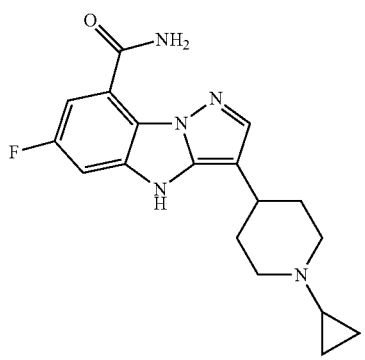 [SMILES: NC(=O)c1cc(F)cc2[nH]c3c(C4CCN(C5CC5)CC4)cnn3c12]

A mixture of (1-ethoxycyclopropoxy)trimethylsilane (115 g, 0.663 mmol), EXAMPLE 1J (40 g, 0.133 mmol), HOAc (79 g, 1.33 mmol) and NaCNBH$_3$ (83 g, 1.33 mmol) in MeOH (10 mL) was stirred at 66° C. for 7 h. The mixture was cooled and then removed of solution in vacuum, and the residue was purified by prep-HPLC to provide the title compound (19.6 g, 43%). $^1$H NMR (400 MHz, METHANOL-d4) δ ppm 0.70-0.79 (m, 4H), 1.84-1.92 (m, 2H), 2.18-2.28 (t, 3H), 2.85-2.94 (m, 3H), 3.42-3.45 (m, 2H), 7.33-7.35 (m, 1H), 7.65-7.68 (m, 2H), 8.395 (s, 1H). LCMS (ESI) m/z: 342 (M+1).

Example 5

3-(1-(cyclopropylmethyl)piperidin-4-yl)-6-fluoro-4H-benzo[4,5]imidazo[1,2-b]pyrazole-8-carboxamide

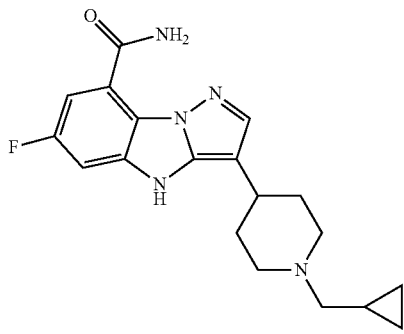 [SMILES: NC(=O)c1cc(F)cc2[nH]c3c(C4CCN(CC5CC5)CC4)cnn3c12]

A mixture of EXAMPLE 1J (12 g, 0.04 mmol), cyclopropanecarbaldehyde (5.58 g, 0.08 mmol) and NaCNBH₃ (50 g, 0.8 mmol) in MeOH (2 mL) was stirred at 10° C. for 16 h. Thereafter, tetraisopropoxytitanium (17 g, 0.06 mmol) was added thereto and continuously stirred for 1 hour. After removal of solution in vacuum, the residue was purified by prep-HPLC to provide the title compound (5.2 g, 37%). $^1$H NMR (400 MHz, METHANOL-d4) ⊠ ppm 0.40-0.44 (m, 2H), 0.75-0.79 (m, 1H), 1.12-1.13 (m, 1H), 2.04 (s, 2H), 2.32-2.36 (d, 2H), 2.9-3.12 (m, 5H), 3.68 (s, 2H), 7.36-7.39 (m, 1H), 7.68-7.73 (m, 2H), 8.50 (s, 1H). LCMS (ESI) m/z: 356 (M+1).

Example 6

6-fluoro-3-(1-(2-hydroxy-2-methylpropyl)piperidin-4-yl)-4H-benzo[4,5]imidazo[1,2-b]pyrazole-8-carboxamide

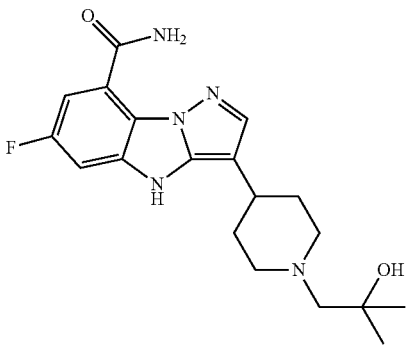 [SMILES: CC(C)(O)CN1CCC(c2cnn3c2[nH]c2cc(F)cc(C(N)=O)c23)CC1]

Example 6A tert-butyl 4-(4-benzyl-8-carbamoyl-6-fluoro-4H-benzo[4,5]imidazo[1,2-b]pyrazol-3-yl)piperidine-1-carboxylate

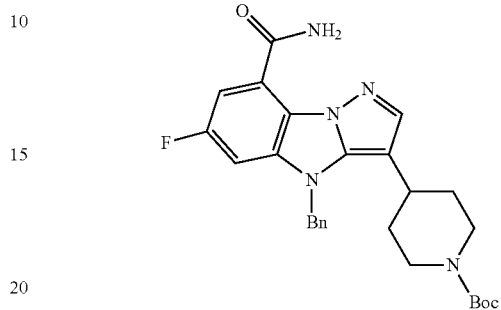

A mixture of EXAMPLE 1I (100 g, 0.25 mmol), (bromomethyl)benzene (127 g, 0.748 mmol) and potassium carbonate (103 g, 0.748 mmol) in acetonitrile (4 mL) was stirred at 60° C. for 4 hours. The mixture was cooled and filtered and the filtrate was evaporated under vacuum to give a residue which was purified by silica gel chromatography to provide the title compound (112.6 g, 91.8%). LCMS (ESI) m/z: 492 (M+1).

Example 6B

4-benzyl-6-fluoro-3-(piperidin-4-yl)-4H-benzo[4,5]imidazo[1,2-b]pyrazole-8-carboxamide

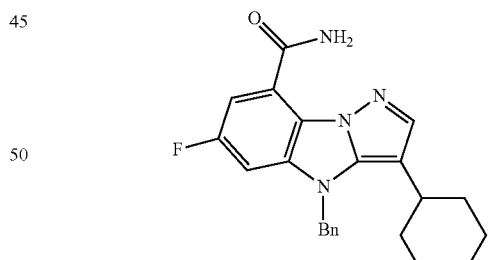

A mixture solution of EXAMPLE 6A (112.6 g, 0.229 mmol) in DCM (9 mL) TFA (3 mL) was stirred at 12° C. for 2 hours. After removal of solution in vacuum, the title compound (115 g, 100%) was provided as yellow solid which could be used directly in the next step without further purification. LCMS (ESI) m/z: 392 (M+1).

Example 6C 4-benzyl-6-fluoro-3-(1-(2-hydroxy-2-methylpropyl)piperidin-4-yl)-4H-benzo[4,5]imidazo[1,2-b]pyrazole-8-carboxamide

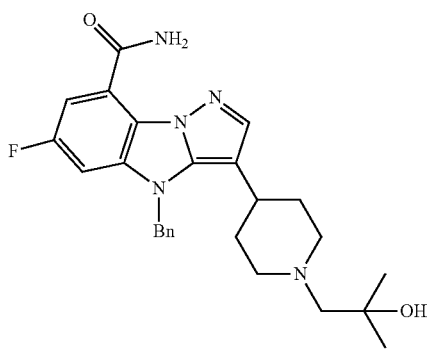 [SMILES: CC(C)(O)CN1CCC(c2cnn3c4c(C(N)=O)cc(F)cc4n(Cc4ccccc4)c23)CC1]

A mixture of EXAMPLE 6B (115 g, 0.229 mmol), 2,2-dimethyloxirane (50 g, 0.690 mmol) and Et$_3$N (116 g, 1.15 mmol) in ethanol (5 ml) was heated at 120° C. under microwave for 1 hour. The mixture was cooled and removed of solution in vacuum, and then the residue was purified by silica gel chromatography to provide the title compound. LCMS (ESI) m/z: 464 (M+1).

Example 6D 6-fluoro-3-(1-(2-hydroxy-2-methylpropyl)piperidin-4-yl)-4H-benzo[4,5]imidazo[1,2-b]pyrazole-8-carboxamide

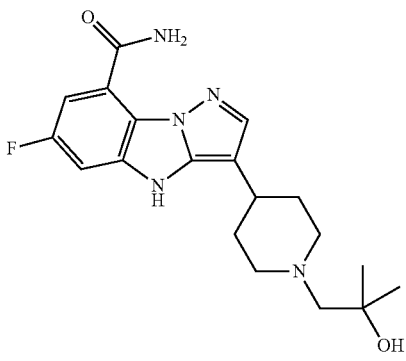 [SMILES: CC(C)(O)CN1CCC(c2cnn3c2[nH]c2cc(F)cc(C(N)=O)c23)CC1]

A mixture of EXAMPLE 6C (32 g, 0.069 mmol) and Pd/C (25 mg) in Methanol (30 mL) was hydrogenated at 50° C. for 4 hours under H$_2$ (1 atm). The mixture was cooled and filtered, and the filtrate was evaporated under vacuum. Thereafter the residue was purified by prep-HPLC to provide the title compound (8.2 g, 32.2%). $^1$H NMR (400 MHz, METHANOL-d$_4$) ppm 1.38 (s, 6H), 2.10-2.30 (m, 4H), 3.12 (s, 5H), 3.57-3.73 (m, 2H), 7.29-7.39 (m, 1H), 7.61-7.69 (m, 1H), 7.69-7.75 (m, 1H), 8.54 (br. s., 1H). LCMS (ESI) m/z: 374 (M+1).

Example 7

6-fluoro-3-(1-(2-fluoro-2-methylpropyl)piperidin-4-yl)-4H-benzo[4,5]imidazo[1,2-b]pyrazole-8-carboxamide

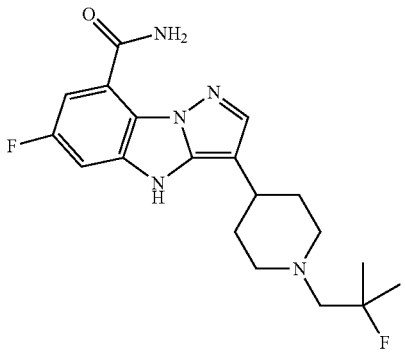 [SMILES: CC(C)(F)CN1CCC(c2cnn3c2[nH]c2cc(F)cc(C(N)=O)c23)CC1]

Example 7A 4-benzyl-6-fluoro-3-(1-(2-fluoro-2-methylpropyl)piperidin-4-yl)-4H-benzo[4,5]imidazo[1,2-b]pyrazole-8-carboxamide

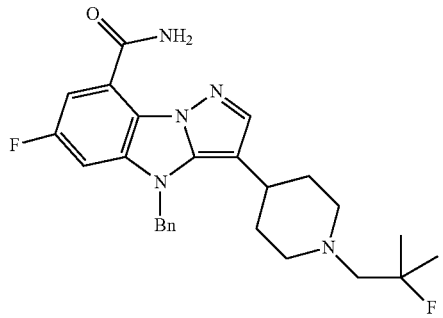 [SMILES: CC(C)(F)CN1CCC(c2cnn3c4c(C(N)=O)cc(F)cc4n(Cc4ccccc4)c23)CC1]

To a mixture of EXAMPLE 6C (32 g, 0.069 mmol) in DCM (10 mL) was added dropwise a solution of DAST (33 g, 0.207 mmol) in DCM (2 mL) at 0° C. under N$_2$ atmosphere. After the dropwise addition was completed, the mixture was stirred at 17° C. for 16 h, and then quenched with saturated sodium bicarbonate solution (10 mL). The aqueous layer was extracted with EtOAc (10 mL×2). The combined organic layers were dried over Na$_2$SO$_4$, filtered and evaporated. The residue was purified by silica gel chromatography to provide the title compound (27 g, 84.4%). LCMS (ESI) m/z: 466 (M+1).

Example 7B 6-fluoro-3-(1-(2-fluoro-2-methylpropyl)piperidin-4-yl)-4H-benzo[4,5]imidazo[1,2-b]pyrazole-8-carboxamide

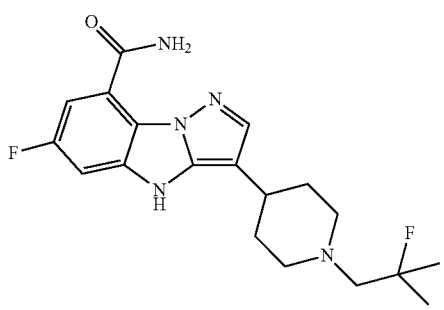 [SMILES: CC(C)(F)CN1CCC(c2cnn3c2[nH]c2cc(F)cc(C(N)=O)c23)CC1]

A mixture of EXAMPLE 7A (27 g, 0.058 mmol) and Pd/C (30 mg) in Methanol (20 mL) was hydrogenated at 45° C. for 16 hours under H₂ (1 atm). The mixture was cooled and filtered and the filtrate was evaporated. The residue was purified by prep-HPLC to provide the title compound (2.1 g, 10%). ¹H NMR (400 MHz, METHANOL-d₄) ppm 1.42 (s, 3H), 1.48 (s, 3H), 1.90-2.03 (m, 2H), 2.04-2.16 (m, 2H), 2.51-2.67 (m, 2H), 2.72-2.90 (m, 3H), 3.23-3.31 (m, 2H), 7.32-7.41 (m, 1H), 7.63-7.75 (m, 2H), 8.27-8.59 (m, 1H). LCMS (ESI) m/z: 376 (M+1)

Example 8

3-(1-(cyclopropylcarbonyl)piperidin-4-yl)-6-fluoro-4H-benzo[4,5]imidazo[1,2-b]pyrazole-8-carboxamide

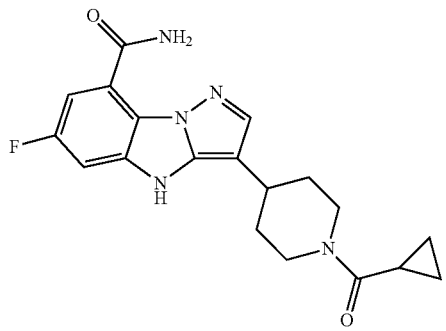 [SMILES: NC(=O)c1cc(F)cc2[nH]c3c(C4CCN(C(=O)C5CC5)CC4)cnn3c12]

A mixture of EXAMPLE 1J (52 g, 0.125 mmol), cyclopropanecarboxylic acid (13 g, 0.150 mmol), Et₃N (50.5 g, 0.5 mmol) and HATU (47.5 g, 0.125 mmol) in acetonitrile (5 mL) was stirred at 50° C. for 3 hours. After the mixture was cooled and removed of solution in vacuum, the residue was purified by prep-HPLC to provide the title compound (12.7 g, 27.3%). LCMS: 370 [M+1]. ¹H NMR (400 MHz, DMSO-d₆) ppm 0.72 (d, J=7.53 Hz, 4H), 1.42-1.69 (m, 2H), 1.88-2.07 (m, 3H), 2.65-2.77 (m, 1H), 2.86-2.98 (m, 1H), 3.14-3.29 (m, 1H), 4.26-4.50 (m, 2H), 7.43-7.50 (m, 1H), 7.51-7.59 (m, 1H), 7.76 (s, 1H). LCMS (ESI) m/z: 370 (M+1).

Example 9

6-fluoro-3-(1-methy piperidin-4-yl)-4H-benzo[4,5]imidazo[1,2-b]pyrazole-8-carboxamide

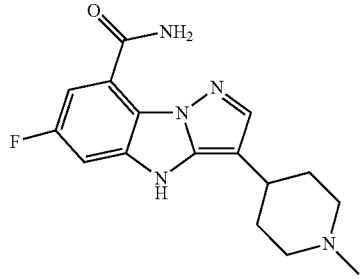 [SMILES: CN1CCC(c2cnn3c2[nH]c2cc(F)cc(C(N)=O)c23)CC1]

This example was prepared as the method described in Example 2. ¹H NMR (400 MHz, METHANOL-d4) δ ppm 1.98-2.01 (d, 2H), 2.29-2.31 (d, 2H), 2.83 (s, 1H), 3.01-3.04 (d, 2H), 3.48 (d, 2H), 7.36-7.39 (m, 1H), 7.68-7.73 (m, 2H), 8.49 (s, 1H). LCMS (ESI) m/z: 316 (M+1).

Example 10

6-fluoro-3-(1-isopropylpiperidin-4-yl)-4H-benzo[4,5]imidazo[1,2-b]pyrazole-8-carboxamide

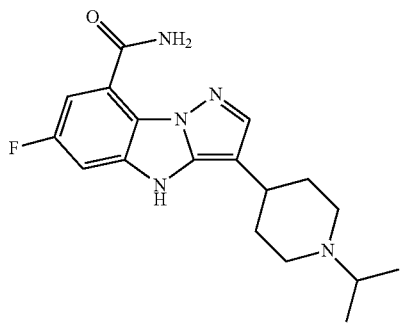 [SMILES: CC(C)N1CCC(c2cnn3c2[nH]c2cc(F)cc(C(N)=O)c23)CC1]

This example was prepared as the method described in Example 2. ¹H NMR (400 MHz, METHANOL-d4) δ ppm 1.38-1.40 (d, 6H), 2.02-2.05 (d, 2H), 2.36-2.40 (d, 2H), 3.06 (m, 1H), 3.19-3.22 (t, 2H), 3.51-3.55 (m, 3H), 7.35-7.38 (m, 1H), 7.66-7.72 (m, 2H), 8.51 (s, 1H). LCMS (ESI) m/z: 344 (M+1).

Example 11

6-fluoro-3-(1-(oxetan-3-yl)piperidin-4-yl)-4H-benzo[4,5]imidazo[1,2-b]pyrazole-8-carboxamide

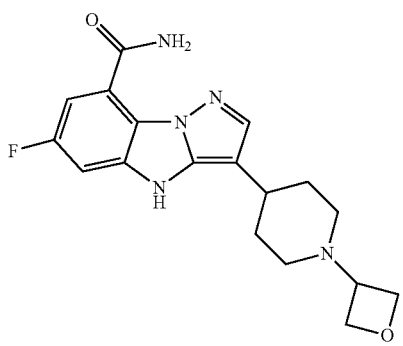 [SMILES: NC(=O)c1cc(F)cc2[nH]c3c(C4CCN(C5COC5)CC4)cnn3c12]

This example was prepared as the method described in Example 2. ¹H NMR (400 MHz, DMSO-d₆) δ ppm 1.66-1.79 (m, 2H), 1.82-1.99 (m, 4H), 2.58-2.69 (m, 1H), 2.70-2.81 (m, 2H), 3.36-3.45 (m, 1H), 4.45 (s, 2H), 4.51-4.58 (m, 2H), 7.36-7.44 (m, 1H), 7.45-7.53 (m, 1H), 7.65-7.75 (m, 1H). LCMS (ESI) m/z: 358 (M+1).

Example 12

6-fluoro-3-(1-propylpiperidin-4-yl)-4H-benzo[4,5]imidazo[1,2-b]pyrazole-8-carboxamide

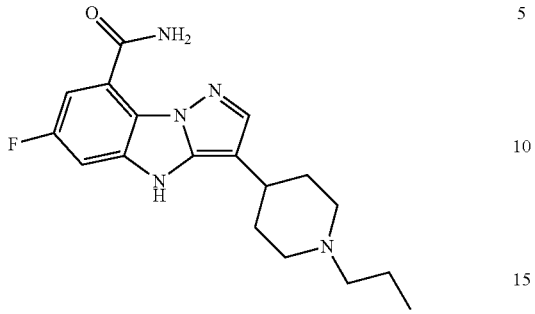

This example was prepared as the method described in Example 2. $^1$H-NMR (400 MHz, METHANOL-d4) δ ppm 1.02-1.06 (t, 3H), 1.76-1.82 (m, 2H), 2.00-2.03 (d, 2H), 2.31-2.34 (d, 2H), 3.01-3.05 (m, 5H), 3.57-3.58 (d, 2H), 7.36-7.39 (m, 1H), 7.68-7.73 (m, 2H), 8.51 (s, 1H). LCMS (ESI) m/z: 344 (M+1).

Example 13

3-(1-(2-aminoethyl)piperidin-4-yl)-6-fluoro-4H-benzo[4,5]imidazo[1,2-b]pyrazole-8-carboxamide

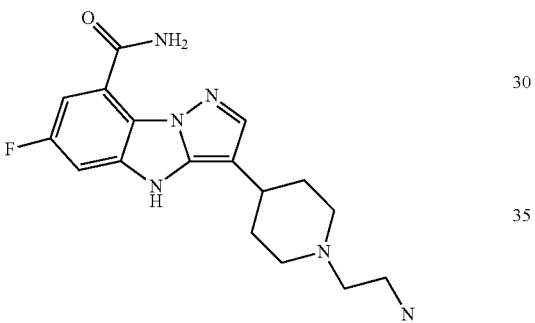

This example was prepared as the method described in Example 2. $^1$H NMR (400 MHz, METHANOL-d$_4$) δ ppm 1.80-1.98 (m, 2H), 2.06-2.17 (m, 2H), 2.30-2.46 (m, 2H), 2.68-2.85 (m, 3H), 3.05-3.19 (m, 4H), 7.30-7.38 (m, 1H), 7.69 (br. s., 2H), 8.28-8.67 (m, 1H). LCMS (ESI) m/z: 345 (M+1).

Example 14

3-(1-(2-(dimethylamino)ethyl)piperidin-4-yl)-6-fluoro-4H-benzo[4,5]imidazo[1,2-b]pyrazole-8-carboxamide

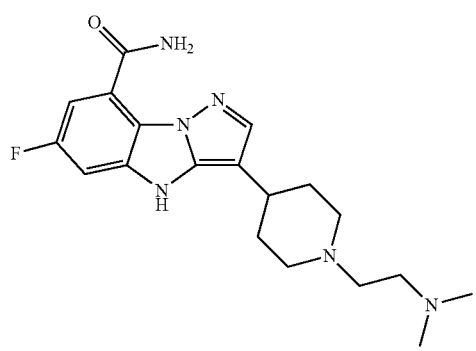 [SMILES: CN(C)CCN1CCC(c2cnn3c2[nH]c2cc(F)cc(C(N)=O)c23)CC1]

This example was prepared as the method described in Example 2. $^1$H NMR (400 MHz, METHANOL-d$_4$) δ ppm 1.83-1.98 (m, 2H), 2.05-2.18 (m, 2H), 2.36-2.48 (m, 2H), 2.68 (s, 6H), 2.80 (t, J=6.46 Hz, 3H), 2.97-3.07 (m, 2H), 3.11-3.25 (m, 2H), 7.25-7.40 (m, 1H), 7.57-7.75 (m, 2H). LCMS (ESI) m/z: 373 (M+1).

Example 15

6-fluoro-3-(1-(2-methoxyethyl)piperidin-4-yl)-4H-benzo[4,5]imidazo[1,2-b]pyrazole-8-carboxamide

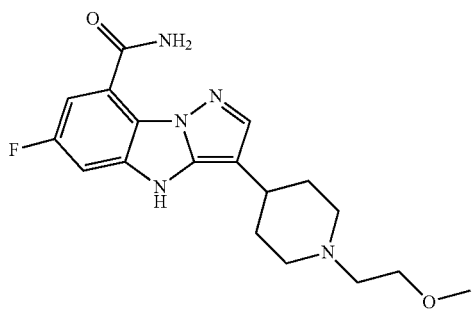 [SMILES: COCCN1CCC(c2cnn3c2[nH]c2cc(F)cc(C(N)=O)c23)CC1]

This example was prepared as the method described in Example 3. $^1$H NMR (400 MHz, METHANOL-d4) ppm 2.00-2.18 (m, 2H), 2.22-2.38 (m, 2H), 2.94-3.08 (m, 1H), 3.08-3.22 (m, 2H), 3.33-3.38 (m, 2H), 3.44 (s, 3H), 3.56-3.70 (m, 2H), 3.71-3.82 (m, 2H), 7.19-7.38 (m, 1H), 7.53-7.64 (m, 1H), 7.68 (s, 1H), 8.42-8.66 (m, 1H). LCMS (ESI) m/z: 360 (M+1).

Example 16

6-fluoro-3-(1-(2-hydroxyethyl)piperidin-4-yl)-4H-benzo[4,5]imidazo[1,2-b]pyrazole-8-carboxamide

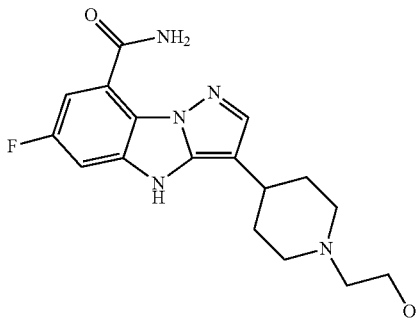

This example was prepared as the method described in Example 3. $^1$H NMR (400 MHz, METHANOL-d$_4$) δ ppm 2.04-2.20 (m, 2H), 2.25-2.37 (m, 2H), 2.98-3.10 (m, 1H), 3.12-3.24 (m, 2H), 3.25-3.31 (m, 2H), 3.62-3.75 (m, 2H), 3.89-3.99 (m, 2H), 7.25-7.38 (m, 1H), 7.57-7.66 (m, 1H), 7.69 (s, 1H), 8.50-8.62 (m, 1H). LCMS (ESI) m/z: 346 (M+1).

Example 17

3-(1-ethylpiperidin-3-yl)-6-fluoro-4H-benzo[4,5]imidazo[1,2-b]pyrazole-8-carboxamide

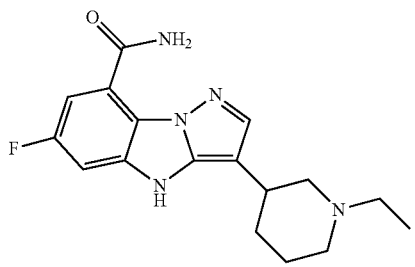 [SMILES: CCN1CCCC(c2cnn3c2[nH]c2cc(F)cc(C(N)=O)c23)C1]

This example was prepared as described in Examples 1 and 2, substituting tert-butyl 3-(hydroxymethyl)piperidine-1-carboxylate for tert-butyl 4-(hydroxymethyl)piperidine-1-carboxylate. $^1$H-NMR (MeOD, 400 MHz) δ: 1.38 (t, 3H), 1.85-2.00 (m, 2H), 2.13-2.26 (m, 2H), 2.94-3.03 (m, 2H), 3.21-3.24 (m, 3H), 3.59-3.73 (m, 2H), 7.37-7.39 (dd, 1H), 7.66-7.69 (dd, 1H), 7.76 (s, 1H), 8.52 (bs, 1H). LCMS (ESI) m/z: 331 (M+1).

Example 18

3-(1-ethylazepan-4-yl)-6-fluoro-4H-benzo[4,5]imidazo[1,2-b]pyrazole-8-carboxamide

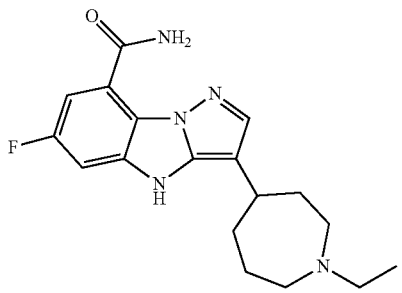 [SMILES: CCN1CCCC(c2cnn3c2[nH]c2cc(F)cc(C(N)=O)c23)CC1]

Example 18A 1-tert-butyl 4-ethyl 5-oxoazepane-1,4-dicarboxylate

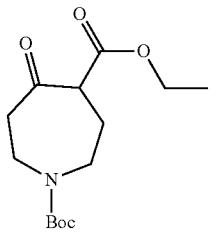 [SMILES: CCOC(=O)C1CCN(C(=O)OC(C)(C)C)CCC1=O]

To a solution of tert-butyl 4-oxopiperidine-1-carboxylate (50 g, 251 mmol) and BF$_3$-Et$_2$O (49.86 g, 351 mmol) in THF (500 ml) was added dropwise ethyl 2-diazo (40.09 g, 351 mmol) at −40° C. under N$_2$ atmosphere. After the dropwise addition was completed, the mixture was stirred at −40° C. for 2 h and then warmed to 15° C. and stirred for 16 h. After the reaction completed, the mixture was quenched with K$_2$CO$_3$ aqueous solution (500 mL). The aqueous layer was extracted with EtOAc (500 mL×2). The combined organic layers were washed with water, and brine, thereafter dried over Na$_2$SO$_4$, filtered and evaporated. The residue was purified by column chromatograph on silica gel to provide the title compound (45 g, yield: 63%). LCMS (ESI) m/z: 286 (M+1).

Example 18B 1-tert-butyl 4-ethyl 5-hydroxyazepane-1,4-dicarboxylate

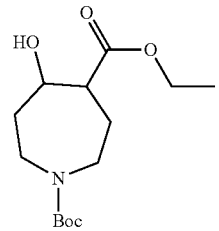

To a solution of EXAMPLE 18A (45 g, 157.7 mmol) in MeOH (420 ml) was added NaBH$_4$ (7.16 g, 189 mmol) in portions at 0° C. After stirring at 0° C. for 1 h, the resultant mixture was quenched with water (400 mL) and the aqueous phase was extracted with EtOAc (400 mL×2). The combined organic layers were washed with water, brine, dried over Na$_2$SO$_4$, filtered and evaporated. The residue was purified by column chromatograph on silica gel to provide the title compound (22.3 g, yield: 49%). LCMS (ESI) m/z: 288 (M+1).

Example 18C 1-tert-butyl 4-ethyl 2,3,6,7-tetrahydro-1H-azepine-1,4-dicarboxylate

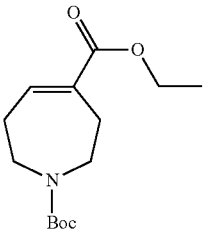 [SMILES: CCOC(=O)C1=CCCN(C(=O)OC(C)(C)C)CC1]

To a solution of EXAMPLE 18B (21 g, 73 mmol), DBU (22 g, 146 mmol) in toluene (200 mL) was added dropwise MsCl (14.56 g, 128 mmol). After the dropwise addition was completed, the mixture was stirred at 110° C. for 2 h, and cooled to room temperature, and then water (200 mL) was added to quench. The aqueous layer was extracted with EtOAc (200 mL×2). The combined organic layers were washed with water, brine, dried over Na$_2$SO$_4$, filtered and evaporated. The residue was purified by column chromatograph on silica gel to provide the title compound (13 g, yield: 66%). LCMS (ESI) m/z: 270 (M+1).

Example 18D 1-tert-butyl 4-methyl azepane-1,4-dicarboxylate

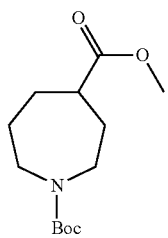 [SMILES: COC(=O)C1CCCN(C(=O)OC(C)(C)C)CC1]

A mixture of EXAMPLE 18C (13 g, 48.27 mmol) and Pd/C (1 g) in MeOH (130 mL) was hydrogenated at 15° C. for 16 h under $H_2$ (1 atm). The mixture was filtered and the filtrate was evaporated to provide the title compound which could be used directly in the next step without further purification (10.7 g, yield: 82%). LCMS (ESI) m/z: 258 (M+1).

Example 18E tert-butyl 4-(hydroxymethyl)azepane-1-carboxylate

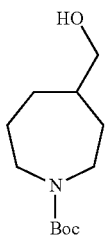

To a solution of EXAMPLE 18D (10.7 g, 39 mmol) in THF (200 mL) was added $LiAlH_4$ (1.48 g, 39 mmol) in portions at 0° C. After stirring at 0° C. for 30 mins, the resultant mixture was quenched with water (10 mL), 15% aq NaOH (10 mL), water (30 mL). The mixture was filtered and the filtrate was evaporated. The residue was purified by column chromatograph on silica gel to provide the title compound (7 g, yield: 77%). LCMS (ESI) m/z: 230 (M+1).

Example 18F 3-(1-ethylazepan-4-yl)-6-fluoro-4H-benzo[4,5]imidazo[1,2-b]pyrazole-8-carboxamide

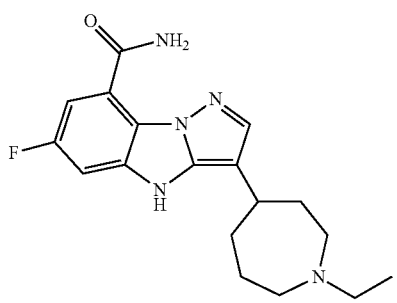 [SMILES: CCN1CCCC(c2cnn3c2[nH]c2cc(F)cc(C(N)=O)c23)CC1]

This example was prepared as described in Examples 1 and 2, substituting tert-butyl 4-(hydroxymethyl)azepane-1-carboxylate for tert-butyl 4-(hydroxymethyl)piperidine-1-carboxylate. $^1$H-NMR (MeOD, 400 MHz) δ: 1.38-1.42 (t, 3H), 1.93-1.96 (m, 2H), 1.99-2.12 (m, 2H), 2.32-2.34 (m, 2H), 3.15-3.30 (m, 1H), 3.32-3.33 (m, 2H), 3.33-3.53 (m, 4H), 7.38-7.40 (dd, 1H), 7.69-7.73 (dd, 1H), 7.74 (s, 1H), 8.50 (bs, 1H). LCMS (ESI) m/z: 344 (M+1).

Example 19

6-fluoro-3-(1-methylazepan-4-yl)-4H-benzo[4,5]imidazo[1,2-b]pyrazole-8-carboxamide

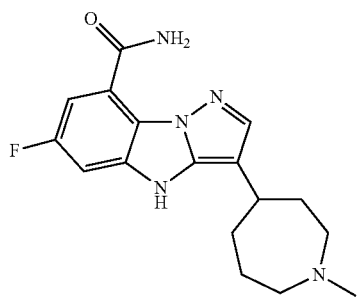 [SMILES: CN1CCCC(c2cnn3c2[nH]c2cc(F)cc(C(N)=O)c23)CC1]

This example was prepared as the method described in Example 18. $^1$H-NMR (MeOD, 400 MHz) δ: 1.95-2.10 (m, 3H), 2.26-2.35 (m, 3H), 2.96 (s, 1H), 3.14-3.17 (m, 1H), 3.36-3.49 (m, 4H), 7.38-7.40 (dd, 1H), 7.69-7.72 (dd, 1H), 7.74 (s, 1H), 8.47 (bs, 1H). LCMS (ESI) m/z: 330 (M+1).

Example 20

6-fluoro-3-(1-methylpyrrolidin-3-yl)-4H-benzo[4,5]imidazo[1,2-b]pyrazole-8-carboxamide

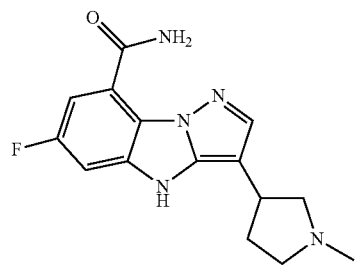 [SMILES: CN1CCC(c2cnn3c2[nH]c2cc(F)cc(C(N)=O)c23)C1]

This example was prepared as described in Examples 1 and 2, substituting tert-butyl 3-(hydroxymethyl)pyrrolidine-1-carboxylate for tert-butyl 4-(hydroxymethyl)piperidine-1-carboxylate. $^1$H-NMR (MeOD, 400 MHz) δ: 2.29-2.35 (m, 1H), 2.59-2.62 (m, 1H), 2.99 (s, 3H), 3.32-3.36 (m, 1H), 3.53-3.55 (m, 2H), 3.76-3.81 (m, 2H), 7.40-7.42 (dd, 1H), 7.70-7.73 (dd, 1H), 7.80 (s, 1H), 8.50 (bs, 1H). LCMS (ESI) m/z: 302 (M+1).

Example 21

3-(1-ethylpyrrolidin-3-yl)-6-fluoro-4H-benzo[4,5]imidazo[1,2-b]pyrazole-8-carboxamide

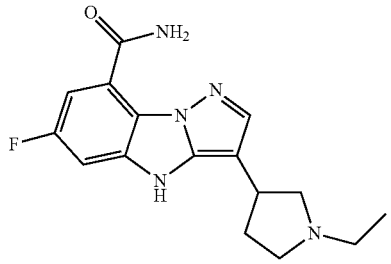 [SMILES: CCN1CCC(c2cnn3c2[nH]c2cc(F)cc(C(N)=O)c23)C1]

This example was prepared as described in Example 20, substituting tert-butyl 3-(hydroxymethyl)pyrrolidine-1-carboxylate for tert-butyl 4-(hydroxymethyl)piperidine-1-carboxylate. $^1$H-NMR (MeOD, 400 MHz) δ: 2.29-2.35 (m, 1H), 2.59-2.62 (m, 1H), 2.99 (s, 3H), 3.32-3.36 (m, 1H), 3.53-3.55 (m, 2H), 3.76-3.81 (m, 2H), 7.40-7.42 (dd, 1H), 7.70-7.73 (dd, 1H), 7.80 (s, 1H), 8.50 (bs, 1H). LCMS (ESI) m/z: 316 (M+1).

Example 22

6-fluoro-3-(1-isopropylpyrrolidin-3-yl)-4H-benzo[4,5]imidazo[1,2-b]pyrazole-8-carboxamide

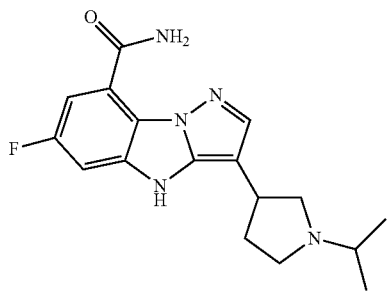 [SMILES: CC(C)N1CCC(c2cnn3c2[nH]c2cc(F)cc(C(N)=O)c23)C1]

This example was prepared as described in Example 20, substituting tert-butyl 3-(hydroxymethyl)pyrrolidine-1-carboxylate for tert-butyl 4-(hydroxymethyl)piperidine-1-carboxylate. $^1$H-NMR (MeOD, 400 MHz) δ: 1.42-1.44 (d, 6H), 2.25-2.31 (m, 1H), 2.57-2.60 (m, 1H), 3.32-3.33 (m, 1H), 3.44-3.55 (m, 3H), 3.68-3.71 (m, 1H), 7.41-7.43 (dd, 1H), 7.71-7.74 (dd, 1H), 7.82 (s, 1H), 8.55 (bs, 1H). LCMS (ESI) m/z: 330 (M+1).

Example 23

6-fluoro-3-(pyrrolidin-2-yl)-4H-benzo[4,5]imidazo[1,2-b]pyrazole-8-carboxamide

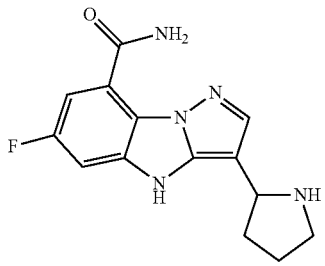

This example was prepared as described in Example 1, substituting tert-butyl 2-(hydroxymethyl)pyrrolidine-1-carboxylate for tert-butyl 4-(hydroxymethyl)piperidine-1-carboxylate. $^1$H-NMR (400 MHz, MethanoL-d$_4$) δ ppm 2.17-2.31 (m, 1H), 2.33-2.51 (m, 2H), 2.52-2.67 (m, 1H), 3.48 (t, J=7.28 Hz, 2H), 7.40 (dd, J=8.03, 2.26 Hz, 1H), 7.65 (dd, J=10.79, 2.26 Hz, 1H), 7.94 (s, 1H), 8.55 (br. s., 1H). LCMS (ESI) m/z: 288 (M+1).

Example 24

6-fluoro-3-(1-propylpyrrolidin-2-yl)-4H-benzo[4,5]imidazo[1,2-b]pyrazole-8-carboxamide

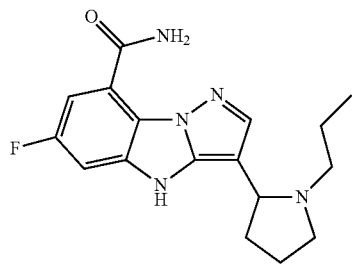 [SMILES: CCCN1CCCC1c1cnn2c1[nH]c1cc(F)cc(C(N)=O)c12]

This example was prepared as described in Example 2, substituting tert-butyl 2-(hydroxymethyl)pyrrolidine-1-carboxylate for tert-butyl 4-(hydroxymethyl)piperidine-1-carboxylate. $^1$H-NMR (400 MHz, MethanoL-d$_4$) δ ppm 0.93 (t, J=7.34 Hz, 3H), 1.54-1.79 (m, 2H), 2.23 (d, J=5.02 Hz, 2H), 2.37-2.53 (m, 2H), 2.76 (br. s., 1H), 3.05 (br. s., 2H), 3.65 (br. s., 1H), 4.31 (br. s., 1H), 7.44 (dd, J=8.09, 2.32 Hz, 1H), 7.73 (dd, J=10.92, 2.38 Hz, 1H), 7.94 (s, 1H), 8.54 (br. s., 1H). LCMS (ESI) m/z: 330 (M+1).

Example 25

6-fluoro-3-(1-methylpyrrolidin-2-yl)-4H-benzo[4,5]imidazo[1,2-b]pyrazole-8-carboxamide

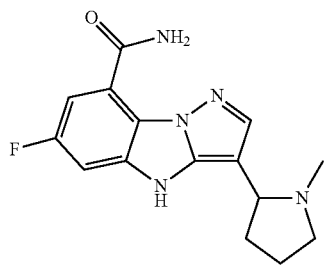 [SMILES: CN1CCCC1c1cnn2c1[nH]c1cc(F)cc(C(N)=O)c12]

This example was prepared as described in Example 2, substituting tert-butyl 2-(hydroxymethyl)pyrrolidine-1-carboxylate for tert-butyl 4-(hydroxymethyl)piperidine-1-carboxylate. $^1$H-NMR (400 MHz, MethanoL-d$_4$) δ ppm 2.25-2.41 (m, 2H), 2.47-2.67 (m, 2H), 2.82 (s, 3H), 3.23-3.30 (m, 1H), 3.66-3.79 (m, 1H), 4.50-4.58 (m, 1H), 7.43 (dd, J=8.16, 2.51 Hz, 1H), 7.64 (dd, J=10.73, 2.57 Hz, 1H), 7.95-8.02 (m, 1H), 8.52 (br. s., 1H). LCMS (ESI) m/z: 302 (M+1).

Example 26

3-(1-ethylpyrrolidin-2-yl)-6-fluoro-4H-benzo[4,5]imidazo[1,2-b]pyrazole-8-carboxamide

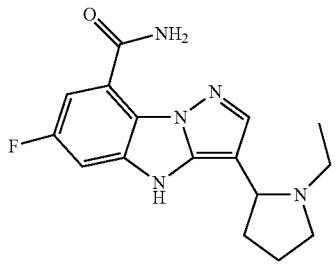 [SMILES: CCN1CCCC1c1cnn2c1[nH]c1cc(F)cc(C(N)=O)c12]

This example was prepared as described in Example 2, substituting tert-butyl 2-(hydroxymethyl)pyrrolidine-1-carboxylate for tert-butyl 4-(hydroxymethyl)piperidine-1-carboxylate. $^1$H-NMR (400 MHz, MethanoL-$d_4$) δ ppm 1.30 (t, J=7.28 Hz, 3H), 2.26-2.37 (m, 2H), 2.46-2.61 (m, 2H), 2.98-3.09 (m, 1H), 3.25 (d, J=10.29 Hz, 2H), 3.68-3.80 (m, 1H), 4.55 (t, J=8.78 Hz, 1H), 7.42 (dd, J=8.16, 2.26 Hz, 1H), 7.64 (dd, J=10.73, 2.32 Hz, 1H), 7.97 (s, 1H), 8.54 (br. s., 1H). LCMS (ESI) m/z: 316 (M+1).

Example 27

3-(1-ethylpiperidin-4-yl)-4H-benzo[4,5]imidazo[1,2-b]pyrazole-8-carboxamide

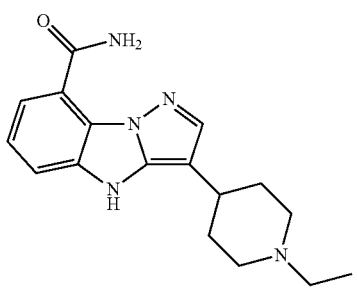 [SMILES: CCN1CCC(c2cnn3c2[nH]c2cccc(C(N)=O)c23)CC1]

This example was prepared as described in Example 1, substituting (2,6-dibromophenyl)hydrazine for (2,6-dibromo-4-fluorophenyl)hydrazine. $^1$H-NMR (400 MHz, METHANOL-d4) δ ppm 1.16-1.20 (t, 3H), 1.84-1.87 (m, 2H), 2.07-2.11 (d, 2H), 2.16-2.19 (d, 2H), 2.51-2.56 (q, 2H), 2.70-2.75 (m, 1H), 3.11-3.13 (d, 2H), 7.40-7.44 (t, 1H), 7.61-7.63 (m, 1H), 7.70 (s, 1H), 7.99-8.02 (m, 1H). LCMS (ESI) m/z: 312 (M+1).

Example 28

6-fluoro-3-(3-methyl-3-azabicyclo[3.1.0]hexan-1-yl)-4H-benzo[4,5]imidazo[1,2-b]pyrazole-8-carboxamide

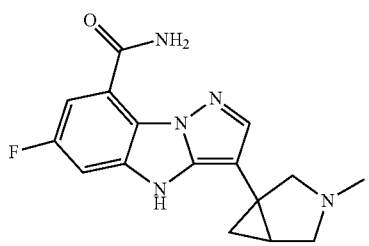 [SMILES: CN1CC2CC2(c2cnn3c2[nH]c2cc(F)cc(C(N)=O)c23)C1]

Example 28A ethyl 1-benzyl-2,5-dihydro-1H-pyrrole-3-carboxylate

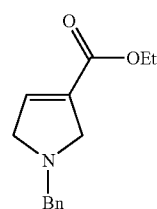

To a solution of N-benzyl-1-methoxy-N-((trimethylsilyl)methyl)methanamine (4.5 g, 61 mmol) and ethyl propiolate (5.0 g, 51 mmol) in DCM (150 mL) was added dropwise Et$_3$N (0.4 mL, 5.2 mmol) at 0° C. After the dropwise addition was completed, the reaction mixture was stirred at 0° C. for 1 h and warmed to 20° C. and stirred for 24 h, and then quenched with saturated NaHCO$_3$ (100 mL).

The aqueous phase was extracted with DCM (250 mL×2). The combined organic layers were washed with brine (150 mL×2) and dried over Na$_2$SO$_4$, filtered and evaporated. The residue was purified by column chromatograph to provide the title compound (10 g, yield: 80%) as a yellow oil. LCMS (ESI) m/z: 232 (M+1).

Example 28B ethyl 3-benzyl-3-azabicyclo[3.1.0]hexane-1-carboxylate

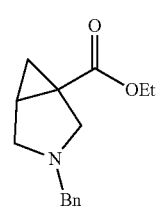 [SMILES: CCOC(=O)C12CC1CN(Cc1ccccc1)C2]

To a mixture of (CH$_3$)$_3$SOI (21.5 g, 97.7 mmol) in DMSO (150 mL) was added portion wise 60% NaH (3.5 g, 87.5 mmol) at 0° C.-5° C. under N$_2$ atmosphere. After the addition was completed, the mixture was stirred at 19° C. for 2 h, and thereafter a solution of EXAMPLE 28A (9 g, 38.9 mmol) was added thereto portionwise at 0° C.-5° C. The mixed reaction solution was stirred at 19° C. for 15 h, and then quenched with saturated NaHCO$_3$ (300 mL). The aqueous phase was extracted with DCM (500 mL×2). The combined organic layers were washed with brine (200 mL×2) and dried over Na$_2$SO$_4$, filtered and evaporated. The residue was purified by column chromatograph to provide the title compound (5.4 g, yield: 32%) as a yellow oil. LCMS (ESI) m/z: 246 (M+1).

Example 28C 3-tert-butyl 1-ethyl
3-azabicyclo[3.1.0]hexane-1,3-dicarboxylate

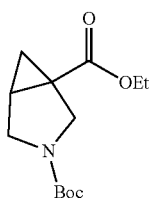 [SMILES: CCOC(=O)C12CC1CN(C(=O)OC(C)(C)C)C2]

A mixture of EXAMPLE 28B (5.4 g, 22 mmol), BOC₂O (10 g, 46 mmol) and 10% Pd/C (600 mg) in MeOH (100 mL) was hydrogenated at 19° C. for 15 h under H₂ (1 atm). The mixture was filtered and the filtrate was evaporated. The residue was purified by column chromatograph to provide the title compound (5.3 g, yield: 94%) as a colorless oil. $^1$H-NMR (400 MHz, CDCl₃) δ ppm 0.83 (t, J=4.96 Hz, 1H), 1.25 (t, J=7.15 Hz, 3H), 1.39-1.48 (m, 9H), 1.56 (dd, J=8.34, 4.58 Hz, 1H), 1.79 (s, 1H), 1.94-2.10 (m, 1H), 3.41 (dd, J=10.73, 3.45 Hz, 1H), 3.50-3.82 (m, 3H), 4.07-4.19 (m, 2H), 4.25 (d, J=7.15 Hz, 1H), 5.05 (s, 1H), 6.61 (t, J=1.88 Hz, 1H), 7.14 (s, 1H), 7.28-7.38 (m, 1H)

Example 28D tert-butyl 1-(hydroxymethyl)-3-azabicyclo[3.1.0]
hexane-3-carboxylate

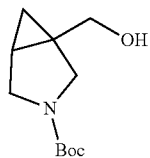 [SMILES: CC(C)(C)OC(=O)N1CC2CC2(CC#N)C1]

A mixture of EXAMPLE 28C (5.3 g, 20.7 mmol) and 1N LiOH (50 mL, 50 mmol) in THF (25 mL) and MeOH (50 mL) was stirred at 60° C. for 2 hours. The mixture was cooled to room temperature and thereafter extracted with EtOAc (100 mL×2). The combined organic layers were washed with water (50 mL×2), brine (50 mL×2), dried over Na₂SO₄ and evaporated to give the residue. The residue was dissolved in THF (100 mL), and thereto was added dropwise 10M BH₃-DMS (10 mL, 100 mmol) at 0° C. under N₂ atmosphere. After the dropwise addition was completed, the mixture was stirred at 19° C. for 15 h, and after completion of the reaction quenched with MeOH (100 mL). The solution was evaporated under vacuum. The residue was purified by column chromatograph to provide the title compound (3.5 g, yield: 89%) as a colorless oil. $^1$H-NMR (400 MHz, CDCl₃) δ ppm 0.51 (br. s., 1H, 0.78 (dd, J=8.09, 5.08 Hz, 1H), 1.37-1.47 (m, 10H), 3.42 (d, J=10.29 Hz, 2H, 3.48-3.78 (m, 4H).

Example 28E tert-butyl 1-(chloromethyl)-3-azabicyclo[3.1.0]
hexane-3-carboxylate

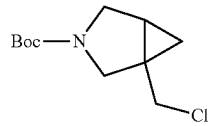

To a mixture of EXAMPLE 28D (3.5 g, 16.43 mmol), DMAP (200 g, 1.6 mmol) and Et₃N (5 mL, 36.14 mmol) in DCM (100 mL) was added portionwise TosCl (3.7 g, 19.47 mmol) at 0° C. After being stirred at 24° C. for 15 h, the mixture was quenched with water (100 mL). The aqueous layer was extracted with DCM (250 mL×2). The combined organic layers were washed with brine, dried over Na₂SO₄, filtered and evaporated. The residue was purified by column chromatograph to provide the title compound (2.6 g, yield: 68%), as a colorless oil. $^1$H-NMR (400 MHz, CDCl₃) δ ppm 0.68 (t, J=4.64 Hz, 1H), 0.90 (dd, J=8.16, 5.27 Hz, 1H), 1.39-1.55 (m, 10H), 3.36-3.46 (m, 2H), 3.48-3.77 (m, 4H).

Example 28F tert-butyl 1-(cyanomethyl)-3-azabicyclo[3.1.0]
hexane-3-carboxylate

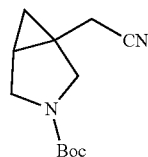

A mixture of EXAMPLE 28E (2.6 g, 11 mmol), NaCN (1.57 g, 32 mmol) and KI (1.87 g, 11 mmol) in DMSO (40 mL) was stirred at 100-120° C. for 2 h. After being cooled to room temperature, the mixture was partitioned between EtOAc (200 mL) and Na₂CO₃ aqueous solution (120 mL). The aqueous layer was extracted with EtOAc (100 mL×2). The combined organic layers were washed with brine, dried over Na₂SO₄, filtered and evaporated. The residue was purified by column chromatograph to provide the title compound (2.4 g, yield: 96%) as a colorless oil. $^1$H-NMR (400 MHz, CDCl₃) δ ppm 0.47-0.72 (m, 1H), 0.81-0.96 (m, 1H), 1.34-1.55 (m, 10H), 2.53-2.80 (m, 2H), 3.30 (d, J=10.54 Hz, 1H), 3.38-3.84 (m, 1H). LCMS (ESI) m/z: 167 (M−55).

Example 28G tert-butyl 1-(1-cyano-2-(dimethylamino)vinyl)-3-
azabicyclo[3.1.0]hexane-3-carboxylate

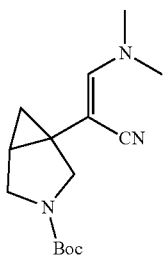 [SMILES: CN(C)/C=C(\C#N)C12CC1CN(C(=O)OC(C)(C)C)C2]

A mixture of 1-tert-butoxy-N,N,N',N'-tetramethylmethanediamine (3.8 g, 21.8 mmol) and EXAMPLE 28F (2.4 g, 10.8 mmol) in DMF (20 mL) was stirred at 70° C. for about 10 h. After being cooled to room temperature, the resultant mixture was evaporated off solvent under vacuum to provide the title compound which could be used directly in the next step without further purification.

Example 28H tert-butyl 1-(1-cyano-2-hydroxyvinyl)-3-azabicyclo[3.1.0]hexane-3-carboxylate

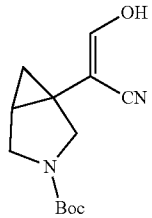 [SMILES: CC(C)(C)OC(=O)N1CC2CC2(/C(C#N)=C/O)C1]

A solution of EXAMPLE 28G (3.0 g, crude, 10.8 mmol) in a mixture of THF/HOAc/Water (1/1/1) (45 mL) was stirred at 24° C. for 5 h. After removal of solution in vacuum, the residue was partitioned between saturated NaHCO₃ (100 mL) and EtOAc (100 mL). The aqueous phase was extracted with EtOAc (100 mL×2). The combined organic layers were washed with water (100 mL×2), brine (100 mL×2), dried over Na₂SO₄, filtered and evaporated. The residue was purified by column chromatography to provide the title compound (1.4 g, yield: 52%) as a yellow oil. LCMS (ESI) m/z: 195 (M−55).

Example 28I 3-(3-azabicyclo[3.1.0]hexan-1-yl)-6-fluoro-4H-benzo[4,5]imidazo[1,2-b]pyrazole-8-carboxamide

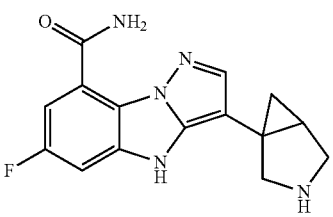 [SMILES: NC(=O)c1cc(F)cc2[nH]c3c(C45CNCC4C5)cnn3c12]

This example was prepared as described in EXAMPLES 1E-1J.

Example 28J 6-fluoro-3-(3-methyl-3-azabicyclo[3.1.0]hexan-1-yl)-4H-benzo[4,5]imidazo[1,2-b]pyrazole-8-carboxamide

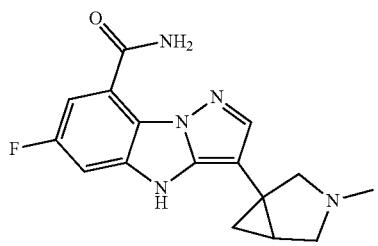 [SMILES: CN1CC2CC2(c2cnn3c2[nH]c2cc(F)cc(C(N)=O)c23)C1]

This example was prepared as the method described in Example 2. ¹H-NMR (400 MHz, MethanoL-d₄) δ ppm 1.32 (d, J=6.40 Hz, 2H), 2.05 (td, J=6.37, 3.95 Hz, 1H), 2.93 (s, 3H), 3.47 (d, J=11.04 Hz, 1H), 3.59 (dd, J=11.11, 3.83 Hz, 1H), 3.67-3.76 (m, 1H), 3.85 (d, J=11.04 Hz, 1H), 7.32 (dd, J=8.16, 2.51 Hz, 1H), 7.58 (dd, J=10.79, 2.51 Hz, 1H), 7.77 (s, 1H), 8.52 (s, 1H). LCMS (ESI) m/z: 314 (M+1).

Example 29

3-(3-ethyl-3-azabicyclo[3.1.0]hexan-1-yl)-6-fluoro-4H-benzo[4,5]imidazo[1,2-b]pyrazole-8-carboxamide

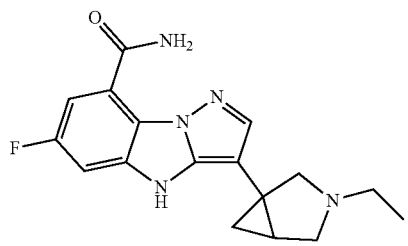 [SMILES: CCN1CC2CC2(c2cnn3c2[nH]c2cc(F)cc(C(N)=O)c23)C1]

This example was prepared as the method described in Example 28. ¹H-NMR (400 MHz, MethanoL-d₄) δ ppm 1.27-1.37 (m, 5H), 1.95-2.11 (m, 1H), 3.22 (q, J=7.19 Hz, 2H), 3.41 (d, J=10.92 Hz, 1H), 3.48-3.57 (m, 1H), 3.69 (s, 1H), 3.86 (d, J=10.92 Hz, 1H), 7.33 (dd, J=8.16, 2.51 Hz, 1H), 7.64 (dd, J=10.85, 2.57 Hz, 1H), 7.79 (s, 1H), 8.51 (s, 1H). LCMS (ESI) m/z: 328 (M+1).

Example 30

3-(3-cyclobutyl-3-azabicyclo[3.1.0]hexan-1-yl)-6-fluoro-4H-benzo[4,5]imidazo[1,2-b]pyrazole-8-carboxamide

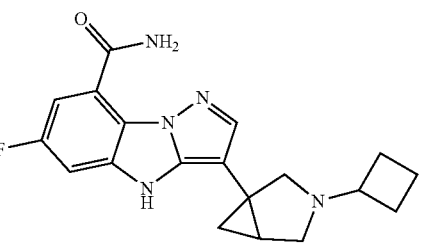

This example was prepared as the method described in Example 28. ¹H-NMR (400 MHz, DMSO-d₆+D₂O) 0.77 (dd, J=7.91, 4.14 Hz, 1H), 1.22 (t, J=4.14 Hz, 1H), 1.51-1.68 (m, 3H), 1.77-1.96 (m, 4H), 2.47 (br. s., 2H), 2.88 (d, J=8.78 Hz, 1H), 2.98-3.13 (m, 2H), 7.44 (dd, J=8.41, 2.51 Hz, 1H), 7.52 (dd, J=10.98, 2.57 Hz, 1H), 7.71 (s, 1H). LCMS (ESI) m/z: 354 (M+1).

Example 31

3-(3-(cyclopropylmethyl)-3-azabicyclo[3.1.0]hexan-1-yl)-6-fluoro-4H-benzo[4,5]imidazo[1,2-b]pyrazole-8-carboxamide

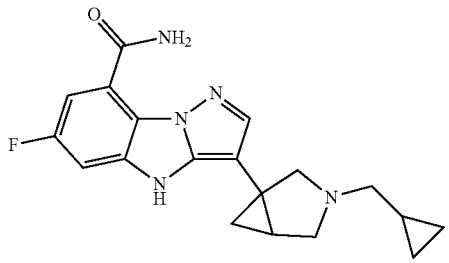 [SMILES: NC(=O)c1cc(F)cc2[nH]c3c(C45CC4CN(CC4CC4)C5)cnn3c12]

This example was prepared as the method described in Example 28. ¹H NMR (400 MHz, METHANOL-d4) ⍰ ppm 0.32-0.35 (m, 2H), 0.65-0.68 (m, 2H), 1.06 (m, 1H), 1.16-1.19 (m, 1H), 1.39-1.42 (t, 1H), 1.92-1.94 (m, 1H), 2.84-2.85 (d, 2H), 3.18-3.21 (m, 1H), 3.56-3.59 (d, 2H), 3.73-3.75 (d, 2H), 7.35-7.39 (dd, 1H), 7.68-7.71 (dd, 1H), 7.78 (s, 1H), 8.55 (s, 1H). LCMS (ESI) m/z: 354 (M+1).

Example 32

6-fluoro-3-(3-isopropyl-3-azabicyclo[3.1.0]hexan-1-yl)-4H-benzo[4,5]imidazo[1,2-b]pyrazole-8-carboxamide

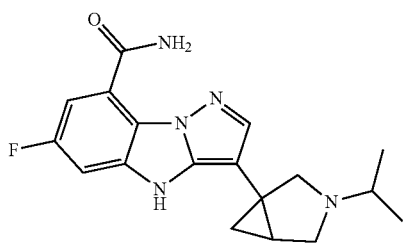 [SMILES: CC(C)N1CC2CC2(c2cnn3c2[nH]c2cc(F)cc(C(N)=O)c23)C1]

This example was prepared as the method described in Example 28. ¹H-NMR (400 MHz, MethanoL-d₄) 1.25-1.43 (m, 8H), 2.00-2.15 (m, 1H), 3.39 (s, 1H), 3.49 (d, J=11.04 Hz, 1H), 3.62 (d, J=3.89 Hz, 1H), 3.71 (s, 1H), 3.90 (d, J=10.92 Hz, 1H), 7.29-7.40 (m, 1H), 7.64 (dd, J=10.85, 2.57 Hz, 1H), 7.79 (s, 1H), 8.52 (br. s., 1H). LCMS (ESI) m/z: 342 (M+1).

Example 33

3-(3-azabicyclo[3.1.0]hexan-6-yl)-6-fluoro-4H-benzo[4,5]imidazo[1,2-b]pyrazole-8-carboxamide

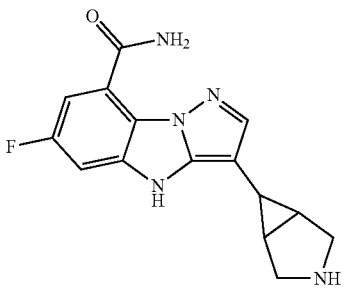 [SMILES: NC(=O)c1cc(F)cc2[nH]c3c(C4C5CNCC54)cnn3c12]

Example 33A ethyl 5-benzyl-4,6-dioxo-1,3a,4,5,6,6a-hexahydro-pyrrolo[3,4-c]pyrazole-3-carboxylate

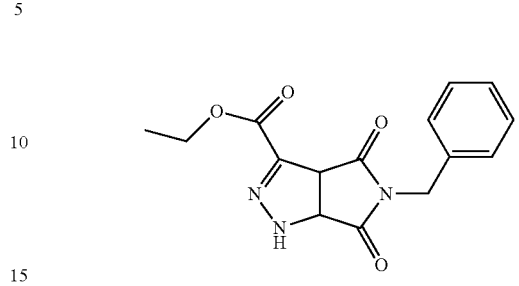

A mixture of 1-benzyl-1H-pyrrole-2,5-dione (5.0 g, 26.7 mmol) and 2-propionyldiazenecarbaldehyde (2.9 ml, 28.0 mmol) in toluene (30 mL) was stirred at 30° C. for 5 h. After removal of solution in vacuum, the residue was purified by silica gel chromatography to provide the title compound (7.67 g, yield 95.4%). LCMS (ESI) m/z: 302 (M+1).

Example 33B ethyl 3-benzyl-2,4-dioxo-3-azabicyclo[3.1.0]hexane-6-carboxylate

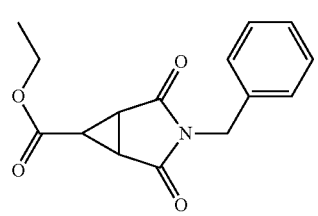 [SMILES: CCOC(=O)C1C2C(=O)N(Cc3ccccc3)C(=O)C12]

EXAMPLE 33A (7.67 g, 25.5 mmol) was heated to 190° C. for 1 hour. The residue was purified by chromatography to provide the title compound (5.353 g, 76.9%) as white solid. LCMS (ESI) m/z: 274 (M+1).

Example 33C (3-benzyl-3-azabicyclo[3.1.0]hexan-6-yl)methanol

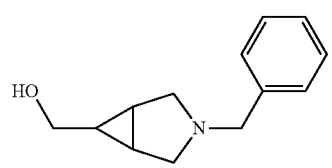 [SMILES: OCC1C2CN(Cc3ccccc3)CC12]

To a suspension of LiAlH₄ (3.055 g, 80.4 mmol) in THF (50 mL) was added dropwise a solution of EXAMPLE 33B (5.353 g, 19.6 mmol) in 30 ml of THF at 0° C. under N₂ atmosphere. After refluxing for 16 h, the reaction mixture was quenched with saturated Na₂SO₄ aqueous solution (5 mL). The organic layer was dried over Na₂SO₄, filtrated and evaporated to give the residue which was purified by chromatography to provide the title compound (1.42 g, 35.8%). LCMS (ESI) m/z: 204 (M+1).

Example 33D tert-butyl 6-(hydroxymethyl)-3-azabicyclo[3.1.0]hexane-3-carboxylate

A mixture of EXAMPLE 33C (1.42 g, 7.0 mmol), Boc$_2$O (1.81 g, 8.4 mmol) and 10% Pd/C (200 mg) in methanol (80 mL) was hydrogenated at 25° C. for 16 h under H$_2$ (1 atm). The mixture was filtered and the filtrate was evaporated to give the residue which was purified by chromatography to provide the title compound 4 (1.14 g, 76%). LCMS (ESI) m/z: 214 (M+1).

Example 33E 3-(3-azabicyclo[3.1.0]hexan-6-yl)-6-fluoro-4H-benzo[4,5]imidazo[1,2-b]pyrazole-8-carboxamide

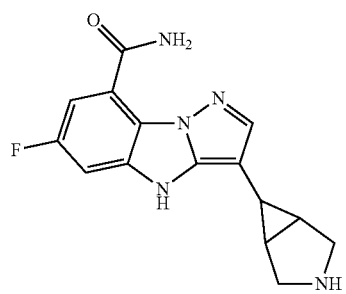 [SMILES: NC(=O)c1cc(F)cc2[nH]c3c(C4C5CNCC54)cnn3c12]

This example was prepared as described in Examples 1E-1J. $^1$H NMR (400 MHz, METHANOL-d4) ppm 1.86-1.95 (m, 1H), 2.12-2.22 (m, 2H), 3.49-3.65 (m, 4H), 7.34-7.42 (m, 1H), 7.64-7.74 (m, 2H), 8.42-8.61 (m, 1H). LCMS (ESI) m/z: 300 (M+1).

Example 34

3-(3-ethyl-3-azabicyclo[3.1.0]hexan-6-yl)-6-fluoro-4H-benzo[4,5]imidazo[1,2-b]pyrazole-8-carboxamide

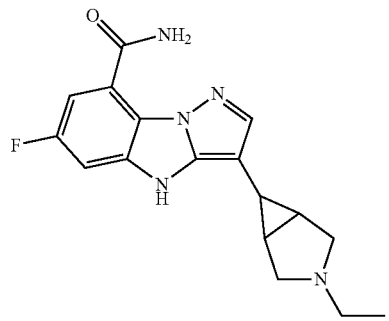 [SMILES: CCN1CC2C(C1)C2c1cnn2c1[nH]c1cc(F)cc(C(N)=O)c12]

This example was prepared as the method described in Example 28. $^1$H NMR (400 MHz, METHANOL-d$_4$) ppm 1.26 (s, 3H), 1.95-2.02 (m, 2H), 2.11-2.18 (m, 1H), 2.85-2.95 (m, 2H), 2.96-3.08 (m, 2H), 3.42-3.58 (m, 2H), 7.30-7.38 (m, 1H), 7.60-7.65 (m, 1H), 7.65-7.70 (m, 1H). LCMS (ESI) m/z: 328 (M+1).

Example 35

3-(8-ethyl-8-azabicyclo[3.2.1]octan-3-yl)-6-fluoro-4H-benzo[4,5]imidazo[1,2-b]pyrazole-8-carboxamide

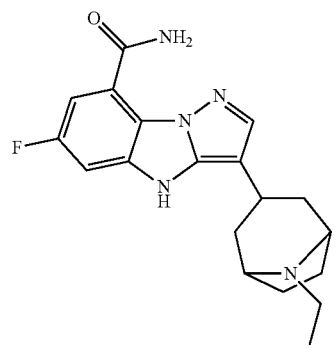 [SMILES: CCN1C2CCC1CC(c1cnn3c1[nH]c1cc(F)cc(C(N)=O)c13)C2]

Example 35A tert-butyl-3-cyano-8-azabicyclo[3.2.1]octane-8-carboxylate

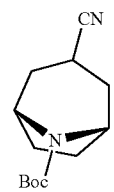

To a mixture of tert-butyl 3-oxo-8-azabicyclo[3.2.1]octane-8-carboxylate (10 g, 44.389 mmol) in DME (300 mL) and EtOH (6.7 mL) was added portionwise t-BuOK (20 g, 177.557 mmol) and TOSMIC (17.33 g, 88.778 mmol) at 0° C. under N$_2$ atmosphere. After being stirred at 60° C. for 16 h, the resultant mixture was quenched with water (100 mL). The aqueous layer was extracted with EtOAc (100 mL×2). The combined organic layers were washed with water, brine, dried over Na$_2$SO$_4$, filtered and evaporated. The residue was purified by column chromatograph to provide the title compound (6.08 g, yield: 57.96%) as a white solid. LCMS (ESI) m/z: 327 (M+1).

Example 35B 8-(tert-butoxycarbonyl)-8-azabicyclo[3.2.1]octane-3-carboxylic acid

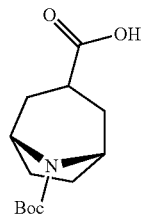 [SMILES: CC(C)(C)OC(=O)N1[C@@H]2CC[C@H]1CC(C(=O)O)C2]

A solution of EXAMPLE 35A (6.58 g, 27.845 mmol) and KOH (9.36 g, 167.069 mmol) in a mixture of EtOH/H$_2$O (1:1, 200 mL) was stirred at 80° C. for 4 h. The resultant mixture was diluted with water (100 mL) and the aqueous phase was adjusted to pH 3-4 with 2 N HCl, and thereafter extracted with EtOAc (100 mL×2). The combined organic layers were washed with water, brine, dried over Na$_2$SO$_4$, filtered and evaporated to provide the title compound as a white solid which was used directly in the next step without further purification (6.01 g, yield: 84.53%).

Example 35C tert-butyl 3-(hydroxymethyl)-8-azabicyclo[3.2.1]octane-8-carboxylate

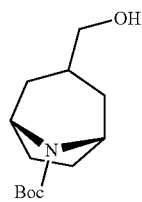 [SMILES: CC(C)(C)OC(=O)N1[C@@H]2CC[C@H]1CC(CO)C2]

To a solution of EXAMPLE 35B (6 g, 23.529 mmol) in THF (60 mL) was added BH$_3$-DMS at 0° C. under N$_2$ atmosphere. After the mixture was stirred at 25° C. for 16 h, MeOH (100 mL) was added to quench. The resultant mixture was evaporated, and the residue was purified by column chromatograph to provide the title compound (5.2 g, yield: 92.69%). LCMS (ESI) m/z: 242 (M+1).

Example 35D 3-(8-ethyl-8-azabicyclo[3.2.1]octan-3-yl)-6-fluoro-4H-benzo[4,5]imidazo[1,2-b]pyrazole-8-carboxamide

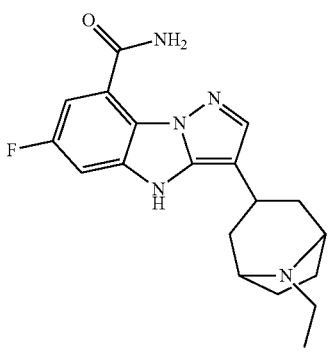 [SMILES: CCN1C2CCC1CC(c1cnn3c1[nH]c1cc(F)cc(C(N)=O)c13)C2]

This example was prepared as described in Examples 1E-1J and 2. $^1$H-NMR (MeOD, 400 MHz) δ: 1.42-1.45 (t, 3H), 2.18-2.36 (m, 8H), 3.16-3.18 (m, 2H), 3.36-3.42 (m, 1H), 4.13 (s, 2H), 7.36-7.37 (dd, 1H), 7.61-7.66 (dd, 1H), 7.68 (s, 1H), 8.62 (bs, 1H). LCMS (ESI) m/z: 356 (M+1).

Example 36

6-fluoro-3-(4-hydroxypyrrolidin-2-yl)-4H-benzo[4,5]imidazo[1,2-b]pyrazole-8-carboxamide

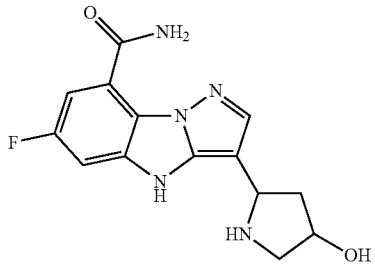 [SMILES: NC(=O)c1cc(F)cc2[nH]c3c(C4CC(O)CN4)cnn3c12]

Example 36A 1-(tert-butyl) 2-methyl 4-((tert-butyldiphenylsilyl)oxy)pyrrolidine-1,2-dicarboxylate

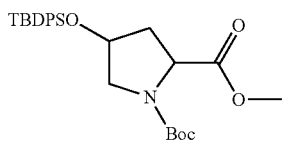

To a mixture of 1-tert-butyl 2-methyl 4-hydroxypyrrolidine-1,2-dicarboxylate (2 g, 8.13 mmol), imidazole (1.1 g, 16.26 mmol) in anhydrous DCM (50 mL) was added portionwise TBDPSCl (2.68 g, 9.76 mmol) at 0° C. under N$_2$ atmosphere. After being stirred at 15° C. for 4 hours, the reaction mixture was washed with water (10 mL×2) and dried over Na$_2$SO$_4$, filtered and evaporated to provide the title compound (3.9 g, yield: 99%) as a colorless oil which could be used directly in the next step without further purification.

Example 36B 1-(tert-butoxycarbonyl)-4-((tert-butyldiphenylsilyl)oxy)pyrrolidine-2-carboxylic acid

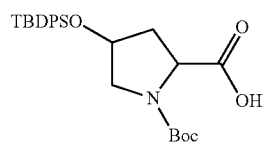

A mixture of EXAMPLE 36A (3.9 g, 8.1 mmol) and LiOH (1 g, 24.2 mmol) in a mixed solution of H$_2$O (20 mL), MeOH (5 mL) and THF (20 mL) was stirred at 15° C. for 16 h. The mixture was diluted with water (50 mL) and adjusted to pH 4-5 with 1 N HCl, and the aqueous layer was extracted with EtOAc (50 mL×3). The combined organic layers were washed with brine, dried over Na$_2$SO$_4$, filtered and evaporated to provide the title compound (3.7 g, yield: 97%) which was used directly in the next step without further purification.

Example 36C tert-butyl 4-((tert-butyldiphenylsilyl)oxy)-2-(hydroxymethyl)pyrrolidine-1-carboxylate

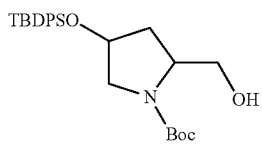

To a mixture of EXAMPLE 36B (3.7 g, 7.89 mmol), Et$_3$N (2.2 g, 15.8 mmol) in THF (100 mL) was added isopropyl carbonochloridate (1.2 g, 9.5 mmol) at 0° C. under N$_2$ atmosphere. After being stirred at 15° C. for 4 h, the mixture was cooled to 0° C. and NaBH$_4$ (1.2 g, 31.56 mmol) was added thereto. The reaction mixture was stirred at 15° C. for 64 hours. After removal of solution in vacuum, the residue was partitioned between water (50 mL) and DCM (50 mL). The aqueous layer was extracted with DCM (50 mL×2). The combined organic layers were washed with brine, dried over Na$_2$SO$_4$, filtered and evaporated. The residue was purified by column chromatograph to provide the title compound (3.5 g, yield: 100%). LCMS (ESI) m/z: 456 (M+1).

Example 36D tert-butyl 4-((tert-butyldiphenylsilyl)oxy)-2-(8-carbamoyl-6-fluoro-4H-benzo[4,5]imidazo[1,2-b]pyrazol-3-yl) pyrrolidine-1-carboxylate

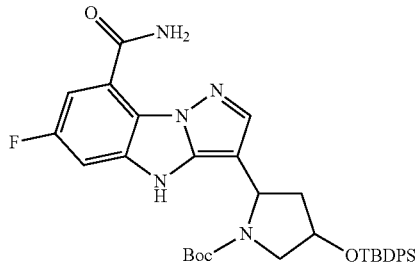

This example was prepared as described in Examples 1E-1J. LCMS (ESI) m/z: 642 (M+1).

Example 36E 6-fluoro-3-(4-hydroxypyrrolidin-2-yl)-4H-benzo[4,5]imidazo[1,2-b]pyrazole-8-carboxamide

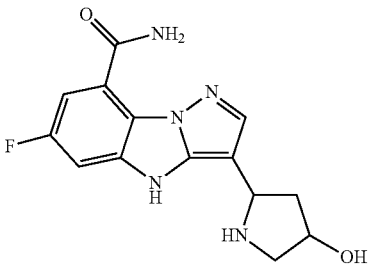

A mixture of EXAMPLE 36D (50 g, 0.078 mmol) in HBr/HOAc (0.5 mL) was stirred at 15° C. for 6 hours. The resultant mixture was evaporated, and the residue was purified by prep-HPLC to provide the title compound (10 g, yield: 43%). $^1$H NMR (400 MHz, DMSO-d$_6$)=8.36 (br. s., 1H), 8.06-7.86 (m, 1H), 7.53 (d, J=9.9 Hz, 2H), 4.91 (dd, J=6.1, 11.5 Hz, 1H), 4.56 (br. s., 1H), 3.45 (d, J=8.8 Hz, 1H), 3.06 (d, J=12.7 Hz, 1H), 2.48-2.41 (m, 1H), 2.21 (dd, J=5.8, 13.0 Hz, 1H). LCMS (ESI) m/z: 304 (M+1).

Example 37

3-cyano-6-fluoro-4H-benzo[4,5]imidazo[1,2-b]pyrazole-8-carboxamide

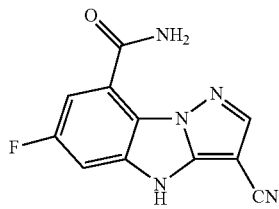 [SMILES: N#Cc1cnn2c1[nH]c1cc(F)cc(C(N)=O)c12]

Example 37A 5-amino-1-(2,6-dibromo-4-fluorophenyl)-1H-pyrazole-4-carbonitrile

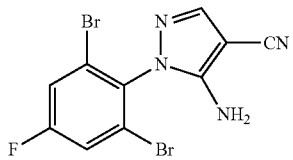 [SMILES: N#Cc1cnn(-c2c(Br)cc(F)cc2Br)c1N]

A mixture of EXAMPLE 1D (4 g, 14 mmol) and 2-(ethoxymethylene)malononitrile (2.24 g, 18.31 mmol) in EtOH (30 mL) was stirred at 80° C. for 1.5 h. The mixture was evaporated under vacuum to provide the title compound (2.8 g, 56%) which could be used directly in the next step without further purification.

Example 37B 8-bromo-6-fluoro-4H-benzo[4,5]imidazo[1,2-b]pyrazole-3-carbonitrile

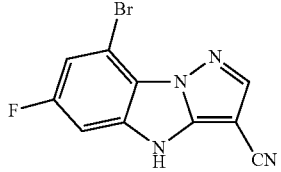 [SMILES: N#Cc1cnn2c1[nH]c1cc(F)cc(Br)c12]

A mixture of EXAMPLE 37A (2.8 g, 7.78 mmol), $N^1,N^2$-dimethylethane-1,2-diamine (68 g, 0.777 mmol), CuI (148 g, 0.777 mmol) and $K_3PO_4$ (1.65 g, 7.78 mmol) in DMF (30 mL) was stirred at 60° C. for 24 h under $N_2$ atmosphere. The mixture was cooled to room temperature and filtered and the filtrate was evaporated to give the residue which was washed with MeOH and water and then dried under vacuum to provide the title compound (1.7 g, 78%) which was used directly in the next step without further purification.

Example 37C methyl 3-cyano-6-fluoro-4H-benzo[4,5]imidazo[1,2-b]pyrazole-8-carboxylate

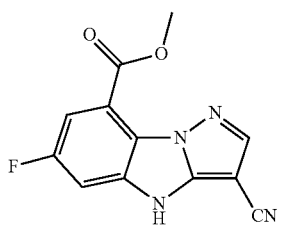 [SMILES: COC(=O)c1cc(F)cc2[nH]c3c(C#N)cnn3c12]

A solution of EXAMPLE 37B (1 g, 3.58 mmol), Pd(OAc)$_2$ (161 g, 0.72 mmol), Pd(dppf)C$_2$ (526 g, 0.72 mmol), Xantphos (420 g, 0.72 mmol), DPPP (296 g, 0.72 mmol), PPh$_3$ (188 g, 0.72 mmol) and Et$_3$N (1.8 g, 18 mmol) in DMF (30 mL) and MeOH (10 mL) was stirred at 120° C. for 12 h under CO atmosphere (3 MPa). After being cooled to room temperature, the mixture was filtered and the filtrate was evaporated to give the residue which was washed with DCM and dried. The resultant title compound (0.5 g, 54%) was used directly in the next step without further purification.

Example 37D 3-cyano-6-fluoro-4H-benzo[4,5]imidazo[1,2-b]pyrazole-8-carboxamide

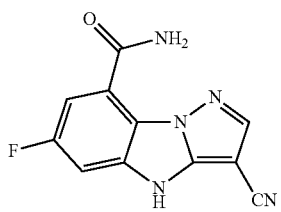 [SMILES: N#Cc1cnn2c1[nH]c1cc(F)cc(C(N)=O)c12]

A mixture of EXAMPLE 37C (20 g, 0.077 mmol) and NH$_4$OH (5 mL) in DMF (1 mL) and MeOH (1 mL) was stirred at 120° C. for 4 h. After removal of solution in vacuum, the resultant residue was purified by prep-HPLC to provide the title compound (2.99 g, 16%). $^1$H-NMR (400 MHz, MeOD-d4) δ ppm 7.52 (dd, J=7.91 Hz, 1H), 7.80 (dd, J=10.67 Hz, 1H), 8.19 (s, 1H). LCMS (ESI) m/z: 244 (M+1).

Example 38

3-cyano-4H-benzo[4,5]imidazo[1,2-b]pyrazole-8-carboxamide

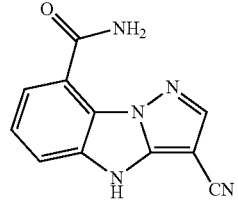 [SMILES: N#Cc1cnn2c1[nH]c1cccc(C(N)=O)c12]

This example was prepared as described in Example 37. $^1$H NMR (400 MHz, D2O) ppm 7.54-7.58 (t, 1H), 7.75-7.77 (d, 1H), 8.10-8.12 (d, 1H), 8.23 (S, 1H). LCMS (ESI) m/z: 226 (M+1).

Example 39

3-(aminomethyl)-6-fluoro-4H-benzo[4,5]imidazo[1,2-b]pyrazole-8-carboxamide

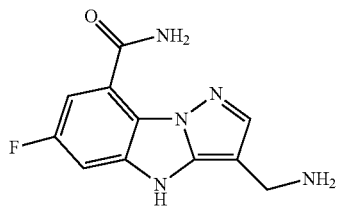 [SMILES: NCc1cnn2c1[nH]c1cc(F)cc(C(N)=O)c12]

To a mixture of EXAMPLE 37D (100 g, 0.4 mmol) in DCM (20 mL) and MeOH (50 mL) was added NiCl$_2$·6H$_2$O (200 g, 0.8 mmol) and NaBH$_4$ (47 g, 1.2 mmol) in protions. After being stirred at 0° C. for 5 min, the reaction mixture was evaporated to give the residue which was purified by prep-HPLC to provide the title compound (45 g, 45%). $^1$H NMR (400 MHz, D2O) ppm 4.2 (S, 2H), 7.269-7.318 (t, 2H), 7.796 (S, 1H), 8.399 (S, 1H). LCMS (ESI) m/z: 248 (M+1).

Example 40

3-(cyclopropanecarboxamidomethyl)-6-fluoro-4H-benzo[4,5]imidazo[1,2-b]pyrazole-8-carboxamide

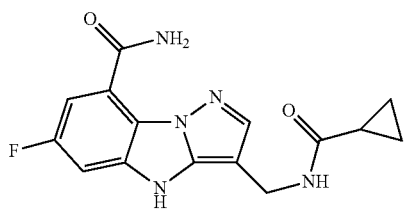 [SMILES: NC(=O)c1cc(F)cc2[nH]c3c(CNC(=O)C4CC4)cnn3c12]

A mixture of EXAMPLE 39 (20 g, 0.081 mmol), cyclopropanecarboxylic acid (8.36 g, 0.098 mmol), HOBt (13.12 g, 0.0979 mmol), EDCl (18.61 g, 0.097 mmol) and Et₃N (25 g, 0.242 mmol) in DMF (5 mL) was stirred at 30° C. for 6 h. After removal of solution in vacuum, the residue was purified by prep-HPLC to provide the title compound (11.9 g, 48%). ¹H NMR (400 MHz, DMSO-d6) • ppm 0.64-0.72 (m, 4H), 1.52-1.57 (m, 1H), 4.25-2.50 (d, 2H), 7.57-7.61 (m, 2H), 7.82 (s, 1H), 8.13 (s, 1H), 8.44-8.46 (t, 1H), 10.46 (s, 1H), 11.93 (br, 1H). LCMS (ESI) m/z: 316 (M+1).

Scheme B

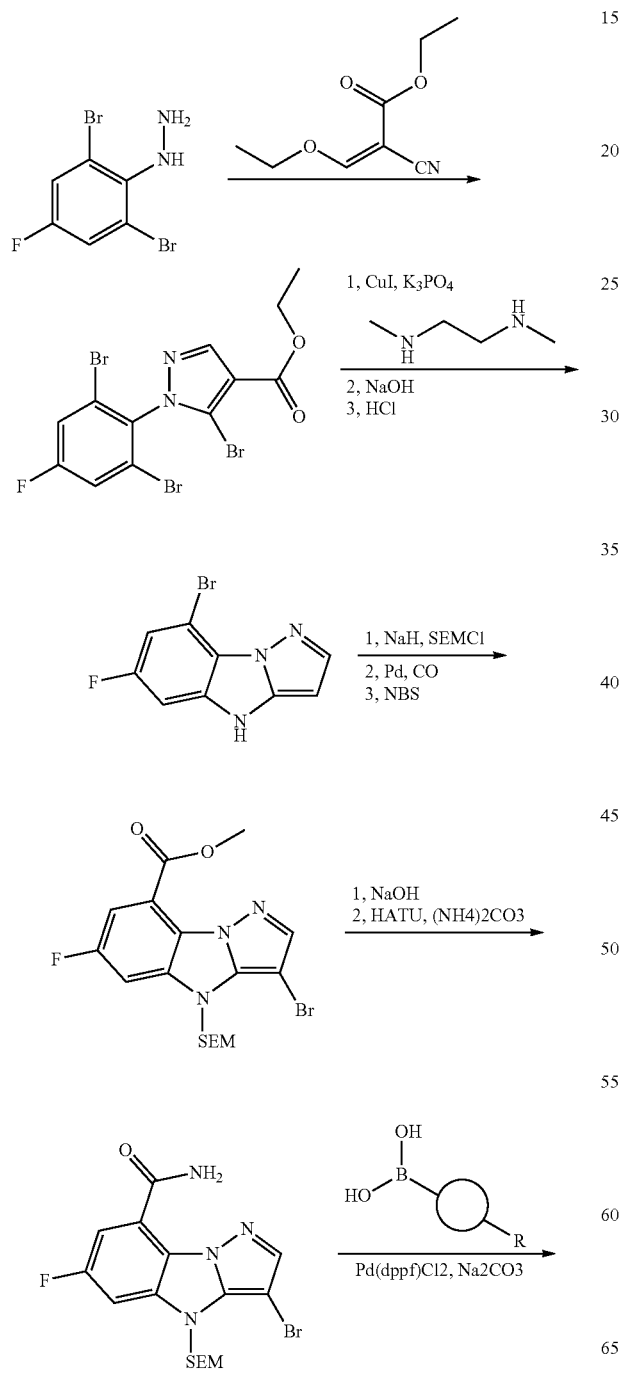

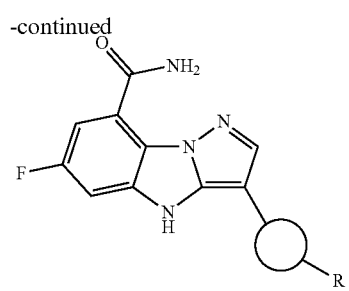

Example 41

6-fluoro-3-(4-fluorophenyl)-4H-benzo[4,5]imidazo[1,2-b]pyrazole-8-carboxamide

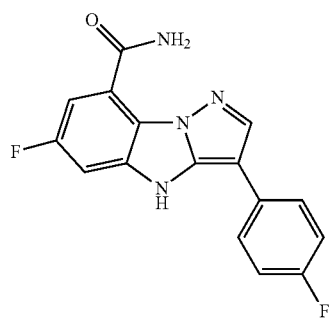 [SMILES: NC(=O)c1cc(F)cc2[nH]c3c(-c4ccc(F)cc4)cnn3c12]

Example 41A ethyl 5-amino-1-(2,6-dibromo-4-fluorophenyl)-1H-pyrazole-4-carboxylate

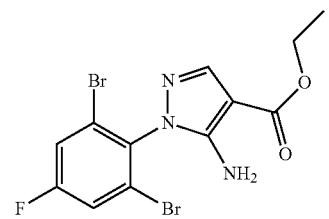 [SMILES: CCOC(=O)c1cnn(-c2c(Br)cc(F)cc2Br)c1N]

A mixture of EXAMPLE 1D (5 g, 17.61 mmol) and ethyl 2-cyano-3-ethoxyacrylate (2.98 g, 17.61 mmol) in EtOH (100 mL) was stirred at 78° C. for 16 h. After removal of solution in vacuum, the residue was purified by column chromatograph to provide the title compound (2.7 g, yield: 38%) which could be used directly in the next step without further purification.

Example 41B ethyl 8-bromo-6-fluoro-4H-benzo[4,5]imidazo[1,2-b]pyrazole-3-carboxylate

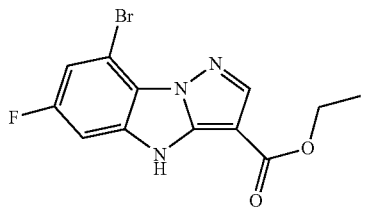 [SMILES: CCOC(=O)c1cnn2c1[nH]c1cc(F)cc(Br)c12]

A mixture of EXAMPLE 41A (2.7 g, 6.63 mmol), CuI (252 g, 1.33 mmol), N¹,N²-dimethylethane-1,2-diamine (233.9 g, 2.65 mmol) and K₃PO₄ (4.22 g, 19.9 mmol) in DMF (60 mL) was stirred at 70° C. for 16 hours under N₂ atmosphere. After being cooled to room temperature, the mixture was filtered and the solvent was evaporated off under vacuum. The resultant residue (2.16 g) could be used directly in the next step without further purification.

Example 41C 8-bromo-6-fluoro-4H-benzo[4,5]imidazo[1,2-b]pyrazole-3-carboxylic acid

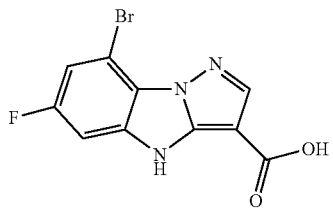 [SMILES: O=C(O)c1cnn2c1[nH]c1cc(F)cc(Br)c12]

A mixture of EXAMPLE 41B (2.16 g, 6.62 mmol) and NaOH (1.06 g, 26.49 mmol) in MeOH (40 mL) and H₂O (10 mL) was stirred at 70° C. for 16 h. After evaporation off solvent, the resultant residue could be used directly in the next step without further purification.

Example 41D 8-bromo-6-fluoro-4H-benzo[4,5]imidazo[1,2-b]pyrazole

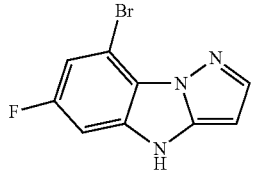 [SMILES: Fc1cc(Br)c2c(c1)[nH]c1ccnn12]

A solution of EXAMPLE 41C (1.97 g, 6.61 mmol) in a mixture of concentrate HCl (20 mL) and H₂O (20 mL) was stirred at 80° C. for 16 h. After neutralized with concentrate NH₄OH, the resultant mixture was filtered. The cake was washed with MeOH and dried under vacuum. The obtained solid (1.58 g) could be used directly in the next step without further purification.

Example 41E 8-bromo-6-fluoro-4-((2-(trimethylsilyl)ethoxy)methyl)-4H-benzo[4,5]imidazo[1,2-b]pyrazole

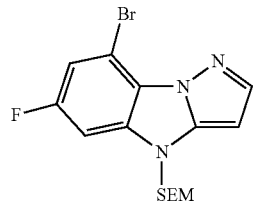 [SMILES: C[Si](C)(C)CCOCn1c2cc(F)cc(Br)c2n2nccc12]

To a solution of NaH (0.746 g, 18.66 mmol) in THF (10 mL) was added a solution of EXAMPLE 41D (1.58 g, 6.22 mmol) in THF (20 mL) at 0° C. under N₂ atmosphere. The mixture was stirred at 0° C. for 0.5 h, and thereafter SEMCl (1.56 g, 9.33 mmol) was added thereto. The mixture was stirred at 0° C. for another 1 h and then quenched with water (20 mL). The aqueous layer was extracted with DCM (20 mL×3). The combined organic layers were dried over Na₂SO₄, filtered and evaporated. The residue was purified by column chromatograph to provide the title compound (0.43 g, yield: 17% for 4 steps). LCMS (ESI) m/z: 384, 386 (M, M+2).

Example 41F methyl 6-fluoro-4-((2-(trimethylsilyl)ethoxy)methyl)-4H-benzo[4,5]imidazo[1,2-b]pyrazole-8-carboxylate

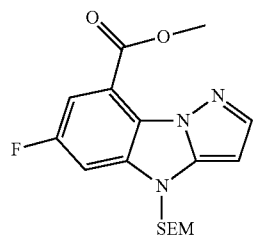 [SMILES: COC(=O)c1cc(F)cc2c1n1nccc1n2COCC[Si](C)(C)C]

A mixture of EXAMPLE 41E (0.43 g, 1.12 mmol), Pd(OAc)₂ (50 g, 0.233 mmol), Pd(dppf)Cl₂ (164 mg, 0.233 mmol), Xantphos (194 g, 0.335 mmol), DPPP (138 g, 0.335 mmol), PPh₃ (88 g, 0.335 mmol) and Et₃N (566 g, 5.59 mmol) in DMF (10 mL) and MeOH (10 mL) was stirred at 80° C. for 24 h under CO atmosphere (3 atms). After being cooled to room temperature, the mixture was filtered and the filtrate was evaporated. The residue was purified by column chromatograph to provide the title compound (0.265 g, yield: 63%). LCMS (ESI) m/z: 364 (M+1).

Example 41G methyl 3-bromo-6-fluoro-4-((2-(trimethylsilyl)ethoxy)methyl)-4H-benzo[4,5]imidazo[1,2-b]pyrazole-8-carboxylate

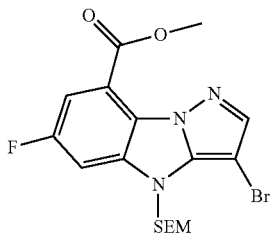 [SMILES: COC(=O)c1cc(F)cc2c1n1ncc(Br)c1n2COCC[Si](C)(C)C]

A mixture of EXAMPLE 41F (0.265 g, 729 mmol) and NBS (117 g, 656 mmol) in DCM (20 mL) was stirred at 10° C. for 20 min. After removal of solution in vacuum, the residue was purified by column chromatograph to provide the title compound (0.24 g, yield: 75%). LCMS (ESI) m/z: 442, 444 (M, M+2).

Example 41H 3-bromo-6-fluoro-4-((2-(trimethylsilyl)ethoxy)methyl)-4H-benzo[4,5]imidazo[1,2-b]pyrazole-8-carboxylic acid

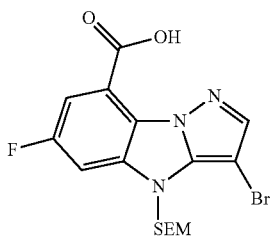 [SMILES: C[Si](C)(C)CCOCn1c2cc(F)cc(C(=O)O)c2n2ncc(Br)c12]

A mixture of EXAMPLE 41G (240 g, 0.542 mmol) and NaOH (108 g, 2.71 mmol) in MeOH (6 mL) and H$_2$O (1.5 mL) was stirred at 60° C. for 0.5 h. After being cooled to room temperature, the mixture was adjusted to pH 4 with 1 N HCl and the aqueous phase was extracted with EtOAc (20 mL×3). The combined organic layers were washed with brine, dried over Na$_2$SO$_4$ and evaporated to provide the title compound (196 g, yield: 84%) which was used directly in the next step without further purification.

Example 41I 3-bromo-6-fluoro-4-((2-(trimethylsilyl)ethoxy)methyl)-4H-benzo[4,5]imidazo[1,2-b]pyrazole-8-carboxamide

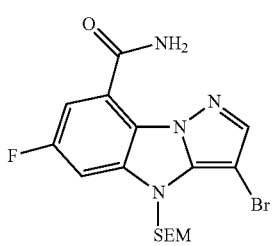

A mixture of EXAMPLE 41H (0.196 g, 0.46 mmol), HATU (0.226 g, 0.595 mmol), (NH$_4$)$_2$CO$_3$ (0.439 g, 4.6 mmol) and Et$_3$N (0.138 g, 1.37 mmol) in DMF (8 mL) was stirred at 40° C. for 16 h under N$_2$ atmosphere. After removal of solution in vacuum, the residue was diluted with water (10 mL). The aqueous layer was extracted with EtOAc (15 mL×3). The combined organic layers were washed with brine, dried over Na$_2$SO$_4$ and evaporated. The residue was purified by column chromatograph to provide the title compound (0.125 g, yield: 64%). LCMS (ESI) m/z: 427, 429 (M, M+2).

Example 41J 6-fluoro-3-(4-fluorophenyl)-4-((2-(trimethylsilyl)ethoxy)methyl)-4H-benzo[4,5]imidazo[1,2-b]pyrazole-8-carboxamide

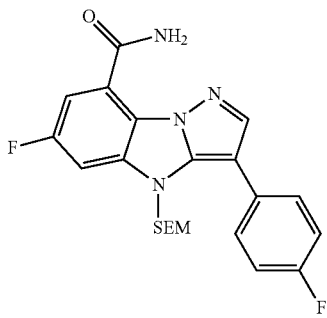 [SMILES: C[Si](C)(C)CCOCn1c2cc(F)cc(C(N)=O)c2n2ncc(-c3ccc(F)cc3)c12]

A mixture of EXAMPLE 41I (50 g, 0.117 mmol), Pd(dppf)Cl$_2$ (17 g, 0.023 mmol), Na$_2$CO$_3$ (31 mg, 0.292 mmol) and (4-fluorophenyl)boronic acid (24 g, 0.175 mmol) in DMF (3 mL) and H$_2$O (0.5 mL) was stirred at 100° C. for 16 h under N$_2$ atmosphere. After removal of solution in vacuum, the residue was diluted with water (10 mL). The aqueous layer was extracted with EtOAc (10 mL×3). The combined organic layers were washed with brine, dried over Na$_2$SO$_4$, filtered and evaporated. The residue was purified by prep-TLC to provide the title compound (40 g, yield: 77%). LCMS (ESI) m/z: 443 (M+1).

Example 41K 6-fluoro-3-(4-fluorophenyl)-4H-benzo[4,5]imidazo[1,2-b]pyrazole-8-carboxamide

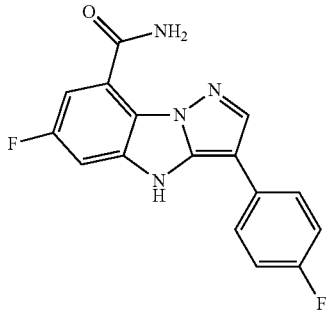 [SMILES: NC(=O)c1cc(F)cc2[nH]c3c(-c4ccc(F)cc4)cnn3c12]

A mixture of EXAMPLE 41J (40 g, 0.090 mmol) in TFA (0.5 mL) and DCM (0.5 mL) was stirred at 10° C. for 5 h.

After removal of the solution in vacuum, to the residue were added MeOH (3 mL) and K₂CO₃ (0.037 g, 0.271 mmol). The mixture was stirred at 10° C. for 2 h. The mixture was filtered and the solvent was evaporated off under vacuum. The residue was purified by prep-HPLC to provide the title compound (6.3 g, yield: 24%). ¹H NMR (400 MHz, DMSO-d6) δ: 8.32 (s, 1H), 7.67-7.71 (m, 2H), 7.59-7.61 (d, 1H), 7.55-7.57 (d, 1H), 7.22-7.27 (t, 2H). LCMS (ESI) m/z: 313 (M+1).

Example 42

6-fluoro-3-(2-fluoro-4-((methylamino)methyl)phenyl)-4H-benzo[4,5]imidazo[1,2-b]pyrazole-8-carboxamide

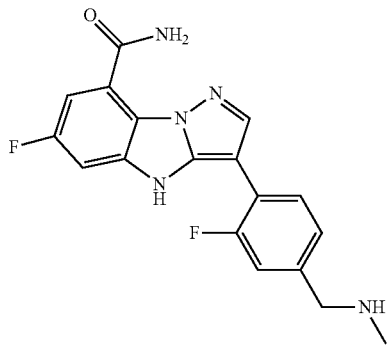 [SMILES: CNCc1ccc(-c2cnn3c2[nH]c2cc(F)cc(C(N)=O)c23)c(F)c1]

Example 42A 1-(4-bromo-3-fluorophenyl)-N-methylmethanamine

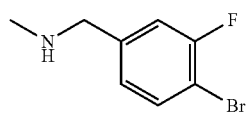

A mixture of 4-bromo-3-fluorobenzaldehyde (2 g, 9.8 mmol) and methanamine (30-40% in EtOH) (10 mL, 16.7 mmol) in EtOH (10 mL) was stirred at 75° C. for 15 h. The mixture was cooled to room temperature, and then added thereto NaBH₄ (745 g, 19.6 mmol) in one portion and stirred for another 30 min. After removal of solution in vacuum, the residue was diluted with saturated NaHCO₃ (20 mL). The aqueous layer was extracted with EtOAc (50 mL×3). The combined organic layers were washed with water (50 mL), brine (50 mL), dried over Na₂SO₄, filtered and evaporated. The residue was purified by column chromatography to provide the title compound (1.47 g, yield: 74%). LCMS (ESI) m/z: 218, 220 (M, M+2).

Example 42B tert-butyl (4-bromo-3-fluorobenzyl)(methyl)carbamate

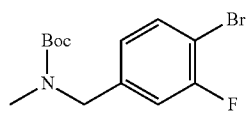 [SMILES: CN(Cc1ccc(Br)c(F)c1)C(=O)OC(C)(C)C]

A mixture of EXAMPLE 42A (1.47 g, 6.77 mmol), Boc₂O (1.77 g, 8.12 mmol) and Et₃N (1.37 g, 13.54 mmol) in DCM (15 mL) was stirred at 18° C. for 2 h. After removal of solution in vacuum, the residue was purified by column chromatograph to provide the title compound (1.83 g, yield: 85%). LCMS (ESI) m/z: 319 (M+1).

Example 42C tert-butyl(3-fluoro-4-(4,4,5,5-tetramethyl-1,3,2-dioxaborolan-2-yl)benzyl)(methyl)carbamate

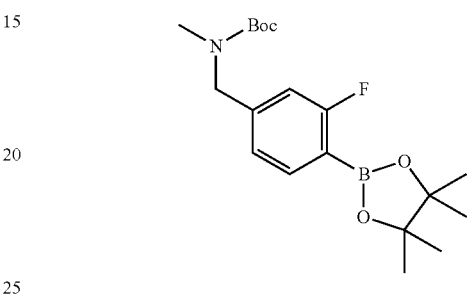

A mixture of 4,4,4',4',5,5,5',5'-octamethyl-2,2'-bi(1,3,2-dioxaborolane) (1.76 g, 6.92 mmol), EXAMPLE 42B (1.83 g, 5.77 mmol), KOAc (1.13 g, 11.54 mmol) and Pd(dppf)Cl₂ (422 g, 0.577 mmol) in DMSO (15 mL) was stirred at 80° C. for 15 h under N₂ atmosphere. After being cooled to room temperature, the mixture was filtered and the filtrate was diluted with water (20 mL). The aqueous layer was extracted with EtOAc (50 mL×2). The combined organic layers were washed with water (30 mL), brine (30 mL), dried over Na₂SO₄, filtered and evaporated. The residue was purified by column chromatography to provide the title compound (2 g, yield: 95%) as colorless oils.

Example 42D tert-butyl (4-(8-carbamoyl-6-fluoro-4-((2-(trimethylsilyl)ethoxy)methyl)-4H-benzo[4,5]imidazo[1,2-b]pyrazol-3-yl)-3-fluorobenzyl)(methyl)carbamate

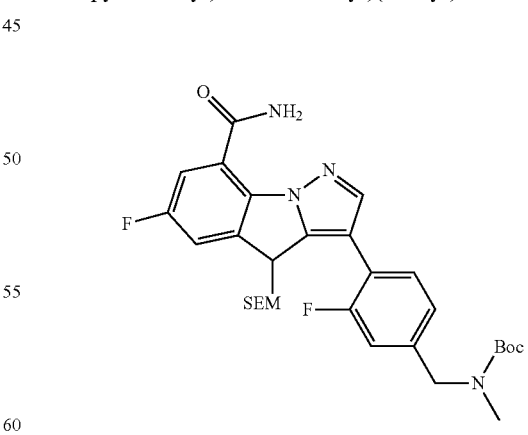

A mixture of EXAMPLE 41I (100 g, 0.23 mmol), EXAMPLE 42C (85.7 g, 0.23 mmol), Na₂CO₃ (50 mg, 0.47 mmol) and Pd(dppf)C₂ (17.1 g, 0.023 mmol) in DMF (5 mL) and H₂O (1 mL) was stirred at 80° C. for 15 h under N₂ atmosphere. After being cooled to room temperature, the mixture was filtered and the filtrate was diluted with water (20 mL). The aqueous layer was extracted with EtOAc (50 mL×2). The combined organic layers were washed with water (30 mL), brine (30 mL), dried over $Na_2SO_4$, filtered and evaporated to give the residue which was purified by prep-TLC to provide the title compound (110 g, yield: 97%). LCMS (ESI) m/z: 586 (M+1).

Example 42E 6-fluoro-3-(2-fluoro-4-((methylamino)methyl)phenyl)-4H-benzo[4,5]imidazo[1,2-b]pyrazole-8-carboxamide

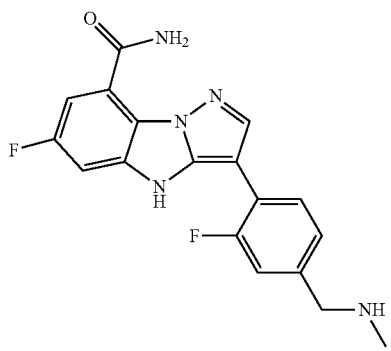 [SMILES: CNCc1ccc(-c2cnn3c2[nH]c2cc(F)cc(C(N)=O)c23)c(F)c1]

A mixture of EXAMPLE 42D (110 g, 0.19 mmol) in TFA (5 mL) and DCM (5 mL) was stirred at 10° C. for 15 h. After removal of solution in vacuum, to the residue were added MeOH (15 mL) and $K_2CO_3$ (53 g, 0.38 mmol). The mixture was stirred at 18° C. for 15 h. The mixture was filtered and the filtrate was evaporated. The residue was partitioned between water (10 mL) and EtOAc (10 mL). The aqueous layer was extracted with EtOAc/THF=3/1 (20 mL×2). The combined organic layers were washed with brine (20 mL), dried over $Na_2SO_4$, filtered and evaporated to give the residue which was purified by prep-HPLC to provide the title compound (22.45 g, yield: 34%) as a white solid. $^1$H NMR (400 MHz, METHANOL-$d_4$) • ppm 2.79 (s, 3H), 4.24 (s, 2H), 4.48-5.29 (m, 27H), 7.37-7.43 (m, 2H), 7.52 (d, J=7.78 Hz, 1H), 7.72 (d, J=9.79 Hz, 1H), 7.78 (t, J=7.78 Hz, 1H), 8.23 (s, 1H), 8.49 (br. s., 1H). LCMS (ESI) m/z: 356 (M+1).

Example 43

6-fluoro-3-(4-((methylamino)methyl)phenyl)-4H-benzo[4,5]imidazo[1,2-b]pyrazole-8-carboxamide

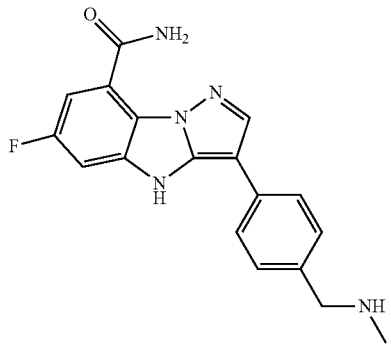 [SMILES: CNCc1ccc(-c2cnn3c2[nH]c2cc(F)cc(C(N)=O)c23)cc1]

This example was prepared as the method described in Example 42. $^1$H-NMR (400 MHz, MethanoL-$d_4$+$D_2O$) 2.77 (s, 3H), 4.21 (s, 2H), 7.46-7.62 (m, 3H), 7.75 (d, J=8.16 Hz, 3H), 8.26 (s, 1H), 8.53 (br. s., 1H). LCMS (ESI) m/z: 338 (M+1).

Example 44

6-fluoro-3-(2-fluoro-5-((methylamino)methyl)phenyl)-4H-benzo[4,5]imidazo[1,2-b]pyrazole-8-carboxamide

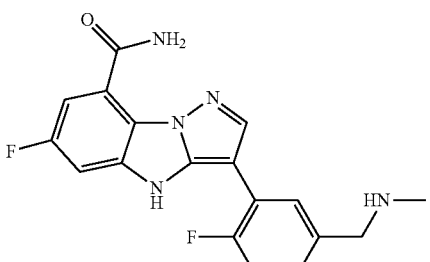

This example was prepared as the method described in Example 42. $^1$H-NMR (400 MHz, DMSO-$d_6$+$D_2O$) 2.59 (br. s., 3H), 4.13 (br. s., 2H), 7.15-7.41 (m, 2H), 7.47-7.68 (m, 2H), 7.95-8.09 (m, 1H), 8.16-8.27 (m, 1H), 8.36 (br. s., 1H). LCMS (ESI) m/z: 356 (M+1).

Example 45

6-fluoro-3-(pyridin-4-yl)-4H-benzo[4,5]imidazo[1,2-b]pyrazole-8-carboxamide

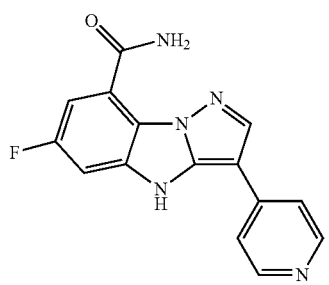 [SMILES: NC(=O)c1cc(F)cc2[nH]c3c(-c4ccncc4)cnn3c12]

This example was prepared as the method described in Example 42. $^1$H-NMR (MeOD, 400 MHz) δ: 7.55-7.63 (m, 2H), 7.73-7.79 (m, 1H), 8.11-8.14 (m, 1H), 8.15-8.19 (m, 1H), 8.48-8.54 (m, 2H), 8.55-8.59 (m, 1H), 10.28-10.36 (m, 1H). LCMS (ESI) m/z: 296 (M+1).

Example 46

6-fluoro-3-(4-(piperidin-3-yl)phenyl)-4H-benzo[4,5]imidazo[1,2-b]pyrazole-8-carboxamide

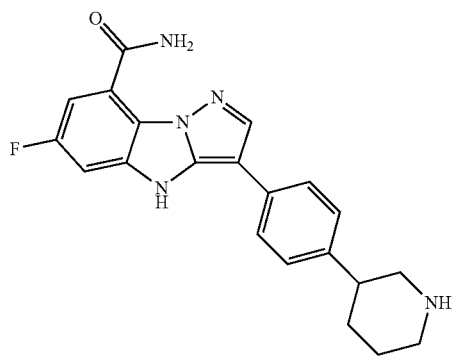 [SMILES: NC(=O)c1cc(F)cc2[nH]c3c(-c4ccc(C5CCCNC5)cc4)cnn3c12]

Example 46A tert-butyl 3-(4-(4,4,5,5-tetramethyl-1,3,2-dioxaborolan-2-yl)phenyl)piperidine-1-carboxylate

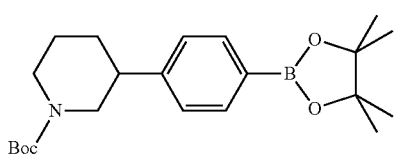 [SMILES: CC(C)(C)OC(=O)N1CCCC(c2ccc(B3OC(C)(C)C(C)(C)O3)cc2)C1]

A mixture of tert-butyl 3-(4-aminophenyl)piperidine-1-carboxylate (0.1 g, 0.362 mmol), 4,4,4',4',5,5,5',5'-octamethyl-2,2'-bi(1,3,2-dioxaborolane) (0.101 g, 0.398 mmol), BPO (1.75 g, 0.00724 mmol) and t-BuONO (0.056 g, 0.542 mmol) in acetonitrile (3 mL) was stirred at 10° C. for 16 h under $N_2$ atmosphere. The solvent was evaporated off under vacuum and the residue was purified by prep-TLC to provide the title compound (0.095 g, yield: 68%).

Example 46B 6-fluoro-3-(4-(piperidin-3-yl)phenyl)-4H-benzo[4,5]imidazo[1,2-b]pyrazole-8-carboxamide

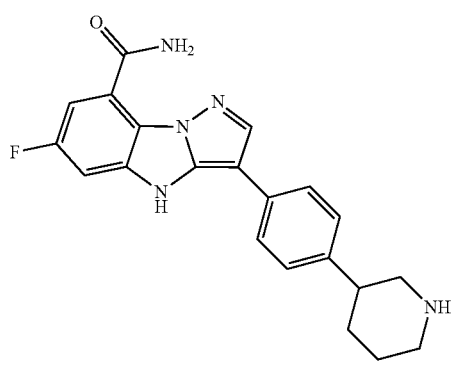 [SMILES: NC(=O)c1cc(F)cc2[nH]c3c(-c4ccc(C5CCCNC5)cc4)cnn3c12]

This example was prepared as the method described in Example 42. $^1$H NMR (300 MHz, METHANOL-d4) δ ppm 1.189 (m, 2H), 2.10-2.01 (m, 2H), 3.03-3.14 (m, 3H), 3.45-3.49 (m, 2H), 7.37-7.40 (d, 2H), 7.44-7.47 (dd, 1H), 7.66-7.68 (d, 2H), 7.74-7.79 (dd, 1H), 8.22 (s, 1H), 8.53 (s, 1H). LCMS (ESI) m/z: 378 (M+1).

Example 47

6-fluoro-3-(tetrahydro-2H-pyran-4-yl)-4H-benzo[4,5]imidazo[1,2-b]pyrazole-8-carboxamide

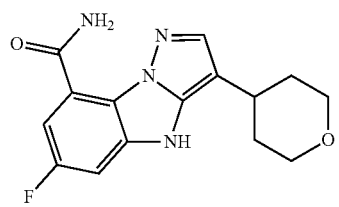 [SMILES: NC(=O)c1cc(F)cc2[nH]c3c(C4CCOCC4)cnn3c12]

Example 47A 3,6-dihydro-2H-pyran-4-yl trifluoromethanesulfonate

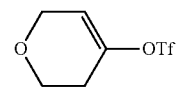

To a solution of dihydro-2H-pyran-4(3H)-one (1.8 g, 18.0 mol) in THF (20 ml) was added LiHMDS (1 M, 21.6 ml, 21.6 mmol) at −78° C. under $N_2$ atmosphere. After stirring for 1 h at −78° C., $(CF_3SO_2)_2$NPh (6.4 g, 18.0 mmol) was added in portions. The mixture was stirred at 15° C. for 16 h and quenched with aq $NH_4Cl$ solution (20 mL). The aqueous layer was extracted with EtOAc (30 mL×2). The combined organic layers were washed with water, brine, dried over $Na_2SO_4$ and concentrated under vacuum. The residue was purified by column chromatograph to provide the title compound as a colorless oil (1.5 g, yield: 35.7%). LCMS (ESI) m/z: 233 (M+1).

Example 47B 2-(3,6-dihydro-2H-pyran-4-yl)-4,4,5,5-tetramethyl-1,3,2-dioxaborolane

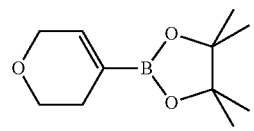

This example was prepared as the method described in Example 42C.

Example 47C 6-fluoro-3-(tetrahydro-2H-pyran-4-yl)-4H-benzo[4,5]imidazo[1,2-b]pyrazole-8-carboxamide

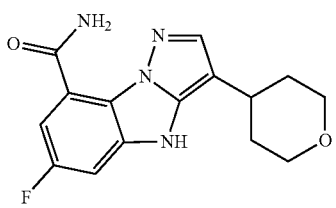 [SMILES: NC(=O)c1cc(F)cc2[nH]c3c(C4CCOCC4)cnn3c12]

This example was prepared as the method described in Example 46B. ¹H-NMR (MeOD, 400 MHz) δ: 1.82-2.03 (m, 4H), 2.93-3.04 (m, 1H), 3.62 (td, J=11.70, 2.45 Hz, 2H), 4.04-4.11 (m, 2H), 7.32-7.39 (m, 1H), 7.66-7.75 (m, 2H), 8.51-8.55 (m, 1H). LCMS (ESI) m/z: 303 (M+1).

Example 48

3-(4-(dimethylamino)cyclohexyl)-6-fluoro-4H-benzo[4,5]imidazo[1,2-b]pyrazole-8-carboxamide

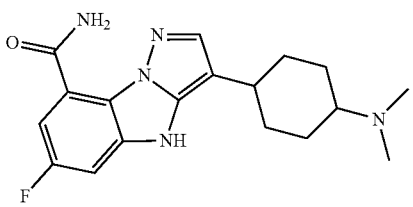 [SMILES: CN(C)C1CCC(c2cnn3c2[nH]c2cc(F)cc(C(N)=O)c23)CC1]

Example 48A 4-((tert-butoxycarbonyl)amino)cyclohex-1-en-1-yl trifluoromethanesulfonate

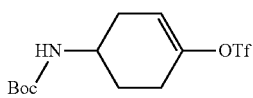

To a solution of tert-butyl (4-oxocyclohexyl)carbamate (1 g, 4.689 mol) in THF (20 mL) was added dropwise LiHMDS (1 M, 9.4 ml, 9.378 mmol) at −78° C. under N₂ atmosphere. After stirring at −78° C. for 1 h, a solution of (CF₃SO₂)₂NPh (1.84 g, 5.158 mmol) in THF (5 mL) was added. The mixture was stirred at 15° C. for 16 h, and then quenched with aq NH₄Cl solution (20 mL). The aqueous layer was extracted with EtOAc (20 mL×2). The combined organic layers were washed with water, brine, dried over Na₂SO₄, filtered and evaporated. The residue was purified by column chromatograph on silica gel to provide the title compound as a white solid (1.16 g, yield: 71.60%). LCMS (ESI) m/z: 347 (M+1).

Example 48B tert-butyl (4-(4,4,5,5-tetramethyl-1,3,2-dioxaborolan-2-yl)cyclohex-3-en-1-yl)carbamate

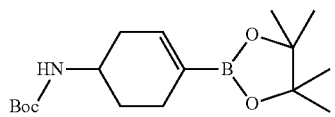

This example was prepared as the method described in Example 47B

Example 48C 3-(4-(dimethylamino)cyclohexyl)-6-fluoro-4H-benzo[4,5]imidazo[1,2-b]pyrazole-8-carboxamide

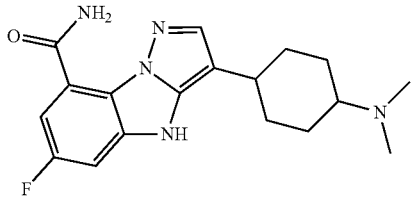 [SMILES: CN(C)C1CCC(c2cnn3c2[nH]c2cc(F)cc(C(N)=O)c23)CC1]

This example was prepared as the methods described in Example 47C and Example 2. ¹H-NMR (MeOD, 400 MHz) δ: 1.63-1.87 (m, 3H), 1.91-2.10 (m, 2H), 2.20-2.46 (m, 3H), 2.81 (s, 4H), 2.90 (s, 3H), 3.19-3.30 (m, 1H), 7.34-7.44 (m, 1H), 7.64-7.75 (m, 2H), 7.78-7.85 (m, 1H), 8.38-8.73 (m, 3H).
LCMS (ESI) m/z: 344 (M+1).

Example 49

6-fluoro-3-(4-methylpiperazine-1-carbonyl)-4H-benzo[4,5]imidazo[1,2-b]pyrazole-8-carboxamide

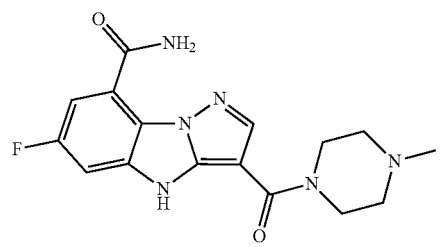 [SMILES: CN1CCN(C(=O)c2cnn3c2[nH]c2cc(F)cc(C(N)=O)c23)CC1]

Example 49A ethyl 8-bromo-6-fluoro-4-((2-(trimethylsilyl)ethoxy)methyl)-4H-benzo[4,5]imidazo[1,2-b]pyrazole-3-carboxylate

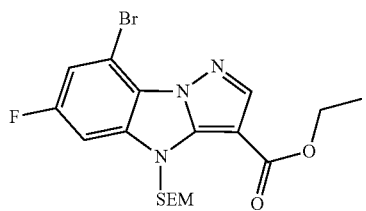 [SMILES: CCOC(=O)c1cnn2c3c(Br)cc(F)cc3n(COCC[Si](C)(C)C)c12]

To a solution of EXAMPLE 41B (3.2 g, 9.812 mol) in THF (50 mL) was added NaH (785 g, 19.625 mmol) in portions at 0° C. under N₂ atmosphere. After stirring at 15° C. for 0.5 h and cooling to 0° C., SEMCl (3.3 g, 19.625 mmol) was added dropwise thereto. The mixture was stirred at 15° C. for another 16 h and then quenched with aq NH₄Cl saturated solution (30 mL). The aqueous layer was extracted with EtOAc (30 mL×3). The combined organic layers were washed with water, brine, dried over Na₂SO₄ and evaporated. The residue was purified by column chromatograph to provide the title compound as a yellow solid (2.16 g, yield: 48.21%). LCMS (ESI) m/z: 456, 458 (M, M+2).

Example 49B 8-bromo-6-fluoro-4-((2-(trimethylsilyl)ethoxy)methyl)-4H-benzo[4,5]imidazo[1,2-b]pyrazole-3-carboxylic acid

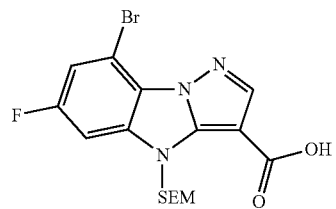 [SMILES: C[Si](C)(C)CCOCn1c2cc(F)cc(Br)c2n2ncc(C(=O)O)c12]

A mixture of EXAMPLE 49A (2.16 g, 4.726 mmol) and NaOH (950 g, 23.632 mmol) in a mixed solvent of MeOH/H₂O (2:1) (30 mL) was stirred at 80° C. for 16 h. The resultant mixture was adjusted to pH 3-4 with 1N HCl. The aqueous layer was extracted with EtOAc (30 mL×2). The combined organic layers were washed with water, brine, dried over Na₂SO₄ and evaporated to provide the title compound (1.73 g, yield: 85.22%) which could be used in the next step without further purification.

Example 49C tert-butyl 4-(8-bromo-6-fluoro-4-((2-(trimethylsilyl)ethoxy)methyl)-4H-benzo[4,5]imidazo[1,2-b]pyrazole-3-carbonyl)piperazine-1-carboxylate

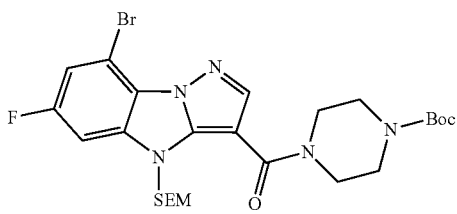 [SMILES: CC(C)(C)OC(=O)N1CCN(C(=O)c2cnn3c4c(Br)cc(F)cc4n(COCC[Si](C)(C)C)c23)CC1]

A mixture of tert-butyl piperazine-1-carboxylate (415 g, 2.241 mmol), EXAMPLE 49B (800 g, 1.868 mmol), HATU (1.42 g, 3.735 mmol) and Et₃N (567 g, 5.603 mmol) in DMF (15 mL) was stirred at 15° C. for 16 h under N₂ atmosphere. The mixture was quenched with H₂O (10 mL). The aqueous layer was extracted with EtOAc (20 mL×2). The combined organic layers were washed with water, brine, dried over Na₂SO₄ and evaporated. The residue was purified by column chromatograph to provide the title compound (1 g, yield: 90%). LCMS (ESI) m/z: 596, 598 (M, M+2).

Example 49D tert-butyl 4-(8-cyano-6-fluoro-4-((2-(trimethylsilyl)ethoxy)methyl)-4H-benzo[4,5]imidazo[1,2-b]pyrazole-3-carbonyl)piperazine-1-carboxylate

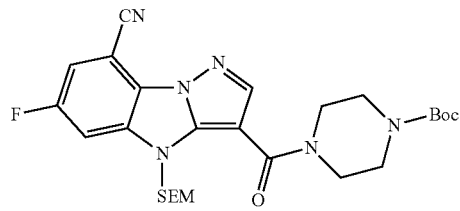 [SMILES: CC(C)(C)OC(=O)N1CCN(C(=O)c2cnn3c4c(C#N)cc(F)cc4n(COCC[Si](C)(C)C)c23)CC1]

A mixture of EXAMPLE 49C (400 g, 0.671 mmol), Zn (87 g, 1.341 mmol), Zn(CN)₂ (158 g, 1.341 mmol), DPPF (75 g, 0.134 mmol) and Pd₂(DBA)₃ (61 g, 0.0671 mmol) in DMF (10 mL) was stirred at 120° C. under N₂ atmosphere for 10 hours. After being cooled to room temperature, the resultant mixture was diluted with water (20 mL). The aqueous layer was extracted with EtOAc (30 mL×3). The combined organic layers were washed with water, brine, dried over Na₂SO₄, filtered and evaporated. The residue was purified by column chromatograph to provide the title compound (350 g, yield: 96.15%). LCMS (ESI) m/z: 543 (M+1).

Example 49E tert-butyl 4-(8-carbamoyl-6-fluoro-4-((2-(trimethylsilyl)ethoxy)methyl)-4H-benzo[4,5]imidazo[1,2-b]pyrazole-3-carbonyl)piperazine-1-carboxylate

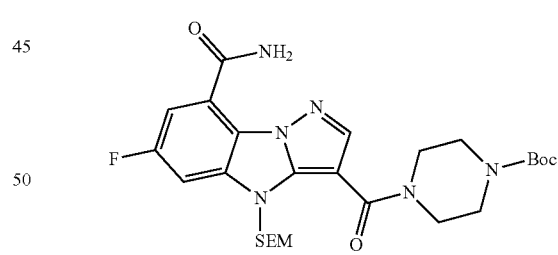

To a mixture of EXAMPLE 49D (400 g, 0.737 mmol) and K₂CO₃ (510 g, 3.685 mmol) in DMSO (10 mL) was added H₂O₂ (5 mL) at 0-5° C. After the dropwise addition was completed, the mixture was stirred at 15° C. for 1 h, and quenched with aq Na₂SO₃ solution (20 mL). The aqueous layer was extracted with EtOAc (30 mL×3). The combined organic layers were washed with water, brine, dried over Na₂SO₄ and evaporated. The residue was purified by column chromatograph to provide the title compound (400 g, yield: 96.85%). LCMS (ESI) m/z: 561 (M+1).

Example 49F 6-fluoro-3-(piperazine-1-carbonyl)-4H-benzo[4,5]imidazo[1,2-b]pyrazole-8-carboxamide

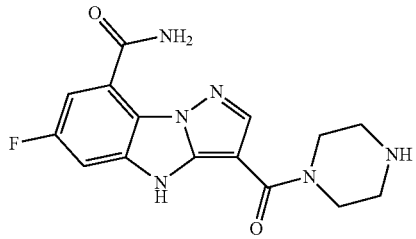 [SMILES: NC(=O)c1cc(F)cc2[nH]c3c(C(=O)N4CCNCC4)cnn3c12]

A mixture of EXAMPLE 49E (100 g, 0.178 mmol) in TFA (1 mL) and DCM (1 mL) was stirred at 15° C. for 16 h. After removal of solution in vacuum, to the residue were added K₂CO₃ (123 g, 0.892 mmol) and MeOH (2 mL). The mixture was stirred at 15° C. for 2 h. The mixture was filtered and the filtrate was evaporated to provide the title compound which could be used directly in the next step without further purification.

Example 49G 6-fluoro-3-(4-methylpiperazine-1-carbonyl)-4H-benzo[4,5]imidazo[1,2-b]pyrazole-8-carboxamide

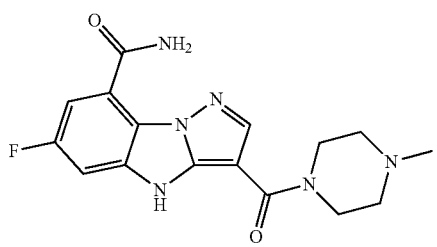 [SMILES: CN1CCN(C(=O)c2cnn3c2[nH]c2cc(F)cc(C(N)=O)c23)CC1]

A mixture of EXAMPLE 49F (59 g, 0.179 mmol), formaldehyde (40 g, 0.358 mmol) and Na(CN)BH₃ (56 g, 0.894 mmol) in MeOH (2 mL) was stirred at 15° C. for 16 h. After evaporation off solvent in vacuum, the residue was purified by prep-HPLC to provide the title compound (8.14 g, yield: 13.23%) as a white solid. ¹H-NMR (MeOD, 400 MHz) δ: 2.68 (s, 3H), 2.99 (d, J=4.64 Hz, 4H), 4.00 (br. s., 4H), 7.46-7.54 (m, 1H), 7.74-7.84 (m, 1H), 8.12-8.20 (m, 1H), 8.24-8.35 (m, 2H). LCMS (ESI) m/z: 345 (M+1).

Example 50

3-(1-(cyclopropylmethyl)piperidin-4-yl)-4,4,6-trifluoro-4H-pyrazolo[15-α]indole-8-carboxamide

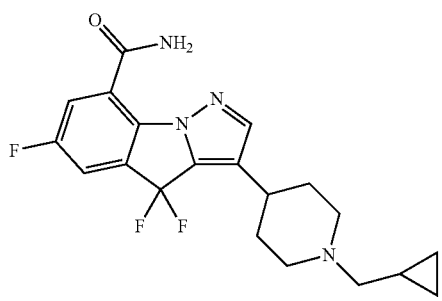 [SMILES: NC(=O)c1cc(F)cc2c1-n1ncc(C3CCN(CC4CC4)CC3)c1C2(F)F]

Example 50A ethyl (E)-4-(dimethylamino)-2-oxobut-3-enoate

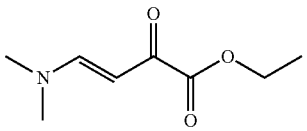

A solution of ethyl 2-oxopropanoate (5.0 g, 43.1 mmol) in DMF-DMA (5.0 g, 42.0 mmol) was stirred at 20° C. for 16 h. The resultant mixture was evaporated to provide the title compound (7.0 g, crude) as brown oil which could be used directly in the next step without further purification.

Example 50B ethyl 1-(2,6-dibromo-4-fluorophenyl)-1H-pyrazole-5-carboxylate

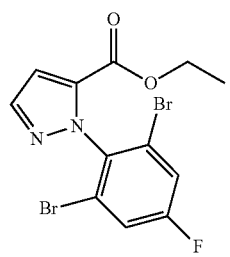 [SMILES: CCOC(=O)c1ccnn1-c1c(Br)cc(F)cc1Br]

A mixture of EXAMPLE 1D (5.0 g, 17.6 mmol), EXAMPLE 50A (6.0 g, 35.2 mmol) in EtOH (100 ml) and conc HCl (2.4 mL) was stirred at 80° C. for 16 h. After removal of solution in vacuum, the residue was purified by column chromatograph to provide the title compound (3.6 g, yield: 46.8%) as a yellow solid.

Example 50C 1-(2,6-dibromo-4-fluorophenyl)-1H-pyrazole-5-carboxylic acid

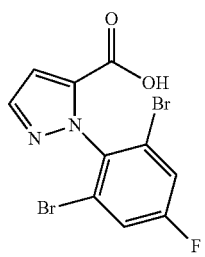 [SMILES: O=C(O)c1ccnn1-c1c(Br)cc(F)cc1Br]

A mixture of EXAMPLE 50B (3.6 g, 9.18 mmol) and NaOH (2.2 g, 55.1 mmol) in MeOH (20 mL) and water (2 mL) was stirred at 20° C. for 1 h. After removal of solution in vacuum, the residue was diluted with water (50 mL) and adjusted to pH 3 with 2 N HCl. The aqueous layer was extracted with dichloromethane (50 mL×3). The combined organic layers were dried over Na$_2$SO$_4$, filtered and evaporated to provide the title compound (3.2 g, 97.0%) which could be used directly in the next step without further purification.

Example 50D 1-(2,6-dibromo-4-fluorophenyl)-N-methoxy-N-methyl-1H-pyrazole-5-carboxamide

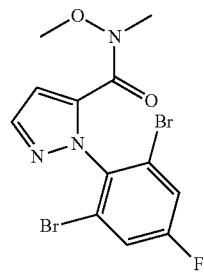 [SMILES: CON(C)C(=O)c1ccnn1-c1c(Br)cc(F)cc1Br]

A mixture of EXAMPLE 50C (3.2 g, 8.82 mmol), O,N-Dimethyl-hydroxylamine (1.7 g, 17.6 mmol), HATU (4.0 g, 10.6 mmol) and Et$_3$N (3.6 g, 35.3 mmol) in dry DMF (2 mL) was stirred at 20° C. for 16 h under N$_2$ atmosphere. After removal of solution in vacuum, the residue was purified by column chromatograph to provide the title compound (3.4 g, yield: 94.4%) as a yellow solid.

Example 50E 8-bromo-6-fluoro-4H-pyrazolo[1,5-α]indol-4-one

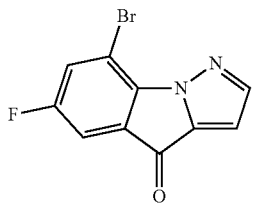 [SMILES: O=C1c2cc(F)cc(Br)c2-n2nccc21]

To a mixture of EXAMPLE 50D (3.2 g, 7.90 mmol) in dry THF (5 mL) was added dropwise n-BuLi (2.8 mL, 7.11 mmol) at −78° C. under N$_2$ atmosphere. After being stirred at −78° C. for 0.5 h, the mixture was quenched with sat aq NH$_4$Cl solution (30 mL). The aqueous layer was extracted with DCM (50 mL×2). The combined organic layers were evaporated. The residue was washed with MeOH (30 mL) to provide the title compound (1.5 g, yield: 71.4%) as a bright yellow solid. LCMS (ESI) m/z: 267, 269 (M, M+2).

Example 50F methyl 6-fluoro-4-oxo-4H-pyrazolo[1,5-α]indole-8-carboxylate

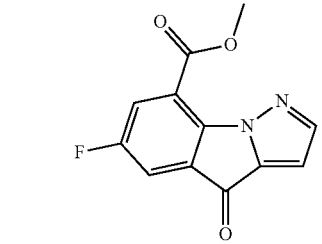 [SMILES: COC(=O)c1cc(F)cc2c1-n1nccc1C2=O]

A mixture of EXAMPLE 50E (1.3 g, 4.89 mmol), Pd(dppf)Cl$_2$ (0.71 g, 0.98 mmol), Pd(OAc)$_2$ (0.22 g, 0.98 mmol), DPPP (0.81 g, 1.96 mmol), PPh$_3$ (0.51 g, 1.96 mmol), Xantphos (1.13 g, 1.96 mmol) and Et$_3$N (3 mL) in MeOH (20 mL) and DMF (60 mL) was stirred at 80° C. for 16 h under CO atmosphere (3 atms). After being cooled to 20° C., the mixture was filtered and the filtrate was evaporated. The residue was purified by column chromatograph to provide the title compound (0.9 g, yield: 75.0%) as a yellow solid. LCMS (ESI) m/z: 247 (M+1).

Example 50G methyl 6-fluorospiro[pyrazolo[1,5-α]indole-4,2'-[1,3]dithiolane]-8-carboxylate

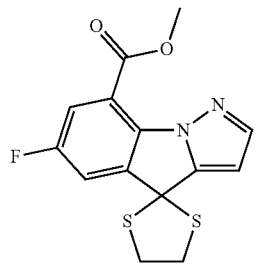 [SMILES: COC(=O)c1cc(F)cc2c1-n1nccc1C21SCCS1]

A mixture of EXAMPLE 50F (0.9 g, 3.66 mmol), 2-ethanedithiol (0.69 g, 7.32 mmol) and BF$_3$-Et$_2$O (1.0 g, 7.32 mmol) in dry DCM (30 mL) was stirred at 50° C. for 24 h under N$_2$ atmosphere. After cooled to room temperature, the mixture was diluted with DCM (30 mL). The combined organic layers were washed with 10% NaOH (30 mL), dried over Na$_2$SO$_4$, filtered and evaporated to give the residue which was purified by column chromatograph on silica gel (PE: EtOAc=10:1) to provide the title compound (0.5 g, yield: 42.4%) as a yellow solid. LCMS (ESI) m/z: 323 (M+1).

Example 50H methyl 3-bromo-6-fluorospiro[pyrazolo[1,5-α]indole-4,2'-[1,3]dithiolane]-8-carboxylate

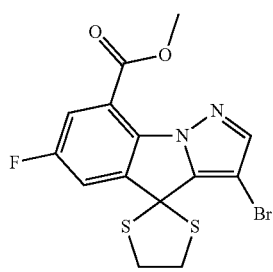 [SMILES: COC(=O)c1cc(F)cc2c1-n1ncc(Br)c1C21SCCS1]

A mixture of EXAMPLE 50G (500 g, 1.55 mmol) and NBS (276 g, 1.55 mmol) in THF (20 mL) was stirred at 40° C. for 16 h. After being cooled to 20° C., the mixture was evaporated and the residue was purified by column chromatograph to provide the title compound (470 g, yield: 75.7%) as a light yellow solid. LCMS (ESI) m/z: 401, 403 (M, M+2).

Example 50I methyl 3-bromo-4,4,6-trifluoro-4H-pyrazolo[1,5-α]indole-8-carboxylate methyl 3-bromo-6-fluoro-4-oxo-4H-pyrazolo[1,5-α]indole-8-carboxylate

50IA

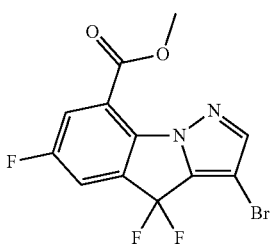

50IB

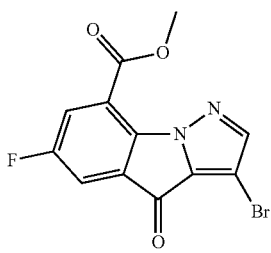

To a solution of NIS (2.1 g, 9.38 mmol) in DCM (20 mL) was added HF.Py (3.5 mL) dropwise at −78° C. under N₂ atmosphere. After stirring at −78° C. for 10 min, EXAMPLE 50H (470 g, 1.17 mmol) was added. The resultant mixture was stirred at −78° C. for 16 h and then quenched with sat aq NaHCO₃ solution (30 mL). The aqueous layer was extracted with EtOAc (30 mL×2). The combined organic layers were washed with sat aq Na₂SO₃ solution (30 mL) and evaporated off solvent under vacuum. The residue was purified by column chromatograph to provide EXAMPLE 50IA as a yellow solid (250 g, yield: 61.6%) and provide EXAMPLE 50IB (110 g, yield: 27.2%) as a white solid.

Example 50J 3-(1-(tert-butoxycarbonyl)-1,2,3,6-tetrahydropyridin-4-yl)-4,4,6-trifluoro-4H-pyrazolo[1,5-α]indole-8-carboxylic acid

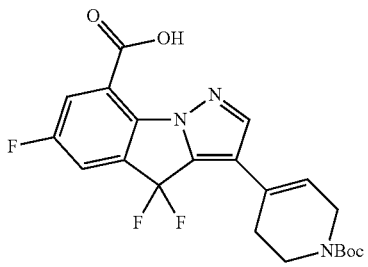 [SMILES: CC(C)(C)OC(=O)N1CC=C(c2cnn3c2C(F)(F)c2cc(F)cc(C(=O)O)c2-3)CC1]

A mixture of EXAMPLE 50IA (200 g, 0.499 mmol), tert-butyl 4-(4,4,5,5-tetramethyl-1,3,2-dioxaborolan-2-yl)-3,6-dihydropyridine-1(2H)-carboxylate (185 g, 0.598 mmol), Pd(dppf)Cl₂ (37 g, 0.050 mmol) and K₂CO₃ (138 g, 0.997 mmol) in DMF (9 mL) and H₂O (3 mL) was stirred at 90° C. for 16 h under N₂ atmosphere. After the mixture was cooled to room temperature and concentrated in vacuum, the residue was dissolved in water (20 mL) and adjusted to pH 3 with 1 N HCl. The aqueous layer was extracted with DCM (50 mL×3).

The combined organic layers were dried over Na₂SO₄, filtered and evaporated to provide the title compound (220 g, crude) without further purification.

Example 50K tert-butyl 4-(8-carbamoyl-4,4,6-trifluoro-4H-pyrazolo[1,5-α]indol-3-yl)-5,6-dihydropyridine-1(2H)-carboxylate

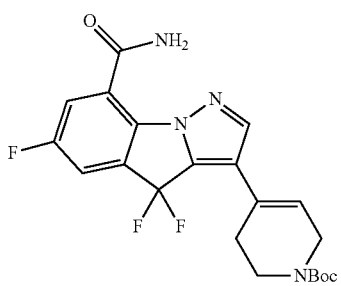 [SMILES: CC(C)(C)OC(=O)N1CC=C(c2cnn3c2C(F)(F)c2cc(F)cc(C(N)=O)c2-3)CC1]

A mixture of EXAMPLE 50J (220 g, 0.51 mmol), (NH₄)₂CO₃ (97 g, 1.01 mmol), Et₃N (0.2 mL, 1.53 mmol) and HATU (252 g, 0.66 mmol) in DMF (8 mL) was stirred at 20° C. for 16 h. The reaction mixture was concentrated under vacuum and the residue was purified by column chromatograph to provide the title compound as a yellow solid (70 g, yield: 32.0%). LCMS (ESI) m/z: 435 (M+1).

Example 50L tert-butyl 4-(8-carbamoyl-4,4,6-trifluoro-4H-pyrazolo[1,5-α]indol-3-yl)piperidine-1-carboxylate

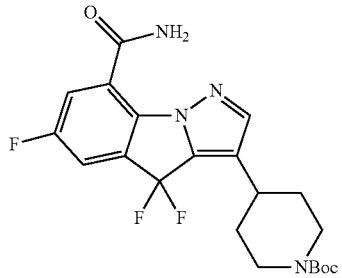 [SMILES: CC(C)(C)OC(=O)N1CCC(c2cnn3c2C(F)(F)c2cc(F)cc(C(N)=O)c2-3)CC1]

A mixture of EXAMPLE 50K (35 g, 0.08 mmol) and 10% Pd/C (20 mg) in dry DCM (20 mL) and MeOH (10 mL) was hydrogenated at 50° C. for 16 h under $H_2$ (1 atm). The mixture was filtered and the filtrate was evaporated to provide the title compound (30 g, yield: 85.7%) which could be used directly in the next step without further purification. LCMS (ESI) m/z: 437 (M+1).

Example 50M 4,4,6-trifluoro-3-(piperidin-4-yl)-4H-pyrazolo[1,5-α]indole-8-carboxamide

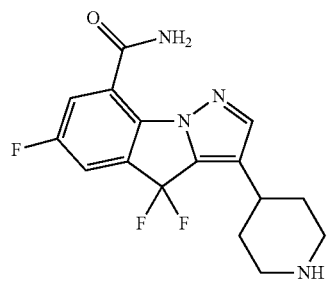 [SMILES: NC(=O)c1cc(F)cc2c1-n1ncc(C3CCNCC3)c1C2(F)F]

A mixture of EXAMPLE 50L (200 g, 0.466 mmol) in TFA (2 mL) and DCM (6 mL) was stirred at 20° C. for 2 h. The resultant mixture was evaporated to provide the title compound which could be used directly in the next step without further purification (30 g, crude).

Example 50N 3-(1-(cyclopropylmethyl)piperidin-4-yl)-4,4,6-trifluoro-4H-pyrazolo[1,5-α]indole-8-carboxamide

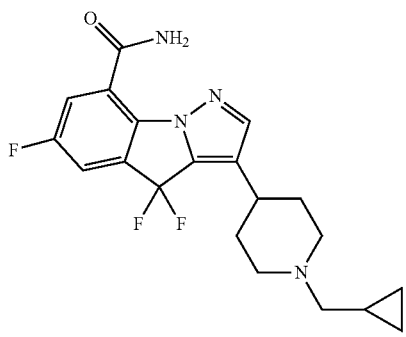 [SMILES: NC(=O)c1cc(F)cc2c1-n1ncc(C3CCN(CC4CC4)CC3)c1C2(F)F]

A mixture of EXAMPLE 50M (30 g, 0.069 mmol), cyclopropanecarbaldehyde (10 g, 0.138 mmol), Ti(O-ipr)$_4$ (39 g, 0.138 mmol) and Na(CN)BH$_3$ (13 g, 0.207 mmol) in MeOH (8 mL) was stirred at 60° C. for 16 h under $N_2$ atmosphere. The resultant mixture was quenched with water (10 mL). The aqueous layer was extracted with DCM (20 mL×3). The combined organic layers were evaporated and the residue was purified by prep-HPLC to provide the title compound as a white solid (5 g, yield: 18.5%). $^1$H-NMR (400 MHz, MethanoL-d$_4$) δ ppm 0.41 (d, J=4.89 Hz, 2H), 0.72-0.81 (m, 2H), 1.13 (br. s., 1H), 1.93-2.13 (m, 2H), 2.31 (d, J=13.93 Hz, 2H), 2.87-3.12 (m, 5H), 3.66 (d, J=11.17 Hz, 2H), 7.78-7.82 (m, 1H), 7.85 (s, 1H), 7.97 (dd, J=9.91, 2.64 Hz, 1H), 8.07 (s, 1H). LCMS (ESI) m/z: 391 (M+1).

Example 51

3-(1-ethylpiperidin-4-yl)-6-fluoro-4-hydroxy-4H-pyrazolo[1,5-α]indole-8-carboxamide

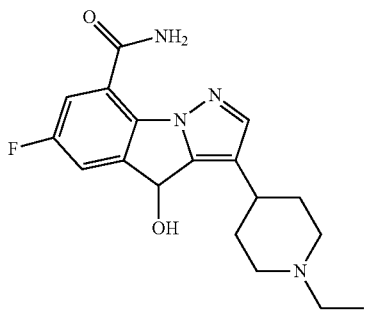 [SMILES: CCN1CCC(c2cnn3c2C(O)c2cc(F)cc(C(N)=O)c2-3)CC1]

Example 51A tert-butyl 4-(8-carbamoyl-6-fluoro-4-oxo-4H-pyrazolo[1,5-α]indol-3-yl)-3,6-dihydropyridine-1(2H)-carboxylate

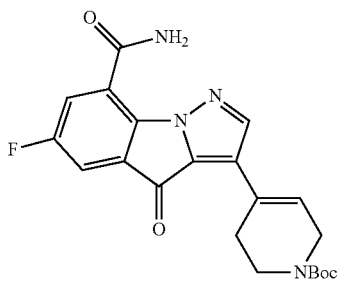 [SMILES: CC(C)(C)OC(=O)N1CC=C(c2cnn3c2C(=O)c2cc(F)cc(C(N)=O)c2-3)CC1]

This example was prepared as described in Example 50K. LCMS (ESI) m/z: 413 (M+1).

Example 51B tert-butyl 4-(8-carbamoyl-6-fluoro-4-hydroxy-4H-pyrazolo[1,5-α]indol-3-yl)piperidine-1-carboxylate

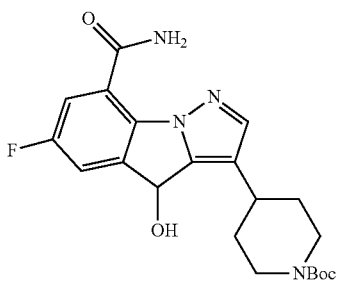 [SMILES: CC(C)(C)OC(=O)N1CCC(c2cnn3c2C(O)c2cc(F)cc(C(N)=O)c2-3)CC1]

A mixture of EXAMPLE 51A (50 g, 0.121 mmol) and 10% Pd/C (10 mg) in dry MeOH (10 mL) was hydrogenated at 50° C. for 16 h under H₂ (1 atm). The mixture was filtered and the filtrate was evaporated to provide the title compound (40 g, yield: 80.0%) which could be used directly in the next step without further purification. LCMS (ESI) m/z: 417 (M+1).

Example 51C 6-fluoro-4-hydroxy-3-(piperidin-4-yl)-4H-pyrazolo[1,5-α]indole-8-carboxamide

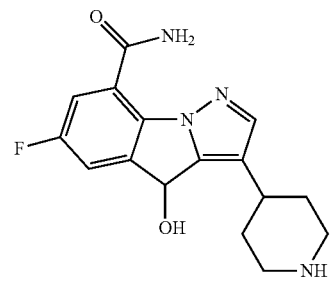 [SMILES: NC(=O)c1cc(F)cc2c1-n1ncc(C3CCNCC3)c1C2O]

This example was prepared as described in Example 50M.

Example 51D 3-(1-ethylpiperidin-4-yl)-6-fluoro-4-hydroxy-4H-pyrazolo[15-α]indole-8-carboxamide

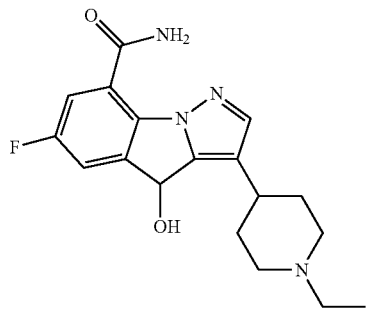 [SMILES: CCN1CCC(c2cnn3c2C(O)c2cc(F)cc(C(N)=O)c2-3)CC1]

A mixture of EXAMPLE 51C (25 g, 0.079 mmol), 40% acetaldehyde (0.1 mL) and Na(CN)BH₃ (20 mg, 0.316 mmol) in MeOH (5 ml) was stirred at 10° C. for 16 h. The resultant mixture was diluted with water (10 mL). The aqueous layer was extracted with DCM (20 mL×3). The combined organic layers were evaporated to give the residue which was purified by prep-HPLC to provide the title compound (9.40 g, yield: 34.8%) as a white solid. ¹H-NMR (400 MHz, MethanoL-d₄) δ ppm 1.11-1.18 (m, 3H), 1.77-1.96 (m, 2H), 2.01-2.16 (m, 2H), 2.61 (br. s., 2H), 2.81 (br. s., 3H), 3.27 (br. s., 2H), 5.72 (s, 1H), 7.59 (dd, J=7.22, 2.45 Hz, 1H), 7.70 (d, J=10.42 Hz, 1H), 7.76 (s, 1H), 7.99 (br. s., 1H), 8.32 (br. s., 1H), 10.09 (br. s., 1H). LCMS (ESI) m/z: 345 (M+1).

Example 52

3-(1-ethylpiperidin-4-yl)-6-fluoro-4-methyl-4H-benzo[4,5]imidazo[1,2-b]pyrazole-8-carboxamide

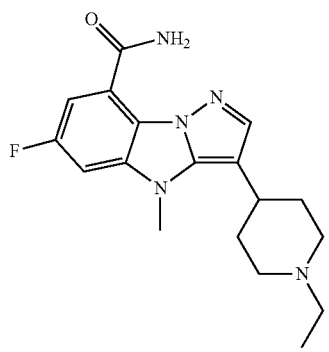

Example 52A tert-butyl 4-(8-carbamoyl-6-fluoro-4-methyl-4H-benzo[4,5]imidazo[1,2-b]pyrazol-3-yl)piperidine-1-carboxylate

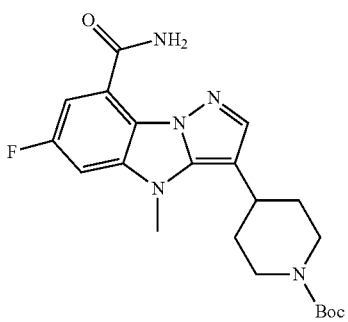 [SMILES: Cn1c2cc(F)cc(C(N)=O)c2n2ncc(C3CCN(C(=O)OC(C)(C)C)CC3)c12]

A mixture of EXAMPLE 1I (30 g, 0.075 mmol), K₂CO₃ (31 g, 0.224 mmol) and CH₃I (32 g, 0.224 mmol) in DMF (3 mL) was stirred at 10° C. for 1 h. The reaction was quenched with water (10 mL). The aqueous layer was extracted with EtOAc (10 mL×3). The combined organic layers were dried over Na₂SO₄, filtered and evaporated to provide the title compound which could be used directly in the next step without further purification.

Example 52B 6-fluoro-4-methyl-3-(piperidin-4-yl)-4H-benzo[4,5]imidazo[1,2-b]pyrazole-8-carboxamide

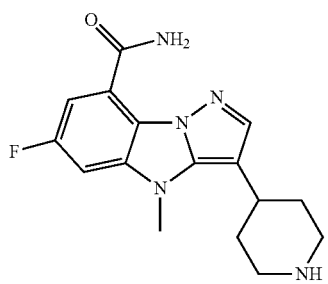 [SMILES: Cn1c2cc(F)cc(C(N)=O)c2n2ncc(C3CCNCC3)c12]

A mixture of EXAMPLE 52A (31 g, 0.074 mmol) in DCM (1 mL) and TFA (0.2 mL) was stirred at 10° C. for 2 h. The mixture was evaporated to provide the title compound which could be used directly in the next step without further purification.

Example 52C 3-(1-ethylpiperidin-4-yl)-6-fluoro-4-methyl-4H-benzo[4,5]imidazo[1,2-b]pyrazole-8-carboxamide

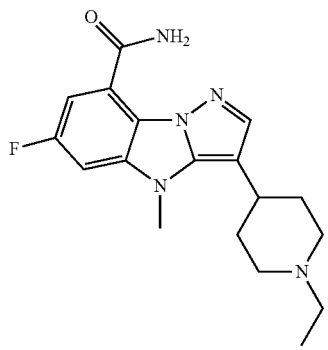

This example was prepared as the method described in Example 51D. $^1$H-NMR (400 MHz, METHANOL-d4) δ ppm 1.23-1.26 (t, 3H), 1.91-1.97 (m, 2H), 2.11-2.14 (d, 2H), 2.55 (t, 2H), 2.78-2.80 (m, 2H), 3.04-3.07 (m, 2H), 3.32 (2H), 3.87 (s, 2H), 7.48-8.50 (m, 1H), 7.64-7.67 (m, 1H), 7.73 (s, 1H), 8.54 (s, 1H). LCMS (ESI) m/z: 344 (M+1).

Scheme C

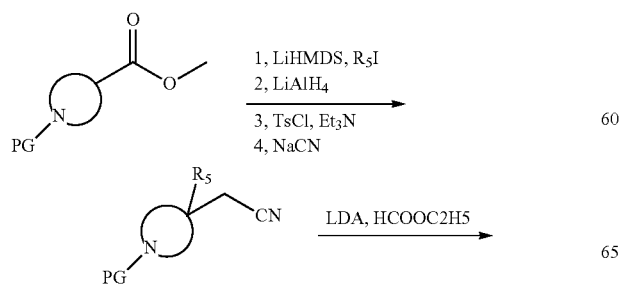

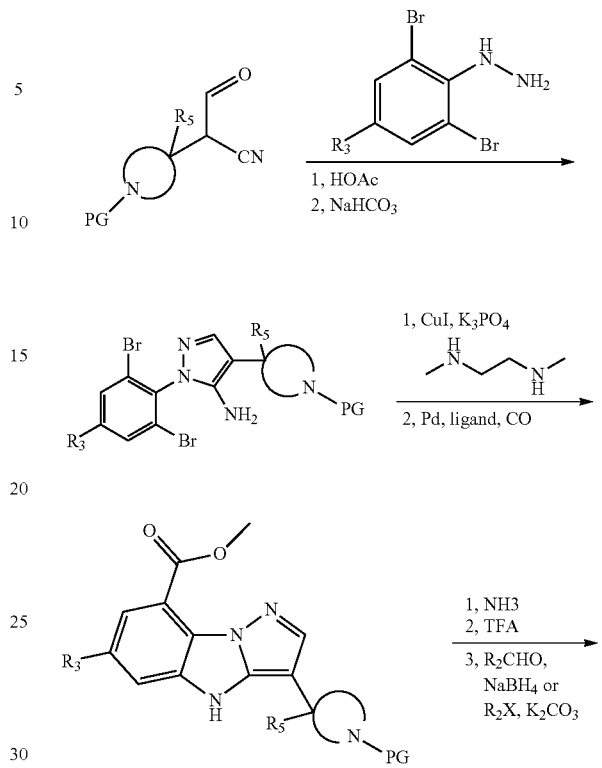

Example 53

6-fluoro-3-(4-methylpiperidin-4-yl)-4H-benzo[4,5]imidazo[1,2-b]pyrazole-8-carboxamide

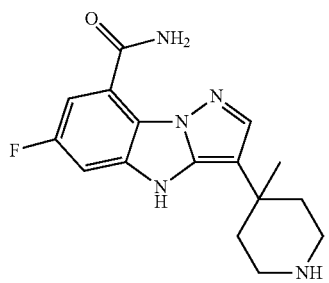 [SMILES: CC1(c2cnn3c2[nH]c2cc(F)cc(C(N)=O)c23)CCNCC1]

Example 53A 1-(tert-butyl) 4-methyl 4-methylpiperidine-1,4-dicarboxylate

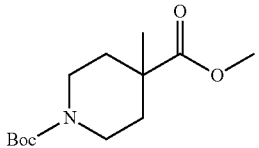

To a solution of 1-tert-butyl 4-methyl piperidine-1,4-dicarboxylate (36.5 g, 0.15 mol) in anhydrous THF (400 mL) was added dropwise LiHMDS (1 M, 300 mL) at −78° C. under N₂ atmosphere. After stirring at −78° C. for 30 min, a solution of MeI (42.6 g, 0.3 mol) in THF (100 mL) was added dropwise thereto. The reaction mixture was stirred at −78° C. for 2 hours and warmed to 15° C. and stirred for further 20 hours. After completion of the reaction, the mixture was quenched with sat aq NH₄Cl solution (500 mL). The aqueous layer was extracted with EtOAc (500 mL×3). The combined organic layers were dried over Na₂SO₄, filtered and evaporated. The residue was purified by column chromatograph to provide the title compound (30 g, yield: 78%). LCMS (ESI) m/z: 258 (M+1).

Example 53B tert-butyl 4-(hydroxymethyl)-4-methylpiperidine-1-carboxylate

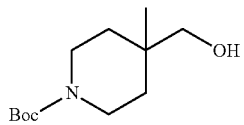 [SMILES: CC1(CC#N)CCN(C(=O)OC(C)(C)C)CC1]

To a solution of LiAlH₄ (3.7 g, 97.5 mmol) in anhydrous THF (40 mL) was added dropwise a solution of EXAMPLE 53A (10 g, 39 mmol) in anhydrous THF (80 mL) at 0° C. under N₂ atmosphere. After the dropwise addition was completed, the reaction mixture was stirred at 0° C. for 2.5 hours, and then quenched with water (4 mL), 15% aq NaOH solution (4 mL) and water (12 mL). The resultant mixture was stirred at 0° C. for further 20 minutes. The mixture was filtered and the solid was washed with EtOAc (50 mL×4). The combined organic layers were dried over Na₂SO₄, filtered and evaporated to provide the title compound (9 g, crude) which could be used directly in the next step without further purification.

Example 53C tert-butyl 4-(cyanomethyl)-4-methylpiperidine-1-carboxylate

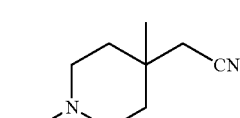

This example was prepared as the method described in Examples 1A-1B.

Example 53D 6-fluoro-3-(4-methylpiperidin-4-yl)-4H-benzo[4,5]imidazo[1,2-b]pyrazole-8-carboxamide

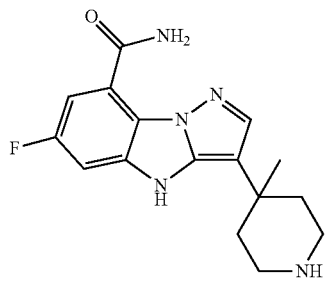 [SMILES: CC1(c2cnn3c2[nH]c2cc(F)cc(C(N)=O)c23)CCNCC1]

This example was prepared as described in Examples 1E-1J. ¹H NMR (400 MHz, MeOD) δ: 8.51 (s, 1H), 7.81 (s, 1H), 7.69 (dd, J=2.4 Hz/J=10.2 Hz, 1H), 7.45 (dd, J=2.4 Hz/J=8.0 Hz, 1H), 3.33-3.39 (m, 2H), 3.12-3.32 (m, 2H), 2.42-2.46 (m, 2H), 2.03-2.08 (m, 2H), 1.46 (s, 3H). LCMS (ESI) m/z: 316 (M+1).

Example 54

3-(1-ethyl-4-methylpiperidin-4-yl)-6-fluoro-4H-benzo[4,5]imidazo[1,2-b]pyrazole-8-carboxamide

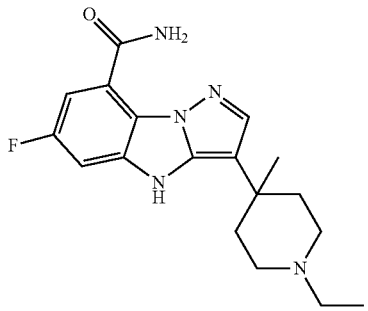 [SMILES: CCN1CCC(C)(c2cnn3c2[nH]c2cc(F)cc(C(N)=O)c23)CC1]

This example was prepared as described in Example 52C (10 g, yield: 38%). ¹H NMR (400 MHz, DMSO) δ: 10.58 (s, 1H), 8.28 (s, 1H), 8.13 (s, 1H), 7.80 (s, 1H), 7.61 (dd, J=2.8 Hz/J=7.2 Hz, 1H), 7.49 (t, J=2.4 Hz, 1H), 2.75-2.78 (m, 2H), 2.50-2.54 (m, 4H), 2.18-2.20 (m, 2H), 1.73-1.78 (m, 2H), 1.30 (s, 3H), 1.05 (t, J=7.2 Hz, 3H). LCMS (ESI) m/z: 344 (M+1).

Example 55

3-(1-cyclopropyl-4-methylpiperidin-4-yl)-6-fluoro-4H-benzo[4,5]imidazo[1,2-b]pyrazole-8-carboxamide

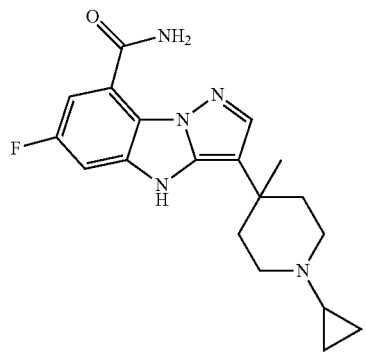 [SMILES: CC1(c2cnn3c2[nH]c2cc(F)cc(C(N)=O)c23)CCN(C2CC2)CC1]

This example was prepared as described in Example 4. $^1$H-NMR (400 MHz, MethanoL-d$_4$) 0.77 (d, J=5.40 Hz, 4H), 1.41-1.45 (m, 3H), 1.90-2.01 (m, 2H), 2.28-2.44 (m, 3H), 3.03 (br. s., 2H), 3.27 (br. s., 2H), 7.39 (dd, J=8.16, 2.51 Hz, 1H), 7.73 (dd, J=10.92, 2.38 Hz, 1H), 7.79 (s, 1H), 8.41 (br. s., 1H). LCMS (ESI) m/z: 356 (M+1).

Example 56

6-fluoro-3-(1-(2-hydroxy-2-methylpropyl)-4-methylpiperidin-4-yl)-4H-benzo[4,5]imidazo[1,2-b]pyrazole-8-carboxamide

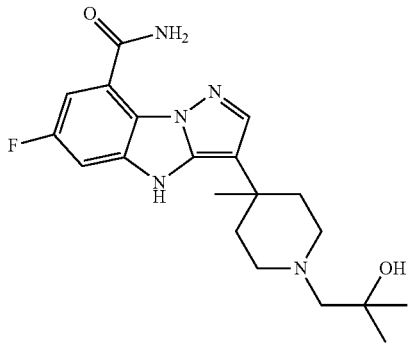 [SMILES: CC(C)(O)CN1CCC(C)(c2cnn3c2[nH]c2cc(F)cc(C(N)=O)c23)CC1]

This example was prepared as the method described in Example 6. $^1$H-NMR (400 MHz, DMSO-d$_4$) δ ppm 1.13 (s, 6H), 1.28 (s, 3H), 1.86 (t, J=10.23 Hz, 2H), 2.20 (d, J=15.43 Hz, 2H), 2.62 (s, 2H), 2.76 (br. s., 2H), 3.04 (d, J=4.02 Hz, 2H), 7.48 (dd, J=8.34, 2.57 Hz, 1H), 7.56 (dd, J=10.92, 2.64 Hz, 1H), 7.79 (s, 1H), 8.31 (s, 1H). LCMS (ESI) m/z: 388 (M+1).

Example 57

3-(1-(cyclopropylmethyl)-4-methylpiperidin-4-yl)-6-fluoro-4H-benzo[4,5]imidazo[1,2-b]pyrazole-8-carboxamide

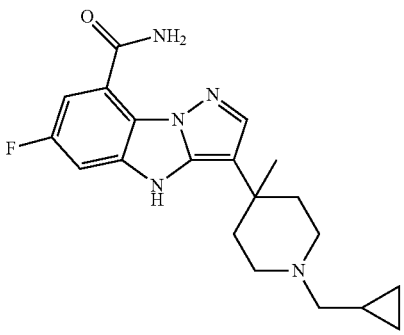 [SMILES: CC1(c2cnn3c2[nH]c2cc(F)cc(C(N)=O)c23)CCN(CC2CC2)CC1]

This example was prepared as the method described in Example 5. $^1$H-NMR (400 MHz, MethanoL-d$_4$) δ ppm 0.37 (d, J=3.89 Hz, 2H), 0.73 (d, J=7.53 Hz, 2H), 1.02-1.14 (m, 1H), 1.44 (br. s., 3H), 2.08 (d, J=11.29 Hz, 2H), 2.37-2.66 (m, 2H), 2.94 (br. s., 3H), 3.34-3.63 (m, 3H), 7.38 (dd, J=8.09, 2.57 Hz, 1H), 7.71 (dd, J=10.92, 2.51 Hz, 1H), 7.79 (s, 1H), 7.77-7.81 (m, 1H), 8.51 (s, 1H). LCMS (ESI) m/z: 370 (M+1).

Example 58

3-(1-(4,4-difluorocyclohexyl)-4-methylpiperidin-4-yl)-6-fluoro-4H-benzo[4,5]imidazo[1,2-b]pyrazole-8-carboxamide

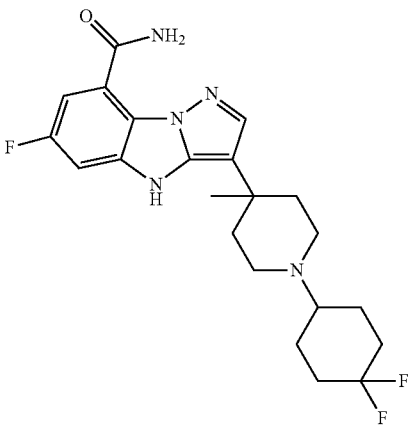 [SMILES: CC1(c2cnn3c2[nH]c2cc(F)cc(C(N)=O)c23)CCN(C2CCC(F)(F)CC2)CC1]

This example was prepared as the method described in Example 5. $^1$H-NMR (400 MHz, DMSO-d$_4$) δ ppm 1.22 (s, 3H), 1.33-1.49 (m, 1H), 1.70 (br. s., 6H), 1.92-2.12 (m, 1H), 2.31-2.38 (m, 1H), 2.59-2.64 (m, 1H), 7.40-7.62 (m, 2H), 7.74 (s, 1H). LCMS (ESI) m/z: 434 (M+1).

Example 59

6-fluoro-3-(4-methyl-1-(tetrahydro-2H-pyran-4-yl)piperidin-4-yl)-4H-benzo[4,5]imidazo[1,2-b]pyrazole-8-carboxamide

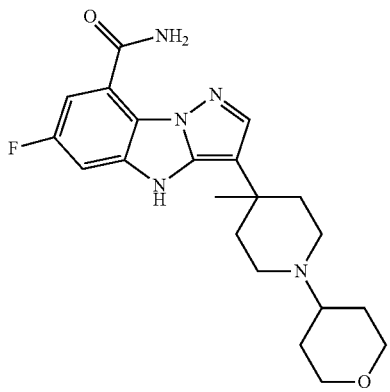 [SMILES: CC1(c2cnn3c2[nH]c2cc(F)cc(C(N)=O)c23)CCN(C2CCOCC2)CC1]

This example was prepared as the method described in Example 5. $^1$H NMR (400 MHz, METHANOL-$d_4$) 1.05 (t, J=7.22 Hz, 1H), 1.36 (s, 3H), 1.50-1.60 (m, 1H), 1.82 (d, J=11.92 Hz, 3H), 2.21-2.27 (m, 1H), 2.44-2.56 (m, 1H), 2.79 (br. s., 2H), 3.35-3.42 (m, 1H), 3.90-4.05 (m, 1H), 7.32-7.38 (m, 1H), 7.71 (s, 1H). LCMS (ESI) m/z: 400 (M+1).

Example 60

6-fluoro-3-(1-(2-fluoroethyl)-4-methylpiperidin-4-yl)-4H-benzo[4,5]imidazo[1,2-b]pyrazole-8-carboxamide

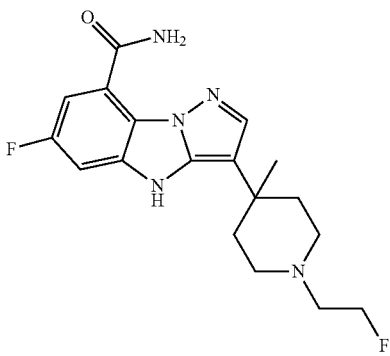 [SMILES: CC1(c2cnn3c2[nH]c2cc(F)cc(C(N)=O)c23)CCN(CCF)CC1]

This example was prepared as the method described in Example 3. $^1$H NMR (400 MHz, METHANOL-$d_4$) ppm 1.45 (s, 3H), 2.01-2.05 (m, 2H), 2.24-2.47 (m, 2H), 3.05 (m, 2H), 3.24-3.25 (m, 1H), 3.26-3.27 (m, 1H), 3.33-3.34 (m, 1H), 4.70-4.72 (m, 1H), 4.82-4.93 (m, 1H), 7.37-7.39 (m, 1H), 7.68-7.79 (d, 1H), 7.81 (s, 1H), 8.45 (br. s., 1H). LCMS (ESI) m/z: 362 (M+1).

Example 61

6-fluoro-3-(4-methyl-1-(2,2,2-trifluoroethyl)piperidin-4-yl)-4H-benzo[4,5]imidazo[1,2-b]pyrazole-8-carboxamide

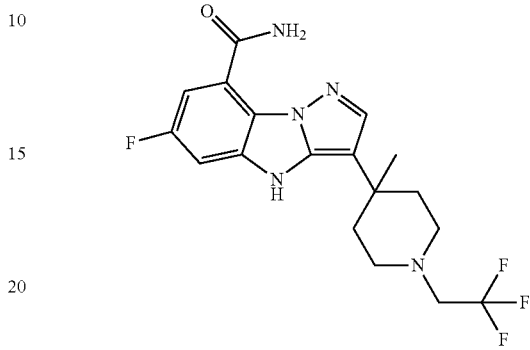

This example was prepared as the method described in Example 3. $^1$H NMR (400 MHz, METHANOL-$d_4$) ppm 1.37 (s, 3H), 1.79-1.91 (m, 2H), 2.16-2.27 (m, 2H), 2.58-2.69 (m, 2H), 2.79-2.89 (m, 2H), 2.98-3.10 (m, 2H), 7.33-7.39 (m, 1H), 7.66-7.75 (m, 2H). LCMS (ESI) m/z: 398 (M+1).

Example 62

6-fluoro-3-(4-methyl-1-(3,3,3-trifluoropropyl)piperidin-4-yl)-4H-benzo[4,5]imidazo[1,2-b]pyrazole-8-carboxamide

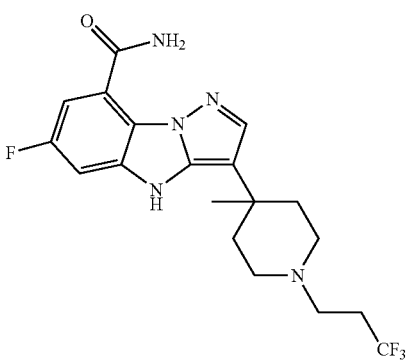 [SMILES: CC1(c2cnn3c2[nH]c2cc(F)cc(C(N)=O)c23)CCN(CCC(F)(F)F)CC1]

This example was prepared as the method described in Example 3. $^1$H NMR (400 MHz, METHANOL-$d_4$) 1.42 (s, 3H), 1.92-2.05 (m, 2H), 2.38 (d, J=14.93 Hz, 2H), 2.54-2.71 (m, 2H), 2.86 (d, J=9.79 Hz, 2H), 2.93-3.07 (m, 2H), 3.14 (d, J=11.17 Hz, 2H), 7.37 (dd, J=8.16, 2.51 Hz, 1H), 7.70 (dd, J=10.92, 2.51 Hz, 1H), 7.76 (s, 1H), 8.37 (br. s., 1H). LCMS (ESI) m/z: 412 (M+1).

Example 63

3-(1-((1-cyanocyclopropyl)methyl)-4-methylpiperidin-4-yl)-6-fluoro-4H-benzo[4,5]imidazo[1,2-b]pyrazole-8-carboxamide

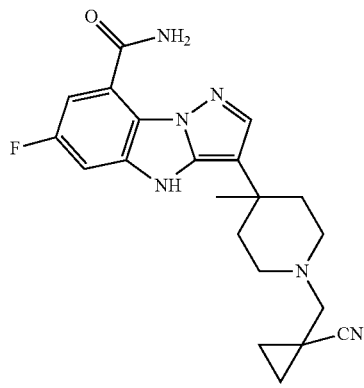 [SMILES: CC1(c2cnn3c2[nH]c2cc(F)cc(C(N)=O)c23)CCN(CC2(C#N)CC2)CC1]

This example was prepared as the method described in Example 3. ¹H NMR (400 MHz, METHANOL-d₄) δ ppm 1.05 (d, J=2.26 Hz, 2H), 1.32-1.38 (m, 2H), 1.40 (s, 3H), 1.89-2.05 (m, 2H), 2.33 (d, J=15.69 Hz, 2H), 2.69 (s, 4H), 3.02 (br. s., 2H), 7.38 (dd, J=8.09, 2.57 Hz, 1H), 7.68-7.83 (m, 2H), 8.28 (br. s., 1H). LCMS (ESI) m/z: 395 (M+1).

Example 64

3-(1-((1-cyanocyclobutyl)methyl)-4-methylpiperidin-4-yl)-6-fluoro-4H-benzo[4,5]imidazo[1,2-b]pyrazole-8-carboxamide

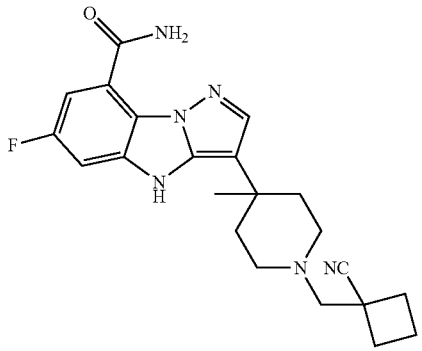 [SMILES: CC1(c2cnn3c2[nH]c2cc(F)cc(C(N)=O)c23)CCN(CC2(C#N)CCC2)CC1]

This example was prepared as the method described in Example 3. ¹H NMR (400 MHz, METHANOL-d₄) 1.38 (s, 3H), 1.85-1.94 (m, 2H), 2.00-2.09 (m, 1H), 2.18-2.31 (m, 5H), 2.42-2.52 (m, 2H), 2.63 (t, J=9.22 Hz, 2H), 2.81 (s, 2H), 2.88 (d, J=5.65 Hz, 2H), 7.36 (dd, J=8.03, 2.26 Hz, 1H), 7.69 (d, J=2.26 Hz, 1H), 7.73 (s, 1H), 8.30 (br. s., 1H). LCMS (ESI) m/z: 409 (M+1).

Example 65

6-fluoro-3-(4-methyl-1-(2-(methylsulfonyl)ethyl)piperidin-4-yl)-4H-benzo[4,5]imidazo[1,2-b]pyrazole-8-carboxamide

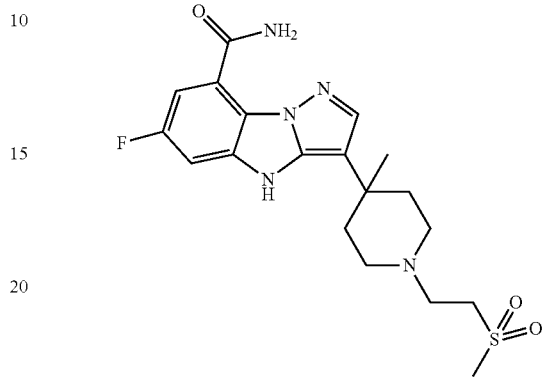

This example was prepared as the method described in Example 3. ¹H NMR (400 MHz, METHANOL-d₄) ppm 1.40 (s, 3H), 1.87-1.98 (m, 2H), 2.28-2.38 (m, 2H), 2.63-2.80 (m, 2H), 2.95-3.05 (m, 2H), 3.07 (s, 3H), 3.07-3.14 (m, 2H), 3.38-3.47 (m, 2H), 7.33-7.40 (m, 1H), 7.66-7.73 (m, 1H), 7.73-7.77 (m, 1H), 8.20-8.37 (m, 1H). LCMS (ESI) m/z: 422 (M+1).

Example 66

6-fluoro-3-(4-methyl-1-((tetrahydro-2H-pyran-4-yl)methyl)piperidin-4-yl)-4H-benzo[4,5]imidazo[1,2-b]pyrazole-8-carboxamide

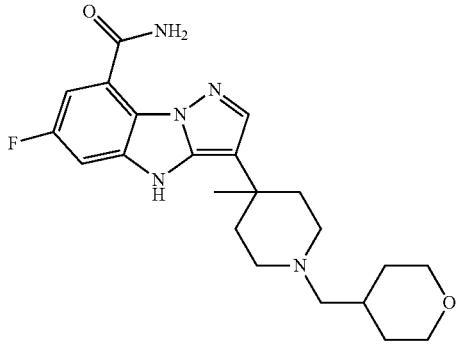 [SMILES: CC1(c2cnn3c2[nH]c2cc(F)cc(C(N)=O)c23)CCN(CC2CCOCC2)CC1]

This example was prepared as the method described in Example 3. ¹H NMR (400 MHz, METHANOL-d₄) 1.25-1.33 (m, 2H), 1.37 (s, 3H), 1.70 (d, J=13.30 Hz, 2H), 1.80-1.89 (m, 3H), 2.22 (br. s., 2H), 2.23 (br. s., 2H), 2.38 (br. s., 2H), 2.67 (br. s., 2H), 3.40-3.47 (m, 2H), 3.94 (dd, J=11.67, 2.89 Hz, 2H), 7.36 (dd, J=8.16, 2.51 Hz, 1H), 7.69 (d, J=2.51 Hz, 1H), 7.72 (br. s., 1H). LCMS (ESI) m/z: 414 (M+1).

Example 67

3-(1-((1-aminocyclopropyl)methyl)-4-methylpiperidin-4-yl)-6-fluoro-4H-benzo[4,5]imidazo[1,2-b]pyrazole-8-carboxamide

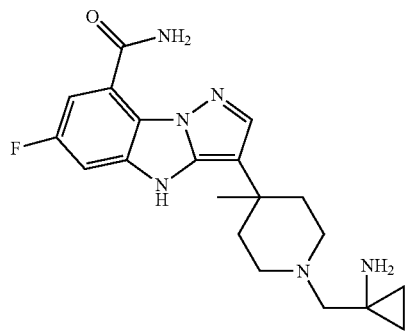 [SMILES: CC1(c2cnn3c2[nH]c2cc(F)cc(C(N)=O)c23)CCN(CC2(N)CC2)CC1]

This example was prepared as the method described in Example 3. $^1$H NMR (400 MHz, METHANOL-$d_4$) ppm 0.72-0.82 (m, 2H), 0.93-1.00 (m, 2H), 1.40 (s, 3H), 1.91-2.03 (m, 2H), 2.26-2.37 (m, 2H), 2.66 (s, 4H), 2.94-3.06 (m, 2H), 7.33-7.41 (m, 1H), 7.67-7.73 (m, 1H), 7.73-7.77 (m, 1H), 8.22-8.48 (m, 2H). LCMS (ESI) m/z: 385 (M+1).

Example 68

6-fluoro-3-(4-methyl-1-(oxetan-3-ylmethyl)piperidin-4-yl)-4H-benzo[4,5]imidazo[1,2-b]pyrazole-8-carboxamide

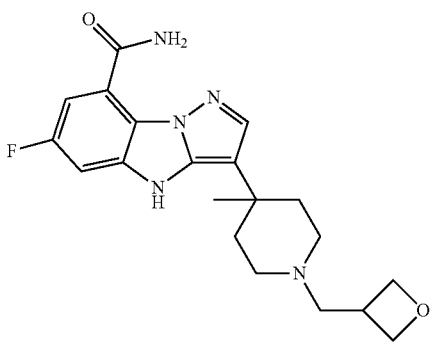 [SMILES: CC1(c2cnn3c2[nH]c2cc(F)cc(C(N)=O)c23)CCN(CC2COC2)CC1]

This example was prepared as the method described in Example 3. $^1$H NMR (400 MHz, CHLOROFORM-d) ppm 1.36 (s, 3H), 1.78-1.88 (m, 2H), 2.17-2.25 (m, 2H), 2.36 (br. s., 2H), 2.57-2.68 (m, 2H), 2.72 (d, J=7.03 Hz, 2H), 4.38-4.47 (m, 2H), 4.60-4.63 (m, 1H), 4.80-4.82 (m, 2H), 7.33-7.39 (m, 1H), 7.68-7.76 (m, 2H). LCMS (ESI) m/z: 386 (M+1).

Example 69

6-fluoro-3-(1-(2-methoxyethyl)-4-methylpiperidin-4-yl)-4H-benzo[4,5]imidazo[1,2-b]pyrazole-8-carboxamide

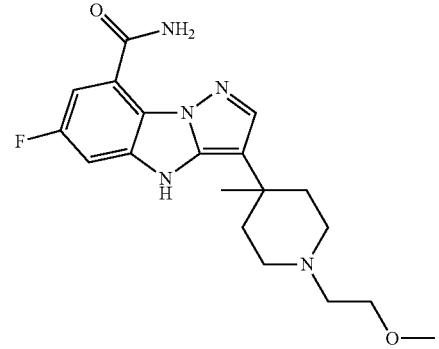 [SMILES: COCCN1CCC(C)(c2cnn3c2[nH]c2cc(F)cc(C(N)=O)c23)CC1]

This example was prepared as the method described in Example 3. $^1$H NMR (400 MHz, METHANOL-$d_4$) 1.45 (s, 3H), 2.07 (ddd, J=14.68, 10.85, 3.58 Hz, 2H), 2.46 (d, J=14.81 Hz, 2H), 3.12 (br. s., 2H), 3.23 (t, J=4.83 Hz, 2H), 3.41 (s, 5H), 3.66-3.73 (m, 2H), 7.39 (dd, J=8.16, 2.51 Hz, 1H), 7.71 (dd, J=10.92, 2.51 Hz, 1H), 7.80 (s, 1H), 8.52 (s, 1H). LCMS (ESI) m/z: 374 (M+1).

Example 70

6-fluoro-3-(1-((1-hydroxycyclopropyl)methyl)-4-methylpiperidin-4-yl)-4H-benzo[4,5]imidazo[1,2-b]pyrazole-8-carboxamide

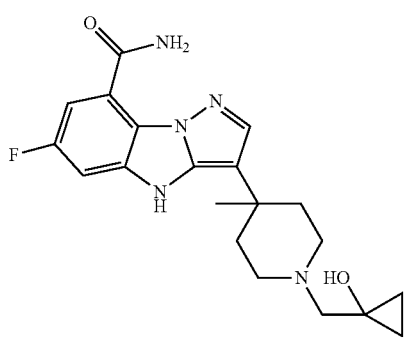 [SMILES: CC1(c2cnn3c2[nH]c2cc(F)cc(C(N)=O)c23)CCN(CC2(O)CC2)CC1]

This example was prepared as the method described in Example 3. $^1$H NMR (400 MHz, METHANOL-$d_4$) δ ppm 0.64-0.74 (m, 2H), 0.84-0.93 (m, 2H), 1.46 (s, 3H), 2.04-2.18 (m, 2H), 2.50 (d, J=15.18 Hz, 2H), 3.16 (br. s., 4H), 3.47-3.68 (m, 2H), 7.36-7.43 (m, 1H), 7.68-7.75 (m, 1H), 7.79-7.84 (m, 1H), 8.48-8.65 (m, 1H). LCMS (ESI) m/z: 386 (M+1).

Example 71

6-fluoro-3-(4-methyl-methyl-((3-methyloxetan-3-yl)methyl)piperidin-4-yl)-4H-benzo[4,5]imidazo[1,2-b]pyrazole-8-carboxamide

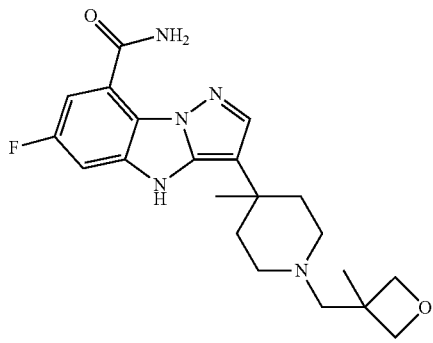 [SMILES: CC1(CN2CCC(C)(c3cnn4c3[nH]c3cc(F)cc(C(N)=O)c34)CC2)COC1]

This example was prepared as the method described in Example 3. $^1$H NMR (400 MHz, METHANOL-$d_4$) ppm 1.38 (s, 3H), 1.46 (s, 3H), 1.81-1.93 (m, 2H), 2.18-2.29 (m, 2H), 2.33-2.54 (m, 2H), 2.54-2.84 (m, 4H), 4.31-4.35 (m, 2H), 4.49-4.54 (m, 2H), 7.34-7.39 (m, 1H), 7.68-7.75 (m, 2H). LCMS (ESI) m/z: 400 (M+1).

Example 72

6-fluoro-3-(1-(3-methoxypropyl)-4-methylpiperidin-4-yl)-4H-benzo[4,5]imidazo[1,2-b]pyrazole-8-carboxamide

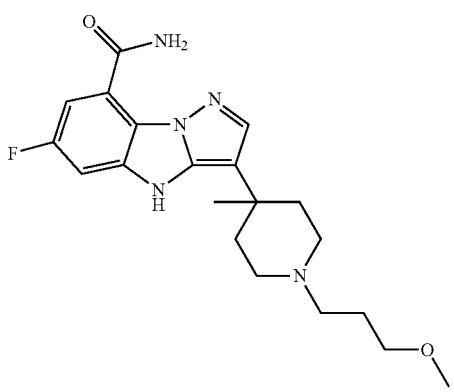 [SMILES: COCCCN1CCC(C)(c2cnn3c2[nH]c2cc(F)cc(C(N)=O)c23)CC1]

This example was prepared as the method described in Example 3. $^1$H NMR (400 MHz, METHANOL-$d_4$) 1.45 (s, 3H), 1.94-2.01 (m, 2H), 2.02-2.12 (m, 2H), 2.47 (d, J=13.05 Hz, 2H), 2.89-3.20 (m, 4H), 3.34 (s, 3H), 3.39 (br. s., 2H), 3.45-3.52 (m, 2H), 7.38 (dd, J=8.09, 2.57 Hz, 1H), 7.71 (dd, J=10.92, 2.51 Hz, 1H), 7.79 (s, 1H), 8.55 (s, 1H). LCMS (ESI) m/z: 434 (M+1).

Example 73

6-fluoro-3-(4-methyl-1-((1-(methylsulfonyl)cyclopropyl)methyl)piperidin-4-yl)-4H-benzo[4,5]imidazo[1,2-b]pyrazole-8-carboxamide

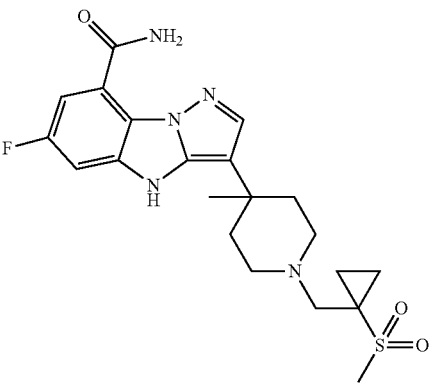 [SMILES: CC1(c2cnn3c2[nH]c2cc(F)cc(C(N)=O)c23)CCN(CC2(S(C)(=O)=O)CC2)CC1]

This example was prepared as the method described in Example 3. $^1$H NMR (400 MHz, METHANOL-$d_4$) 0.95-1.01 (m, 2H), 1.38 (s, 3H), 1.41-1.49 (m, 2H), 1.83-1.96 (m, 2H), 2.27 (d, J=13.30 Hz, 2H), 2.55 (br. s., 2H), 2.86 (s, 2H), 2.92 (br. s., 2H), 3.24 (s, 3H), 7.36 (dd, J=8.16, 2.51 Hz, 1H), 7.67-7.78 (m, 2H). LCMS (ESI) m/z: 448 (M+1).

Example 74

6-fluoro-3-(4-methyl-1-(thiazol-2-ylmethyl)piperidin-4-yl)-4H-benzo[4,5]imidazo[1,2-b]pyrazole-8-carboxamide

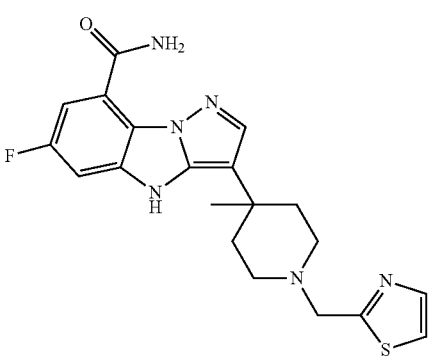 [SMILES: CC1(c2cnn3c2[nH]c2cc(F)cc(C(N)=O)c23)CCN(Cc2nccs2)CC1]

This example was prepared as the method described in Example 3. $^1$H NMR (400 MHz, METHANOL-$d_4$) ppm 1.36-1.42 (m, 3H), 1.86-1.97 (m, 2H), 2.23-2.33 (m, 2H), 2.63-2.73 (m, 2H), 2.89-2.98 (m, 2H), 4.02-4.07 (m, 2H), 7.32-7.40 (m, 1H), 7.58-7.63 (m, 1H), 7.68-7.73 (m, 1H), 7.74 (s, 1H), 7.75-7.79 (m, 1H), 8.25-8.35 (m, 1H). LCMS (ESI) m/z: 413 (M+1).

Example 75

6-fluoro-3-(4-methyl-1-(methylsulfonyl)piperidin-4-yl)-4H-benzo[4,5]imidazo[1,2-b]pyrazole-8-carboxamide

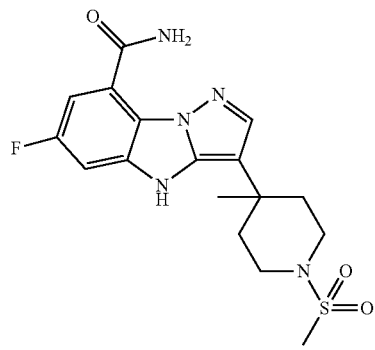 [SMILES: CC1(c2cnn3c2[nH]c2cc(F)cc(C(N)=O)c23)CCN(S(C)(=O)=O)CC1]

This example was prepared as the method described in Example 3. ¹H-NMR (MeOD, 400 MHz) δ: 1.38-1.46 (m, 3H), 1.88 (ddd, J=13.68, 9.66, 3.76 Hz, 2H), 2.32 (d, J=15.06 Hz, 2H), 2.78 (s, 3H), 3.00-3.17 (m, 2H), 3.46-3.53 (m, 2H), 7.35-7.41 (m, 1H), 7.69-7.75 (m, 1H), 7.77-7.79 (m, 1H), 8.46-8.53 (m, 1H). LCMS (ESI) m/z: 394 (M+1).

Example 76

6-fluoro-3-(1-(3-fluorocyclobutyl)-4-methylpiperidin-4-yl)-4H-benzo[4,5]imidazo[1,2-b]pyrazole-8-carboxamide

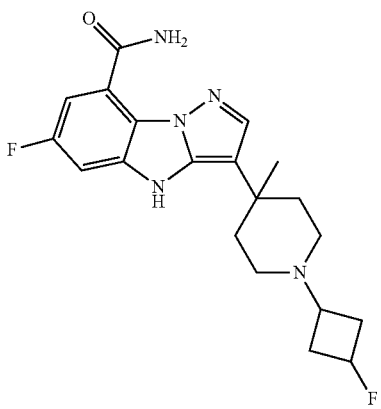 [SMILES: CC1(c2cnn3c2[nH]c2cc(F)cc(C(N)=O)c23)CCN(C2CC(F)C2)CC1]

This example was prepared as the method described in Example 2. ¹H-NMR (400 MHz, MethanoL-d₄) δ ppm 1.45 (s, 3H), 1.96-2.18 (m, 2H), 2.38-2.74 (m, 6H), 2.94 (br. s., 4H), 3.74-3.93 (m, 1H), 5.12-5.32 (m, 1H), 7.41 (dd, J=8.16, 2.38 Hz, 1H), 7.67 (dd, J=10.79, 2.26 Hz, 1H), 7.79 (s, 1H), 8.52 (br. s., 1H). LCMS (ESI) m/z: 388 (M+1).

Example 77

6-fluoro-3-(4-methyl-1-(thiophen-2-ylmethyl)piperidin-4-yl)-4H-benzo[4,5]imidazo[1,2-b]pyrazole-8-carboxamide

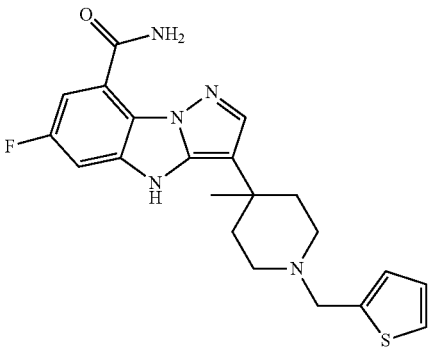

This example was prepared as the method described in Example 2. ¹H NMR (400 MHz, METHANOL-d₄) 1.34 (s, 3H), 1.82 (ddd, J=13.36, 9.41, 3.45 Hz, 2H), 2.13-2.27 (m, 1H), 2.32-2.53 (m, 1H), 2.69 (br. s., 2H), 3.72 (s, 2H), 6.87-7.01 (m, 2H), 7.25-7.39 (m, 2H), 7.62-7.75 (m, 2H). LCMS (ESI) m/z: 412 (M+1).

Example 78

3-(1-((1-ethylpiperidin-4-yl)methyl)-4-methylpiperidin-4-yl)-6-fluoro-4H-benzo[4,5]imidazo[1,2-b]pyrazole-8-carboxamide

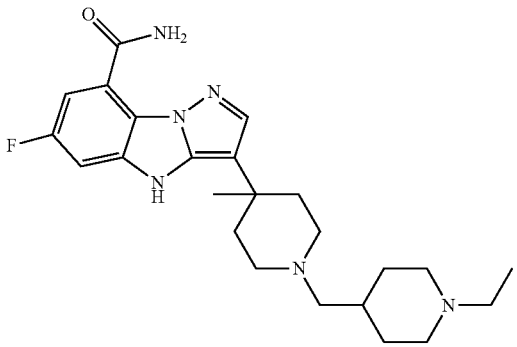 [SMILES: CCN1CCC(CN2CCC(C)(c3cnn4c3[nH]c3cc(F)cc(C(N)=O)c34)CC2)CC1]

This example was prepared as the method described in Example 2. ¹H-NMR (400 MHz, METHANOL-d4) δ ppm 1.32-1.35 (t, 3H), 1.42 (s, 3H), 1.47-1.51 (d, 2H), 1.99-2.08 (m, 5H), 2.35-2.38 (d, 2H), 2.64-2.65 (d, 2H), 2.89 (m, 2H), 3.06 (t, 2H), 3.11-3.15 (m, 4H), 3.51-3.54 (d, 2H), 7.37-7.39 (m, 1H), 7.70-7.74 (m, 1H), 7.77 (s, 1H), 8.446 (s, 2H). LCMS (ESI) m/z: 441 (M+1).

Example 79

6-fluoro-3-(4-methyl-1-((1-methylazetidin-3-yl)methyl)piperidin-4-yl)-4H-benzo[4,5]imidazo[1,2-b]pyrazole-8-carboxamide

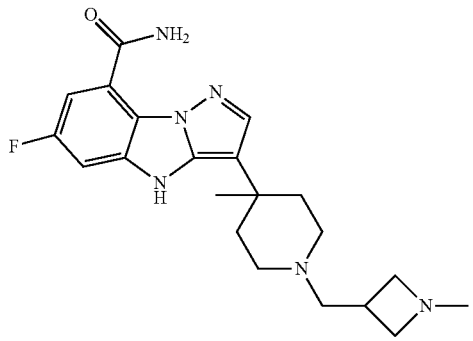 [SMILES: CN1CC(CN2CCC(C)(c3cnn4c3[nH]c3cc(F)cc(C(N)=O)c34)CC2)C1]

This example was prepared as the method described in Example 2. $^1$H-NMR (400 MHz, METHANOL-d4) δ ppm 1.32 (s, 3H), 1.89-1.95 (m, 2H), 2.29-2.33 (d, 2H), 2.60 (d, 2H), 2.86-2.91, 2.64-2.65 (m, 7H), 3.18 (m, 1H), 3.84-3.88 (t, 2H), 4.15-4.20 (t, 2H), 7.36-7.39 (m, 1H), 7.70-7.73 (m, 1H), 7.77 (s, 1H), 8.41 (s, 2H). LCMS (ESI) m/z: 399 (M+1).

Example 80 ethyl 2-((4-(8-carbamoyl-6-fluoro-4H-benzo[4,5]imidazo[1,2-b]pyrazol-3-yl)-4-methylpiperidin-1-yl)methyl)cyclopropanecarboxylate

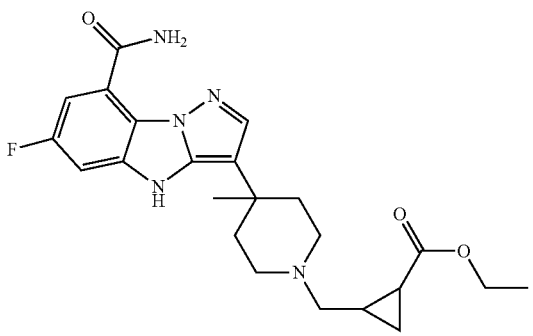 [SMILES: CCOC(=O)C1CC1CN1CCC(C)(c2cnn3c2[nH]c2cc(F)cc(C(N)=O)c23)CC1]

This example was prepared as the method described in Example 2. $^1$H NMR (400 MHz, METHANOL-d$_4$) 0.86-1.34 (m, 6H), 1.35-1.49 (m, 2H), 1.57-2.01 (m, 4H), 2.09-2.28 (m, 2H), 2.44-2.70 (m, 2H), 2.99-3.27 (m, 2H), 3.36-3.47 (m, 2H), 3.53-3.75 (m, 2H), 4.06-4.26 (m, 3H), 7.50-7.65 (m, 1H), 7.74-7.85 (m, 1H), 8.05 (br. s., 1H). LCMS (ESI) m/z: 442 (M+1).

Example 81 ethyl 3-(1-((2-(dimethylcarbamoyl)cyclopropyl)methyl)-4-methylpiperidin-4-yl)-6-fluoro-4H-benzo[4,5]imidazo[1,2-b]pyrazole-8-carboxamide

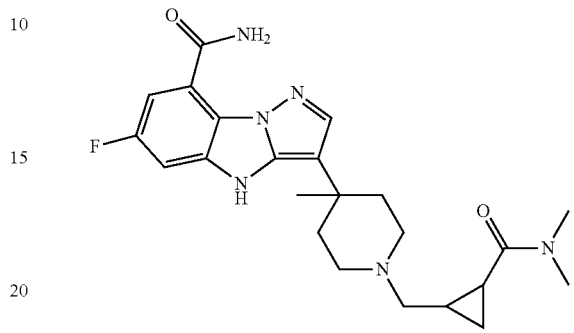

This example was prepared as the method described in Example 2. $^1$H NMR (400 MHz, METHANOL-d$_4$) 0.97-1.29 (m, 2H), 1.47 (s, 2H), 1.65 (s, 1H), 2.08-2.30 (m, 3H), 2.63 (d, J=15.3 Hz, 1H), 2.85 (s, 1H), 2.92-3.01 (m, 3H), 3.01-3.12 (m, 2H), 3.12-3.27 (m, 2H), 3.29 (s, 2H), 3.34-3.47 (m, 2H), 3.55-3.77 (m, 2H), 7.56-7.70 (m, 1H), 7.78-7.85 (m, 1H), 8.12 (d, J=6.5 Hz, 1H). LCMS (ESI) m/z: 441 (M+1).

Example 82

6-fluoro-3-(1-isobutyl-4-methylpiperidin-4-yl)-4H-benzo[4,5]imidazo[1,2-b]pyrazole-8-carboxamide

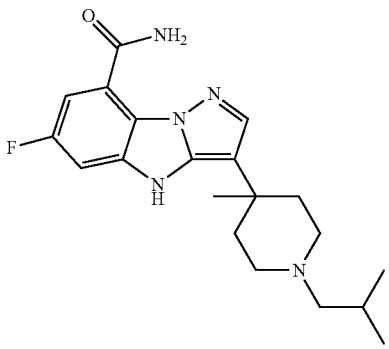 [SMILES: CC(C)CN1CCC(C)(c2cnn3c2[nH]c2cc(F)cc(C(N)=O)c23)CC1]

This example was prepared as the method described in Example 2. $^1$H-NMR (MeOD, 400 MHz) δ: 1.00-1.02 (d, 6H), 1.43 (s, 3H), 2.03-2.07 (m, 3H), 2.10-2.11 (d, 2H), 2.81-2.83 (d, 2H), 3.03 (bs, 2H), 3.31 (bs, 2H), 7.35-7.38 (dd, 1H), 7.67-7.71 (s, 1H), 7.77 (s, 1H), 8.53 (bs, 1H). LCMS (ESI) m/z: 372 (M+1).

Example 83

6-fluoro-3-(4-methyl-1-((4-methylthiazol-5-yl)methyl)piperidin-4-yl)-4H-benzo[4,5]imidazo[1,2-b]pyrazole-8-carboxamide

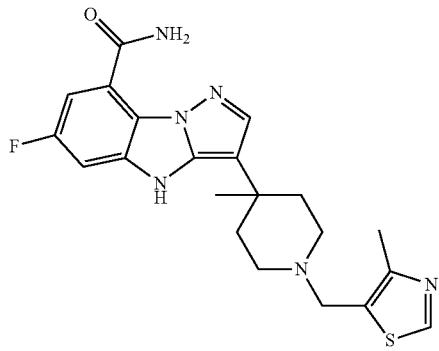 [SMILES: Cc1ncsc1CN1CCC(C)(c2cnn3c2[nH]c2cc(F)cc(C(N)=O)c23)CC1]

This example was prepared as the method described in Example 2. $^1$H NMR (400 MHz, METHANOL-d4) δ ppm 1.41 (s, 3H), 1.89-2.01 (m, 2H), 2.30-2.39 (m, 2H), 2.43 (s, 3H), 2.73-2.86 (m, 2H), 2.97-3.15 (m, 2H), 4.01-4.20 (m, 2H), 7.30-7.47 (m, 1H), 7.65-7.86 (m, 2H), 8.90-9.04 (m, 1H). LCMS (ESI) m/z: 427 (M+1).

Example 84

6-fluoro-3-(4-methyl-1-((1-methyl-1H-imidazol-2-yl)methyl)piperidin-4-yl)-4H-benzo[4,5]imidazo[1,2-b]pyrazole-8-carboxamide

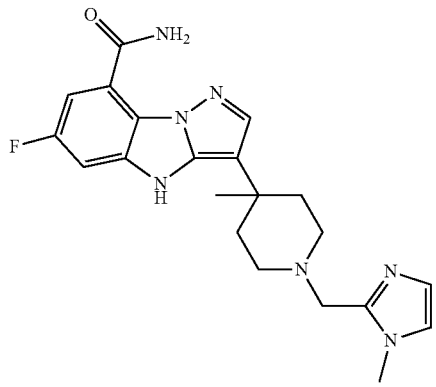 [SMILES: Cn1ccnc1CN1CCC(C)(c2cnn3c2[nH]c2cc(F)cc(C(N)=O)c23)CC1]

This example was prepared as the method described in Example 2. $^1$H NMR (400 MHz, METHANOL-d$_4$) δ ppm 1.32-1.44 (m, 3H), 1.78-1.96 (m, 2H), 2.18-2.33 (m, 2H), 2.46-2.62 (m, 2H), 2.71-2.88 (m, 2H), 3.73-3.77 (m, 2H), 3.81 (s, 3H), 7.01-7.11 (m, 1H), 7.18-7.23 (m, 1H), 7.33-7.40 (m, 1H), 7.73 (s, 2H), 8.28-8.44 (m, 1H). LCMS (ESI) m/z: 410 (M+1).

Example 85

3-(1-((1,2-dimethyl-1H-imidazol-5-yl)methyl)-4-methylpiperidin-4-yl)-6-fluoro-4H-benzo[4,5]imidazo[1,2-b]pyrazole-8-carboxamide

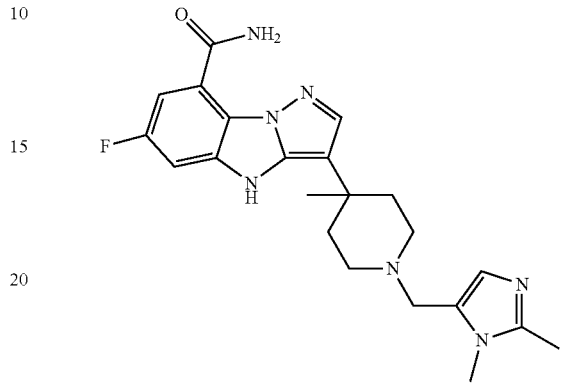

This example was prepared as the method described in Example 2. $^1$H NMR (400 MHz, METHANOL-d$_4$) δ ppm 1.38 (s, 3H), 1.83-1.92 (m, 2H), 2.27 (d, J=13.80 Hz, 2H), 2.54 (s, 5H), 2.86 (d, J=10.92 Hz, 2H), 3.70 (s, 2H), 3.75 (s, 3H), 7.17 (s, 1H), 7.36 (dd, J=8.16, 2.51 Hz, 1H), 7.66-7.80 (m, 2H), 8.38 (br. s., 1H). LCMS (ESI) m/z: 424 (M+1).

Example 86

3-(1'-ethyl-4-methyl-[1,4'-bipiperidin]-4-yl)-6-fluoro-4H-benzo[4,5]imidazo[1,2-b]pyrazole-8-carboxamide

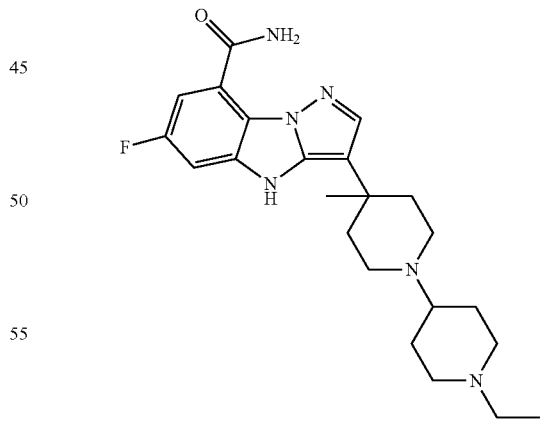

This example was prepared as the method described in Example 2. $^1$H-NMR (400 MHz, MethanoL-d$_4$) 1.09 (t, J=7.09 Hz, 3H), 1.27 (s, 3H), 1.50-1.70 (m, 2H), 1.72-1.85 (m, 2H), 1.92 (d, J=11.54 Hz, 2H), 2.34 (br. s., 2H), 2.75 (d, J=7.40 Hz, 7H), 2.86 (br. s., 2H), 3.23 (d, J=10.42 Hz, 2H), 7.49 (d, J=8.41 Hz, 1H), 7.58 (dd, J=10.85, 2.20 Hz, 1H), 7.79 (s, 1H), 8.28 (s, 2H). LCMS (ESI) m/z: 427 (M+1).

Example 87

6-fluoro-3-(4-methyl-1-((6-oxo-1,6-dihydro-pyridazin-3-yl)methyl)piperidin-4-yl)-4H-benzo[4,5]imidazo[1,2-b]pyrazole-8-carboxamide

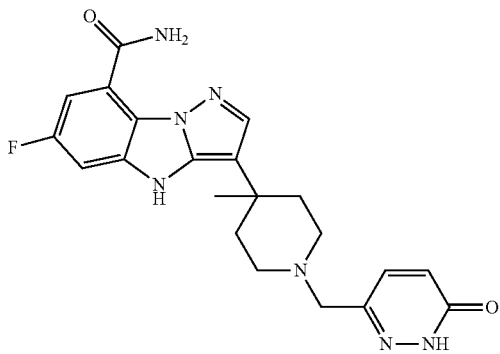 [SMILES: CC1(c2cnn3c2[nH]c2cc(F)cc(C(N)=O)c23)CCN(Cc2ccc(=O)[nH]n2)CC1]

This example was prepared as the method described in Example 2. $^1$H NMR (400 MHz, MeOD) δ: 8.35 (s, 1H), 7.70-7.74 (m, 2H), 7.57-7.60 (d, 1H), 7.36-7.38 (t, 1H), 6.98-7.00 (d, 1H), 3.63 (s, 2H), 2.86 (m, 2H), 2.61-2.63 (m, 2H), 2.26-2.30 (d, 2H), 1.87-1.94 (m, 2H), 1.39 (s, 3H). LCMS (ESI) m/z: 424 (M+1).

Example 88

3-(1-(2-cyanoethyl)-4-methylpiperidin-4-yl)-6-fluoro-4H-benzo[4,5]imidazo[1,2-b]pyrazole-8-carboxamide

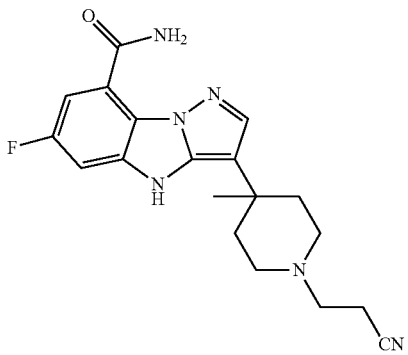 [SMILES: CC1(c2cnn3c2[nH]c2cc(F)cc(C(N)=O)c23)CCN(CCC#N)CC1]

A mixture of EXAMPLE 53D (52 g, 0.125 mmol), acrylonitrile (66 g, 1.25 mmol) and potassium carbonate (172 g, 1.25 mmol) in DMF (18 mL) was stirred at 28° C. for 1 hour. After completion, the reaction was quenched with water (10 mL). The aqueous layer was extracted with EtOAc (20 mL×3). The combined organic layers were dried over Na$_2$SO$_4$, filtered and evaporated. The residue was purified by prep-HPLC to provide the title compound (31 g, yield 66.0%). $^1$H NMR (400 MHz, METHANOL-d$_4$) ppm 1.39 (s, 3H), 1.86-1.97 (m, 2H), 2.25-2.36 (m, 2H), 2.60-2.70 (m, 2H), 2.74 (s, 2H), 2.84-2.98 (m, 4H), 7.33-7.41 (m, 1H), 7.68-7.73 (m, 1H), 7.74 (s, 1H), 8.21-8.32 (m, 1H). LCMS (ESI) m/z: 369 (M+1).

Example 89

6-chloro-3-(1-ethyl-4-methylpiperidin-4-yl)-4H-benzo[4,5]imidazo[1,2-b]pyrazole-8-carboxamide

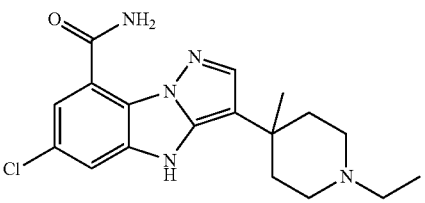 [SMILES: CCN1CCC(C)(c2cnn3c2[nH]c2cc(Cl)cc(C(N)=O)c23)CC1]

This example was prepared as described in Example 53, substituting (2,6-dibromo-4-chlorophenyl)hydrazine for (2,6-dibromo-4-fluorophenyl)hydrazine. $^1$H-NMR (MeOD, 400 MHz) δ: 1.32-1.39 (t, 3H), 1.46 (m, 1H), 2.52-2.55 (s, 3H), 2.06-2.08 (m, 2H), 2.47-2.48 (m, 2H), 3.09-3.11 (m, 3H), 3.34-3.41 (m, 3H), 7.63 (s, 1H), 7.83 (s, 1H), 7.97-7.97 (d, 1H), 8.54 (bs, 1H). LCMS (ESI) m/z: 360 (M+1).

Example 90

3-(1-ethyl-3-methylpyrrolidin-3-yl)-6-fluoro-4H-benzo[4,5]imidazo[1,2-b]pyrazole-8-carboxamide

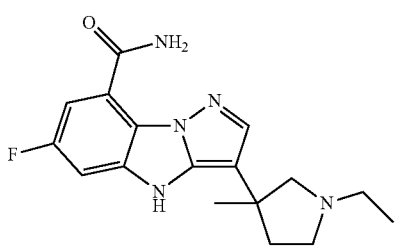 [SMILES: CCN1CCC(C)(c2cnn3c2[nH]c2cc(F)cc(C(N)=O)c23)C1]

This example was prepared as described in Example 53, substituting tert-butyl 3-(hydroxymethyl)-3-methylpyrrolidine-1-carboxylate for tert-butyl 4-(hydroxymethyl)-4-methylpiperidine-1-carboxylate. $^1$H NMR (400 MHz, METHANOL-d$_4$) ppm 1.38 (s, 3H), 1.64 (s, 3H), 2.25-2.42 (m, 1H), 2.59-2.76 (m, 1H), 3.27-3.32 (m, 2H), 3.39-3.53 (m, 1H), 3.54-3.71 (m, 2H), 3.71-3.88 (m, 1H), 7.33-7.39 (m, 1H), 7.57-7.70 (m, 1H), 7.76-7.90 (m, 1H), 8.28-8.80 (m, 1H). LCMS (ESI) m/z: 330 (M+1).

Example 91

3-(1,3-dimethylpyrrolidin-3-yl)-6-fluoro-4H-benzo[4,5]imidazo[1,2-b]pyrazole-8-carboxamide

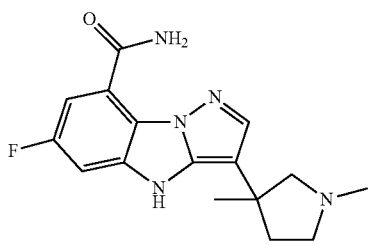 [SMILES: CN1CCC(C)(c2cnn3c2[nH]c2cc(F)cc(C(N)=O)c23)C1]

This example was prepared as the method described in Example 90. ¹H-NMR (400 MHz, MethanoL-d₄) δ ppm 8.52 (br. s., 1H), 7.84 (s, 1H), 7.67 (dd, J=2.5, 10.9 Hz, 1H), 7.38 (dd, J=2.5, 8.0 Hz, 1H), 3.74 (d, J=11.3 Hz, 1H), 3.67-3.49 (m, 2H), 3.40 (d, J=11.3 Hz, 1H), 2.96 (s, 3H), 2.73-2.60 (m, 1H), 2.34 (td, J=7.8, 13.4 Hz, 1H), 1.64 (s, 3H). LCMS (ESI) m/z: 316 (M+1).

Example 92

6-fluoro-3-(1-isopropyl-3-methylpyrrolidin-3-yl)-4H-benzo[4,5]imidazo[1,2-b]pyrazole-8-carboxamide

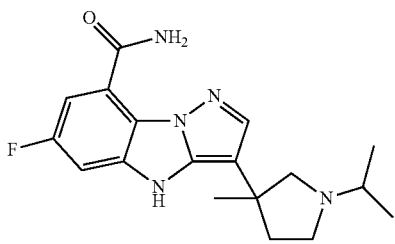 [SMILES: CC(C)N1CCC(C)(c2cnn3c2[nH]c2cc(F)cc(C(N)=O)c23)C1]

This example was prepared as the method described in Example 90. ¹H NMR (400 MHz, METHANOL-d₄) ppm 1.38-1.52 (m, 6H), 1.71 (d, J=2.26 Hz, 3H), 2.32-2.46 (m, 1H), 2.63-2.82 (m, 1H), 3.38-3.70 (m, 3H), 3.76-4.11 (m, 2H), 7.58-7.70 (m, 1H), 7.76-7.86 (m, 1H), 8.15-8.29 (m, 1H). LCMS (ESI) m/z: 344 (M+1).

Example 93

3-(1-(cyclopropylmethyl)-3-methylpyrrolidin-3-yl)-6-fluoro-4H-benzo[4,5]imidazo[1,2-b]pyrazole-8-carboxamide

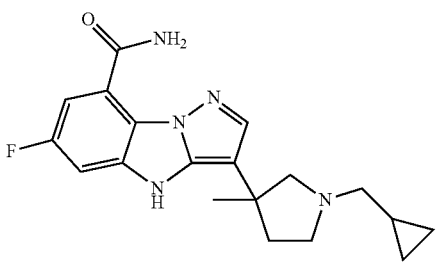 [SMILES: CC1(c2cnn3c2[nH]c2cc(F)cc(C(N)=O)c23)CCN(CC2CC2)C1]

This example was prepared as the method described in Example 5. ¹H NMR (400 MHz, METHANOL-d₄) ppm 0.41-0.52 (m, 2H), 0.70-0.82 (m, 2H), 1.10-1.26 (m, 1H), 1.66 (s, 3H), 2.27-2.39 (m, 1H), 2.63-2.75 (m, 1H), 3.17 (d, J=7.15 Hz, 2H), 3.44-3.58 (m, 1H), 3.59-3.78 (m, 2H), 3.79-3.94 (m, 1H), 7.27-7.40 (m, 1H), 7.55-7.67 (m, 1H), 7.77-7.89 (m, 1H), 8.43-8.69 (m, 1H). LCMS (ESI) m/z: 356 (M+1).

Example 94

6-fluoro-3-(3-methyl-1-(oxetan-3-yl)pyrrolidin-3-yl)-4H-benzo[4,5]imidazo[1,2-b]pyrazole-8-carboxamide

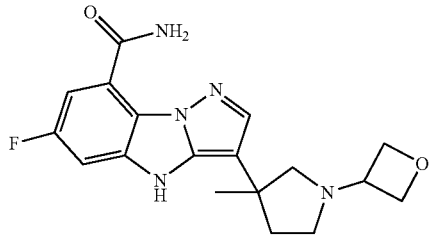 [SMILES: CC1(c2cnn3c2[nH]c2cc(F)cc(C(N)=O)c23)CCN(C2COC2)C1]

This example was prepared as the method described in Example 5. ¹H NMR (400 MHz, METHANOL-d₄) δ ppm 1.58 (s, 3H), 2.01-2.10 (m, 1H), 2.26-2.35 (m, 1H), 2.68-2.74 (m, 1H), 2.79-2.87 (m, 1H), 2.87-2.96 (m, 1H), 2.96-3.03 (m, 1H), 3.78-3.85 (m, 1H), 4.62-4.72 (m, 1H), 4.74-4.81 (m, 1H), 7.31-7.40 (m, 1H), 7.64-7.71 (m, 1H), 7.72-7.77 (m, 1H). LCMS (ESI) m/z: 358 (M+1).

Example 95

6-fluoro-3-(1-(2-fluoroethyl)-3-methylpyrrolidin-3-yl)-4H-benzo[4,5]imidazo[1,2-b]pyrazole-8-carboxamide

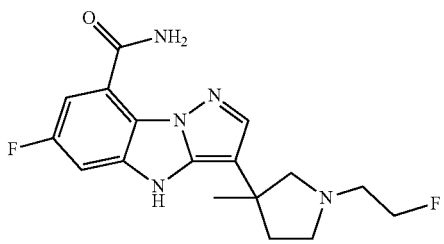 [SMILES: CC1(c2cnn3c2[nH]c2cc(F)cc(C(N)=O)c23)CCN(CCF)C1]

This example was prepared as the method described in Example 3. ¹H-NMR (MeOD, 400 MHz) δ: 1.635 (s, 1H), 2.243-2.263 (m, 1H), 2.522-2.554 (m, 1H), 3.288-3.321 (d, 1H), 3.325 (s, 2H), 3.329-3.337 (m, 1H), 3.391-3.414 (m, 1H), 3.632-3.659 (d, 1H), 4.730-4.860 (dt, 2H), 7.291-7.317 (dd, 1H), 7.586-7.619 (dd, 1H), 7.788 (s, 1H), 8.445 (bs, 1H), LCMS (ESI) m/z: 348 (M+1).

Example 96

3-(1-((2,2-difluorocyclopropyl)methyl)-3-methylpyrrolidin-3-yl)-6-fluoro-4H-benzo[4,5]imidazo[1,2-b]pyrazole-8-carboxamide

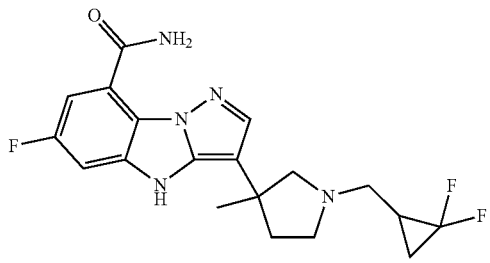 [SMILES: CC1(c2cnn3c2[nH]c2cc(F)cc(C(N)=O)c23)CCN(CC2CC2(F)F)C1]

This example was prepared as the method described in Example 3. ¹H NMR (400 MHz, METHANOL-$d_4$) ppm 1.34-1.46 (m, 1H) 1.64 (s, 3H) 1.67-1.79 (m, 1H) 2.03-2.11 (m, 1H) 2.20-2.31 (m, 1H) 2.52-2.63 (m, 1H) 3.13-3.24 (m, 1H) 3.24-3.31 (m, 2H) 3.37-3.48 (m, 1H) 3.48-3.58 (m, 1H) 3.59-3.67 (m, 1H) 7.29-7.39 (m, 1H) 7.57-7.67 (m, 1H) 7.76-7.84 (m, 1H) 8.35-8.54 (m, 1H) LCMS (ESI) m/z: 392 (M+1).

Example 97

6-fluoro-3-(3-methyl-1-(2,2,2-trifluoroethyl)pyrrolidin-3-yl)-4H-benzo[4,5]imidazo[1,2-b]pyrazole-8-carboxamide

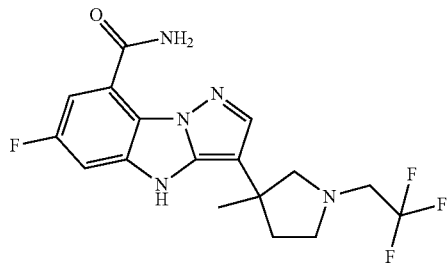 [SMILES: CC1(c2cnn3c2[nH]c2cc(F)cc(C(N)=O)c23)CCN(CC(F)(F)F)C1]

This example was prepared as the method described in Example 3. ¹H NMR (400 MHz, METHANOL-$d_4$) ppm 1.74 (s, 3H), 2.39-2.54 (m, 1H), 2.74-2.88 (m, 1H), 3.69-3.82 (m, 1H), 3.82-3.95 (m, 2H), 3.97-4.14 (m, 1H), 4.36-4.50 (m, 2H), 7.55-7.64 (m, 1H), 7.73-7.83 (m, 1H), 8.12-8.20 (m, 1H). LCMS (ESI) m/z: 384 (M+1).

Example 98

6-fluoro-3-(3-methyl-1-(2-(methylsulfonyl)ethyl)pyrrolidin-3-yl)-4H-benzo[4,5]imidazo[1,2-b]pyrazole-8-carboxamide

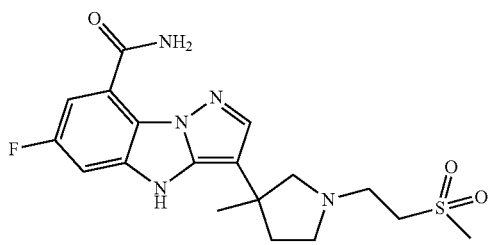 [SMILES: CC1(c2cnn3c2[nH]c2cc(F)cc(C(N)=O)c23)CCN(CCS(C)(=O)=O)C1]

This example was prepared as the method described in Example 3. ¹H NMR (400 MHz, METHANOL-$d_4$) ppm 1.60 (s, 3H), 2.05-2.15 (m, 1H), 2.18-2.28 (m, 1H), 2.63-2.69 (m, 1H), 2.69-2.78 (m, 1H), 3.01-3.10 (m, 1H), 3.11 (s, 3H), 3.26-3.31 (m, 1H), 3.34-3.41 (m, 2H), 3.41-3.50 (m, 1H), 3.50-3.60 (m, 1H), 7.35-7.45 (m, 1H), 7.63-7.70 (m, 1H), 7.72 (s, 1H), 8.22 (s, 1H). LCMS (ESI) m/z: 408 (M+1).

Example 99

6-fluoro-3-(3-methyl-1-(3,3,3-trifluoropropyl)pyrrolidin-3-yl)-4H-benzo[4,5]imidazo[1,2-b]pyrazole-8-carboxamide

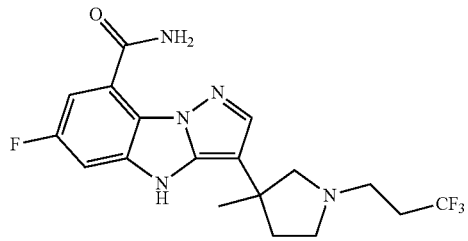 [SMILES: CC1(c2cnn3c2[nH]c2cc(F)cc(C(N)=O)c23)CCN(CCC(F)(F)F)C1]

This example was prepared as the method described in Example 3. ¹H NMR (400 MHz, METHANOL-$d_4$) ppm 1.62 (s, 3H), 2.16-2.25 (m, 1H), 2.43-2.53 (m, 1H), 2.58-2.72 (m, 1H), 3.08-3.14 (m, 1H), 3.16-3.29 (m, 1H), 3.34-3.39 (m, 1H), 3.41-3.47 (m, 1H), 7.32-7.41 (m, 1H), 7.63-7.71 (m, 1H), 7.74-7.83 (m, 1H), 8.24-8.34 (m, 1H). LCMS (ESI) m/z: 398 (M+1).

Example 100

3-(1-((1-aminocyclopropyl)methyl)-3-methylpyrrolidin-3-yl)-6-fluoro-4H-benzo[4,5]imidazo[1,2-b]pyrazole-8-carboxamide

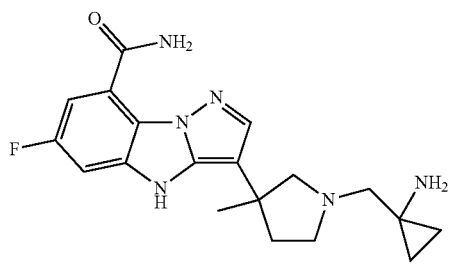 [SMILES: CC1(c2cnn3c2[nH]c2cc(F)cc(C(N)=O)c23)CCN(CC2(N)CC2)C1]

This example was prepared as the method described in Example 3. ¹H NMR (400 MHz, METHANOL-$d_4$) ppm 0.85 (s, 1H), 1.00 (s, 1H), 1.62 (s, 3H), 2.07-2.17 (m, 1H), 2.34-2.44 (m, 1H), 2.85 (s, 1H), 2.94-3.01 (m, 1H), 3.04-3.12 (m, 1H), 3.20 (d, J=9.41 Hz, 1H), 7.33-7.39 (m, 1H), 7.64-7.70 (m, 1H), 7.75-7.80 (m, 1H), 7.83-7.85 (m, 1H), 8.02-8.05 (m, 1H), 8.34-8.47 (m, 1H). LCMS (ESI) m/z: 371 (M+1).

Example 101

3-(1-((1-cyanocyclobutyl)methyl)-3-methylpyrrolidin-3-yl)-6-fluoro-4H-benzo[4,5]imidazo[1,2-b]pyrazole-8-carboxamide

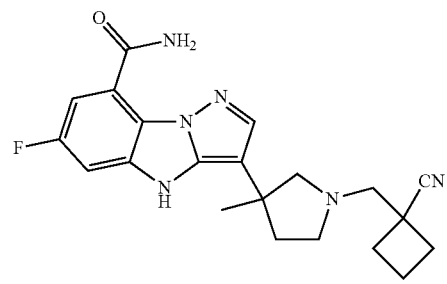 [SMILES: CC1(c2cnn3c2[nH]c2cc(F)cc(C(N)=O)c23)CCN(CC2(C#N)CCC2)C1]

This example was prepared as the method described in Example 3. ¹H NMR (400 MHz, METHANOL-d₄) 1.60 (s, 3H), 2.00-2.11 (m, 2H), 2.13-2.23 (m, 1H), 2.25-2.40 (m, 3H), 2.45-2.58 (m, 2H), 2.65-2.70 (m, 1H), 2.72-2.80 (m, 1H), 2.93 (s, 1H), 2.99-3.06 (m, 1H), 3.14-3.23 (m, 2H), 7.38-7.44 (m, 1H), 7.69 (dd, J=10.85, 2.57 Hz, 1H), 7.74 (s, 1H), 8.33 (br. s., 1H).

LCMS (ESI) m/z: 395 (M+1).

Example 102

3-(1-((1-cyanocyclopropyl)methyl)-3-methylpyrrolidin-3-yl)-6-fluoro-4H-benzo[4,5]imidazo[1,2-b]pyrazole-8-carboxamide

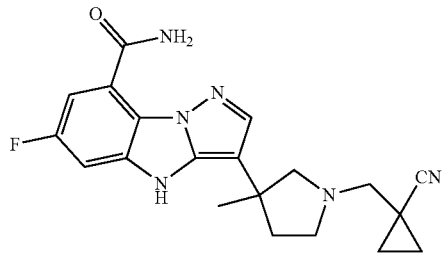 [SMILES: CC1(c2cnn3c2[nH]c2cc(F)cc(C(N)=O)c23)CCN(CC2(C#N)CC2)C1]

This example was prepared as the method described in Example 3. ¹H NMR (400 MHz, DMSO-d₆) ppm 0.92 (d, J=2.26 Hz, 2H), 1.16-1.24 (m, 2H), 1.48 (s, 3H), 1.87-1.97 (m, 1H), 2.05 (s, 1H), 2.55 (d, J=7.53 Hz, 4H), 2.91 (s, 2H), 7.43-7.50 (m, 1H), 7.51-7.61 (m, 1H), 7.79 (s, 1H). LCMS (ESI) m/z: 381 (M+1).

Example 103

3-(1-(2-cyanoethyl)-3-methylpyrrolidin-3-yl)-6-fluoro-4H-benzo[4,5]imidazo[1,2-b]pyrazole-8-carboxamide

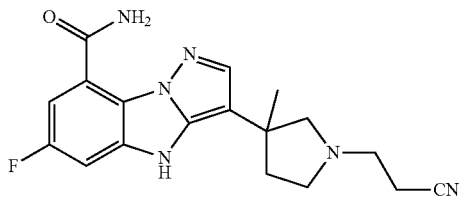 [SMILES: CC1(c2cnn3c2[nH]c2cc(F)cc(C(N)=O)c23)CCN(CCC#N)C1]

This example was prepared as the method described in Example 88. ¹H NMR (400 MHz, METHANOL-d₄) ppm 1.61 (s, 3H), 2.06-2.16 (m, 1H), 2.23-2.33 (m, 1H), 2.80 (d, J=6.40 Hz, 1H), 2.83-2.91 (m, 1H), 2.93-3.02 (m, 1H), 3.03-3.12 (m, 1H), 3.27 (d, J=9.29 Hz, 2H), 7.37-7.44 (m, 1H), 7.64-7.72 (m, 1H), 7.76 (s, 1H), 8.14-8.26 (m, 1H). LCMS (ESI) m/z: 355 (M+1).

Example 104

3-(1-(cyclopropylmethyl)-3-methylazetidin-3-yl)-6-fluoro-4H-benzo[4,5]imidazo[1,2-b]pyrazole-8-carboxamide

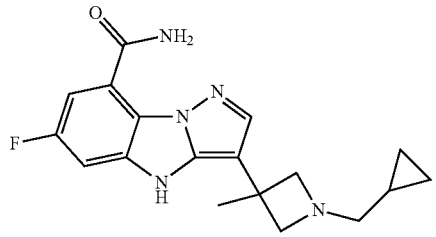 [SMILES: CC1(c2cnn3c2[nH]c2cc(F)cc(C(N)=O)c23)CN(CC2CC2)C1]

This example was prepared as the method described in Example 93. ¹H NMR (400 MHz, MeOD) δ: 8.51 (s, 1H), 7.96 (s, 1H), 7.70-7.73 (dd, 1H), 7.39-7.41 (dd, 1H), 4.39-4.32 (d, 2H), 4.23-4.26 (d, 2H), 3.15-3.17 (d, 2H), 1.87 (s, 3H), 1.06-1.08 (m, 1H), 0.69-0.74 (m, 2H), 0.42-0.46 (m, 2H). LCMS (ESI) m/z: 342 (M+1).

Scheme D

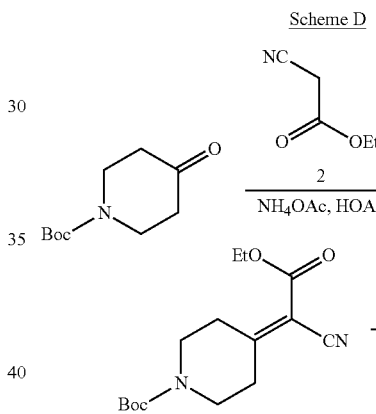

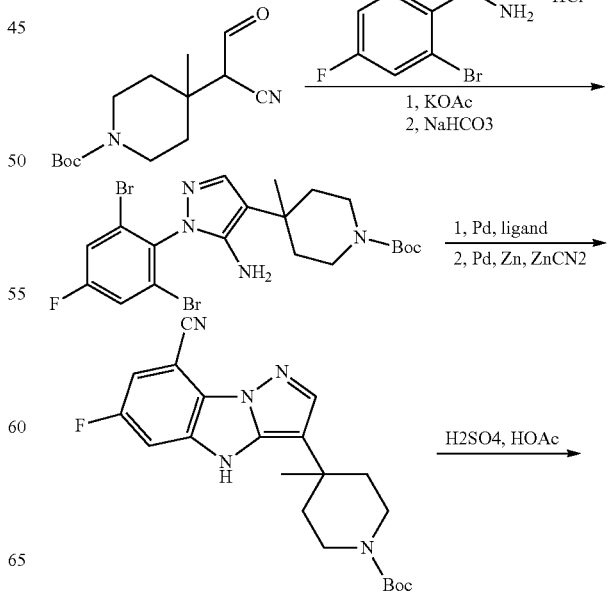

-continued

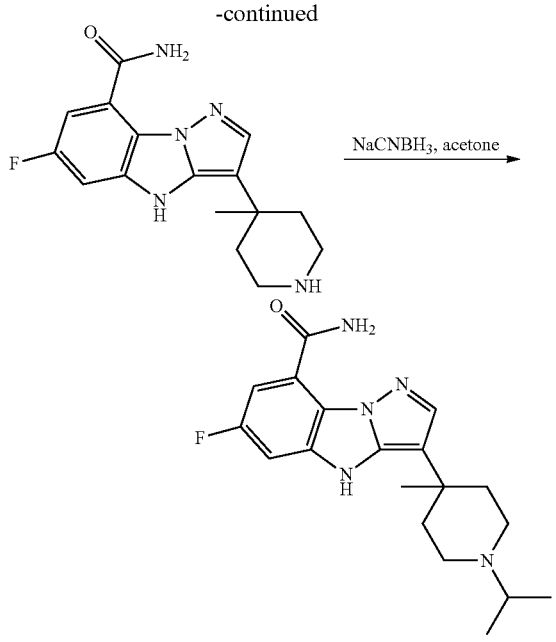

Example 105

6-fluoro-3-(1-isopropyl-4-methylpiperidin-4-yl)-4H-benzo[4,5]imidazo[1,2-b]pyrazole-8-carboxamide

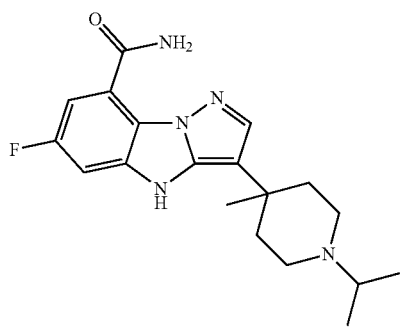 [SMILES: CC(C)N1CCC(C)(c2cnn3c2[nH]c2cc(F)cc(C(N)=O)c23)CC1]

Example 105A tert-butyl 4-(1-cyano-2-ethoxy-2-oxoethylidene)-4-piperidine-1-carboxylate

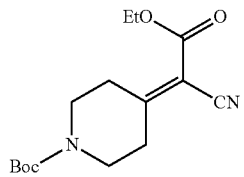 [SMILES: CCOC(=O)C(C#N)=C1CCN(C(=O)OC(C)(C)C)CC1]

A mixture of tert-butyl 4-oxopiperidine-1-carboxylate (100 g, 0.5 mol), ethyl 2-cyanoacetate (56.5 g, 0.5 mol), NH₄OAc (19.2 g, 0.25 mol) and HOAc (15 g, 0.25 mol) in toluene (1 L) was stirred at 120° C. for 5-6 h to remove water by a Dean-Stark trap. After removal of solvent in vacuum, the residue was partitioned between EtOAc (500 mL) and water (500 mL), the aqueous layer was extracted with EtOAc (500 mL×3). The combined organic layers were washed with brine (500 mL), dried over Na₂SO₄, filtered and evaporated. The residue was purified by pulping with PE/EtOAc=10/1 (300 mL). The white solid was collected by filtration to provide the title compound (90 g, 61% yield). $^1$H NMR (400 MHz, CHLOROFORM-d) δ ppm 1.38 (t, J=7.15 Hz, 3H), 1.50 (s, 9H), 2.79 (t, J=5.90 Hz, 2H), 3.15 (t, J=5.83 Hz, 2H), 3.56 (t, J=5.71 Hz, 2H), 3.63 (t, J=5.83 Hz, 2H), 4.31 (q, J=7.15 Hz, 2H). LCMS (ESI) m/z: 295 (M+1).

Example 105B tert-butyl 4-(1-cyano-2-ethoxy-2-oxoethyl)-4-methylpiperidine-1-carboxylate

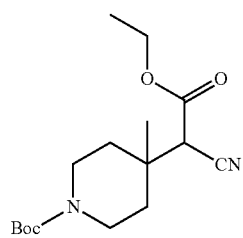 [SMILES: CCOC(=O)C(C#N)C1(C)CCN(C(=O)OC(C)(C)C)CC1]

To a mixture of CuI (86.3 g, 0.454 mol) in dry THF (1.7 L) was added dropwise 3M methylmagnesium bromide (378 mL, 1.13 mol) at −60-70° C. under N₂ atmosphere. After stirring at −10° C.-0° C. for 1 h and cooling to −60-70° C., a solution of EXAMPLE 105A (133.5 g, 0.454 mol) in THF (300 mL) was added. The mixture was stirred at 20° C. for 15 h and then cooled to 0° C. and quenched with sat aq NH₄Cl solution (1.2 L). After filtration through a pad of Celite, the aqueous layer was extracted with EtOAc (600 mL×3). The combined organic layers were washed with brine (500 mL), dried over Na₂SO₄, filtered and evaporated to provide the crude title compound (142 g) as a yellow oil which was used directly in the next step without further purification.

Example 105C 2-(1-(tert-butoxycarbonyl)-4-methylpiperidin-4-yl)-2-cyanoacetic acid

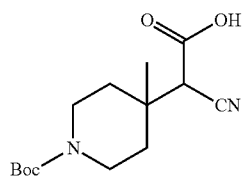

To a solution of EXAMPLE 105B (142 g, crude, 0.458 mol) in a mixture of THF/MeOH=10:1 (1.2 L) was added dropwise a solution of NaOH (73.3 g, 1.82 mol) in water (320 mL) at 0° C. After the dropwise addition was completed, the mixture was stirred at 20° C. for 2 h, and then diluted by adding water (320 mL). The aqueous layer was extracted with EtOAc (500 mL×3). The combined organic layers were washed with water (200 mL×2). The combined aqueous layer was adjusted to pH 3-4 by 1N HCl and extracted with DCM/MeOH=10:1 (300 mL×6). The combined DCM/MeOH organic layer was washed with brine (800 mL) and then dried over Na₂SO₄, filtered and evaporated to provide the crude title compound (111.5 g) as a yellow solid which was used directly in the next step without further purification.

Example 105D tert-butyl 4-(cyanomethyl)-4-methylpiperidine-1-carboxylate

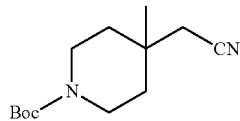

A mixture of EXAMPLE 105C (111.5 g, crude, 0.395 mol) and Cu₂O (11.4 g, 79.08 mmol) in acetonitrile (900 mL) was stirred at 80° C. for 2 h. After being cooled to room temperature, the mixture was evaporated and the residue was dissolved in EtOAc (1 L) and filtered through a pad of Celite to remove insolubles. The filter residue was washed with EtOAc (250 mL×2). To the filtrate was added THF (150 mL) to dissolve the precipitates. The organic layer was washed with water, water/brine=1:1 (300 mL), dried over Na₂SO₄, filtered and evaporated. The residue was purified by pulping with PE/EtOAc=10/1 (300 mL). The white solid was collected by filtration to provide the title compound (98 g). LCMS (ESI) m/z: 239 (M+1).

Example 105E tert-butyl 4-(1-cyano-2-oxoethyl)-4-methylpiperidine-1-carboxylate

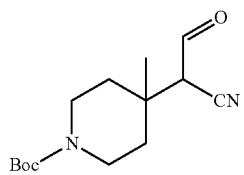 [SMILES: CC(C)(C)OC(=O)N1CCC(C)(C(C#N)C=O)CC1]

To a mixture of EXAMPLE 105D (50 g, 0.21 mol) in THF (400 mL) was added dropwise 2M LDA (160 mL, 0.32 mol) at −60-70° C. under N₂ atmosphere. After stirring at −60-70° C. for 1 h, ethyl formate (32 g, 0.43 mol) was added dropwise till completion, followed by slowly warming up to 15° C. and stirring for another 4 h. After completion, the reaction was quenched with aq NH₄Cl solution (500 mL). The aqueous layer was extracted with EtOAc (200 mL×3). The combined organic layers were washed with water (200 mL), 1N HCl (300 mL×3), brine (200 mL), thereafter dried over Na₂SO₄, filtered and evaporated to give the residue which was purified by pulping with PE/EtOAc=10/1 (200 mL). The white solid was collected by filtration to provide the title compound (45 g, 80% yield). LCMS (ESI) m/z: 267 (M+1).

Example 105F (2,6-dibromo-4-fluorophenyl)hydrazine hydrochloride

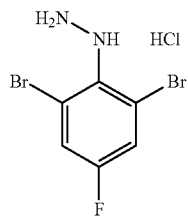

To a mixture of 2,6-dibromo-4-fluoroaniline (50 g, 0.186 mol) in conc HCl (190 mL) was added dropwise a solution of NaNO₂ (14.1 g, 0.205 mol) in water (70 mL) at −5-0° C. After being stirred at −5-0° C. for 40 min, the above reaction mixture was added dropwise in into a solution of SnCl₂·2H₂O (62.95 g, 0.279 mol) in conc HCl (240 mL) at −5-0° C. The resultant mixture was slowly warmed up to 20° C. and stirred for 12 h. The solid was collected by filtration, washed with i-PrOH (200 mL) and thereafter dried in vacuum to provide the title compound (47 g, 78% yield) which could be used directly in the next step without further purification. ¹H NMR (400 MHz, DMSO-d₆) δ ppm 2.37-2.68 (m, 1H), 6.94-7.28 (m, 1H), 7.80 (d, J=8.03 Hz, 2H), 10.13 (br. s., 3H).

Example 105G tert-butyl 4-(5-amino-1-(2,6-dibromo-4-fluorophenyl)-1H-pyrazol-4-yl)-4-methylpiperidine-1-carboxylate

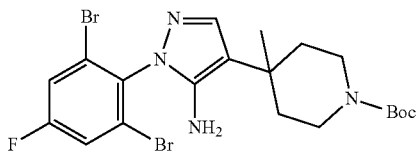 [SMILES: CC(C)(C)OC(=O)N1CCC(C)(c2cnn(-c3c(Br)cc(F)cc3Br)c2N)CC1]

A mixture of EXAMPLE 105E (50 g, 187.73 mmol), KOAc (27.64 g, 281.73 mmol) and EXAMPLE 105F (72.17 g, 225.28 mmol) in ethanol (500 ml) was stirred at 60° C. for 5 h. After the reaction was completed, to the mixture was added NaHCO₃ (31.57 g, 375.78 mmol) while stirring at 80° C. for another 15 h. After being cooled to room temperature, the resultant mixture was evaporated and the residue was dissolved with EtOAc (200 mL) and water (200 mL). The aqueous layer was extracted with EtOAc (200 mL×3). The combined organic layers were washed with brine (200 mL), dried over Na₂SO₄, filtered and evaporated. The residue was purified by pulping with PE/EtOAc=10/1 (200 mL). The white solid was collected by filtration to provide the title compound (75 g, 75% yield) which could be used directly in the next step without further purification.

Example 105H tert-butyl 4-(8-bromo-6-fluoro-4H-benzo[4,5]imidazo[1,2-b]pyrazol-3-yl)-4-methylpiperidine-1-carboxylate

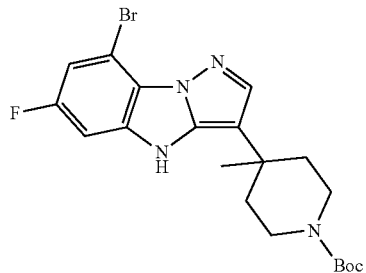 [SMILES: CC(C)(C)OC(=O)N1CCC(C)(c2cnn3c2[nH]c2cc(F)cc(Br)c23)CC1]

A mixture of EXAMPLE 105G (35 g, 65.78 mmol), Pd$_2$(dba)$_3$ (6.02 g, 6.57 mmol), Xantphos (7.61 g, 13.16 mmol) and Cs$_2$CO$_3$ (42.77 g, 131.58 mmol) in DMF (300 mL) was stirred at 130° C. for 9 h under N$_2$ atmosphere. After being cooled to room temperature, the resultant mixture was filtered and the filtrate was evaporated. The residue was dissolved in EtOAc (500 mL). The organic layer was washed with water (200 mL×2), brine (200 mL×2), dried over Na$_2$SO$_4$, filtered and evaporated to provide the crude title compound as brown oil which could be used in the next step without further purification. LCMS (ESI) m/z: 451, 453 (M, M+2).

Example 105I tert-butyl 4-(8-cyano-6-fluoro-4H-benzo[4,5]imidazo[1,2-b]pyrazol-3-yl)-4-methylpiperidine-1-carboxylate

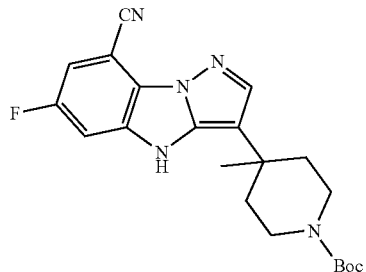 [SMILES: CC(C)(C)OC(=O)N1CCC(C)(c2cnn3c2[nH]c2cc(F)cc(C#N)c23)CC1]

A mixture of EXAMPLE 105H (29.7 g, crude, 65.8 mmol), Zn(CN)$_2$ (15.4 g, 131.71 mmol), Pd$_2$(dba)$_3$ (6.02 g, 6.58 mmol), DPPF (7.30 g, 13.17 mmol) and Zn (8.65 g, 131.71 mmol) in DMF (300 mL) was stirred at 120° C. for 5 h under N$_2$ atmosphere. After being cooled to room temperature, the mixture was filtered and the filtrate was evaporated to give the residue which was purified by column chromatography to provide the crude title compound (35 g, crude) as yellow foam. LCMS (ESI) m/z: 398 (M+1).

Example 105J tert-butyl 4-(8-carbamoyl-6-fluoro-4H-benzo[4,5]imidazo[1,2-b]pyrazol-3-yl)-4-methylpiperidine-1-carboxylate

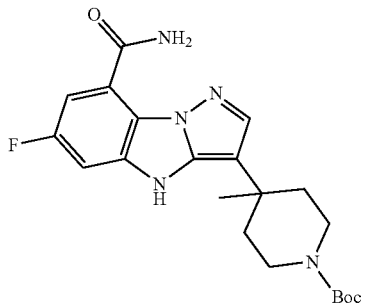 [SMILES: CC(C)(C)OC(=O)N1CCC(C)(c2cnn3c2[nH]c2cc(F)cc(C(N)=O)c23)CC1]

To a solution of EXAMPLE 105I (35 g, crude, 88.17 mmol) and 1N NaOH (140 mL, 140 mmol) in DMSO (100 mL) was added dropwise 30% H$_2$O$_2$ (40 mL) at 0° C. After the dropwise addition was completed, the reaction solution was warmed to 40-50° C. and stirred for 2 hours, and thereafter diluted with water (200 mL) and extracted with EtOAc/THF=3/1 (200 mL×2). The combined organic layers were washed with water (150 mL×2), brine (150 mL×2), dried over Na$_2$SO$_4$, filtered and evaporated. The residue was purified by column chromatography to provide the title compound (12.2 g, yield: 45%) as yellow solids. LCMS (ESI) m/z: 416 (M+1).

Example 105K 6-fluoro-3-(4-methylpiperidin-4-yl)-4H-benzo[4,5]imidazo[1,2-b]pyrazole-8-carboxamide

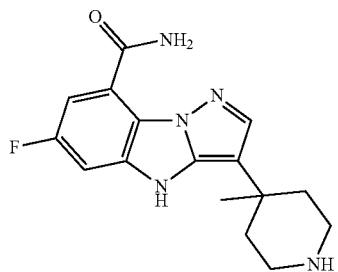 [SMILES: CC1(c2cnn3c2[nH]c2cc(F)cc(C(N)=O)c23)CCNCC1]

A solution of EXAMPLE 105J (5 g, 12 mmol) in a mixture of DCM/TFA (50 mL/10 mL) was stirred at 20° C. for 2 h. The resultant mixture was evaporated to provide the title compound as yellow oil which could be used in the next step without further purification.

Example 105L 6-fluoro-3-(1-isopropyl-4-methylpiperidin-4-yl)-4H-benzo[4,5]imidazo[1,2-b]pyrazole-8-carboxamide

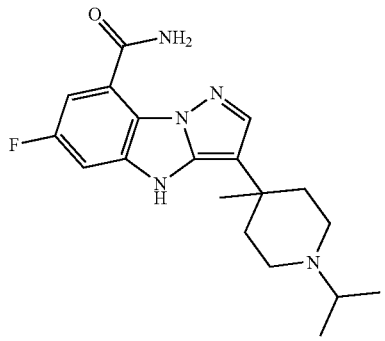 [SMILES: CC(C)N1CCC(C)(c2cnn3c2[nH]c2cc(F)cc(C(N)=O)c23)CC1]

A solution of EXAMPLE 105K (3.8 g, crude, 12 mmol), Na(CN)BH₃ (2.8, 60 mmol) in a mixture of acetone (2.0 g, 34 mmol) and methanol (50 mL) was stirred at 25° C. for 3 h. After removal of solution in vacuum, the residue was dissolved in EtOAc/THF=5/1 (200 mL). The organic layers were washed with water (50 mL×2), brine (50 mL), then dried over Na₂SO₄, filtered and evaporated. The residue was purified by column chromatograph to provide the title compound (4 g, yield: 90%). ¹H-NMR (400 MHz, DMSO-d₆) δ ppm 1.11-1.61 (m, 9H), 1.89-2.29 (m, 2H), 2.47 (br. s., 1H), 2.55 (br. s., 1H), 2.77 (d, J=12.05 Hz, 1H), 3.09-3.66 (m, 4H), 7.53 (dd, J=8.28, 2.51 Hz, 1H), 7.63 (dt, J=10.92, 2.26 Hz, 1H), 7.79-7.99 (m, 1H), 8.17 (br. s., 1H), 10.23-10.75 (m, 2H), 12.49-12.93 (m, 1H). LCMS (ESI) m/z: 358 (M+1).

Example 106

6-fluoro-3-(4-methyl-1,1-dioxidotetrahydro-2H-thiopyran-4-yl)-4H-benzo[4,5]imidazo[1,2-b]pyrazole-8-carboxamide

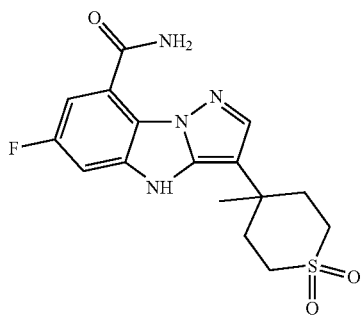 [SMILES: CC1(c2cnn3c2[nH]c2cc(F)cc(C(N)=O)c23)CCS(=O)(=O)CC1]

Example 106A 8-bromo-6-fluoro-3-(4-methyltetrahydro-2H-thiopyran-4-yl)-4H-benzo[4,5]imidazo[1,2-b]pyrazole

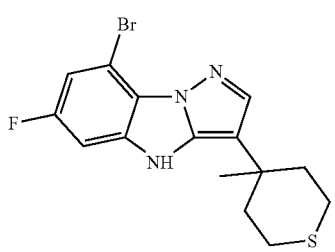 [SMILES: CC1(c2cnn3c2[nH]c2cc(F)cc(Br)c23)CCSCC1]

This example was prepared as described in Examples 105A-105H, substituting dihydro-2H-thiopyran-4(3H)-one for tert-butyl 4-oxopiperidine-1-carboxylate. LCMS (ESI) m/z: 368, 370 (M, M+2).

Example 106B 4-(8-bromo-6-fluoro-4H-benzo[4,5]imidazo[1,2-b]pyrazol-3-yl)-4-methyltetrahydro-2H-thiopyran 1,1-dioxide

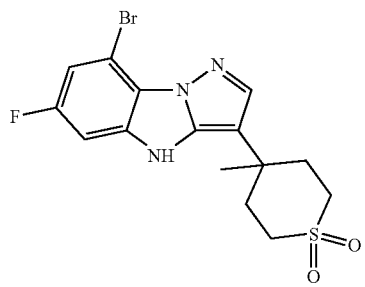 [SMILES: CC1(c2cnn3c2[nH]c2cc(F)cc(Br)c23)CCS(=O)(=O)CC1]

A mixture of EXAMPLE 106A (0.1 g, 0.271 mmol) and mCPBA (0.94 g, 0.542 mmol) in DCM (15 mL) and THF (3 mL) was stirred at 25° C. for 3 h. The mixture was quenched with sat aq Na₂SO₃ solution (20 mL). The aqueous layer was extracted with DCM (15 mL×3). The combined organic layers were washed with sat aq NaHCO₃ solution (20 mL), brine (15 mL), dried over Na₂SO₄, filtered and evaporated to provide the title compound which could be used directly in the next step without further purification.

Example 106C 6-fluoro-3-(4-methyl-1,1-dioxidotetrahydro-2H-thiopyran-4-yl)-4H-benzo[4,5]imidazo[1,2-b]pyrazole-8-carboxamide

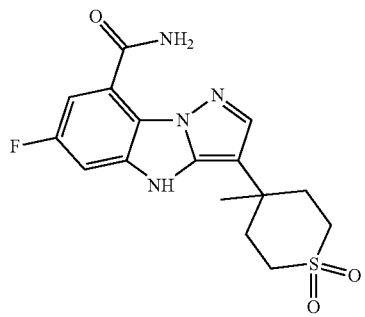 [SMILES: CC1(c2cnn3c2[nH]c2cc(F)cc(C(N)=O)c23)CCS(=O)(=O)CC1]

This example was prepared as described in Examples 105I and 105J. ¹H NMR (400 MHz, MeOD) δ: 7.8798 (s, 1H), 7.56-7.59 (d, 1H), 7.46-7.48 (d, 1H), 3.11 (m, 2H), 2.95-3.01 (m, 2H), 2.52 (m, 2H), 2.13-2.19 (m, 2H), 1.35 (s, 3H). LCMS (ESI) m/z: 365 (M+1).

Example 107

3-(1,4-diethylpiperidin-4-yl)-6-fluoro-4H-benzo[4,5]imidazo[1,2-b]pyrazole-8-carboxamide

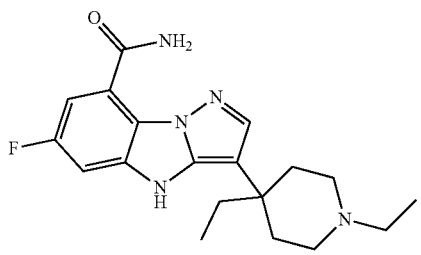 [SMILES: CCN1CCC(CC)(c2cnn3c2[nH]c2cc(F)cc(C(N)=O)c23)CC1]

Example 107A tert-butyl 4-(1-cyano-2-ethoxy-2-oxoethyl)-4-ethyl-piperidine-1-carboxylate

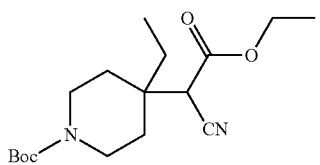 [SMILES: CCOC(=O)C(C#N)C1(CC)CCN(C(=O)OC(C)(C)C)CC1]

1,4-ethylpiperidin-4-yl

To a mixture of EXAMPLE 105A (1.0 g, 3.4 mmol) in THF (20 mL) was added dropwise ethylmagnesium bromide (2.83 mL, 8.49 mmol) at −78° C. under $N_2$ atmosphere. After being stirred at −78° C. for 1 h, the mixture was warmed to 32° C. and stirred for 15 h and then quenched with sat $NH_4Cl$ aq solution (100 mL). The aqueous layer was extracted with EtOAc (100 mL×2). The combined organic layers were washed with brine (200 mL), dried over $Na_2SO_4$, filtered and evaporated. The residue was purified by column chromatograph to provide the title compound (0.8 g, yield: 73%) as a colorless oil. LCMS (ESI) m/z: 325 (M+1).

Example 107B 3-(1,4-diethylpiperidin-4-yl)-6-fluoro-4H-benzo[4,5]imidazo[1,2-b]pyrazole-8-carboxamide

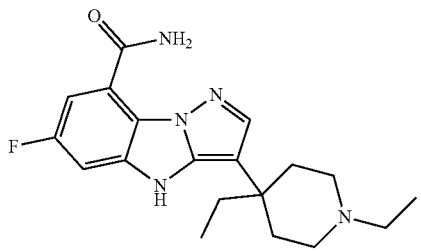 [SMILES: CCN1CCC(CC)(c2cnn3c2[nH]c2cc(F)cc(C(N)=O)c23)CC1]

This example was prepared as described in Example 105. $^1$H-NMR (400 MHz, MethanoL-$d_4$) δ ppm 0.80 (t, J=7.47 Hz, 3H), 1.28 (t, J=7.34 Hz, 3H), 1.72 (d, J=7.40 Hz, 1H), 1.89-2.14 (m, 1H), 2.41-2.61 (m, 1H), 3.06 (d, J=7.28 Hz, 3H), 3.37-3.58 (m, 1H), 7.35 (dd, J=8.16, 2.51 Hz, 1H), 7.69 (dd, J=10.92, 2.64 Hz, 1H), 7.76 (s, 1H), 8.52 (s, 1H). LCMS (ESI) m/z: 358 (M+1).

Example 108

3-(4-cyano-1-(cyclopropylmethyl)piperidin-4-yl)-6-fluoro-4H-benzo[4,5]imidazo[1,2-b]pyrazole-8-carboxamide

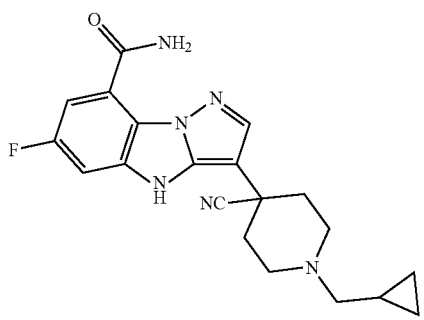 [SMILES: N#CC1(c2cnn3c2[nH]c2cc(F)cc(C(N)=O)c23)CCN(CC2CC2)CC1]

Example 108A tert-butyl 4-cyano-4-(cyanomethyl)piperidine-1-carboxylate

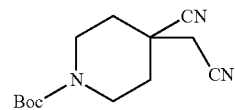

A solution of EXAMPLE 105A (2.0 g, 6.8 mmol) and KCN (1.71 g, 26.3 mmol) in a mixture of ethanol (20 mL)/Water (4 mL) was stirred at 70-80° C. for 15 h. After removal of solution in vacuum, the residue was dissolved by adding water (100 mL). The aqueous phase was extracted with EtOAc (100 mL×2). The combined organic layers were washed with brine (200 mL), dried over $Na_2SO_4$, filtered and evaporated. The residue was purified by column chromatograph to provide the title compound (1.3 g, yield: 79%) as a white solid. LCMS (ESI) m/z: 250 (M+1).

Example 108B tert-butyl 4-(5-amino-1-(2,6-dibromo-4-fluorophenyl)-1H-pyrazol-4-yl)-4-cyanopiperidine-1-carboxylate

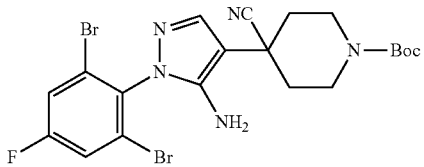 [SMILES: CC(C)(C)OC(=O)N1CCC(C#N)(c2cnn(-c3c(Br)cc(F)cc3Br)c2N)CC1]

This example was prepared as described in Examples 105E-105G.

Example 108C tert-butyl 4-(8-bromo-6-fluoro-4H-benzo[4,5]imidazo[1,2-b]pyrazol-3-yl)-4-cyanopiperidine-1-carboxylate

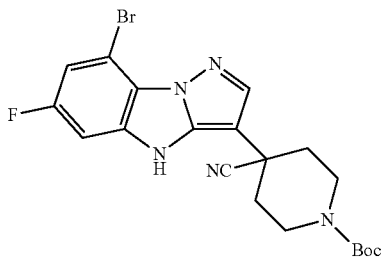 [SMILES: CC(C)(C)OC(=O)N1CCC(C#N)(c2cnn3c2[nH]c2cc(F)cc(Br)c23)CC1]

A mixture of EXAMPLE 108B (660 g, 1.22 mmol), CuI (70 g, 0.37 mmol), $N^1,N^2$-dimethylethane-1,2-diamine (65 g, 0.74 mmol) and $K_3PO_4$ (780 g, 3.68 mmol) in DMF (15 mL) was stirred at 70° C. for 10 hours under $N_2$ atmosphere. After being cooled to room temperature, the resultant mixture was filtered through a pad of Celite. The filtrate was evaporated and the residue was purified by column chromatography to provide the title compound (470 g, yield: 78%) as white solids. LCMS (ESI) m/z: 462, 464 (M, M+2).

Example 108D 3-(4-cyanopiperidine-4-yl)-6-fluoro-4H-benzo[4,5]imidazo[1,2-b]pyrazole-8-carboxamide

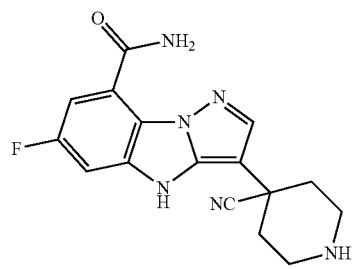 [SMILES: N#CC1(c2cnn3c2[nH]c2cc(F)cc(C(N)=O)c23)CCNCC1]

This example was prepared as described in Examples 1G-1J. LCMS (ESI) m/z: 327 (M+1).

Example 108E 3-(4-cyano-1-(cyclopropylmethyl)piperidin-4-yl)-6-fluoro-4H-benzo[4,5]imidazo[1,2-b]pyrazole-8-carboxamide

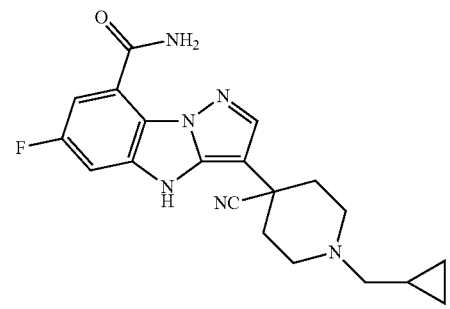 [SMILES: N#CC1(c2cnn3c2[nH]c2cc(F)cc(C(N)=O)c23)CCN(CC2CC2)CC1]

This example was prepared as the method described in Example 5. $^1$H-NMR (400 MHz, MethanoL-$d_4$) δ ppm 0.34 (d, J=5.90 Hz, 2H), 0.67-0.75 (m, 2H), 0.99-1.13 (m, 1H), 2.37 (br. s., 2H), 2.58 (br. s., 2H), 2.75 (d, J=6.90 Hz, 2H), 2.89-3.07 (m, 2H), 3.39-3.61 (m, 2H), 7.44 (dd, J=8.09, 2.57 Hz, 1H), 7.75 (dd, J=10.85, 2.57 Hz, 1H), 7.90 (s, 1H), 8.34-8.47 (m, 1H). LCMS (ESI) m/z: 381 (M+1).

Example 109

3-(1-(cyclopropylmethyl)-4-(hydroxymethyl)piperidin-4-yl)-6-fluoro-4H-benzo[4,5]imidazo[1,2-b]pyrazole-8-carboxamide

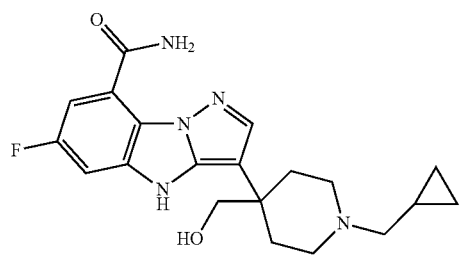 [SMILES: NC(=O)c1cc(F)cc2[nH]c3c(C4(CO)CCN(CC5CC5)CC4)cnn3c12]

Example 109A 4-(8-bromo-6-fluoro-4H-benzo[4,5]imidazo[1,2-b]pyrazol-3-yl)-1-(tert-butoxycarbonyl)piperidine-4-carboxylic acid

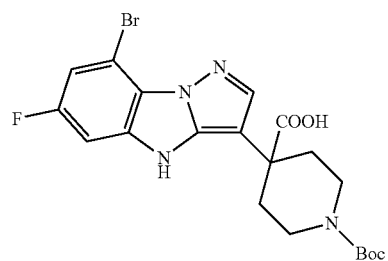 [SMILES: CC(C)(C)OC(=O)N1CCC(C(=O)O)(c2cnn3c2[nH]c2cc(F)cc(Br)c23)CC1]

A mixture of EXAMPLE 108C (800 g, 1.73 mmol) and 40% NaOH aq solution (5 mL) in ethanol (25 mL) was stirred at 80-90° C. for 15 h. After being cooled to room temperature, the mixture was acidified to pH 3-4 by 1N HCl and extracted with EtOAc (100 mL×2). The combined organic layers were washed with water (50 mL×2), brine (50 mL×2), dried over $Na_2SO_4$, filtered and evaporated to provide the title compound (850 g, purity: 79% yield: 98%) as a yellow solid which was used directly in the next step without further purification. LCMS (ESI) m/z: 481, 483 (M, M+2).

Example 109B tert-butyl 4-(8-bromo-6-fluoro-4H-benzo[4,5]imidazo[1,2-b]pyrazol-3-yl)-4-(hydroxymethyl)piperidine-1-carboxylate

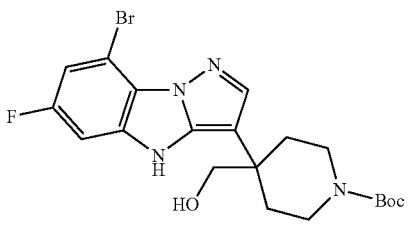 [SMILES: CC(C)(C)OC(=O)N1CCC(CO)(c2cnn3c2[nH]c2cc(F)cc(Br)c23)CC1]

To a mixture of EXAMPLE 109A (800 g, 1.56 mmol) in THF (15 mL) was added 10 M BH$_3$-DMS (1 mL, 10 mmol) at 0° C. under N$_2$ atmosphere. After the dropwise addition was completed, the mixture was stirred at 0° C. for 2 hours, and then quenched with MeOH (20 mL) and evaporated off solvent in vacuum. The residue was purified by column chromatography to provide the title compound as white solids. (508 g, yield: 70%). LCMS (ESI) m/z: 467, 469 (M, M+2).

Example 109C tert-butyl 4-(8-cyano-6-fluoro-4H-benzo[4,5]imidazo[1,2-b]pyrazol-3-yl)-4-(hydroxymethyl)piperidine-1-carboxylate

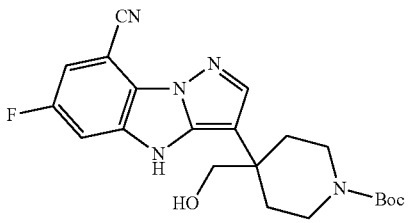 [SMILES: CC(C)(C)OC(=O)N1CCC(CO)(c2cnn3c2[nH]c2cc(F)cc(C#N)c23)CC1]

A mixture of EXAMPLE 109B (450 g, 0.96 mmol), Zn(CN)$_2$ (225 g, 1.92 mmol), Pd$_2$(dba)$_3$ (176 mg, 0.19 mmol), DPPF (215 g, 0.38 mmol) and Zn (125 g, 1.92 mmol) in DMF (5 mL) was stirred at 120° C. for 15 h under N$_2$ atmosphere. After being cooled to room temperature, the resultant mixture was filtered and the filtrate was concentrated in vacuum. The residue was purified by column chromatography to provide the title compound as brown solids (387 g, yield: 87%). LCMS (ESI) m/z: 414 (M+1).

Example 109D tert-butyl 4-(8-carbamoyl-6-fluoro-4H-benzo[4,5]imidazo[1,2-b]pyrazol-3-yl)-4-(hydroxymethyl)piperidine-1-carboxylate

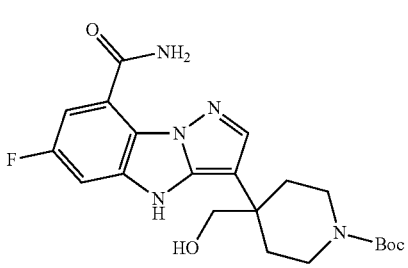 [SMILES: CC(C)(C)OC(=O)N1CCC(CO)(c2cnn3c2[nH]c2cc(F)cc(C(N)=O)c23)CC1]

To a mixture of EXAMPLE 109C (350 g, 0.85 mmol) and K$_2$CO$_3$ (600 g, 4.34 mmol) in DMSO (10 mL) was added dropwise 30% H$_2$O$_2$ (10 mL) at 0° C. After the dropwise addition was completed, the mixture was stirred at 25° C. for 10 h, and then diluted with water (50 mL). The aqueous layer was extracted with EtOAc (100 mL×2). The combined organic layers were washed with water (50 mL×2), brine (50 mL×2), dried over Na$_2$SO$_4$, filtered and evaporated. The residue was purified by column chromatography to provide the title compound as yellow solids (270 g, yield: 68%). LCMS (ESI) m/z: 432 (M+1).

Example 109E 6-fluoro-3-(4-(hydroxymethyl)piperidin-4-yl)-4H-benzo[4,5]imidazo[1,2-b]pyrazole-8-carboxamide

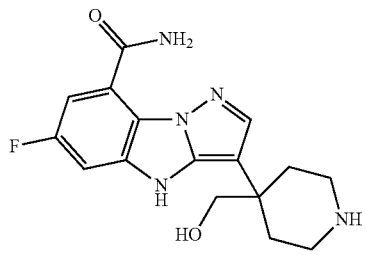 [SMILES: NC(=O)c1cc(F)cc2[nH]c3c(C4(CO)CCNCC4)cnn3c12]

A mixture of EXAMPLE 109D (100 g, 0.23 mmol) in DCM (10 mL) and TFA (3 mL) was stirred at 25° C. for 3 h. The resultant mixture was evaporated to give the title compound as yellow oil which could be used directly in the next step without further purification. LCMS (ESI) m/z: 332 (M+1).

Example 109F 3-(1-(cyclopropylmethyl)-4-(hydroxymethyl)piperidin-4-yl)-6-fluoro-4H-benzo[4,5]imidazo[1,2-b]pyrazole-8-carboxamide

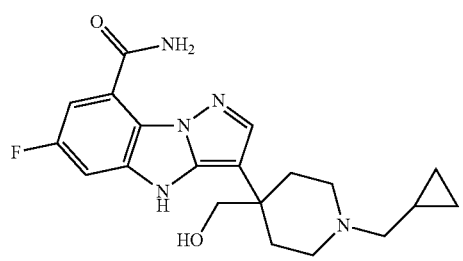 [SMILES: NC(=O)c1cc(F)cc2[nH]c3c(C4(CO)CCN(CC5CC5)CC4)cnn3c12]

This example was prepared as the method described in Example 108E. $^1$H-NMR (400 MHz, DMSO-d$_6$+D$_2$O) δ ppm 0.06-0.35 (m, 2H), 0.44-0.70 (m, 2H), 0.81-1.14 (m, 1H), 1.57-2.01 (m, 1H), 2.05-2.47 (m, 1H), 2.57-2.98 (m, 1H), 3.08-3.28 (m, 1H), 3.32-3.52 (m, 1H), 7.38-7.69 (m, 2H), 7.80 (s, 1H), 8.34 (s, 1H). LCMS (ESI) m/z: 386 (M+1).

Example 110 methyl 4-(8-carbamoyl-6-fluoro-4H-benzo[4,5]imidazo[1,2-b]pyrazol-3-yl)-1-(cyclopropylmethyl)piperidine-4-carboxylate

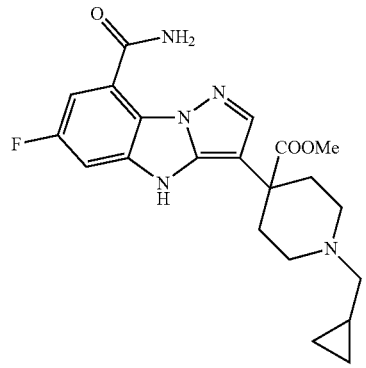 [SMILES: COC(=O)C1(c2cnn3c2[nH]c2cc(F)cc(C(N)=O)c23)CCN(CC2CC2)CC1]

Example 110A 1-(tert-butyl) 4-methyl 4-(8-bromo-6-fluoro-4H-benzo[4,5]imidazo[1,2-b]pyrazol-3-yl)piperidine-1,4-dicarboxylate

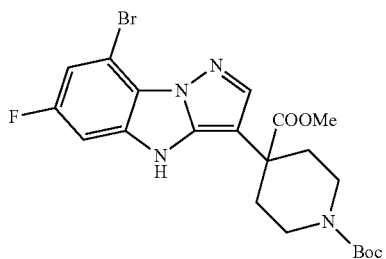 [SMILES: COC(=O)C1(c2cnn3c2[nH]c2cc(F)cc(Br)c23)CCN(C(=O)OC(C)(C)C)CC1]

A solution of EXAMPLE 109A (250 g, 0.52 mmol) in a mixture of MeOH/DCM=10/1 (1 mL) was added dropwise TMSCH$_2$N$_2$ (0.52 mL, 1.04 mmol) at 0° C. under N$_2$ atmosphere. After being stirred at 0° C. for 5 min, the reaction solution was quenched with HOAc/H$_2$O=1/10 (20 mL). The aqueous layer was extracted with CH$_2$Cl$_2$ (50 mL×2). The combined organic layers were washed with brine, dried over Na$_2$SO$_4$, filtered and evaporated. The residue was purified by column chromatograph to provide the title compound (200 g, yield: 78%). LCMS (ESI) m/z: 495, 497 (M, M+2).

Example 110B methyl 4-(8-carbamoyl-6-fluoro-4H-benzo[4,5]imidazo[1,2-b]pyrazol-3-yl)-1-(cyclopropylmethyl)piperidine-4-carboxylate

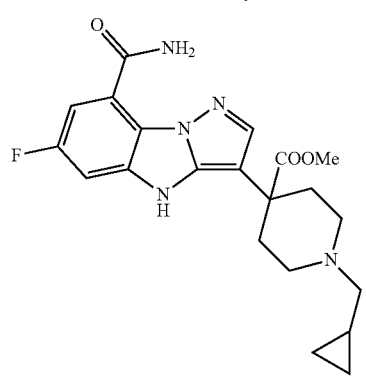

This example was prepared as the method described in Examples 109C-109F. (11 g, yield: 37%). LCMS (ESI) m/z: 414 (M+1). $^1$H-NMR (400 MHz, MethanoL-d4) δ ppm 0.34 (d, J=5.90 Hz, 2H), 0.67-0.75 (m, 2H), 0.99-1.13 (m, 1H), 2.37 (br. s., 2H), 2.58 (br. s., 2H), 2.75 (d, J=6.90 Hz, 2H), 2.89-3.07 (m, 2H), 3.39-3.61 (m, 2H), 7.44 (dd, J=8.09, 2.57 Hz, 1H), 7.75 (dd, J=10.85, 2.57 Hz, 1H), 7.90 (s, 1H), 8.34-8.47 (m, 1H). LCMS (ESI) m/z: 414 (M+1).

Scheme E

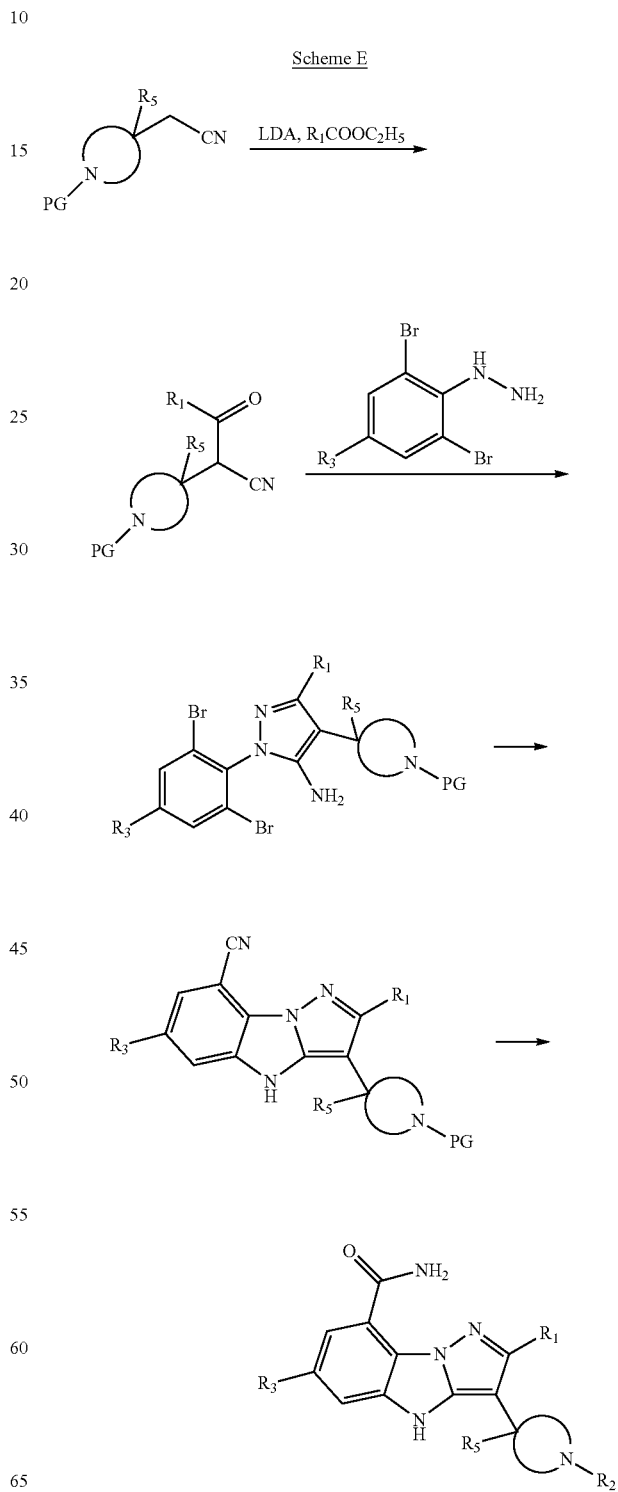

Example 111

3-(1-(cyclopropylmethyl)-4-methylpiperidin-4-yl)-6-fluoro-2-methyl-4H-benzo[4,5]imidazo[1,2-b]pyrazole-8-carboxamide

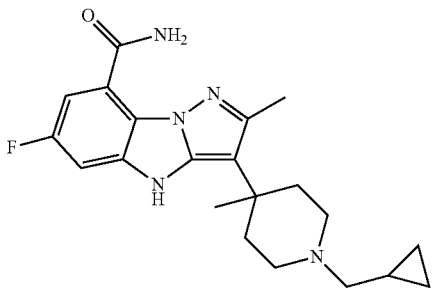 [SMILES: Cc1nn2c([nH]c3cc(F)cc(C(N)=O)c32)c1C1(C)CCN(CC2CC2)CC1]

Example 111A tert-butyl 4-(1-cyano-2-oxopropyl)-4-methylpiperidine-1-carboxylate

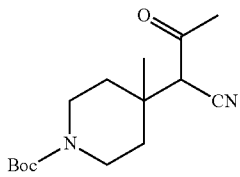 [SMILES: CC(=O)C(C#N)C1(C)CCN(C(=O)OC(C)(C)C)CC1]

To a solution of EXAMPLE 53C (5.0 g, 21.0 mmol) in dry THF (60 mL) was added dropwise LDA (26 mL, 52.0 mmol) at −78° C. under N₂ atmosphere, followed by dropwise addition of Ac₂O (5.4 g, 52.0 mmol) after stirring at −78° C. for 1 h. The resultant mixture was slowly warmed to room temperature and stirred for 30 min. The mixture was quenched with sat aq NH₄Cl solution (30 mL). The aqueous layer was extracted with EtOAc (30 mL×2). The combined organic layers were evaporated and the residue was purified by column chromatograph to provide the title compound (4.5 g, yield: 76.5%) as yellow oil. LCMS (ESI) m/z: 281 (M+1).

Example 111B tert-butyl-4-(1-cyano-2-(2-(2,6-dibromo-4-fluorophenyl)hydrazono)propyl)-4-methylpiperidine-1-carboxylate

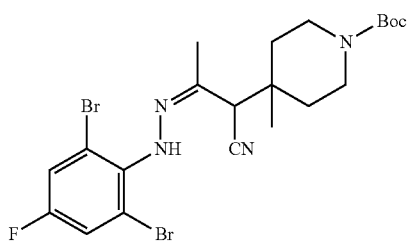 [SMILES: C/C(=N/Nc1c(Br)cc(F)cc1Br)C(C#N)C1(C)CCN(C(=O)OC(C)(C)C)CC1]

A mixture of EXAMPLE 111A (2.0 g, 7.14 mmol), HOAc (0.2 mL) and EXAMPLE 1D (2.4 g, 8.57 mmol) in EtOH (30 mL) was stirred at 70° C. for 16 h. After removal of solution in vacuum, the residue was purified by column chromatograph to provide the title compound (2.1 g, yield: 53.8%) as a light yellow solid.

Example 111C tert-butyl 4-(5-amino-1-(2,6-dibromo-4-fluorophenyl)-3-methyl-1H-pyrazol-4-yl)-4-methylpiperidine-1-carboxylate

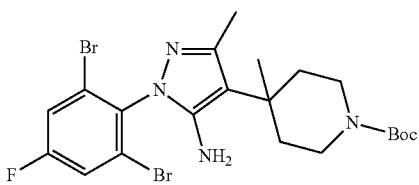 [SMILES: Cc1nn(-c2c(Br)cc(F)cc2Br)c(N)c1C1(C)CCN(C(=O)OC(C)(C)C)CC1]

A mixture of EXAMPLE 111B (2.1 g, 3.84 mmol) and K₂CO₃ (2.1 g, 15.4 mmol) in EtOH (30 mL) was heated to 80° C. and stirred for 4 h. After removal of solution in vacuum, the residue was purified by column chromatograph to provide the title compound (0.8 g, yield: 54.4%) as a light red solid.

Example 111D tert-butyl 4-(8-bromo-6-fluoro-2-methyl-4H-benzo[4,5]imidazo[1,2-b]pyrazol-3-yl)-4-methylpiperidine-1-carboxylate

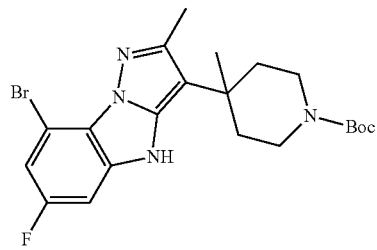 [SMILES: Cc1nn2c([nH]c3cc(F)cc(Br)c32)c1C1(C)CCN(C(=O)OC(C)(C)C)CC1]

A mixture of EXAMPLE 111C (700 g, 1.28 mmol), CuI (73 g, 0.38 mmol), K₃PO₄ (814 g, 3.84 mmol) and N,N-dimethyl-1,2-ethane-1,2-diamine (68 g, 0.76 mmol) in DMF (15 mL) was stirred at 70° C. for 5 h under N₂ atmosphere. After being cooled to room temperature, the mixture was filtered and the filtrate was concentrated in vacuum. The residue was purified by column chromatograph to provide the title compound (400 g, yield: 67.0%) as a yellow solid. LCMS (ESI) m/z: 465, 467 (M, M+2).

Example 111E tert-butyl 4-(8-cyano-6-fluoro-2-methyl-4H-benzo[4,5]imidazo[1,2-b]pyrazol-3-yl)-4-methylpiperidine-1-carboxylate

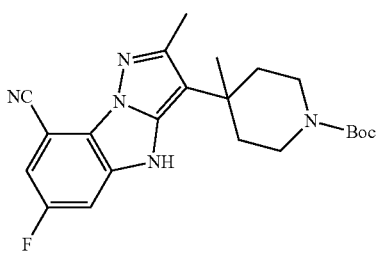 [SMILES: Cc1nn2c([nH]c3cc(F)cc(C#N)c32)c1C1(C)CCN(C(=O)OC(C)(C)C)CC1]

A mixture of EXAMPLE 111D (650 g, 1.39 mmol), Zn(CN)$_2$ (326 g, 2.78 mmol), Pd$_2$(dba)$_3$ (254 mg, 0.28 mmol), DPPF (309 g, 0.56 mmol) and Zn (181 g, 2.78 mmol) in DMF (8 mL) was stirred at 120° C. for 3 h under N$_2$ atmosphere. After being cooled to room temperature, the resultant mixture was filtered and concentrated in vacuum. The residue was purified by column chromatography to provide the title compound (450 g, yield: 78.5%) as yellow solids. LCMS (ESI) m/z: 412 (M+1).

Example 111F tert-butyl 4-(8-carbamoyl-6-fluoro-2-methyl-4H-benzo[4,5]imidazo[1,2-b]pyrazol-3-yl)-4-methylpiperidine-1-carboxylate

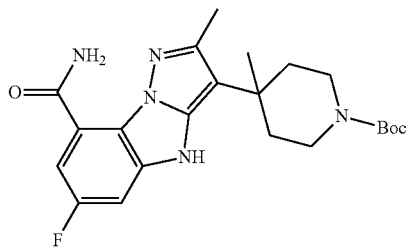 [SMILES: Cc1nn2c([nH]c3cc(F)cc(C(N)=O)c32)c1C1(C)CCN(C(=O)OC(C)(C)C)CC1]

To a mixture of EXAMPLE 111E (450 g, 1.09 mmol) and K$_2$CO$_3$ (906 g, 6.56 mmol) in DMSO (10 mL) was added 30% H$_2$O$_2$ (6 mL) at 0° C. After the dropwise addition was completed, the mixture was stirred at 25° C. for 16 h, and then diluted with water (50 mL). The aqueous phase was extracted with EtOAc (50 mL×2). The combined organic layers were washed with sat Na$_2$SO$_3$ aq solution (50 mL×2), brine (100 mL), dried over Na$_2$SO$_4$, filtered and evaporated. The residue was purified by column chromatograph to provide the title compound (450 g, yield: 95.7%) as a white solids. LCMS (ESI) m/z: 430 (M+1).

Example 111G 3-(1-(cyclopropylmethyl)-4-methylpiperidin-4-yl)-6-fluoro-2-methyl-4H-benzo[4,5]imidazo[1,2-b]pyrazole-8-carboxamide

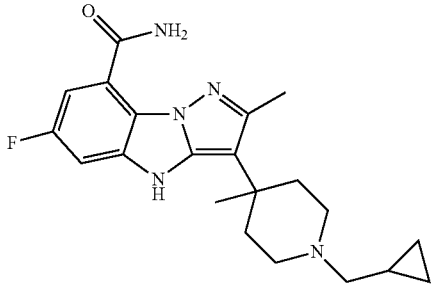 [SMILES: Cc1nn2c([nH]c3cc(F)cc(C(N)=O)c32)c1C1(C)CCN(CC2CC2)CC1]

This example was prepared as described in Examples 109E and 109F. (50 g, yield: 56.2%). $^1$H-NMR (400 MHz, MethanoL-d$_4$) δ ppm 0.41 (d, J=4.52 Hz, 2H), 0.64-0.83 (m, 2H), 1.12 (br. s., 1H), 1.47 (br. s., 3H), 2.09 (br. s., 2H), 2.50 (s, 3H), 2.54-2.71 (m, 2H), 2.84-3.29 (m, 4H), 3.52 (br. s., 2H), 7.28 (d, J=8.03 Hz, 1H), 7.48-7.69 (m, 1H), 8.63 (br. s., 1H). LCMS (ESI) m/z: 384 (M+1).

Example 112

3-(1-ethyl-4-methylpiperidin-4-yl)-6-fluoro-2-methyl-4H-benzo[4,5]imidazo[1,2-b]pyrazole-8-carboxamide

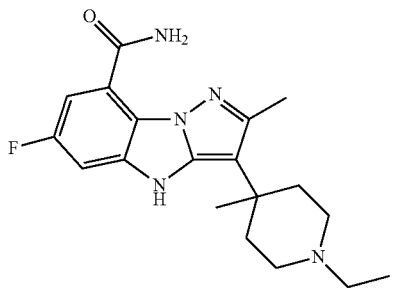 [SMILES: CCN1CCC(C)(c2c(C)nn3c2[nH]c2cc(F)cc(C(N)=O)c23)CC1]

This example was prepared as the method described in Example 111. $^1$H-NMR (400 MHz, MethanoL-d$_4$) δ ppm 1.20-1.61 (m, 6H), 2.09 (br. s., 2H), 2.49 (s, 3H), 2.52-2.77 (m, 2H), 3.17 (br. s., 4H), 3.49 (br. s., 2H), 7.16-7.34 (m, 1H), 7.46-7.63 (m, 1H), 8.46 (s, 1H). LCMS (ESI) m/z: 358 (M+1).

Example 113

6-fluoro-3-(1-isobutyl-4-methylpiperidin-4-yl)-2-methyl-4H-benzo[4,5]imidazo[1,2-b]pyrazole-8-carboxamide

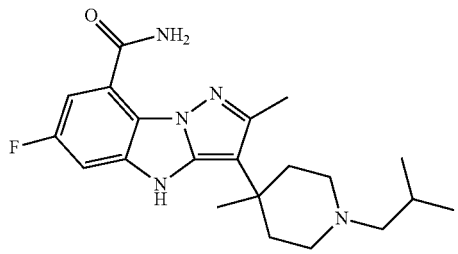 [SMILES: Cc1nn2c([nH]c3cc(F)cc(C(N)=O)c32)c1C1(C)CCN(CC(C)C)CC1]

This example was prepared as the method described in Example 111. ¹H NMR (400 MHz, DMSO-d₆) 0.84 (d, J=6.5 Hz, 7H), 1.26 (s, 3H), 1.76 (d, J=6.8 Hz, 3H), 2.00 (d, J=7.3 Hz, 2H), 2.13-2.29 (m, 3H), 2.34 (s, 1H), 2.41 (s, 3H), 2.68 (s, 1H), 7.36 (dd, J=2.5, 8.3 Hz, 1H), 7.55 (dd, J=2.5, 11.0 Hz, 1H), 8.04 (s, 1H), 8.29 (br, s, 1H), 10.63 (s, 1H). LCMS (ESI) m/z: 386 (M+1).

Example 114

6-fluoro-3-(1-isopropyl-4-methylpiperidin-4-yl)-2-methyl-4H-benzo[4,5]imidazo[1,2-b]pyrazole-8-carboxamide

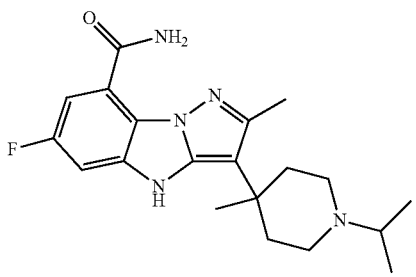 [SMILES: Cc1nn2c([nH]c3cc(F)cc(C(N)=O)c32)c1C1(C)CCN(C(C)C)CC1]

This example was prepared as the method described in Example 111. ¹H-NMR (400 MHz, MethanoL-d₄) δ ppm 1.34 (d, J=5.52 Hz, 6H), 1.47 (br. s., 3H), 2.11 (br. s., 2H), 2.51 (s, 3H), 2.53-2.72 (m, 2H), 3.11 (br. s., 2H), 3.44 (br. s., 3H), 7.20-7.38 (m, 1H), 7.59 (dd, J=10.92, 2.64 Hz, 1H), 8.66 (br. s., 1H). LCMS (ESI) m/z: 372 (M+1).

Example 115

3-(1,4-dimethylpiperidin-4-yl)-6-fluoro-2-methyl-4H-benzo[4,5]imidazo[1,2-b]pyrazole-8-carboxamide

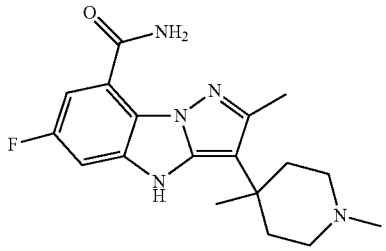 [SMILES: Cc1nn2c([nH]c3cc(F)cc(C(N)=O)c32)c1C1(C)CCN(C)CC1]

This example was prepared as the method described in Example 111. ¹H-NMR (400 MHz, MethanoL-d₄) δ ppm 1.46 (s, 3H), 2.05 (br. s., 2H), 2.50 (s, 3H), 2.56 (d, J=11.67 Hz, 2H), 2.79 (s, 3H), 3.09 (br. s., 2H), 3.34-3.41 (m, 2H), 7.31 (dd, J=8.09, 2.32 Hz, 1H), 7.63 (dd, J=10.98, 2.20 Hz, 1H), 8.55 (br. s., 1H). LCMS (ESI) m/z: 344 (M+1).

Example 116

6-fluoro-3-(1-(2-hydroxy-2-methylpropyl)-4-methylpiperidin-4-yl)-2-methyl-4H-benzo[4,5]imidazo[1,2-b]pyrazole-8-carboxamide

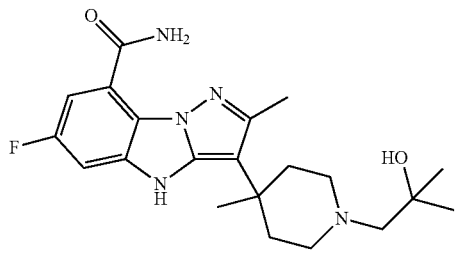 [SMILES: Cc1nn2c([nH]c3cc(F)cc(C(N)=O)c32)c1C1(C)CCN(CC(C)(C)O)CC1]

This example was prepared as the method described in Example 111. ¹H NMR (400 MHz, DMSO-d₆) 1.02-1.14 (m, 6H), 1.26 (s, 3H), 1.69-1.81 (m, 2H), 2.11-2.24 (m, 4H), 2.32-2.44 (m, 6H), 2.68 (br, s, 2H), 7.37 (dd, J=2.5, 8.3 Hz, 1H), 7.56 (dd, J=2.5, 11.0 Hz, 1H), 8.06 (s, 1H), 8.28 (s, 1H), 10.65 (s, 1H). LCMS (ESI) m/z: 402 (M+1).

Example 117

3-(1-ethyl-2,4-dimethylpiperidin-4-yl)-6-fluoro-2-methyl-4H-benzo[4,5]imidazo[1,2-b]pyrazole-8-carboxamide

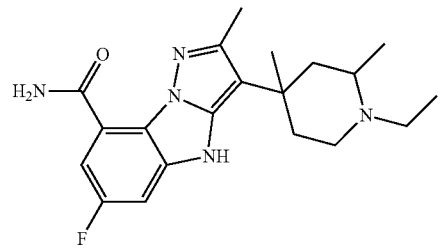 [SMILES: CCN1CCC(C)(c2c(C)nn3c2[nH]c2cc(F)cc(C(N)=O)c23)CC1C]

This example was prepared as the method described in Example 111. ¹H NMR (400 MHz, DMSO-d₆) 1.07 (t, J=7.0 Hz, 3H), 1.13 (d, J=6.0 Hz, 3H), 1.41 (s, 3H), 1.84-1.72 (m, 1H), 1.97 (d, J=10.8 Hz, 2H), 2.05-2.16 (m, 1H), 2.44 (s, 3H), 2.54-2.70 (m, 2H), 2.77 (br, s, 1H), 2.90-3.03 (m, 2H), 7.41 (dd, J=2.4, 8.4 Hz, 1H), 7.55 (dd, J=2.5, 11.0 Hz, 1H), 8.05 (s, 1H), 8.33 (s, 1H), 10.63 (s, 1H). LCMS (ESI) m/z: 372 (M+1).

Example 118

3-(1-ethyl-3-methylpyrrolidin-3-yl)-6-fluoro-2-methyl-4H-benzo[4,5]imidazo[1,2-b]pyrazole-8-carboxamide

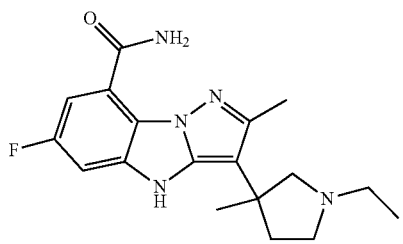 [SMILES: CCN1CCC(C)(c2c(C)nn3c2[nH]c2cc(F)cc(C(N)=O)c23)C1]

This example was prepared as the method described in Example 111. ¹H-NMR (MeOD, 400 MHz) δ: 1.37-1.41 (t, 3H), 1.58 (s, 3H), 2.47-2.49 (m, 1H), 2.51 (s, 3H), 2.67-2.74 (m, 1H), 3.29-3.30 (m, 2H), 3.34-3.67 (m, 4H), 7.33-7.35 (d, 1H), 7.66-7.69 (d, 1H), 8.52 (bs, 1H). LCMS (ESI) m/z: 344 (M+1).

Example 119

6-fluoro-3-(1-isopropyl-3-methylpyrrolidin-3-yl)-2-methyl-4H-benzo[4,5]imidazo[1,2-b]pyrazole-8-carboxamide

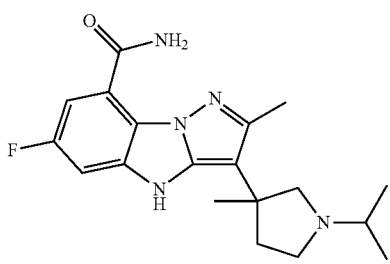 [SMILES: Cc1nn2c([nH]c3cc(F)cc(C(N)=O)c32)c1C1(C)CCN(C(C)C)C1]

This example was prepared as the method described in Example 111. ¹H-NMR (MeOD, 400 MHz) δ: 1.36-1.45 (m, 6H), 1.52-1.59 (m, 3H), 2.48 (s, 4H), 2.61-2.73 (m, 1H), 3.45-3.53 (m, 1H), 3.55-3.82 (m, 4H), 7.24-7.33 (m, 1H), 7.56-7.68 (m, 1H), 8.40-8.55 (bs, 1H). LCMS (ESI) m/z: 358 (M+1).

Example 120

3-(1-(cyclopropylmethyl)-3-methylpyrrolidin-3-yl)-6-fluoro-2-methyl-4H-benzo[4,5]imidazo[1,2-b]pyrazole-8-carboxamide

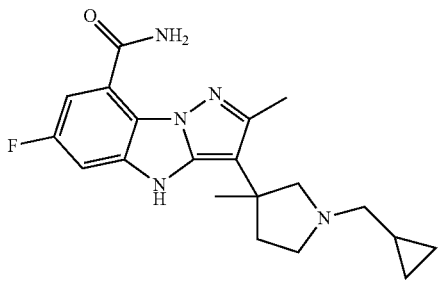 [SMILES: Cc1nn2c([nH]c3cc(F)cc(C(N)=O)c32)c1C1(C)CCN(CC2CC2)C1]

This example was prepared as the method described in Example 111. ¹H-NMR (MeOD, 400 MHz) δ: 0.59 (d, 2H), 0.96-1.06 (m, 1H), 1.53 (s, 3H), 2.12-2.22 (m, 1H), 2.48 (s, 5H), 2.83-2.94 (m, 1H), 2.98-3.08 (m, 2H), 3.11-3.20 (m, 1H), 7.33-7.36 (m, 1H), 7.61-7.74 (m, 1H). LCMS (ESI) m/z: 370 (M+1).

Example 121

3-(1,3-dimethylazetidin-3-yl)-6-fluoro-2-methyl-4H-benzo[4,5]imidazo[1,2-b]pyrazole-8-carboxamide

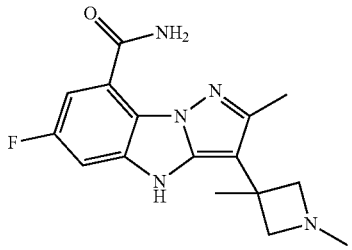 [SMILES: Cc1nn2c([nH]c3cc(F)cc(C(N)=O)c32)c1C1(C)CN(C)C1]

This example was prepared as the method described in Example 111. ¹H-NMR (400 MHz, MethanoL-d₄) δ ppm 1.74 (s, 3H), 2.37 (s, 3H), 2.94 (s, 3H), 4.27 (d, J=9.79 Hz, 2H), 4.43 (d, J=9.29 Hz, 2H), 7.29 (d, J=8.28 Hz, 1H), 7.62 (d, J=10.92 Hz, 1H), 8.51 (br. s., 1H). LCMS (ESI) m/z: 316 (M+1).

Example 122

3-(1-ethyl-3-methylazetidin-3-yl)-6-fluoro-2-methyl-4H-benzo[4,5]imidazo[1,2-b]pyrazole-8-carboxamide

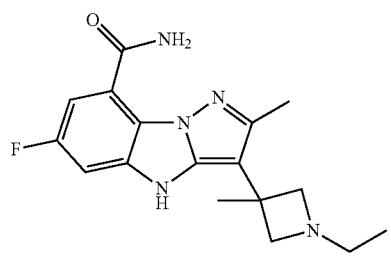 [SMILES: CCN1CC(C)(c2c(C)nn3c2[nH]c2cc(F)cc(C(N)=O)c23)C1]

This example was prepared as the method described in Example 111. ¹H-NMR (MeOD, 400 MHz) δ: 1.01-1.08 (m, 3H), 1.65-1.70 (m, 3H), 2.34 (s, 3H), 2.55-2.65 (m, 2H), 3.47-3.53 (m, 2H), 3.59-3.66 (m, 2H), 7.28-7.36 (dd, 1H), 7.63-7.73 (dd, 1H). LCMS (ESI) m/z: 330 (M+1).

Example 123

6-fluoro-3-(1-isopropyl-3-methylazetidin-3-yl)-2-methyl-4H-benzo[4,5]imidazo[1,2-b]pyrazole-8-carboxamide

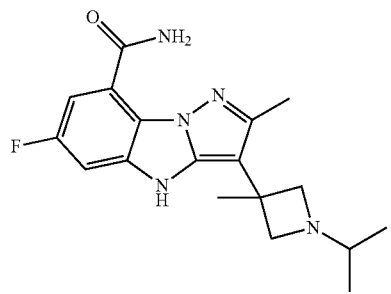 [SMILES: Cc1nn2c([nH]c3cc(F)cc(C(N)=O)c32)c1C1(C)CN(C(C)C)C1]

This example was prepared as the method described in Example 111. ¹H-NMR (MeOD, 400 MHz) δ: 1.26 (d, J=6.53 Hz, 6H), 1.75 (s, 3H), 2.40 (s, 3H), 3.38 (d, J=5.90 Hz, 1H), 4.20-4.28 (m, 2H), 4.33-4.44 (m, 2H), 7.27-7.43 (dd, 1H), 7.62-7.76 (dd, 1H), 8.43-8.58 (bs, 1H). LCMS (ESI) m/z: 344 (M+1).

Example 124

3-(1-(cyclopropylmethyl)-3-methylazetidin-3-yl)-6-fluoro-2-methyl-4H-benzo[4,5]imidazo[1,2-b]pyrazole-8-carboxamide

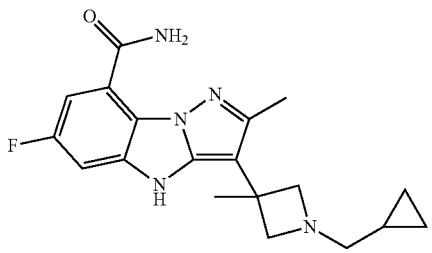 [SMILES: Cc1nn2c([nH]c3cc(F)cc(C(N)=O)c32)c1C1(C)CN(CC2CC2)C1]

This example was prepared as the method described in Example 111. ¹H-NMR (400 MHz, MethanoL-d₄) δ ppm 0.46 (d, J=4.02 Hz, 2H), 0.66-0.82 (m, 2H), 1.09 (d, J=6.02 Hz, 1H), 1.76 (s, 3H), 2.37 (s, 3H), 3.19 (br. s., 2H), 4.19-4.40 (m, 2H), 4.54 (d, J=9.16 Hz, 2H), 7.24 (br. s., 1H), 7.57 (br. s., 1H), 8.53 (br. s., 1H). LCMS (ESI) m/z: 356 (M+1).

Example 125

6-fluoro-3-(1-(2-hydroxy-2-methylpropyl)-3-methyl-azetidin-3-yl)-2-methyl-4H-benzo[4,5]imidazo[1,2-b]pyrazole-8-carboxamide

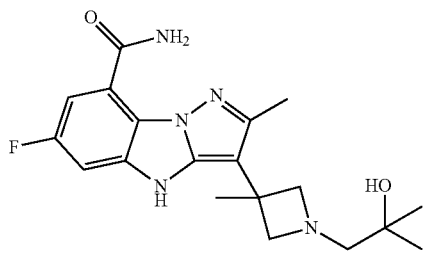 [SMILES: Cc1nn2c([nH]c3cc(F)cc(C(N)=O)c32)c1C1(C)CN(CC(C)(C)O)C1]

This example was prepared as the method described in Example 111. ¹H-NMR (400 MHz, MethanoL-d₄) δ ppm 1.32 (s, 6H), 1.75 (s, 3H), 2.30-2.43 (m, 3H), 3.24 (s, 2H), 4.35 (d, J=9.91 Hz, 2H), 4.52 (d, J=9.29 Hz, 2H), 7.26 (d, J=8.03 Hz, 1H), 7.61 (d, J=11.04 Hz, 1H), 8.50 (br. s., 1H). LCMS (ESI) m/z: 374 (M+1).

Example 126

6-fluoro-3-(1-isopropyl-4-methylpiperidin-4-yl)-2-methoxy-4H-benzo[4,5]imidazo[1,2-b]pyrazole-8-carboxamide

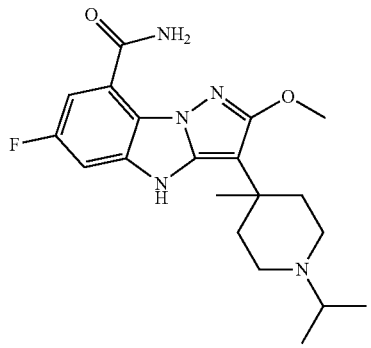 [SMILES: COc1nn2c([nH]c3cc(F)cc(C(N)=O)c32)c1C1(C)CCN(C(C)C)CC1]

Example 126A tert-butyl 4-(1-cyano-2-(2-(2,6-dibromo-4-fluoro-phenyl)hydrazinyl)-2-oxoethyl)-4-methylpiperidine-1-carboxylate

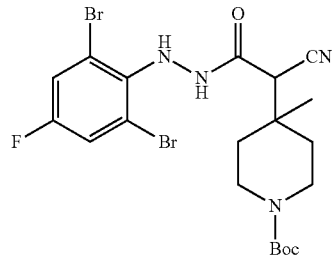 [SMILES: CC(C)(C)OC(=O)N1CCC(C)(C(C#N)C(=O)NNc2c(Br)cc(F)cc2Br)CC1]

A mixture of EXAMPLE 105C (2.73 g, crude, 9.67 mmol), HATU (5.51 g, 0.26 mmol), EXAMPLE 1D (3.29 g, 11.60 mmol) and Et₃N (2.84 g, 29.01 mmol) in DMF (20 mL) was stirred at 25° C. for 10 h under N₂ atmosphere. After completion the reaction mixture was quenched with water (100 mL) and extracted with EtOAc (100 mL×2). The combined organic layers were washed with water (50 mL×2) and brine (50 mL×2), dried over Na₂SO₄, filtered and evaporated. The residue was purified by column chromatograph to provide the title compound (4.50 g, yield: 85%) as yellow solids.

Example 126B tert-butyl 4-(5-amino-1-(2,6-dibromo-4-fluorophenyl)-3-hydroxy-1H-pyrazol-4-yl)-4-methylpiperidine-1-carboxylate

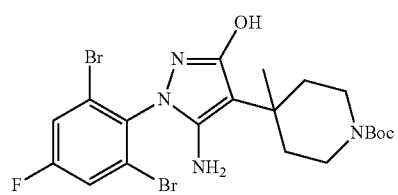 [SMILES: CC(C)(C)OC(=O)N1CCC(C)(c2c(O)nn(-c3c(Br)cc(F)cc3Br)c2N)CC1]

A mixture of EXAMPLE 126A (4.50 g, 8.21 mmol) and K₂CO₃ (2.27 g, 16.42 mmol) in ethanol (100 mL) was stirred at 80° C. for 15 h. After removal of solution in vacuum, the residue was diluted with water (100 mL). The aqueous layer was extracted with EtOAc (100 mL×2). The combined organic layers were washed with water (50 mL×2) and brine (50 mL×2), dried over Na₂SO₄, filtered and evaporated. The residue was purified by column chromatograph to provide the title compound (3.81 g, yield: 84%) as a yellow solid.

Example 126C tert-butyl 4-(5-amino-1-(2,6-dibromo-4-fluorophenyl)-3-methoxy-1H-pyrazol-4-yl)-4-methylpiperidine-1-carboxylate

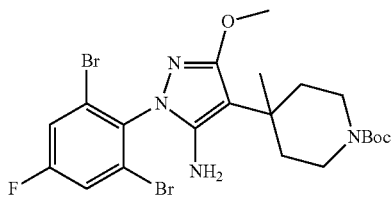 [SMILES: COc1nn(-c2c(Br)cc(F)cc2Br)c(N)c1C1(C)CCN(C(=O)OC(C)(C)C)CC1]

A mixture of EXAMPLE 126B (2.3 g, 3.65 mmol), MeI (517.80 g, 3.65 mmol) and K₂CO₃ (1.51 g, 10.94 mmol) in DMF (50 ml) was stirred at 25° C. for 15 h. After removal of solution in vacuum, the residue was diluted with water (100 mL). The aqueous layer was extracted with EtOAc (100 mL×2). The combined organic layers were washed with water (50 mL×2), brine (50 mL×2), dried over Na₂SO₄, filtered and evaporated. The residue was purified by column chromatograph to provide the title compound (590 g, yield: 28.76%) as a yellow solid.

Example 126D tert-butyl 4-(8-bromo-6-fluoro-2-methoxy-4H-benzo[4,5]imidazo[1,2-b]pyrazol-3-yl)-4-methylpiperidine-1-carboxylate

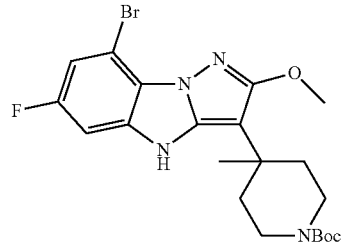 [SMILES: COc1nn2c([nH]c3cc(F)cc(Br)c32)c1C1(C)CCN(C(=O)OC(C)(C)C)CC1]

A mixture of EXAMPLE 126C (680 g, 1.21 mmol), CuI (69 g, 0.36 mmol), N¹,N²-dimethylethane-1,2-diamine (64 g, 0.73 mmol) and K₃PO₄ (770 g, 3.63 mmol) in DMF (15 mL) was stirred at 70° C. for 10 h under N₂ atmosphere. After being cooled to room temperature, the resultant mixture was filtered and the filtrate was evaporated. The residue was purified by column chromatography to provide the title compound (455 g, yield: 78%) as white solids. LCMS (ESI) m/z: 481, 483 (M, M+2).

Example 126E tert-butyl 4-(8-cyano-6-fluoro-2-methoxy-4H-benzo[4,5]imidazo[1,2-b]pyrazol-3-yl)-4-methylpiperidine-1-carboxylate

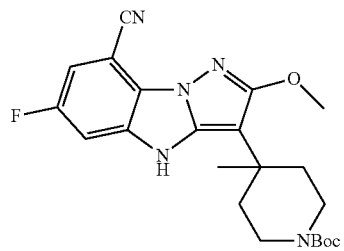 [SMILES: COc1nn2c([nH]c3cc(F)cc(C#N)c32)c1C1(C)CCN(C(=O)OC(C)(C)C)CC1]

A mixture of EXAMPLE 126D (400 g, 0.83 mmol), Zn(CN)₂ (108 g, 1.69 mmol), Pd₂(dba)₃ (152 mg, 0.16 mmol), DPPF (185 g, 0.33 mmol) and Zn (108 g, 1.66 mmol) in DMF (8 mL) was stirred at 120° C. for 15 h under N₂ atmosphere. After being cooled to room temperature, the resultant mixture was filtered and the filtrate was evaporated. The residue was purified by column chromatography to provide the title compound (330 g, yield: 81%) as yellow solids. LCMS (ESI) m/z: 428 (M+1).

Example 126F tert-butyl 4-(8-carbamoyl-6-fluoro-2-methoxy-4H-benzo[4,5]imidazo[1,2-b]pyrazol-3-yl)-4-methylpiperidine-1-carboxylate

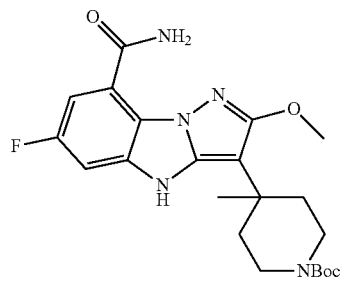 [SMILES: COc1nn2c([nH]c3cc(F)cc(C(N)=O)c32)c1C1(C)CCN(C(=O)OC(C)(C)C)CC1]

To a mixture of EXAMPLE 126E (200 g, 0.47 mmol) and K₂CO₃ (300 g, 2.17 mmol) in DMSO (5 mL) was added 30% H₂O₂ (5 mL) at 0° C. After being stirred at 25° C. for 15 h, the mixture was diluted with water (50 mL). The aqueous layer was extracted with EtOAc (50 mL×3). The combined organic layers were washed with water (50 mL) and brine (50 mL), dried over Na₂SO₄, filtered and evaporated. The residue was purified by column chromatography to provide the title compound (195 g, yield: 93%) as white solids. LCMS (ESI) m/z: 446 (M+1).

Example 126G 6-fluoro-2-methoxy-3-(4-methylpiperidin-4-yl)-4H-benzo[4,5]imidazo[1,2-b]pyrazole-8-carboxamide

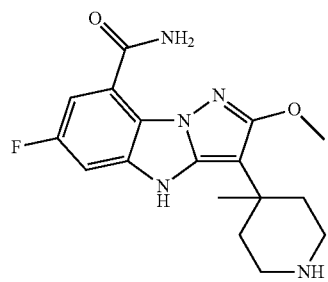 [SMILES: COc1nn2c([nH]c3cc(F)cc(C(N)=O)c32)c1C1(C)CCNCC1]

A solution of EXAMPLE 126F (100 g, 0.22 mmol) in a mixture of DCM/TFA (10 mL/3 mL) was stirred at 25° C. for 3 h. After removal of solution in vacuum, the title compound was provided and used directly in the next step without further purification.

Example 126H 6-fluoro-3-(1-isopropyl-4-methylpiperidin-4-yl)-2-methoxy-4H-benzo[4,5]imidazo[1,2-b]pyrazole-8-carboxamide

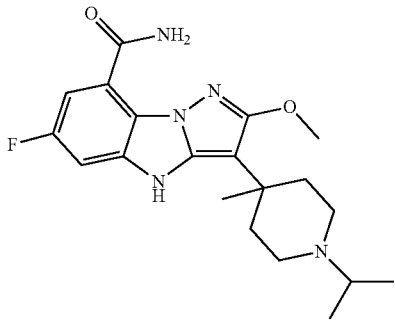 [SMILES: COc1nn2c([nH]c3cc(F)cc(C(N)=O)c32)c1C1(C)CCN(C(C)C)CC1]

A mixture of EXAMPLE 126G (78 g, crude, 0.22 mmol), acetone (70 g, 1.2 mmol) and Na(CN)BH$_3$ (140 g, 2.22 mmol) in a mixture of THF/MeOH (15 mL/5 mL) was stirred at 24° C. for 15 h. The mixture was diluted with water (20 mL). The aqueous layer was extracted with EtOAc (30 mL×2). The combined organic layers were washed with water (20 mL) and brine (20 mL), dried over Na$_2$SO$_4$, filtered and evaporated. The residue was purified by prep-HPLC to provide the title compound (35 g, yield: 41%) as a white solid. $^1$H-NMR (400 MHz, MethanoL-d$_4$) δ ppm 1.27-1.52 (m, 9H), 1.77-2.19 (m, 2H), 2.69 (br. s., 2H), 2.84-3.28 (m, 2H), 3.39-3.55 (m, 3H), 4.06 (s, 3H), 7.31 (dd, J=8.03, 2.51 Hz, 1H), 7.66 (dd, J=10.98, 2.45 Hz, 1H), 8.55 (br. s., 1H). LCMS (ESI) m/z: 388 (M+1).

Example 127

2-(benzyloxy)-6-fluoro-3-(1-isopropyl-4-methylpiperidin-4-yl)-4H-benzo[4,5]imidazo[1,2-b]pyrazole-8-carboxamide

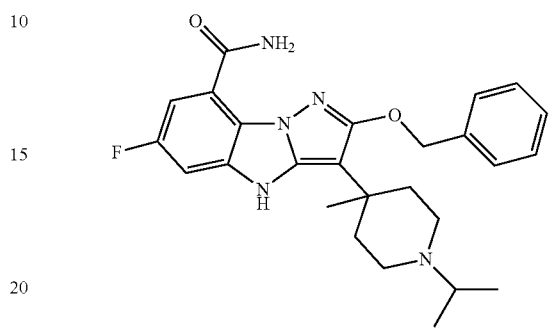

Example 127A

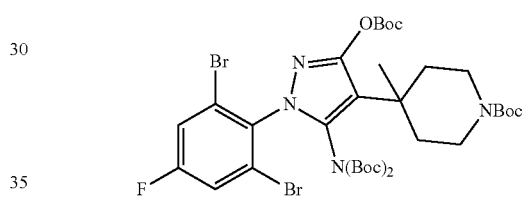

A mixture of EXAMPLE 126B (3.0 g, 5.48 mmol), Boc$_2$O (10.0 g, 45.8 mmol) and DMAP (670 g, 5.48 mmol) was stirred at 80° C. for 3 hours. After being cooled to room temperature, the mixture was diluted with aq NaHCO$_3$ solution (30 mL). The aqueous layer was extracted with DCM (100 mL×3). The combined organic layers were dried over Na$_2$SO$_4$, filtered and evaporated to provide the title compound (4.5 g crude) which could be used directly in the next step without further purification.

Example 127B

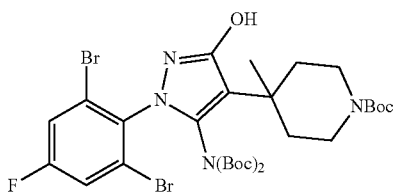

A mixture of EXAMPLE 127A (4.5 g, 5.31 mmol) and K$_2$CO$_3$ (1.46 g, 10.62 mmol) in MeOH (40 mL) was stirred at 20° C. for 4 h. The mixture was filtered and the filtrate was evaporated. The residue was purified by chromatography to provide the title compound (3.1 g, yield: 80%) as a yellow solid.

Example 127C

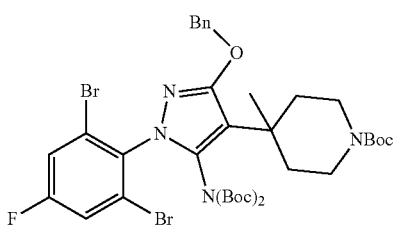

A mixture of EXAMPLE 127B (2.5 g, 3.35 mmol), K₂CO₃ (925 g, 6.7 mmol) and BnBr (626 g, 3.68 mmol) in MeOH (30 mL) was stirred at 60° C. for 8 h. The mixture was filtered and the filtrate was evaporated. The residue was purified by chromatography to provide the title compound (1.4 g crude) as a white solid.

Example 127D 3-(benzyloxy)-1-(2,6-dibromo-4-fluorophenyl)-4-(4-methylpiperidin-4-yl)-1H-pyrazol-5-amine

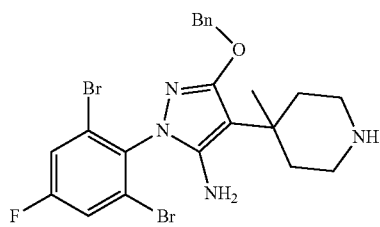 [SMILES: CC1(c2c(OCc3ccccc3)nn(-c3c(Br)cc(F)cc3Br)c2N)CCNCC1]

A solution of EXAMPLE 127C (1.4 g, 1.63 mmol) in 4M HCl/EtOAc (20 mL) was stirred at 10° C. for 3 hours. After removal of solution in vacuum, the title compound was provided (1.0 g, yield: 100%) as a yellow solid and used directly in the next step without further purification.

Example 127E tert-butyl 4-(5-amino-3-(benzyloxy)-1-(2,6-dibromo-4-fluorophenyl)-1H-pyrazol-4-yl)-4-methylpiperidine-1-carboxylate

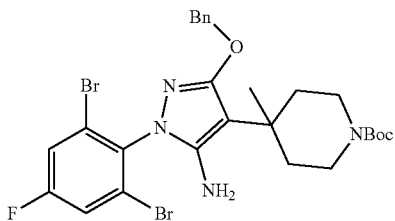 [SMILES: CC(C)(C)OC(=O)N1CCC(C)(c2c(OCc3ccccc3)nn(-c3c(Br)cc(F)cc3Br)c2N)CC1]

A mixture of EXAMPLE 127D (1.0 g, 1.78 mmol), Et₃N (362 g, 3.56 mmol) and Boc₂O (776 g, 3.56 mmol) in DCM (15 mL) was stirred at 10° C. for 4 hours. The mixture was diluted with H₂O (20 mL). The aqueous layer was extracted with DCM (15 mL×2). The combined organic layers were washed with water, brine, dried over Na₂SO₄, filtered and evaporated. The residue was purified by column chromatograph to provide the title compound (1.0 g crude) as a white solid.

Example 127F 2-(benzyloxy)-6-fluoro-3-(1-isopropyl-4-methylpiperidin-4-yl)-4H-benzo[4,5]imidazo[1,2-b]pyrazole-8-carboxamide

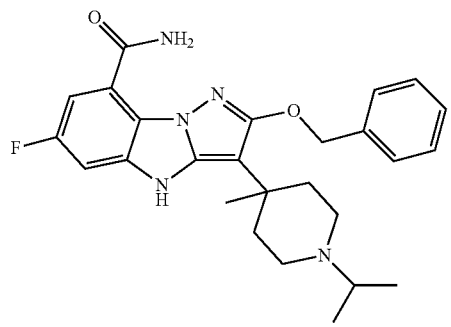 [SMILES: CC(C)N1CCC(C)(c2c(OCc3ccccc3)nn3c2[nH]c2cc(F)cc(C(N)=O)c23)CC1]

This example was prepared as described in Examples 126D-126H. $^1$H NMR (400 MHz, DMSO-d₆) 0.95 (d, J=6.5 Hz, 6H), 1.24 (s, 3H), 1.60-1.72 (m, 2H), 2.34 (br, s, 4H), 2.66-2.77 (m, 3H), 5.32 (s, 2H), 7.29-7.55 (m, 7H), 8.04 (s, 1H), 8.34 (br, s, 1H), 10.20 (s, 1H). LCMS (ESI) m/z: 464 (M+1).

Scheme F

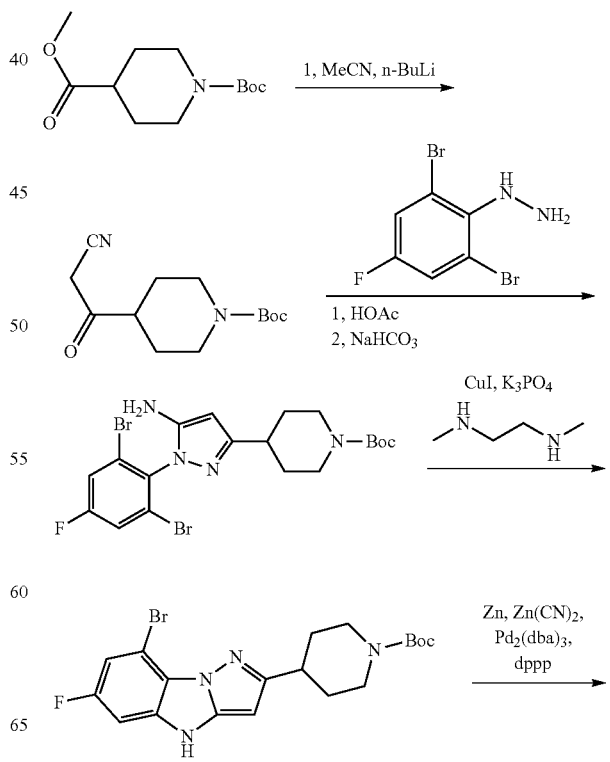

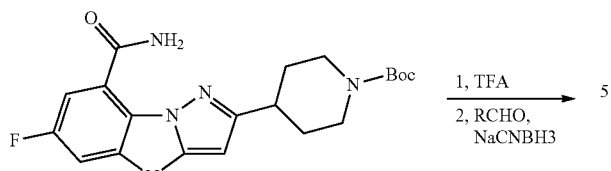

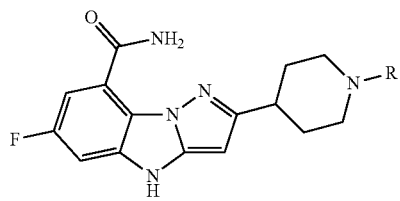

Example 128

6-fluoro-2-(piperidin-4-yl)-4H-benzo[4,5]imidazo[1,2-b]pyrazole-8-carboxamide

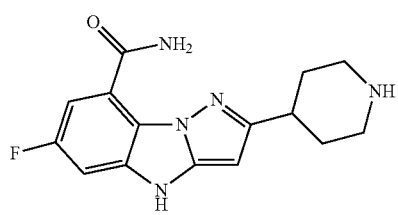 [SMILES: NC(=O)c1cc(F)cc2[nH]c3cc(C4CCNCC4)nn3c12]

Example 128A tert-butyl 4-(2-cyanoacetyl)piperidine-1-carboxylate

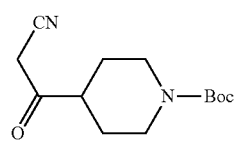 [SMILES: CC(C)(C)OC(=O)N1CCC(C(=O)CC#N)CC1]

To a solution of acetonitrile (5.06 g, 123.4 mmol) in dry THF (200 mL) was added n-BuLi (39.5 mL, 98.6 mmol) dropwise at −78° C. under nitrogen atmosphere. The mixture was stirred at −78° C. for 2 h. Thereafter, a solution of 1-(tert-butyl) 4-methyl piperidine-1,4-dicarboxylate (20 g, 82.2 mmol) in tetrahydrofuran (100 mL) was added dropwise into the above mixture. After the dropwise addition was completed, the resultant mixture was warmed to 15° C. and stirred for 16 h and subsequently quenched with sat aq NH₄Cl solution (100 mL). The aqueous phase was extracted with EtOAc (100 mL×2). The combined organic layers were dried over Na₂SO₄, filtered and evaporated. The residue was purified by column chromatograph to provide the title compound (7.9 g, yield: 38.1%) as a yellow solid. LCMS (ESI) m/z: 253 (M+1).

Example 128B tert-butyl-4-(2-cyano-1-(2-(2,6-dibromo-4-fluorophenyl)hydrazono)ethyl)piperidine-1-carboxylate

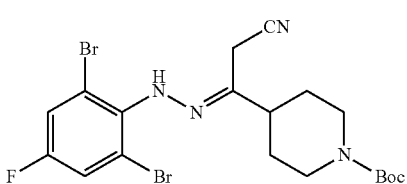 [SMILES: CC(C)(C)OC(=O)N1CCC(/C(CC#N)=N/Nc2c(Br)cc(F)cc2Br)CC1]

A mixture of EXAMPLE 128A (6.35 g, 25.16 mmol) and EXAMPLE 1D (10 g, 35.2 mmol) in ethanol (80 mL) and HOAc (80 mL) was stirred at 85° C. for 16 h. After being cooled to room temperature, the mixture was evaporated to provide the title compound (15 g, crude) which could be used directly in the next step with out further purification.

Example 128C tert-butyl 4-(5-amino-1-(2,6-dibromo-4-fluorophenyl)-1H-pyrazol-3-yl)piperidine-1-carboxylate

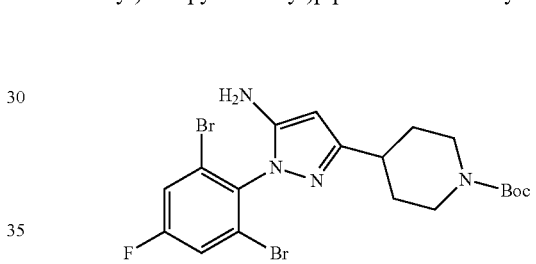

A mixture of EXAMPLE 128B (13 g, 25.1 mmol) and Et₃N (12.7 g, 125.5 mmol) in ethanol (100 mL) was heated to 80° C. for about 16 h. After being cooled to room temperature, the mixture was evaporated. The residue was purified by column chromatograph to provide the title compound (11 g, yield: 84.6%) as a yellow solid.

Example 128D tert-butyl 4-(8-bromo-6-fluoro-4H-benzo[4,5]imidazo[1,2-b]pyrazol-2-yl)piperidine-1-carboxylate

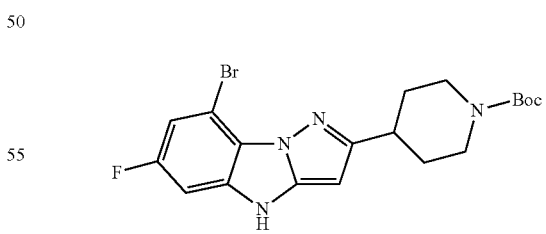

A mixture of EXAMPLE 128C (1.5 g, 2.9 mmol), CuI (166 g, 0.87 mmol), K₃PO₄ (1.8 g, 8.7 mmol) and N¹,N²-dimethylethane-1,2-diamine (153 g, 1.74 mmol) in DMF (8 mL) was stirred at 55° C. for 18 h under N₂ atmosphere. After being cooled to room temperature, the resultant mixture was diluted with water (20 mL). The aqueous layer was extracted with EtOAc (20 mL×2). The combined organic layers were washed with water (20 mL), brine (20 mL), dried over Na₂SO₄, filtered and evaporated. The residue was purified by column chromatograph to provide the title compound (350 g, yield: 27.6%) as a yellow solid. LCMS (ESI) m/z: 437, 439 (M, M+2).

Example 128E tert-butyl 4-(8-carbamoyl-6-fluoro-4H-benzo[4,5]imidazo[1,2-b]pyrazol-2-yl)piperidine-1-carboxylate

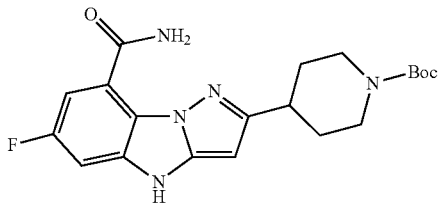 [SMILES: CC(C)(C)OC(=O)N1CCC(c2cc3[nH]c4cc(F)cc(C(N)=O)c4n3n2)CC1]

A mixture of EXAMPLE 128D (350 g, 0.8 mmol), Zn(CN)₂ (188 g, 1.6 mmol), Pd₂(dba)₃ (110 g, 0.12 mmol), DPPF (133 g, 0.24 mmol), and Zn powder (104 g, 1.6 mmol) in DMF (4 mL) was stirred at 120° C. for 2 h under N₂ atmosphere. After being cooled to room temperature, the resultant mixture was filtered and the filtrate was evaporated. The residue was purified by prep-TLC to provide the title compound (50 g, yield: 16.2%) as a yellow solid. LCMS (ESI) m/z: 402 (M+1).

Example 128F 6-fluoro-2-(piperidin-4-yl)-4H-benzo[4,5]imidazo[1,2-b]pyrazole-8-carboxamide

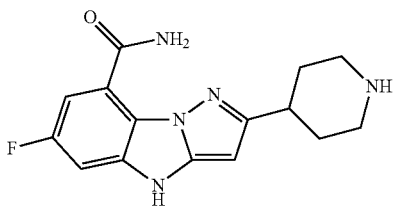 [SMILES: NC(=O)c1cc(F)cc2[nH]c3cc(C4CCNCC4)nn3c12]

A mixed solution of EXAMPLE 128E (50 g, 0.125 mmol) in TFA (1 mL) and DCM (6 mL) was stirred at 20° C. for 2 h. The resultant mixture was evaporated. The residue was purified by prep-HPLC to provide the title compound (23 g, yield: 59.0%) as a white solid. ¹H-NMR (400 MHz, Methanol-d₄) δ ppm 1.07-1.27 (m, 9H), 2.51 (d, J=1.51 Hz, 2H), 2.76-2.97 (m, 2H), 3.34 (d, J=3.26 Hz, 2H), 5.74 (br. s., 1H), 7.36~7.39 (m, 1H), 7.68~7.72 (m, 1H). LCMS (ESI) m/z: 302 (M+1).

Example 129

2-(1-ethylpiperidin-4-yl)-6-fluoro-4H-benzo[4,5]imidazo[1,2-b]pyrazole-8-carboxamide

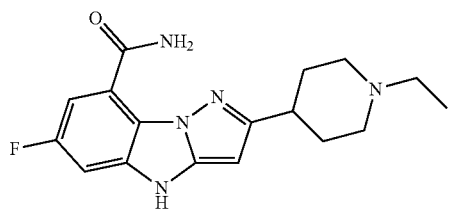 [SMILES: CCN1CCC(c2cc3[nH]c4cc(F)cc(C(N)=O)c4n3n2)CC1]

A mixture of EXAMPLE 128F (20 g, 0.066 mmol), 40% acetaldehyde (0.2 mL) and Na(CN)BH₃ (17 mg, 0.264 mmol) in MeOH (5 mL) was stirred at 10° C. for 16 h. After the reaction was complete, the resultant mixture was diluted with water (5 mL). The aqueous layer was extracted with DCM (20 mL×2). The combined organic layers were evaporated. The residue was purified by prep-HPLC to provide the title compound (17.36 g, yield: 78.9%) as a light yellow solid. ¹H-NMR (400 MHz, MethanoL-d₄) δ ppm 1.38 (t, J=7.28 Hz, 3H), 1.98-2.23 (m, 2H), 2.28-2.49 (m, 2H), 2.92-3.25 (m, 5H), 3.57 (d, J=11.54 Hz, 2H), 5.83 (s, 1H), 7.29 (dd, J=8.28, 2.51 Hz, 1H), 7.61 (dd, J=10.92, 2.51 Hz, 1H), 8.60 (br. s., 1H). LCMS (ESI) m/z: 330 (M+1).

In Vitro Studies

Cellular PARylation Assay

HCC1937 cells were planted into 96 well plates at 4×10⁴ cells/well and incubated at 37° C. in an incubator overnight. After being treated with a test compound for 30 min, cells were then treated with 1 mM H₂O₂ for 10 min. The cells were washed with 200 ul pre-chilled PBS twice and fixed with 100 ul pre-chilled methanol/acetone (7:3) on ice for 30 min. After being air-dried, the plates were blocked using PBS-Tween blocking solution (0.05%) with dissolved 5% nonfat dry milk for 30 min at room temperature. The cells were incubated with anti-PAR antibody 10H (1:100) at room temperature for 1 hour followed by washing with PBS-Tween20 for 3 times; and then added into a blocking solution including goat anti-mouse fluorescein isothiocyanate (FITC)-coupled secondary antibody and 1 μg/mL DAPI to incubate away from light at room temperature for 1 hour. After being washed with PBS-Tween20 for 3 times, the plate was analyzed with a fluorescence microplate counter (Flexstation III, Molecular Device).

PARP Enzymatic Assay (Following the Manual of HT Universal Colorimetric PARP1 Assay Kit).

Histone proteins were coated on a 96-well plate and incubated overnight at 4° C. After be washed 3 times with 200 ul PBST solution, the plate was blocked with a blocking solution and incubated for 30 min at room temperature, and then washed with PBST solution 3 times. A compound to be tested was treated and added to the plate. Thereafter, 20 μl of diluted PARP1 (1 nM) or 20 μl of PARP2 (3 nM) solution was added into the reaction system and incubated for 1 or 2 hours. 50 ul of streptavidin-HRP mixture (1:50) was added into the plate and incubated for 30 min at room temperature. The plate was then washed with three times with PBST buffer. 100 μl of (HRP) (Chemiluminescent substrate A and substrate B (1:1)) was added into the plate, and the plate was immediately read on a microplate reader (Envision, PerkinElmer).

Anti-Proliferation Assay

MDA-MB-436 and MDA-MB-231 cells were seeded in 96-well plates at the density of 500 and 2000 cells per well respectively and cultured overnight in a medium RPMI1640 supplemented with 10% (v/v) FBS and 1% (v/v) Penicillin-Streptomycin. After adding a compound to be tested, the cells were treated for 8 days. Cellular viabilities were measured by CCK8 kit following the specific method: adding 10 ul CCK8 reagent each well and incubating for 3 hours at 37° C. in 5% CO2 incubator. After shaking for 10 min, the optical density values (OD) were measured at 450 nm by Flexstation III (Molecular Device).

For the compound combination test (in combination with drugs for DNA damages), the PF50 value is calculated to measure a synergetic effect of a drug. PF50=[IC50 of a tested compound]/[IC50 of the tested compound at a fixed conc. of a drug for DNA damages]. Temozolomide (TMZ) was used as the drug for DNA damages in this study.

The data of PARP-1 enzymatic inhibition $IC_{50}$ and cellular PARylation $EC_{50}$ of the compounds of this invention were provided in Table I below. Compounds with $IC_{50}$ between 1 nM to 100 nM were designated as +++; compounds with $IC_{50}$ between 101 nM to 1000 nM were designated as ++, and compounds with $IC_{50}$ above 1000 nM were designated as +.

TABLE 1

| Tested/ Example Title Compounds | $IC_{50}$ (nM) | $EC_{50}$ (nM) |
| --- | --- | --- |
| ABT-888 | +++ | +++ |
| MK-4827 | +++ | +++ |
| BMN-673 | +++ | +++ |
| 1 | +++ | ++ |
| 2 | +++ | +++ |
| 3 | +++ | +++ |
| 4 | +++ | +++ |
| 5 | +++ | +++ |
| 6 | +++ | +++ |
| 7 | +++ | +++ |
| 8 | +++ | ++ |
| 9 | +++ | +++ |
| 10 | +++ | +++ |
| 11 | +++ | ++ |
| 12 | +++ | +++ |
| 13 | +++ | ++ |
| 14 | +++ | +++ |
| 15 | +++ | +++ |
| 16 | +++ | +++ |
| 17 | +++ | ++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | ++ |
| 25 | +++ | +++ |
| 26 | +++ | ++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | ++ |
| 34 | +++ | ++ |
| 35 | +++ | ++ |
| 36 | +++ | ++ |
| 37 | +++ | + |
| 38 | ++ | + |
| 39 | +++ | ++ |
| 40 | +++ | + |
| 41 | ++ | + |
| 42 | +++ | ++ |
| 43 | +++ | ++ |
| 44 | ++ | ++ |
| 45 | ++ | + |
| 46 | ++ | + |
| 47 | +++ | + |
| 48 | +++ | +++ |
| 49 | +++ | ++ |
| 50 | ++ | + |
| 64 | +++ | ++ |
| 65 | +++ | +++ |
| 66 | +++ | +++ |
| 67 | +++ | +++ |
| 68 | +++ | +++ |
| 69 | +++ | +++ |
| 70 | +++ | +++ |
| 71 | +++ | +++ |
| 72 | +++ | +++ |
| 73 | +++ | +++ |

TABLE 1-continued

| Tested/ Example Title Compounds | $IC_{50}$ (nM) | $EC_{50}$ (nM) |
| --- | --- | --- |
| 74 | +++ | ++ |
| 75 | +++ | ++ |
| 76 | +++ | +++ |
| 77 | +++ | +++ |
| 78 | +++ | +++ |
| 79 | +++ | +++ |
| 80 | +++ | +++ |
| 81 | +++ | +++ |
| 82 | +++ | +++ |
| 83 | +++ | +++ |
| 84 | +++ | +++ |
| 85 | +++ | +++ |
| 86 | +++ | +++ |
| 87 | +++ | ++ |
| 88 | +++ | +++ |
| 89 | +++ | ++ |
| 90 | +++ | +++ |
| 91 | +++ | +++ |
| 92 | +++ | +++ |
| 93 | +++ | +++ |
| 94 | +++ | ++ |
| 95 | +++ | +++ |
| 96 | +++ | +++ |
| 97 | +++ | ++ |
| 98 | +++ | ++ |
| 99 | +++ | +++ |
| 100 | +++ | +++ |
| 101 | +++ | ++ |
| 102 | +++ | ++ |
| 103 | +++ | ++ |
| 104 | +++ | +++ |
| 105 | +++ | +++ |
| 106 | +++ | ++ |
| 107 | +++ | +++ |
| 108 | +++ | +++ |
| 109 | +++ | ++ |
| 110 | +++ | ++ |
| 111 | +++ | +++ |
| 112 | +++ | +++ |
| 113 | +++ | +++ |
| 114 | +++ | +++ |
| 115 | +++ | +++ |
| 116 | +++ | +++ |

What is claimed is:

1. A compound of formula (I) or a pharmaceutically acceptable salt thereof,

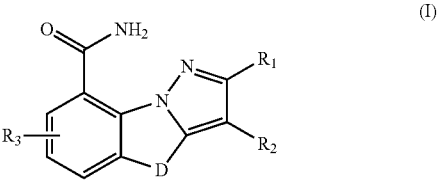

wherein,
D is selected from the group consisting of —C($R_{d1}$)($R_{d2}$)—, —C(═O)N($R_{d3}$)—, —N($R_{d4}$)—, —C(═N$R_{d5}$)—, —S(═O)$_2$N($R_{d6}$)—, —S(═O)N($R_{d7}$)—, —O—, —S—, —C(═O)O—, —C(═O)—, —C(═S)—, —S(═O)—, and —S(═O)$_2$—;

$R_{1-3}$, $R_{d1}$, and $R_{d2}$ are separately and independently selected from the group consisting of H, F, Cl, Br, I, CN, OH, SH, and NH$_2$, or selected from the group, optionally substituted by $R_{01}$, consisting of $C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl;

$R_{01}$ is selected from the group consisting of F, Cl, Br, I, CN, OH, SH, $NH_2$, and $R_{02}$;

$R_{02}$ is selected from the group consisting of $C_{1-10}$ alkyl, $C_{1-10}$ alkylamino, N,N-di($C_{1-10}$ alkyl) amino, $C_{1-10}$ alkyloxyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

heteroatom or heteroatomic group is separately and independently selected from the group consisting of —C(=O)N($R_{d3}$)—, —N($R_{d4}$)—, —C(=N$R_{d5}$)—, —S(=O)$_2$N($R_{d6}$)—, —S(=O) N($R_{d7}$)—, —O—, —S—, —C(=O)O—, —C(=O)—, —C(=S)—, —S(=O)—, and/or —S(=O)$_2$—;

$R_{d3-d7}$ are separately and independently selected from the group consisting of H, and $R_{03}$;

$R_{03}$ is selected from the group consisting of $C_{1-10}$ alkyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

$R_{02}$, and $R_{03}$ are optionally substituted by $R_{001}$;

$R_{001}$ is selected from the group consisting of F, Cl, Br, I, CN, OH, $N(CH_3)_2$, $NH(CH_3)$, $NH_2$, $CF_3$, $(NH_2)CH_2$, $(HO)CH_2$, $CH_3$, $CH_3O$, $CH_3C(=O)$, $CH_3O$ $C(=O)$, $CH_3S(=O)_2$, and $CH_3S(=O)$; and the number of $R_{01}$, $R_{001}$, the heteroatom, or heteroatomic group is separately and independently selected from 0, 1, 2, and 3.

2. The compound of claim 1 or a pharmaceutically acceptable salt thereof, wherein the D is selected from —NH—, —N($CH_3$)—, —C(F)$_2$—, —C(H) (F)— and —C(H)(OH)—.

3. The compound of claim 1 or 2, or a pharmaceutically acceptable salt thereof, wherein $R_{1-3}$ are separately and independently selected from the group consisting of H, F, Cl, Br, I, CN, OH, SH, $NH_2$, $C_{1-6}$ alkyl, $C_{1-6}$ alkyloxyl, benzyloxyl, —$CH_2N(R_{21})(R_{22})$,

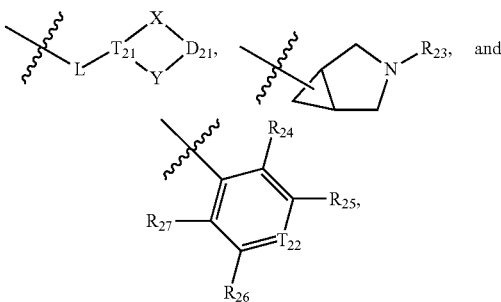

in which,

L and $D_{21}$ are separately and independently selected from the group consisting of —C($R_{d1}$)($R_{d2}$)—, —C(=O)N($R_{d3}$)—, —N($R_{d4}$)—, —C(=N$R_{d6}$)—, —S(=O)$_2$N($R_{d6}$)—, —S(=O) N($R_{d7}$)—, —O—, —S—, —C(=O)—, —C(=O)O—, —C(=S)—, —S(=O)—, and —S(=O)$_2$—;

L may also be a single bond for a linkage purpose only;

$T_{21-22}$ are separately and independently selected from the group consisting of C($R_t$) and N;

X is selected from $(CH_2)_n$ optionally substituted by $R_{01}$, and n is selected from 0, 1, 2, or 3;

Y is selected from $(CH_2)_m$ optionally substituted by $R_{01}$, and m is selected from 0, 1, 2, or 3;

$R_{21-23}$ and $R_{d3-d7}$ are separately and independently selected from the group consisting of H and $R_{03}$;

$R_{24-27}$, $R_{d1}$, $R_{d2}$, and $R_t$ are separately and independently selected from the group consisting of H, F, Cl, Br, I, CN, OH, SH, and $NH_2$, or selected from the group, optionally substituted by $R_{01}$, consisting of $C_{1-10}$alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl;

$R_{01}$ is selected from the group consisting of F, Cl, Br, I, CN, OH, SH, $NH_2$, and $R_{02}$;

$R_{02}$ is selected from the group consisting of $C_{1-10}$alkyl, $C_{1-10}$alkylamino, N,N-di($C_{1-10}$alkyl) amino, $C_{1-10}$ alkyloxyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

the heteroatom or heteroatomic group is separately and independently selected from the group consisting of —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, —C(=O)O—, —C(=O)—, —C(=S)—, —S(=O)—, and/or —S(=O)$_2$—;

$R_{d3-d7}$ are separately and independently selected from the group consisting of H, and $R_{03}$;

$R_{03}$ is selected from the group consisting of $C_{1-10}$alkyl, $C_{1-10}$alkylacyl, $C_{1-10}$alkyloxylcarbonyl, $C_{1-10}$ alkylsulfonyl, $C_{1-10}$alkylsulfinyl, $C_{3-10}$ cycloalkyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

$R_{02}$, and $R_{03}$ are optionally substituted by $R_{001}$;

$R_{001}$ is selected from the group consisting of F, Cl, Br, I, CN, OH, $N(CH_3)_2$, $NH(CH_3)$, $NH_2$, $CF_3$, $(NH_2)CH_2$, $(HO)CH_2$, $CH_3$, $CH_3O$, HC(=O), $CH_3O$ C(=O), $CH_3S(=O)_2$, and $CH_3S(=O)$; and the number of $R_{01}$, $R_{001}$, the heteroatom, or heteroatomic group is separately and independently selected from 0, 1, 2, or 3.

4. The compound of claim 3 or a pharmaceutically acceptable salt thereof, wherein the $R_1$ and $R_3$ are separately and independently selected from the group consisting of H, F, Cl, Br, I, CN, OH, SH, $NH_2$, $C_{1-3}$ alkyl, $C_{1-3}$ alkyloxyl, benzyloxyl, and

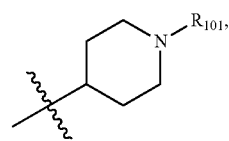

in which $R_{101}$ is selected from the group consisting of H, methyl, ethyl, n-propyl, or isopropyl.

5. The compound of claim 3 or a pharmaceutically acceptable salt thereof, wherein $R_2$ is selected from —$CH_2N$ ($R_{201}$)($R_{202}$), in which $R_{201}$ and $R_{202}$ are separately and independently selected from the group consisting of H, $C_{1-3}$ alkyl, $C_{1-3}$ alkylacyl, $C_{3-6}$ cycloalkylacyl, or $C_{3-6}$ cycloalkyl.

6. The compound of claim 3 or a pharmaceutically acceptable salt thereof, wherein $R_2$ is selected from the group consisting of

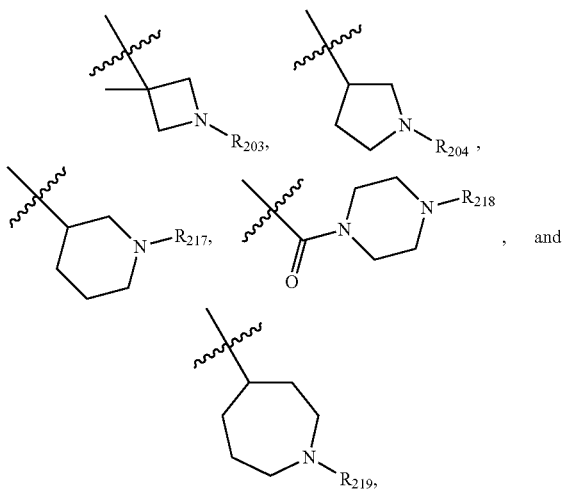

in which $R_{203}$, $R_{204}$, $R_{217}$, and $R_{218}$ are separately and independently selected from the group consisting of H, substituted or unsubstituted $C_{1-3}$ alkyl, cyclopropyl, or cyclopropylmethylene, the substituent is selected from the group consisting of F, Cl, Br, I, CN, OH, $NH_2$, methyl, or methyloxyl, and the number of substituents is 0, 1, 2, or 3.

7. The compound of claim 3 or a pharmaceutically acceptable salt thereof, wherein $R_2$ is selected from

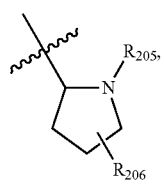

in which $R_{205}$ and $R_{206}$ are separately and independently selected from the group consisting of H, substituted or unsubstituted $C_{1-3}$ alkyl, cyclopropyl, and cyclopropylmethylene, wherein the substituent is selected from the group consisting of F, Cl, Br, I, CN, OH, $NH_2$, methyl, or methyloxyl, and the number of substituents is 0, 1, 2, or 3.

8. The compound of claim 3 or a pharmaceutically acceptable salt thereof, wherein $R_2$ is selected from

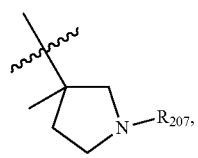

in which $R_{207}$ is selected from the group consisting of H, substituted or unsubstituted $C_{1-3}$ alkyl, cyclopropyl, cyclopropylmethylene, cyclobutyl, cyclobutylmethylene, oxacyclobutyl or oxacyclobutylalkylene, where the substituent is selected from the group consisting of F, Cl, Br, I, CN, OH, $NH_2$, methyl, $CF_3$, methyloxyl, and methylsulfonyl, and the number of substituents is 0, 1, 2, or 3.

9. The compound of claim 3 or a pharmaceutically acceptable salt thereof, wherein $R_2$ is selected from the group consisting of

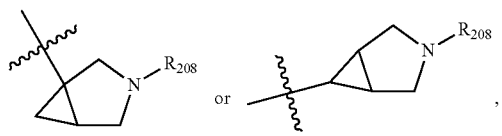

in which $R_{208}$ is selected from the group consisting of H, substituted or unsubstituted $C_{1-4}$ alkyl, wherein the substituent is selected from the group consisting of F, Cl, Br, I, CN, OH, $NH_2$, methyl, $CF_3$, methyloxyl, and methylsulfonyl, and the number of substituents is 0, 1, 2, or 3.

10. The compound of claim 3 or a pharmaceutically acceptable salt thereof, wherein $R_2$ is selected from

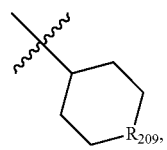

in which $R_{209}$ is selected from the group consisting of $-C(R_{d1})(R_{d2})-$, $-C(=O)N(R_{d3})-$, $-N(R_{d4})-$, $-C(=NR_{d6})-$, $-S(=O)_2N(R_{d6})-$, $-S(=O)N(R_{d7})-$, $-O-$, $-S-$, $-C(=O)O-$, $-C(=O)-$, $-C(=S)-$, $-S(=O)-$, or $-S(=O)_2-$, $R_{d1-d7}$ are as defined in claim 1.

11. The compound of claim 3 or a pharmaceutically acceptable salt thereof, wherein $R_2$ is selected from

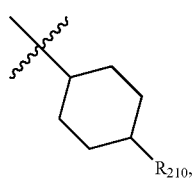

in which $R_{210}$ is selected from the group consisting of H, F, Cl, Br, I, CN, OH, $NH_2$, N,N-di($C_{1-3}$ alkyl)amino, and $C_{1-3}$ alkylamino.

12. The compound of claim 3 or a pharmaceutically acceptable salt thereof, wherein $R_2$ is selected from

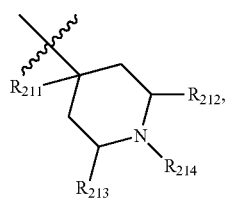

in which $R_{211-214}$ are selected from the group consisting of H or substituted or unsubstituted $C_{1-4}$ alkyloxylcarbonyl, $C_{1-4}$ alkyl, $C_{3-6}$ cycloalkyl, $C_{3-6}$ cycloalkylmethylene, or unsaturated $C_{5-6}$ heterocyclohydrocarbyl, $R_{211-213}$ are also selected from the group consisting of F, Cl, Br, I, CN, OH, and NH$_2$, the cycloalkyl or unsaturated heterocyclohydrocarbyl has O, S or NR$_{216}$ with a number of 0, 1 or 2; R$_{216}$ is selected from the group consisting of H and C$_{1-4}$alkyl substituted by R$_{215}$, R$_{215}$ is selected from the group consisting of F, Cl, Br, I, CN, OH, NH$_2$, methyl, ethyl, methyloxyl, ethyloxyl, formyl, acetyl, methylsulfonyl, ethylsulfonyl, methyloxylcarbonyl, ethyloxylcarbonyl, dimethylamino, diethylamino, dimethylaminocarbonyl, diethylaminocarbonyl, oxo, the number of R$_{215}$ is 1, 2, or 3.

13. The compound of claim 3 or a pharmaceutically acceptable salt thereof, wherein R$_2$ is selected from

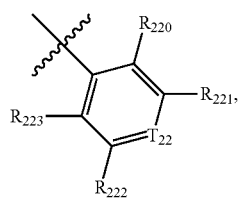

in which T22 is selected from the group consisting of N or C(R$_{224}$), R$_{220-224}$ are separately and independently selected from the group consisting of H, F, Cl, Br, I, CN, OH, SH, NH$_2$, C$_{1-3}$ alkylamino-C$_{1-3}$ alkyl, and

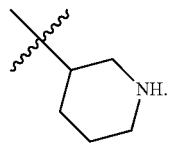 [SMILES: *C1CCCNC1]

14. The compound of claim 1 or a pharmaceutically acceptable salt thereof, wherein the compound is selected from the group consisting of:
1) 6-fluoro-3-(piperidin-4-yl)-4H-benzo[4,5]imidazo[1,2-b]pyrazole-8-carboxamide;
2) 3-(1-ethylpiperidin-4-yl)-6-fluoro-4H-benzo[4,5]imidazo[1,2-b]pyrazole-8-carboxamide;
3) 6-fluoro-3-(1-(2-fluoroethyl)piperidin-4-yl)-4H-benzo[4,5]imidazo[1,2-b]pyrazole-8-carboxamide;
4) 3-(1-cyclopropylpiperidin-4-yl)-6-fluoro-4H-benzo[4,5]imidazo[1,2-b]pyrazole-8-carboxamide;
5) 3-(1-(cyclopropylmethyl)piperidin-4-yl)-6-fluoro-4H-benzo[4,5]imidazo[1,2-b]pyrazole-8-carboxamide;
6) 6-fluoro-3-(1-(2-hydroxy-2-methylpropyl)piperidin-4-yl)-4H-benzo[4,5]imidazo[1,2-b]pyrazole-8-carboxamide;
7) 6-fluoro-3-(1-(2-fluoro-2-methylpropyl)piperidin-4-yl)-4H-benzo[4,5]imidazo[1,2-b]pyrazole-8-carboxamide;
8) 3-(1-(cyclopropanecarbonyl)piperidin-4-yl)-6-fluoro-4H-benzo[4,5]imidazo[1,2-b]pyrazole-8-carboxamide;
9) 6-fluoro-3-(1-methylpiperidin-4-yl)-4H-benzo[4,5]imidazo[1,2-b]pyrazole-8-carboxamide;
10) 6-fluoro-3-(1-isopropylpiperidin-4-yl)-4H-benzo[4,5]imidazo[1,2-b]pyrazole-8-carboxamide;
11) 6-fluoro-3-(1-(oxetan-3-yl)piperidin-4-yl)-4H-benzo[4,5]imidazo[1,2-b]pyrazole-8-carboxamide;
12) 6-fluoro-3-(1-propylpiperidin-4-yl)-4H-benzo[4,5]imidazo[1,2-b]pyrazole-8-carboxamide;
13) 3-(1-(2-aminoethyl)piperidin-4-yl)-6-fluoro-4H-benzo[4,5]imidazo[1,2-b]pyrazole-8-carboxamide;
14) 3-(1-(2-(dimethylamino)ethyl)piperidin-4-yl)-6-fluoro-4H-benzo[4,5]imidazo[1,2-b]pyrazole-8-carboxamide;
15) 6-fluoro-3-(1-(2-methoxyethyl)piperidin-4-yl)-4H-benzo[4,5]imidazo[1,2-b]pyrazole-8-carboxamide;
16) 6-fluoro-3-(1-(2-hydroxyethyl)piperidin-4-yl)-4H-benzo[4,5]imidazo[1,2-b]pyrazole-8-carboxamide;
17) 3-(1-ethylpiperidin-3-yl)-6-fluoro-4H-benzo[4,5]imidazo[1,2-b]pyrazole-8-carboxamide;
18) 3-(1-ethylazepan-4-yl)-6-fluoro-4H-benzo[4,5]imidazo[1,2-b]pyrazole-8-carboxamide;
19) 6-fluoro-3-(1-methylazepan-4-yl)-4H-benzo[4,5]imidazo[1,2-b]pyrazole-8-carboxamide;
20) 6-fluoro-3-(1-methylpyrrolidin-3-yl)-4H-benzo[4,5]imidazo[1,2-b]pyrazole-8-carboxamide;
21) 3-(1-ethylpyrrolidin-3-yl)-6-fluoro-4H-benzo[4,5]imidazo[1,2-b]pyrazole-8-carboxamide;
22) 6-fluoro-3-(1-isopropylpyrrolidin-3-yl)-4H-benzo[4,5]imidazo[1,2-b]pyrazole-8-carboxamide;
23) 6-fluoro-3-(pyrrolidin-2-yl)-4H-benzo[4,5]imidazo[1,2-b]pyrazole-8-carboxamide;
24) 6-fluoro-3-(1-propylpyrrolidin-2-yl)-4H-benzo[4,5]imidazo[1,2-b]pyrazole-8-carboxamide; 6-fluoro-3-(1-methylpyrrolidin-2-yl)-4H-benzo[4,5]imidazo[1,2-b]pyrazole-8-carboxamide;
25) 3-(1-ethylpyrrolidin-2-yl)-6-fluoro-4H-benzo[4,5]imidazo[1,2-b]pyrazole-8-carboxamide;
26) 3-(1-ethylpiperidin-4-yl)-4H-benzo[4,5]imidazo[1,2-b]pyrazole-8-carboxamide;
27) 6-fluoro-3-(1-propylpyrrolidin-2-yl)-4H-benzo[4,5]imidazo[1,2-b]pyrazole-8-carboxamide;
28) 6-fluoro-3-(3-methyl-3-azabicyclo[3.1.0]hexan-1-yl)-4H-benzo[4,5]imidazo[1,2-b]pyrazole-8-carboxamide;
29) 3-(3-ethyl-3-azabicyclo[3.1.0]hexan-1-yl)-6-fluoro-4H-benzo[4,5]imidazo[1,2-b]pyrazole-8-carboxamide;
30) 3-(3-cyclobutyl-3-azabicyclo[3.1.0]hexan-1-yl)-6-fluoro-4H-benzo[4,5]imidazo[1,2-b]pyrazole-8-carboxamide;
31) 3-(3-(cyclopropylmethylene)-3-azabicyclo[3.1.0]hexan-1-yl)-6-fluoro-4H-benzo[4,5]imidazo[1,2-b]pyrazole-8-carboxamide;
32) 6-fluoro-3-(3-isopropyl-3-azabicyclo[3.1.0]hexan-1-yl)-4H-benzo[4,5]imidazo[1,2-b]pyrazole-8-carboxamide;
33) 3-(3-azabicyclo[3.1.0]hexan-6-yl)-6-fluoro-4H-benzo[4,5]imidazo[1,2-b]pyrazole-8-carboxamide;
34) 3-(3-ethyl-3-azabicyclo[3.1.0]hexan-6-yl)-6-fluoro-4H-benzo[4,5]imidazo[1,2-b]pyrazole-8-carboxamide;
35) 3-(8-ethyl-8-azabicyclo[3.2.1]octan-3-yl)-6-fluoro-4H-benzo[4,5]imidazo[1,2-b]pyrazole-8-carboxamide;
36) 6-fluoro-3-(4-hydroxypyrrolidin-2-yl)-4H-benzo[4,5]imidazo[1,2-b]pyrazole-8-carboxamide;
37) 3-cyano-6-fluoro-4H-benzo[4,5]imidazo[1,2-b]pyrazole-8-carboxamide;
38) 3-cyano-4H-benzo[4,5]imidazo[1,2-b]pyrazole-8-carboxamide;
39) 3-(aminomethyl)-6-fluoro-4H-benzo[4,5]imidazo[1,2-b]pyrazole-8-carboxamide;
40) 3-(cyclopropanecarboxamidomethylene)-6-fluoro-4H-benzo[4,5]imidazo[1,2-b]pyrazole-8-carboxamide;
41) 6-fluoro-3-(4-fluorophenyl)-4H-benzo[4,5]imidazo[1,2-b]pyrazole-8-carboxamide;
42) 6-fluoro-3-(2-fluoro-4-((methylamino)methylene)phenyl)-4H-benzo[4,5]imidazo[1,2-b]pyrazole-8-carboxamide;

43) 6-fluoro-3-(4-((methylamino)methyl)phenyl)-4H-benzo[4,5]imidazo[1,2-b]pyrazole-8-carboxamide;
44) 6-fluoro-3-(2-fluoro-5-((methylamino)methyl)phenyl)-4H-benzo[4,5]imidazo[1,2-b]pyrazole-8-carboxamide;
45) 6-fluoro-3-(pyridin-4-yl)-4H-benzo[4,5]imidazo[1,2-b]pyrazole-8-carboxamide;
46) 6-fluoro-3-(4-(piperidin-3-yl)phenyl)-4H-benzo[4,5]imidazo[1,2-b]pyrazole-8-carboxamide;
47) 6-fluoro-3-(tetrahydro-2H-pyran-4-yl)-4H-benzo[4,5]imidazo[1,2-b]pyrazole-8-carboxamide;
48) 3-(4-(dimethylamino)cyclohexyl)-6-fluoro-4H-benzo[4,5]imidazo[1,2-b]pyrazole-8-carboxamide;
49) 6-fluoro-3-(4-methylpiperazine-1-carbonyl)-4H-benzo[4,5]imidazo[1,2-b]pyrazole-8-carboxamide;
50) 3-(1-(cyclopropylmethyl)piperidin-4-yl)-4,4,6-trifluoro-4H-pyrazolo[1,5-α]indole-8-carboxamide;
51) 3-(1-ethylpiperidin-4-yl)-6-fluoro-4-hydroxy-4H-pyrazolo[1,5-α]indole-8-carboxamide;
52) 3-(1-ethylpiperidin-4-yl)-6-fluoro-4-methyl-4H-benzo[4,5]imidazo[1,2-b]pyrazole-8-carboxamide;
53) 6-fluoro-3-(4-methylpiperidin-4-yl)-4H-benzo[4,5]imidazo[1,2-b]pyrazole-8-carboxamide;
54) 3-(1-ethyl-4-methylpiperidin-4-yl)-6-fluoro-4H-benzo[4,5]imidazo[1,2-b]pyrazole-8-carboxamide;
55) 3-(1-cyclopropyl-4-methylpiperidin-4-yl)-6-fluoro-4H-benzo[4,5]imidazo[1,2-b]pyrazole-8-carboxamide;
56) 6-fluoro-3-(1-(2-hydroxy-2-methylpropyl)-4-methylpiperidin-4-yl)-4H-benzo[4,5]imidazo[1,2-b]pyrazole-8-carboxamide;
57) 3-(1-(cyclopropylmethylene)-4-methylpiperidin-4-yl)-6-fluoro-4H-benzo[4,5]imidazo[1,2-b]pyrazole-8-carboxamide;
58) 3-(1-(4,4-difluorocyclohexyl)-4-methylpiperidin-4-yl)-6-fluoro-4H-benzo[4,5]imidazo[1,2-b]pyrazole-8-carboxamide;
59) 6-fluoro-3-(4-methyl-1-(tetrahydro-2H-pyran-4-yl)piperidin-4-yl)-4H-benzo[4,5]imidazo[1,2-b]pyrazole-8-carboxamide;
60) 6-fluoro-3-(1-(2-fluoroethyl)-4-methylpiperidin-4-yl)-4H-benzo[4,5]imidazo[1,2-b]pyrazole-8-carboxamide;
61) 6-fluoro-3-(4-methyl-1-(2,2,2-trifluoroethyl)piperidin-4-yl)-4H-benzo[4,5]imidazo[1,2-b]pyrazole-8-carboxamide;
62) 6-fluoro-3-(4-methyl-1-(3,3,3-trifluoropropyl)piperidin-4-yl)-4H-benzo[4,5]imidazo[1,2-b]pyrazole-8-carboxamide;
63) 3-(1-((1-cyanocyclopropyl)methyl)-4-methylpiperidin-4-yl)-6-fluoro-4H-benzo[4,5]imidazo[1,2-b]pyrazole-8-carboxamide;
64) 3-(1-((1-cyanocyclobutyl)methyl)-4-methylpiperidin-4-yl)-6-fluoro-4H-benzo[4,5]imidazo[1,2-b]pyrazole-8-carboxamide;
65) 6-fluoro-3-(4-methyl-1-(2-(methylsulfonyl)ethyl)piperidin-4-yl)-4H-benzo[4,5]imidazo[1,2-b]pyrazole-8-carboxamide;
66) 6-fluoro-3-(4-methyl-1-((tetrahydro-2H-pyran-4-yl)methyl)piperidin-4-yl)-4H-benzo[4,5]imidazo[1,2-b]pyrazole-8-carboxamide;
67) 3-(1-((1-aminocyclopropyl)methyl)-4-methylpiperidin-4-yl)-6-fluoro-4H-benzo[4,5]imidazo[1,2-b]pyrazole-8-carboxamide;
68) 6-fluoro-3-(4-methyl-1-(oxetan-3-ylmethyl)piperidin-4-yl)-4H-benzo[4,5]imidazo[1,2-b]pyrazole-8-carboxamide;
69) 6-fluoro-3-(1-(2-methoxyethyl)-4-methylpiperidin-4-yl)-4H-benzo[4,5]imidazo[1,2-b]pyrazole-8-carboxamide;
70) 6-fluoro-3-(1-((1-hydroxycyclopropyl)methyl)-4-methylpiperidin-4-yl)-4H-benzo[4,5]imidazo[1,2-b]pyrazole-8-carboxamide;
71) 6-fluoro-3-(4-methyl-1-((3-methyloxetan-3-yl)methyl)piperidin-4-yl)-4H-benzo[4,5]imidazo[1,2-b]pyrazole-8-carboxamide;
72) 6-fluoro-3-(1-(3-methoxypropyl)-4-methylpiperidin-4-yl)-4H-benzo[4,5]imidazo[1,2-b]pyrazole-8-carboxamide;
73) 6-fluoro-3-(4-methyl-1-((1-(methylsulfonyl)cyclopropyl)methyl)piperidin-4-yl)-4H-benzo[4,5]imidazo[1,2-b]pyrazole-8-carboxamide;
74) 6-fluoro-3-(4-methyl-1-(thiazol-2-ylmethyl)piperidin-4-yl)-4H-benzo[4,5]imidazo[1,2-b]pyrazole-8-carboxamide;
75) 6-fluoro-3-(4-methyl-1-(methylsulfonyl)piperidin-4-yl)-4H-benzo[4,5]imidazo[1,2-b]pyrazole-8-carboxamide;
76) 6-fluoro-3-(1-(3-fluorocyclobutyl)-4-methylpiperidin-4-yl)-4H-benzo[4,5]imidazo[1,2-b]pyrazole-8-carboxamide;
77) 6-fluoro-3-(4-methyl-1-(thiophen-2-ylmethyl)piperidin-4-yl)-4H-benzo[4,5]imidazo[1,2-b]pyrazole-8-carboxamide;
78) 3-(1-((1-ethylpiperidin-4-yl)methyl)-4-methylpiperidin-4-yl)-6-fluoro-4H-benzo[4,5]imidazo[1,2-b]pyrazole-8-carboxamide;
79) 6-fluoro-3-(4-methyl-1-((1-methylazetidin-3-yl)methyl)piperidin-4-yl)-4H-benzo[4,5]imidazo[1,2-b]pyrazole-8-carboxamide;
80) ethyl 2-((4-(8-carbamoyl-6-fluoro-4H-benzo[4,5]imidazo[1,2-b]pyrazol-3-yl)-4-methylpiperidin-1-yl)methyl)cyclopropanecarboxylate;
81) 3-(1-((2-(dimethylcarbamoyl)cyclopropyl)methyl)-4-methylpiperidin-4-yl)-6-fluoro-4H-benzo[4,5]imidazo[1,2-b]pyrazole-8-carboxamide;
82) 6-fluoro-3-(1-isobutyl-4-methylpiperidin-4-yl)-4H-benzo[4,5]imidazo[1,2-b]pyrazole-8-carboxamide;
83) 6-fluoro-3-(4-methyl-1-((4-methylthiazol-5-yl)methyl)piperidin-4-yl)-4H-benzo[4,5]imidazo[1,2-b]pyrazole-8-carboxamide;
84) 6-fluoro-3-(4-methyl-1-((1-methyl-1H-imidazol-2-yl)methyl)piperidin-4-yl)-4H-benzo[4,5]imidazo[1,2-b]pyrazole-8-carboxamide;
85) 3-(1-((1,2-dimethyl-1H-imidazol-5-yl)methyl)-4-methylpiperidin-4-yl)-6-fluoro-4H-benzo[4,5]imidazo[1,2-b]pyrazole-8-carboxamide
86) 3-(1'-ethyl-4-methyl-[1,4'-bipiperidin]-4-yl)-6-fluoro-4H-benzo[4,5]imidazo[1,2-b]pyrazole-8-carboxamide;
87) 6-fluoro-3-(4-methyl-1-((6-oxo-1,6-dihydropyridazin-3-yl)methyl)piperidin-4-yl)-4H-benzo[4,5]imidazo[1,2-b]pyrazole-8-carboxamide;
88) 3-(1-(2-cyanoethyl)-4-methylpiperidin-4-yl)-6-fluoro-4H-benzo[4,5]imidazo[1,2-b]pyrazole-8-carboxamide;
89) 6-chloro-3-(1-ethyl-4-methylpiperidin-4-yl)-4H-benzo[4,5]imidazo[1,2-b]pyrazole-8-carboxamide;
90) 3-(1-ethyl-3-methylpyrrolidin-3-yl)-6-fluoro-4H-benzo[4,5]imidazo[1,2-b]pyrazole-8-carboxamide;
91) 3-(1,3-dimethylpyrrolidin-3-yl)-6-fluoro-4H-benzo[4,5]imidazo[1,2-b]pyrazole-8-carboxamide;
92) 6-fluoro-3-(1-isopropyl-3-methylpyrrolidin-3-yl)-4H-benzo[4,5]imidazo[1,2-b]pyrazole-8-carboxamide;

93) 3-(1-(cyclopropylmethyl)-3-methylpyrrolidin-3-yl)-6-fluoro-4H-benzo[4,5]imidazo[1,2-b]pyrazole-8-carboxamide;
94) 6-fluoro-3-(3-methyl-1-(oxetan-3-yl)pyrrolidin-3-yl)-4H-benzo[4,5]imidazo[1,2-b]pyrazole-8-carboxamide;
95) 6-fluoro-3-(1-(2-fluoroethyl)-3-methylpyrrolidin-3-yl)-4H-benzo[4,5]imidazo[1,2-b]pyrazole-8-carboxamide;
96) 3-(1-((2,2-difluorocyclopropyl)methyl)-3-methylpyrrolidin-3-yl)-6-fluoro-4H-benzo[4,5]imidazo[1,2-b]pyrazole-8-carboxamide;
97) 6-fluoro-3-(3-methyl-1-(2,2,2-trifluoroethyl)pyrrolidin-3-yl)-4H-benzo[4,5]imidazo[1,2-b]pyrazole-8-carboxamide;
98) 6-fluoro-3-(3-methyl-1-(2-(methylsulfonyl)ethyl)pyrrolidin-3-yl)-4H-benzo[4,5]imidazo[1,2-b]pyrazole-8-carboxamide;
99) 6-fluoro-3-(3-methyl-1-(3,3,3-trifluoropropyl)pyrrolidin-3-yl)-4H-benzo[4,5]imidazo[1,2-b]pyrazole-8-carboxamide;
100) 3-(1-((1-aminocyclopropyl)methyl)-3-methylpyrrolidin-3-yl)-6-fluoro-4H-benzo[4,5]imidazo[1,2-b]pyrazole-8-carboxamide;
101) 3-(1-((1-cyanocyclobutyl)methyl)-3-methylpyrrolidin-3-yl)-6-fluoro-4H-benzo[4,5]imidazo[1,2-b]pyrazole-8-carboxamide;
102) 3-(1-((1-cyanocyclopropyl)methyl)-3-methylpyrrolidin-3-yl)-6-fluoro-4H-benzo[4,5]imidazo[1,2-b]pyrazole-8-carboxamide;
103) 3-(1-(2-cyanoethyl)-3-methylpyrrolidin-3-yl)-6-fluoro-4H-benzo[4,5]imidazo[1,2-b]pyrazole-8-carboxamide;
104) 3-(1-(cyclopropylmethyl)-3-methylazetidin-3-yl)-6-fluoro-4H-benzo[4,5]imidazo[1,2-b]pyrazole-8-carboxamide;
105) 6-fluoro-3-(1-isopropyl-4-methylpiperidin-4-yl)-4H-benzo[4,5]imidazo[1,2-b]pyrazole-8-carboxamide;
106) 6-fluoro-3-(4-methyl-1,1-dioxido-2H-thiopyran-4-yl)-4H-benzo[4,5]imidazo[1,2-b]pyrazole-8-carboxamide;
107) 3-(1,4-diethylpiperidin-4-yl)-6-fluoro-4H-benzo[4,5]imidazo[1,2-b]pyrazole-8-carboxamide;
108) 3-(4-cyano-1-(cyclopropylmethyl)piperidin-4-yl)-6-fluoro-4H-benzo[4,5]imidazo[1,2-b]pyrazole-8-carboxamide;
109) 3-(1-(cyclopropylmethyl)-4-(hydroxymethyl)piperidin-4-yl)-6-fluoro-4H-benzo[4,5]imidazo[1,2-b]pyrazole-8-carboxamide;
110) Methyl 4-(8-carbamoyl-6-fluoro-4H-benzo[4,5]imidazo[1,2-b]pyrazol-3-yl)-1-(cyclopropylmethyl)piperidine-4-carboxylate;
111) 3-(1-(cyclopropylmethyl)-4-methylpiperidin-4-yl)-6-fluoro-2-methyl-4H-benzo[4,5]imidazo[1,2-b]pyrazole-8-carboxamide;
112) 3-(1-ethyl-4-methylpiperidin-4-yl)-6-fluoro-2-methyl-4H-benzo[4,5]imidazo[1,2-b]pyrazole-8-carboxamide;
113) 6-fluoro-3-(1-isobutyl-4-methylpiperidin-4-yl)-2-methyl-4H-benzo[4,5]imidazo[1,2-b]pyrazole-8-carboxamide;
114) 6-fluoro-3-(1-isopropyl-4-methylpiperidin-4-yl)-2-methyl-4H-benzo[4,5]imidazo[1,2-b]pyrazole-8-carboxamide;
115) 3-(1,4-dimethylpiperidin-4-yl)-6-fluoro-2-methyl-4H-benzo[4,5]imidazo[1,2-b]pyrazole-8-carboxamide;
116) 6-fluoro-3-(1-(2-hydroxy-2-methylpropyl)-4-methylpiperidin-4-yl)-2-methyl-4H-benzo[4,5]imidazo[1,2-b]pyrazole-8-carboxamide;
117) 3-(1-ethyl-2,4-dimethylpiperidin-4-yl)-6-fluoro-2-methyl-4H-benzo[4,5]imidazo[1,2-b]pyrazole-8-carboxamide;
118) 3-(1-ethyl-3-methylpyrrolidin-3-yl)-6-fluoro-2-methyl-4H-benzo[4,5]imidazo[1,2-b]pyrazole-8-carboxamide;
119) 6-fluoro-3-(1-isopropyl-3-methylpyrrolidin-3-yl)-2-methyl-4H-benzo[4,5]imidazo[1,2-b]pyrazole-8-carboxamide;
120) 3-(1-(cyclopropylmethyl)-3-methylpyrrolidin-3-yl)-6-fluoro-2-methyl-4H-benzo[4,5]imidazo[1, 2-b]pyrazole-8-carboxamide;
121) 3-(1,3-dimethylazetidin-3-yl)-6-fluoro-2-methyl-4H-benzo[4,5]imidazo[1,2-b]pyrazole-8-carboxamide;
122) 3-(1-ethyl-3-methylazetidin-3-yl)-6-fluoro-2-methyl-4H-benzo[4,5]imidazo[1,2-b]pyrazole-8-carboxamide;
123) 6-fluoro-3-(1-isopropyl-3-methylazetidin-3-yl)-2-methyl-4H-benzo[4,5]imidazo[1,2-b]pyrazole-8-carboxamide;
124) 3-(1-(cyclopropylmethyl)-3-methylazetidin-3-yl)-6-fluoro-2-methyl-4H-benzo[4,5]imidazo[1,2-b]pyrazole-8-carboxamide;
125) 6-fluoro-3-(1-(2-hydroxy-2-methylpropyl)-3-methylazetidin-3-yl)-2-methyl-4H-benzo[4,5]imidazo[1,2-b]pyrazole-8-carboxamide;
126) 6-fluoro-3-(1-isopropyl-4-methylpiperidin-4-yl)-2-methoxy-4H-benzo[4,5]imidazo[1,2-b]pyrazole-8-carboxamide;
127) 2-(benzyloxy)-6-fluoro-3-(1-isopropyl-4-methylpiperidin-4-yl)-4H-benzo[4,5]imidazo[1,2-b]pyrazole-8-carboxamide;
128) 6-fluoro-2-(piperidin-4-yl)-4H-benzo[4,5]imidazo[1,2-b]pyrazole-8-carboxamide; and
129) 2-(1-ethylpiperidin-4-yl)-6-fluoro-4H-benzo[4,5]imidazo[1,2-b]pyrazole-8-carboxamide.

15. The compound of claim 4 or a pharmaceutically acceptable salt thereof, wherein the $R_1$ is selected from the group consisting of H, methyl, methyloxyl, benzyloxyl,

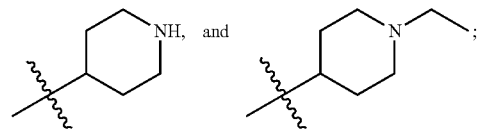

$R_3$ is selected from the group consisting of H, F, Cl, Br, CN, and methyl.

16. The compound of claim 6 or a pharmaceutically acceptable salt thereof, wherein $R_{203}$ is selected from the group consisting of methyl, ethyl, n-propyl, isopropyl, $-CH_2C(CH_3)(CH_3)(OH)$, and cyclopropylmethylene, $R_{204}$ is selected from the group consisting of methyl, ethyl, n-propyl, and isopropyl, $R_{217-219}$ are separately and independently selected from the group consisting of methyl and ethyl.

17. The compound of claim 8 or a pharmaceutically acceptable salt thereof, wherein $R_{207}$ is selected from the group consisting of H, methyl, ethyl, n-propyl, isopropyl, $-CH_2CF_3$, $-CH_2CH_2CF_3$, $-CH_2CH_2F$, $-CH_2CH_2S(=O)_2CH_3$, $-CH_2CH_2CN$,

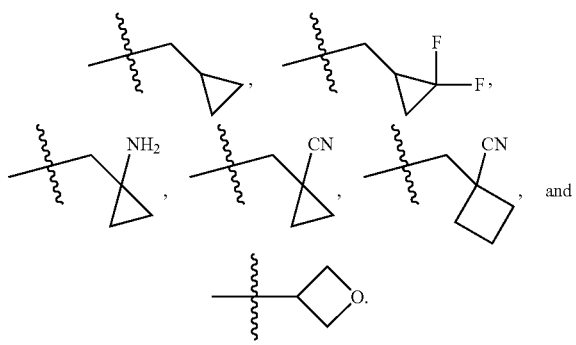

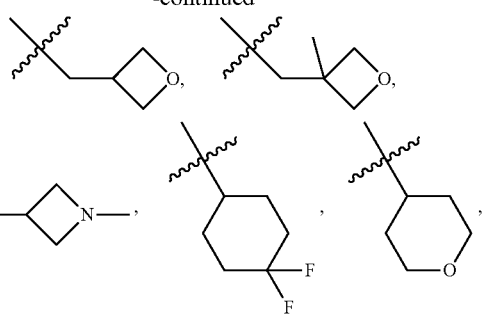

18. The compound of claim 9 or a pharmaceutically acceptable salt thereof, wherein $R_{208}$ is selected from the group consisting of H, methyl, ethyl, n-propyl, isopropyl, cyclopropylmethylene, and cyclobutyl.

19. The compound of claim 12 or a pharmaceutically acceptable salt thereof, wherein $R_{211}$ is selected from the group consisting of H, F, Cl, Br, I, CN, OH, $NH_2$, methyl, ethyl, hydroxylmethyl, and methyloxylcarbonyl, $R_{212}$ is selected from the group consisting of H, F, Cl, Br, I, CN, OH, $NH_2$, and methyl, $R_{213}$ is selected from the group consisting of H, F, Cl, Br, I, CN, OH, and $NH_2$, $R_{214}$ is selected from the group consisting of H, methyl, ethyl, n-propyl, isopropyl, n-butyl, isobutyl, tert-butyl, —$CH_2CH(OH)(CH_3)_2$, —$CH_2CH(F)(CH_3)_2$, —$CH_2CH_2F$, —$CH_2CF_3$, —$CH_2CH_2CF_3$, —$CH_2CH_2NH_2$, —$CH_2CH_2OH$, —$CH_2CH_2OCH_3$, —$CH_2CH_2CH_2OCH_3$, —$CH_2CH_2N(CH_3)_2$, —$S(=O)_2CH_3$, —$CH_2CH_2S(=O)_2CH_3$,

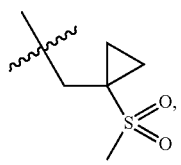 [SMILES: *CC1(S(C)(=O)=O)CC1]

cyclopropyl, cyclopropylmethylene,

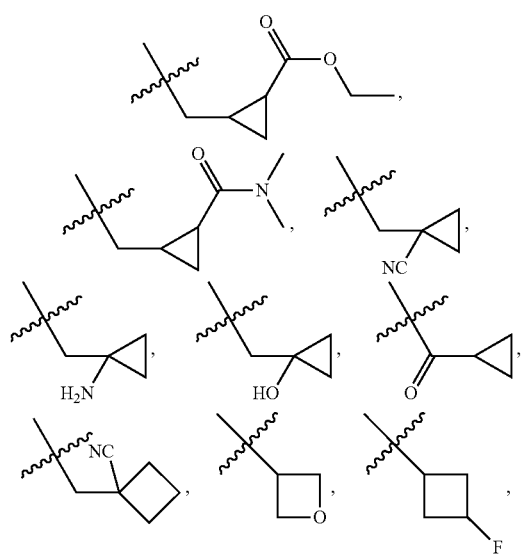

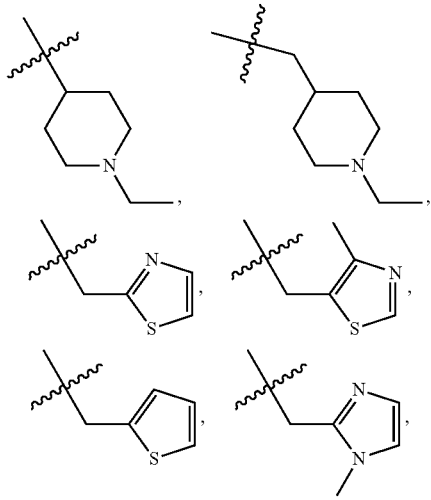

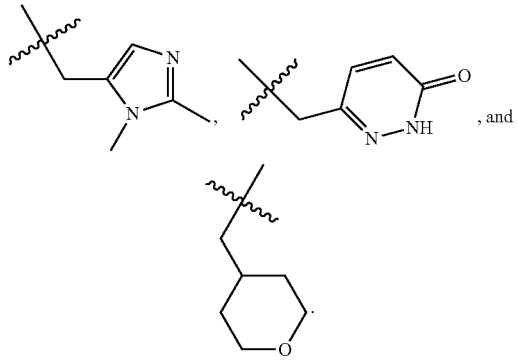

20. The compound of claim 12 or a pharmaceutically acceptable salt thereof, wherein $R_2$ is selected from the group consisting of

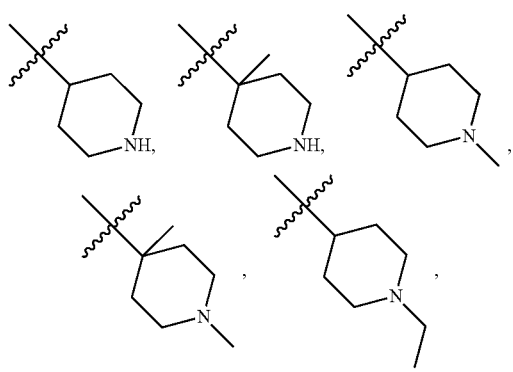

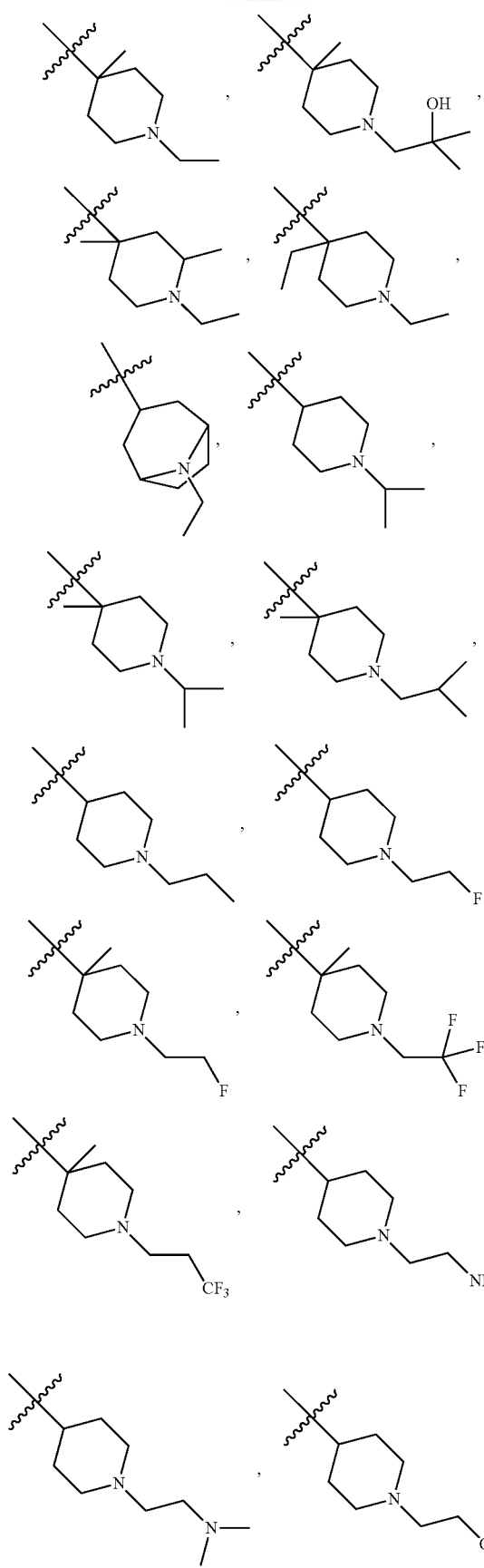
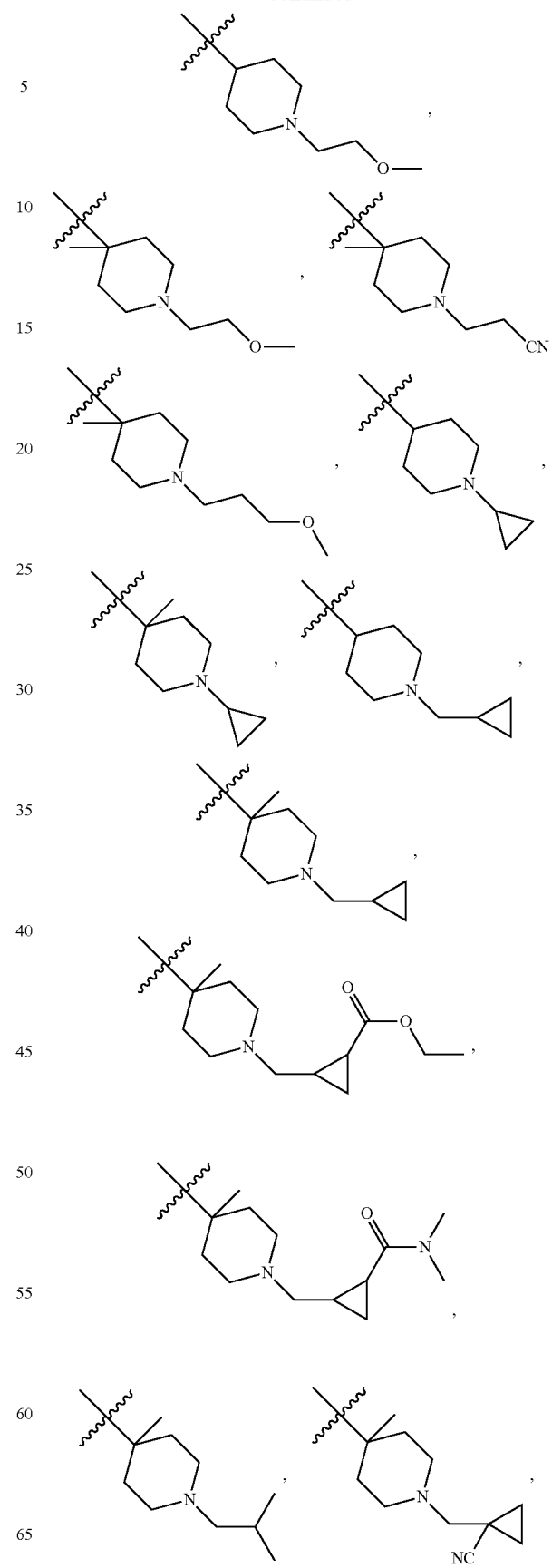

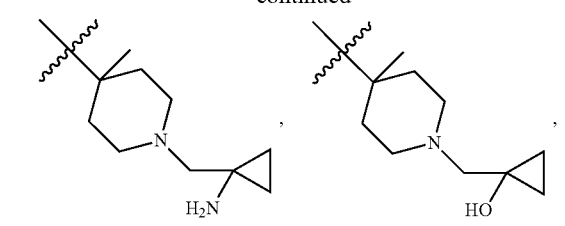
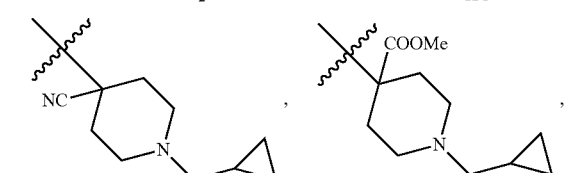
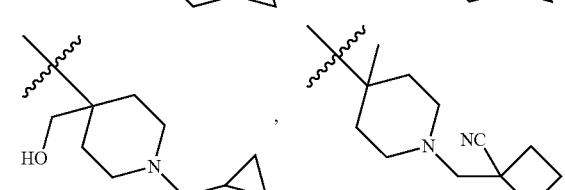
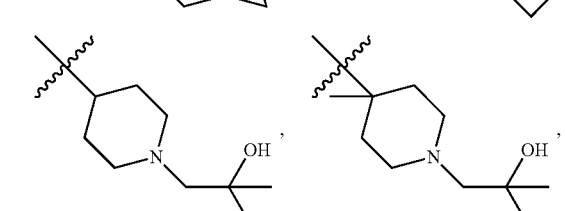
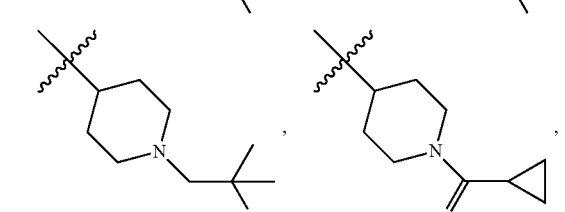
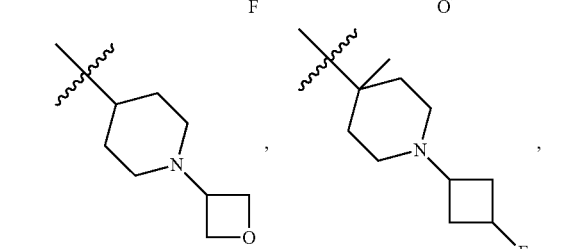
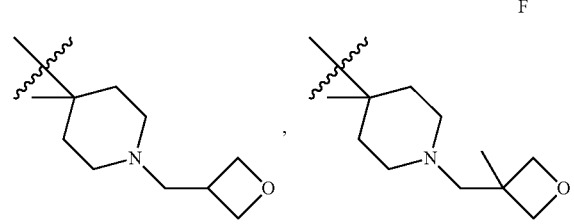
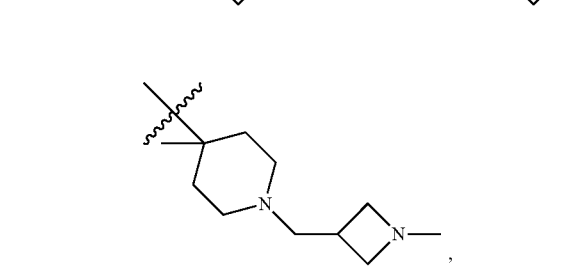
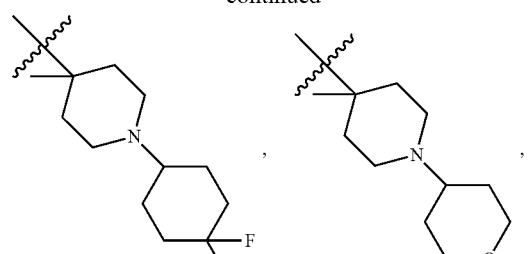
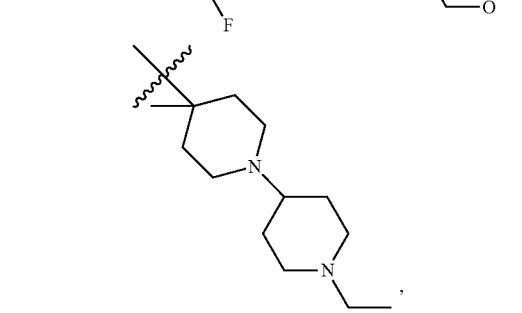
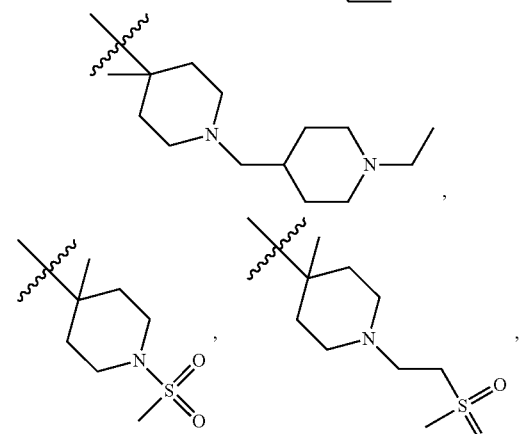
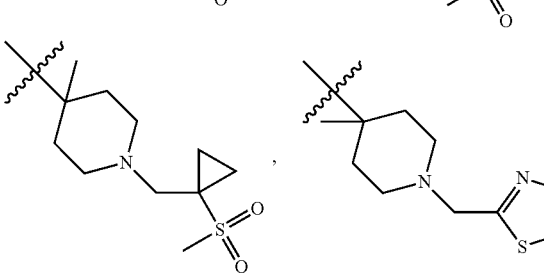
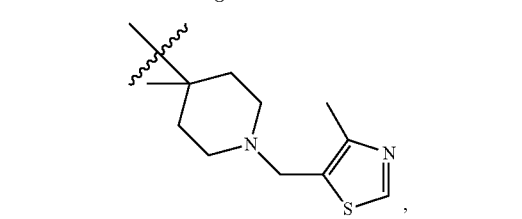
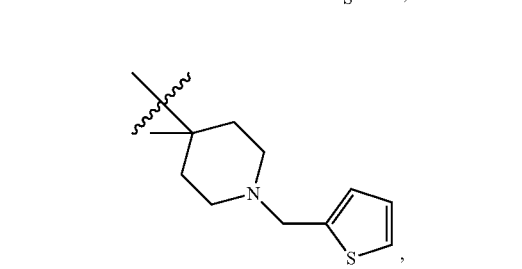

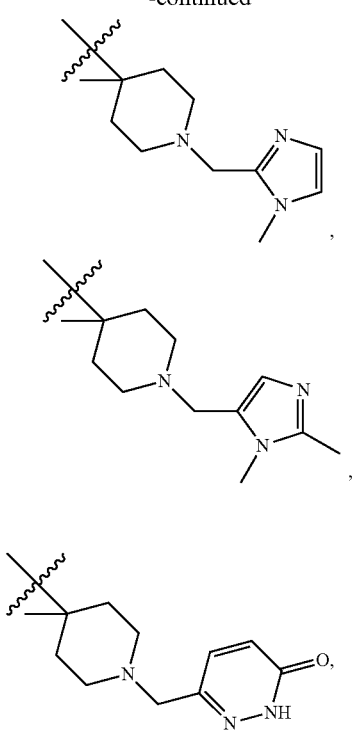
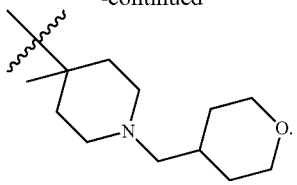
21. The compound of claim 7 or a pharmaceutically acceptable salt thereof, wherein $R_2$ is selected from the group consisting of
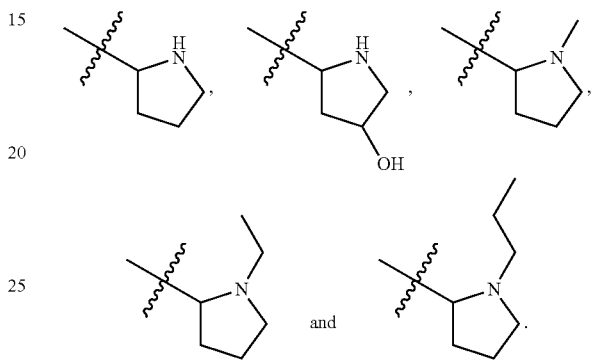
* * * * *